US010174087B2

(12) United States Patent
Meuser et al.

(10) Patent No.: US 10,174,087 B2
(45) Date of Patent: Jan. 8, 2019

(54) ENHANCED PRODUCTIVITY BY ATTENUATION OF CHLOROPHYLL BINDING PROTEIN GENES

(71) Applicant: Synthetic Genomics, Inc., La Jolla, CA (US)

(72) Inventors: Jonathan E. Meuser, Fort Myers, FL (US); Christen G. DiPetrillo, Santa Clara, CA (US); Jay McCarren, Cardiff, CA (US); Shaun Bailey, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 15/299,457

(22) Filed: Oct. 20, 2016

(65) Prior Publication Data

US 2017/0114107 A1 Apr. 27, 2017

Related U.S. Application Data

(60) Provisional application No. 62/244,079, filed on Oct. 20, 2015.

(51) Int. Cl.

| | |
|---|---|
| ***C12N 1/12*** | (2006.01) |
| ***C12N 15/113*** | (2010.01) |
| ***C12N 15/11*** | (2006.01) |
| ***C12N 15/90*** | (2006.01) |
| ***C07K 14/405*** | (2006.01) |

(52) U.S. Cl.

CPC .............. *C07K 14/405* (2013.01); *C12N 1/12* (2013.01); *C12N 15/113* (2013.01); *C12N 15/902* (2013.01); *C12N 2800/80* (2013.01)

(58) Field of Classification Search

CPC ...... C07K 14/405; C12N 1/12; C12N 15/113; C12N 15/8269; C12N 15/01; C12N 15/8218; C12N 15/8247; C12N 15/902; C12N 1/36; C12N 2310/20; C12N 2800/80; C12P 7/64; C12P 21/00; C12P 7/6445; C12P 7/6463; C12P 7/649; A61K 9/127; A61K 9/167; A61K 9/19

See application file for complete search history.

(56) References Cited

FOREIGN PATENT DOCUMENTS

WO PCT/US16/58000 * 10/2016

OTHER PUBLICATIONS

Weeks et al Proc Natl Acad Sci U S A. Dec. 27, 2011; 108(52): 20859-20860.*

International Search Report dated Apr. 25, 2017, regarding PCT/US2016/058000.

Kilian, et al.: "*High-efficiency homologous recombination in the oil-producing alga Nannochloropsis sp.*"; Proc Natl Acad Sci USA 2011, 108(52):21265-9.

Specht; "*Improving the genetic tractability of the green alga Chlamydomonas reinhardtii.*"; PhD Thesis (2014) [Retrieved from the Internet Jan. 16, 2017: <http://escholarship.org/uc/item/4x37x9rv>]; p. 16, 17.

Zetsche et al.: "*Cpf1 is a single RNA-guided endonuclease of a class 2 CRISPR-Cas system*"; Cell, Epub Sep. 25, 2015, 163(3):759-71.

"Cpf1 Is a Single RNAGuided Endonuclease of a Class 2 CRISPRCas System" [retrieved on from http://www.cell.com/cell/abstract/S0092-8674(15)01200-?_returnURL=http%3A°02F%2Flinkinghub.elseviercom%2Fretrieve%2Fpii%2FS00928674150 12003%3Fshowall%3Dtrue] The hyperlink listed is available as of Sep. 25, 2015).

* cited by examiner

*Primary Examiner* — Padmavathi Baskar

(74) *Attorney, Agent, or Firm* — DLA Piper LLP (US)

(57) ABSTRACT

Mutant photosynthetic algae having increased biomass productivity are provided. The mutants have attenuated expression of violaxanthin chlorophyll a binding proteins (VCP) or fucoxanthin chlorophyll a/c binding proteins (FCP), reduced chlorophyll, higher apparent ETR(II), little to no reduction in $P_{max}$ per cell, and decreased NPQ over a wide range of light intensities. Provided herein are constructs for attenuating or disrupting VCP or FCP genes. Also provided are methods of culturing VCP or FCP mutants for the production of biomass or other products.

13 Claims, 22 Drawing Sheets

Specification includes a Sequence Listing.

A.

B.

A.

| Strain # | FIRe, Absorption spectroscopy | | | | | | | | Chlorophyll | Productivity |
|---|---|---|---|---|---|---|---|---|---|---|
| | $F_V/F_M$ | $\sigma_{PSII}$ (Å$^2$, 450nm) | $\sigma_{PSII}$ (Å$^2$, 530nm) | $\tau'_{Qa}$ (ms) | $N_{chl}$/PSII | a_chl ($m^2$/g Chl)_ white | [PSII]/TOC (relative) | NPQ | (Chl a/ TOC) | CL-SCPA (gTOC $m^2$ $day^{-1}$) |
| WE-03730 | 0.531 | 462 | 159 | 6.5 | 286 | 4.3 | 11 | 1.35 | 0.047 | 24.8 |
| GE-15853 | 0.485 | 379 | 128 | 5.4 | 199 | 5.0 | 12 | 1.66 | 0.040 | 23.5 |
| GE-16152 | 0.594 | 284 | 80 | 4.7 | 130 | 5.2 | 11 | 1.03 | 0.029 | 27.0 |
| GE-16373 | 0.630 | 151 | 42 | 3.8 | 53 | 6.6 | 9 | 0.36 | 0.019 | 24.1 |
| GE-16374 | 0.639 | 152 | 43 | 4.4 | 51 | 6.8 | 8 | 0.60 | 0.018 | 22.7 |

B.

| Strain # | Strain description | FIRe | | | | $O_2$ | | Chl/TOC % | Productivity |
|---|---|---|---|---|---|---|---|---|---|
| | | **$F_V/F_M$ (r.u.)** | **$\sigma^{450}_{PSII}$ (Å$^2$)** | **$\sigma^{530}_{PSII}$ (Å$^2$)** | **$NPQ_{max}$ (r.u.)** | **$\alpha$*$10^5$** (nmol $O^2$ $m^2$/ µg TOC/ µmol photon) | **$P_{max}$** (nmol $O_2$/ µg TOC/ hour) | | **g/m2/day** |
| **WT-3730** | Wild type | 0.53 | 461. | 182 | 1.8 | 10.44 | 9.44 | 6.7 | 22.5 |
| **GE-8145** | *Vcp2,2'* KO | 0.62 | 340 | 115 | 0.63 | 7.56 | 9.65 | 5.1 | 24.2 |

ENHANCED PRODUCTIVITY BY ATTENUATION OF CHLOROPHYLL BINDING PROTEIN GENES

CROSS-REFERENCE TO RELATED APPLICATIONS

This application claims priority under U.S.C. § 119(e) to U.S. Provisional Patent Application No. 62/244,079, filed Oct. 20, 2015, the entire contents of which is herein incorporated by reference.

INCORPORATION OF SEQUENCE LISTING

The material in the accompanying sequence listing is hereby incorporated by reference into this application. The accompanying sequence listing text file, name SGI1970_1_Sequence_Listing, was created on Jan. 4, 2017, and is 168 kb. The file can be assessed using Microsoft Word on a computer that uses Windows OS.

FIELD OF THE DISCLOSURE

The present disclosure relates to algal mutants having reduced expression levels of VCP or FCP genes and increased productivity and methods of their use. The present disclosure also relates, in some embodiments, to genes encoding antennae pigment binding proteins, to constructs that include at least a portion of the regulator genes, and to methods of engineering photosynthetic alga using such constructs.

BACKGROUND

The light harvesting antenna in eukaryotic algae is a complex component of the multi-subunit photosystem complexes. In response to environment conditions, such as variable irradiance, the composition can be appropriately modified as part of an acclimation response. Components of this variable component of the photosystem include multiple light harvesting polypeptides and pigments, such as chlorophyll and a variety of carotenoids. The light harvesting antenna in *Nannochloropsis* includes auxiliary pigments including vaucheriaxanthin and violaxanthin. Three violaxanthin-chlorophyll a binding protein (VCP) genes have been identified in the *Nannochloropsis* genome. While the precise function of these proteins and mechanism of their interaction with other components of the photosystem super-complexes are only poorly characterized, they are members of the LHC family that are believed to function in the binding of auxiliary light harvesting antenna components, including violaxanthin, vaucheriaxanthin, and chlorophyll. In vascular plants and green algae, light-harvesting complexes (LHC) are composed of a family of intrinsic membrane polypeptides that non-covalently bind chlorophyll (chl) a, chl b, xanthophylls, and carotenoids; these polypeptides have been designated LHC (Green and Durnford, 1996 *Annu. Rev. Plant Physiol*. Plant Mol. Biol. 47:685-714; Grossman et al., 1995, *Ann. Rev. Genetics* 29:231-88). The LHC polypeptides are encoded by a nuclear gene family that has been extensively examined in vascular plants (Bhaya and Grossman, 1993, *Nucleic Acids Res.* 21:4458-66; Green and Durnford, 1996, *Annu. Rev. Plant Physiol. Plant Mol. Biol.* 47:685-714). Polypeptides related to plant and green algae LHCs are present in the chromophytic algae (algae that have chlorophyll c), such as the diatoms (bacillariophytes), chrysophytes, and dinoflagellates. The major LHC of the chromophytes is a fucoxanthin-chl a/c complex (FCPC), that harvests light energy and transfers the absorbed energy to chl a of the photosynthetic reaction centers (Joshi-Deo et al., 2010, *J. Exp. Bot.*, June 61(11):3079-87). The constituent polypeptides of this complex, designated fucoxanthin-chlorophyll binding proteins (FCPs) are usually between 17 kDa and 22 kDa and share significant similarity to the LHC of vascular plants (Fawley and Grossman, 1986, *Plant Physiol.* May; 81(1):149-55; Caron and Brown, 1987, *Plant Cell Physiol.* 28:775-785; Green et al, 1991, *Trends Biochem. Sci.* 16:181-6). Sequences of the FCPs have been deduced from gene sequences characterized from diatoms, phaeophytes, a raphidophyte, a chrysophyte, and a haptophyte (Bhaya and Grossman, 1993, *Nucleic Acids Res.* 21:4458-66). Amino acid sequence comparisons between FCP and LHC polypeptides reveal extensive sequence similarities, especially in the three chl-binding domains that span the thylakoid membranes. The greatest similarities between the FCPs and the LHCs are within or near the first and third membrane-spanning domains; similarities include conserved residues that are involved in chl binding and are critical for the maintenance of the proper tertiary structure of the protein (Grossman et al., 1990, *Mol. Gen. Genet.* 224: 91-100; Kuhlbrandt et al., 1994, *Nature* 367:614-21; Sukenik et al, 2000, *J. Phycol.* 36, 563-570). In the diatoms and brown algae, the FCPs are encoded in the nuclear genome by a family of 6 to 12 conserved genes (Bhaya and Grossman, 1993, *Nucleic Acids Res.* 21:4458-66; Apt et al., 1995, *Mol. Gen. Genet.* 246:455-64; Durnford et al., 1996, *Mol. Gen. Genet.* 253: 377-86; Eppard and Rhiel, 1998, *Mol. Gen. Genet.* 260:335-45). The eustigmatophyte algae, along with the diatoms, phaeophytes, xanthophytes, raphidophytes, and chrysophytes, belong to the heterokont class of algae (Ochrophytes). In contrast to vascular plants and most other algal groups, eustigmatophyte algae have neither chl b nor chl c. The major polypeptide of their LHC is a violaxanthin-chl a binding protein (VCP). Initial characterization of a LHC from *Nannochloropsis* was reported by Brown (1987, *Plant Physiol.* 66:434-7) and from other eustigmatophyte species by Arsalane et al. (1992 *J. Phycol.* 28:32-6). The VCPs, which bind violaxanthin and chlorophyll a, are structurally similar to FCPs (Sukenik et al., 1992, *Plant and Cell Physiol.* 33:1041-48; Sukenik et al, 2000).

SUMMARY

The present disclosure describes the attenuation of genes encoding particular chlorophyll-binding polypeptides, such as violaxanthin and chlorophyll a binding proteins (VCPs) and fucoxanthin-chlorophyll binding proteins (FCPs), in algae, which confers increased productivity.

In some aspects the present disclosure provides a mutant alga (i.e., a recombinant or classically-mutagenized alga) that has attenuated expression of at least one violaxanthin chlorophyll a-binding protein (VCP) gene or at least one fucoxanthin-chlorophyll binding protein (FCP) gene. In some examples, the recombinant or classically-mutagenized alga has at least two VCP or FCP genes attenuated. In some examples, the recombinant or classically-mutagenized alga has attenuated expression of at least three VCP or FCP genes. In some examples, the recombinant or classically-mutagenized alga has attenuated expression of all VCP and FCP genes of the alga. Attenuation of gene expression can be attenuation of expression by at least 50%, at least 65%, at least 80%, at least 90%, at least 95%, or greater than 95%. In some examples, the expression of one or more, for example all, VCP or FCP genes of the mutant alga may be reduced to undetectable levels.

The mutant alga may be a species of heterokont, e.g., an ochrophyte alga, such as a member of the bacillariophyte (diatom), xanthophyte, phaeophyte, chrysophyte, raphidophyte, haptophyte, or eustigmatophyte class. In some examples the mutant alga is a diatom (bacillariophyte) and has attenuated expression of at least one, at least two, or all of its FCP genes. Alternative, the mutant alga (i.e., recombinant or classically-mutagenized alga) may be a eustigmatophyte and may have attenuated expression of at least one, at least two, or all of its VCP genes.

The present disclosure provides a recombinant or classically-mutagenized mutant alga which has attenuation of expression of at least one, at least two, at least three, or all VCP gene/s or FCP gene/s by means of any of gene disruption, promoter disruption, RNAi, CRISPRi, antisense RNA, or one or more ribozymes. In some examples, the amount of RNA transcribed by the at least one attenuated VCP or FCP gene in the mutant alga is less than 50%, 45%, 40%, 35%, 30%, 25%, 20%, 15%, 10%, 5% or 3% of the amount of RNA transcribed by the corresponding VCP gene or genes or FCP gene or genes in a control or wild type alga. In some examples, the amount of RNA transcribed by the at least one attenuated VCP gene or FCP gene is undetectable or not significantly increased above background noise compared to the RNA transcribed from the corresponding VCP gene or genes or FCP gene or genes in a wild type or control alga. Alternatively or in addition, the amount of RNA transcribed by all of the VCP genes or all of the FCP genes in the mutant alga is less than 50%, 45%, 40%, 35%, 30%, 25%, 20%, 15%, 10%, 5% or 3% of the amount of RNA transcribed by the VCP genes or FCP genes in a control or wild type alga. In some examples, the amount of RNA transcribed by all of the VCP genes, or all of the FCP genes, is undetectable or not significantly increased above background noise compared to the RNA transcribed from the VCP genes or FCP genes in a wild type or control alga.

For example, a recombinant or classically-mutagenized mutant alga as provided herein can have at least one VCP or FCP gene disrupted. In some examples, the mutant alga has at least two VCP or FCP genes disrupted. In some examples, the mutant alga has at least three VCP or FCP genes disrupted. In some examples, the mutant alga has all VCP or FCP genes of the alga's genome disrupted. In some examples the disruption is by insertional mutagenesis, deletion of all or a portion of the gene, homologous recombination, and/or CRISPR RNA-guided endonuclease cleavage. In some examples the RNA-guided endonuclease is Cas9 or Cbf1.

A recombinant or classically-mutagenized mutant alga as provided herein that has attenuated expression of at least one VCP gene or at least one FCP gene can in some examples exhibit a higher Electron Transport Rate (ETR) than a control alga substantially identical to the mutant alga with the exception that the mutant alga does not have attenuated expression or disruption of at least one VCP gene or at least one FCP gene. In some examples, the ETR (which can be apparent ETR as measured by a Walz Dual-PAM fluorometer) is increased by at least 10% at all irradiances between 200 and 2000 μE. In some examples, the ETR is increased by at least 20% at all irradiances between 300 and 2000 μE. In some examples, the ETR is increased by at least 30% at all irradiances between 500 and 2000 μE. In some examples, the ETR is increased by at least 10%, at least 20%, or at least 30% at the light intensity at which photosynthesis saturates for the control alga.

In various examples the maximal rate of oxygen evolution (Pmax) of a recombinant or classically-derived algal mutant as provided herein can be at least 80% of the Pmax of a wild type or control alga/strain, and/or can be, for example, within about 10% of the wild type/control value and/or can be at least 5%, at least 10%, at least 15%, or at least 20% higher than the wild type or control value.

Alternatively or in addition, a recombinant or classically-mutagenized mutant alga as provided herein can exhibit lower Non-Photochemical Quenching (NPQ) induction than a control alga substantially identical to the mutant alga with the exception that the mutant alga does not have attenuated expression or disruption of at least one VCP or FCP gene. In some examples, the NPQ induction is decreased by at least 10% at all irradiances between 200 and 2000 μE. In some examples, the NPQ induction is decreased by at least 30% at all irradiances between 300 and 2000 μE. In some examples, the NPQ induction is decreased by at least 50% at all irradiances between 500 and 2000 μE. In some examples, the NPQ is decreased by at least 10%, at least 30%, or at least 50% at the light intensity at which photosynthesis is saturated for the control alga.

Also provided herein is a recombinant or classically-mutagenized mutant alga having attenuated expression of at least one VCP gene or at least one FCP gene, wherein the mutant alga has reduced chlorophyll with respect to a control alga. In some examples, total chlorophyll is reduced by at least 15% on a per cell basis.

In some aspects the present disclosure provides a recombinant or classically-mutagenized mutant alga having attenuated expression of at least one VCP gene or at least one FCP gene, such as any disclosed herein, where the mutant alga has increased productivity with respect to a control alga, for example, biomass productivity or productivity of a bioproduct such as lipid. In some examples, the biomass productivity is at least 5% increased with respect to a control alga. In some examples, the biomass productivity is at least 7%, at least 8%, at least 10%, at least 12%, at least 13%, at least 15%, at least 20%, or at least 23% increased with respect to a control alga. In some examples, the biomass productivity is increased between 5% and 500% with respect to a control alga. In some examples, the biomass productivity is increased between 10% and 100% with respect to a control alga. In some examples, the productivity increase is demonstrated over at least 5, 7, 10, or 14 days of semi-continuous or continuous growth. In some examples the mutant alga exhibits greater productivity each day for at least 5, 6, 7, 10, or 14 days of semi-continuous or continuous growth. A recombinant or classically-mutagenized mutant alga as provided herein can exhibit greater productivity, for example, greater biomass productivity, for at least 5, 6, 7, 10, or 14 days of semi-continuous or continuous growth in a culture system that experiences a diel cycle, and, in some examples, experiences a diel cycle that includes a day, or light, period in which the light varies in intensity over the course of the day. Alternatively, a recombinant or classically-mutagenized mutant alga as provided herein can exhibit greater productivity, for example, greater biomass productivity, for at least 5, 6, 7, 10, or 14 days of semi-continuous or continuous growth in a culture system that experiences constant light, for example, constant light of greater than about 100, 200, 400, 500, 600, 800, 1000, 1200, 1400, 1600, 1800, or 2000 μE.

In some aspects the present disclosure provides a recombinant or classically-derived mutant alga, wherein the mutant alga cell belongs to a genus selected from the group consisting of *Achnanthes, Amphiprora, Amphora, Ankis-*

*trodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*.

In some aspects the present disclosure provides a recombinant or classically-derived mutant alga, wherein the mutant alga is a heterokont alga. In some examples, the mutant heterokont alga belongs to the diatoms (bacillariophytes), eustigmatophytes, xanthophytes, phaeophytes, chrysophytes, or raphidophytes. In some examples, the mutant heterokont alga belongs to a genus selected from the group consisting of *Amphiprora, Amphora, Chaetoceros, Cyclotella, Eustigmatos, Fragilaria, Fragilaropsis, Hantzschia, Monodus, Nannochloropsis, Navicula, Nitzschia, Phaeodactylum, Pseudostaurastrum, Vischeria, Phaeodactylum, Skeletonema*, and *Thalassiosira*. In some examples, the mutant alga is a Bacillariophyte alga that has attenuated expression of at least one FCP gene. In some examples, the mutant alga is a Eustigmatophyte alga that has attenuated expression of at least one VCP gene. In some examples, the Eustigmatophyte alga belongs to a genus selected from the group consisting of *Chloridella, Chlorobptrys, Ellipsoidion, Eustigmatos, Goniochloris, Monodopsis, Monodus, Nannochloropsis, Pseudocharaciopsis, Pseudostaruastrum, Pseudotetraedriella*, and *Vischeria*. In some examples, the mutant alga cell is a *Nannochloropsis* species.

In a further aspect the present disclosure provides a microbial biomass comprising a mutant alga (e.g., a recombinant alga or classically derived algal mutant) as disclosed herein.

In another aspect the present disclosure provides a method for producing an algal biomass comprising culturing a mutant alga as provided herein to produce biomass. In some examples, the culturing is under photoautotrophic conditions. The method can further comprise recovering biomass from culture. Also provided is a method for producing a bioproduct comprising culturing a recombinant or classically-derived mutant alga as provided herein to produce a bioproduct. In some examples, the culturing is under photoautotrophic conditions. In some examples, the method for producing a bioproduct comprises culturing a mutant alga, wherein the mutant alga produces a bioproduct, and isolating the bioproduct from the culture. In some examples, the culturing is under photoautotrophic conditions. In some examples, the bioproduct is a lipid, protein, peptide, one or more amino acids, an amino acid, one or more nucleotides, vitamin, cofactor, hormone, pigment, colorant, antioxidant, or some combination thereof. In some examples, the bioproduct is a lipid.

In a further aspect the present disclosure provides a bioproduct produced by and isolated from a cultured biomass of mutant alga. In some examples, the culturing is under photoautotrophic conditions. In some examples, the bioproduct comprises or is a lipid, protein, peptide, one or more amino acids, an amino acid, one or more nucleotides, a vitamin, a cofactor, a hormone, a pigment, a colorant, an antioxidant, or a combination thereof. In some examples, the bioproduct comprises or is a lipid. In some examples, the bioproduct can be defined as a food, feed, biofuel, biochemical, pharmaceutical, and/or medicinal product.

In some aspects the present disclosure provides a nucleic acid molecule construct for homologous recombination comprising a nucleotide sequence from or adjacent to a naturally-occurring algal gene encoding a VCP or FCP. For example, a homologous recombinant construct can include a nucleotide sequence from or adjacent to a naturally-occurring algal gene encoding a polypeptide having an amino acid sequence with at least 55%, at least 60%, at least 65%, at least 70%, at least 75%, at least 80%, at least 85%, at least 90%, at least 95%, or at least 99% identity to SEQ ID NO:1, SEQ ID NO:2, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45. In some examples, the nucleic acid molecule comprises a selectable marker gene, e.g., a selectable marker gene positioned between sequences of or adjacent to the VCP or FCP gene(s).

In some aspects the present disclosure provides a nucleic acid molecule construct for expression of an antisense RNA, shRNA, microRNA, or ribozyme comprising a nucleotide sequence complementary to at least a portion of a naturally-occurring gene encoding a VCP or FCP. For example, a nucleic acid molecule construct for attenuating expression of a VCP or FCP gene can comprise a nucleotide sequence complementary to at least a portion of a naturally-occurring gene encoding a polypeptide having an amino acid sequence with at least 55%, at least 60%, at least 65%, at least 70%, at least 75%, at least 80%, at least 85%, at least 90%, at least 95%, or at least 99% identity to SEQ ID NO:1, SEQ ID NO:2, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or combinations thereof. In some examples, the nucleic acid molecule comprises a heterologous promoter operably linked to the nucleic acid sequence complementary to at least a portion of a naturally-occurring VCP or FCP gene.

In some aspects the present disclosure provides a nucleic acid molecule encoding a guide RNA of a CRISPR system, wherein the guide RNA targets at least a portion of a naturally-occurring algal gene encoding a polypeptide having an amino acid sequence with at least 55%, at least 60%, at least 65%, at least 70%, at least 75%, at least 80%, at least 85%, at least 90%, at least 95%, or at least 99% identity to SEQ ID NO:1, SEQ ID NO:2, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or combinations thereof.

BRIEF DESCRIPTION OF THE DRAWINGS

FIGS. 18A-18B. (A) Table summarizing photophysiology of wild type, strains. (B) Table summarizing photophysiology of GE-8145, a strain that does not express VCP genes.

FIGS. 22A and 22B show the kinetics of nonphotochemical quenching (NPQ) of attenuated strains.

DETAILED DESCRIPTION

Definitions

Figure 1A:
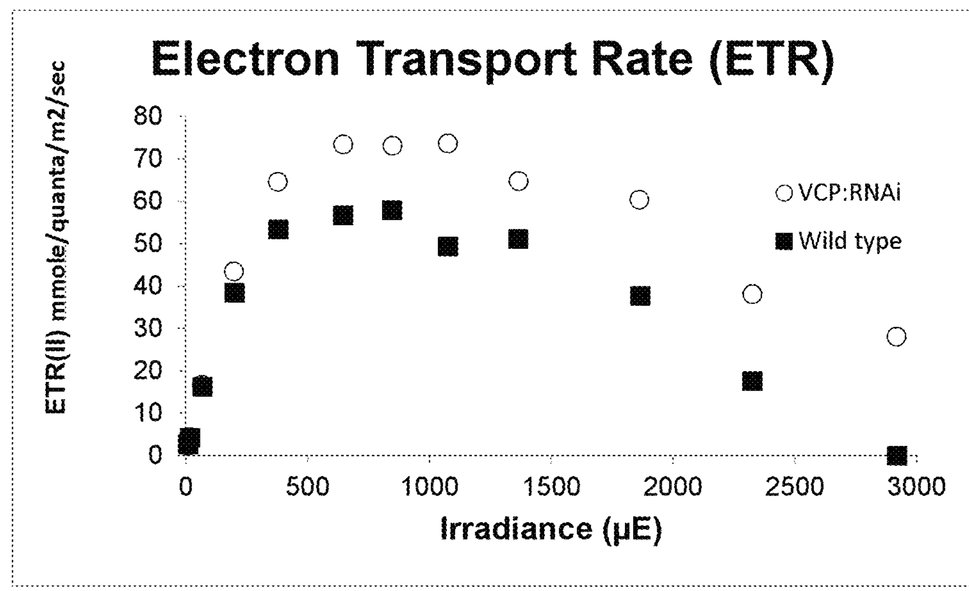
FIGS. 1A-1D. Phenotyping of VCP:RNAi strains. Graphs of (A) electron transport rate and (B) non-photochemical quenching are shown for wild type (WT-3730) and a representative VCP:RNAi line created in a wild type background. Additionally, graphs of (C) electron transport rate and (D) non-photochemical quenching are shown for Lar1 (NE-5282) and a representative VCP:RNAi line created in a Lar1 background.

Although aspects of the invention relate to attenuated VCP or FCP production or attenuated expression of VCP or FCP genes in algae, as well as mutant algae, it should be understood that any microorganism having native VCP or FCP genes can be mutated, i.e., can be a mutant microorganism, and/or can have the expression of its VCP or FCP genes attenuated by the methods disclosed herein.

All headings are for the convenience of the reader and do not limit the invention in any way. As used herein, the terms "aspect" and "embodiment" do not necessarily imply mutually exclusive features and/or combinations of the invention and do not limit this disclosure in any way.

Unless defined otherwise, all technical and scientific terms used herein have the same meaning as commonly understood by one of ordinary skill in the art to which this disclosure belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

To facilitate an understanding of the present disclosure, a number of terms and phrases are defined below.

As used in the present disclosure and claims, the singular forms "a," "an," and "the" include plural forms unless the context clearly dictates otherwise.

As used herein, the terms "about" or "approximately" when referring to any numerical value are intended to mean a value of plus or minus 10% of the stated value. For example, "about 50 degrees C." (or "approximately 50 degrees C.") encompasses a range of temperatures from 45 degrees C. to 55 degrees C., inclusive. Similarly, "about 100 mM" (or "approximately 100 mM") encompasses a range of concentrations from 90 mM to 110 mM, inclusive. Alternatively, "about" or "approximately" can mean within 5% of the stated value, or in some cases within 2.5% of the stated value, or, "about" can mean rounded to the nearest significant digit. All ranges provided within the application are inclusive of the values of the upper and lower ends of the range.

The term "and/or" as used in a phrase such as "A and/or B" herein is intended to include "A and B", "A or B", "A", and "B".

"Bioproduct" is used herein to refer to a product made by cells, which can be, for example, a molecule, including a polymeric molecule, class of molecules, or molecular complex. As nonlimiting examples, a bioproduct can be a lipid, protein, carbohydrate, triglyceride, wax ester, fatty alcohol, fatty acid, fatty aldehyde, hydrocarbon (e.g., alkane or alkene), amino acid, sugar, alcohol, alkaloid, sterol, polyketide, carotenoid, xanthophyll, nucleotide, nucleic acid molecule, vitamin, small molecule cofactor, pigment, colorant, or antioxidant.

A "control alga", "control cell", or "control alga" is either a wild type alga, cell, or alga from which the mutant alga, cell, or alga is directly or indirectly derived, or is an alga, cell or alga that is substantially identical to the manipulated, recombinant, or mutant cell referred to, with the exception that the control cell does not have the genetic manipulation of the mutant alga, cell, or alga, i.e., does not have attenuated expression of at least one VCP or FCP gene.

"The same conditions" or "the same culture conditions", as used herein, means substantially the same conditions, that is, any differences between the referenced conditions are minor and not relevant to the function or properties of the alga that are material to the disclosure, e.g., lipid production or biomass production.

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. In some examples, a gene may only refer to a protein-encoding portion of a DNA or RNA molecule, which may or may not include introns. A gene is preferably greater than 50 nucleotides in length, more preferably greater than 100 nucleotide in length, and can be, for example, between 50 nucleotides and 500,000 nucleotides in length, such as between 100 nucleotides and 100,000 nucleotides in length or between about 200 nucleotides and about 50,000 nucleotides in length, or about 200 nucleotides and about 20,000 nucleotides in length. Genes can be obtained from a variety of sources, including cloning from a source of interest or synthesizing from known or predicted sequence information.

The term "nucleic acid" or "nucleic acid molecule" refers to, a segment of DNA or RNA (e.g., mRNA), and also includes nucleic acids having modified backbones (e.g., peptide nucleic acids, locked nucleic acids) or modified or non-naturally-occurring nucleobases. The nucleic acid molecules can be double-stranded or single-stranded; a single stranded nucleic acid that comprises a gene or a portion thereof can be a coding (sense) strand or a non-coding (antisense) strand.

A nucleic acid molecule may be "derived from" an indicated source, which includes the isolation (in whole or in part) of a nucleic acid segment from an indicated source. A nucleic acid molecule may also be derived from an indicated source by, for example, direct cloning, PCR amplification, or artificial synthesis from the indicated polynucleotide source or based on a sequence associated with the indicated polynucleotide source. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other molecular biology techniques, or by chemical synthesis, or any combination thereof. A gene or nucleic acid molecule that is derived from a referenced gene or nucleic acid molecule that encodes a functional RNA or polypeptide can encode a functional RNA or polypeptide having at least 75%, at least 80%, at least 85%, at least 90%, or at least 95%, sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable.

The terms "naturally-occurring" and "wild type" refer to a form found in nature. For example, a naturally occurring or wild type nucleic acid molecule, nucleotide sequence or protein may be present in and isolated from a natural source, and is not intentionally modified by human manipulation.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be due to a mutation or a disruption in the gene (e.g., a gene disrupted by partial or total deletion, truncation, frameshifting, or insertional mutation) or may have decreased expression due to alteration, replacement, and/or elimination of one or more gene regulatory sequences. A mutant alga having attenuated expression of a gene, such as a VCP or FCP gene, can be a recombinant alga in which the attenuation is the result of genetic engineering, i.e., by human intervention that includes, typically, introduction of one or more non-native nucleic acid molecules or polypeptides into the alga. Alternatively, gene attenuation can be by classical mutagenesis according to protocols known in the art or adapted therefrom.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and so "heterologous"), or from the same species (and so "homologous"), relative to the cell being transformed. An "endogenous" nucleic acid molecule, gene or protein is a native nucleic acid molecule, gene or protein as it occurs in, or is naturally produced by, the host.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a cell, subjected to laboratory manipulation, and introduced or reintroduced into a host cell is considered "non-native." Synthetic or partially synthetic genes introduced into a host cell are "non-native." Non-native genes further include genes endogenous to the host alga operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering.

When applied to organisms, the term recombinant, engineered, or genetically engineered refers to organisms that have been manipulated by introduction of a heterologous or exogenous (e.g., non-native) recombinant nucleic acid sequence into the organism, and includes, without limitation, gene knockouts, targeted mutations, and gene replacement, promoter replacement, deletion, or insertion, or transfer of a nucleic acid molecule, e.g., a transgene, synthetic gene, promoter, or other sequence into the organism. Recombinant or genetically engineered organisms can also be organisms into which constructs for gene "knock down" have been introduced. Such constructs include, but are not limited to, one or more guide RNAs, RNAi, microRNA, shRNA, siRNA, antisense, and ribozyme constructs. Also included are organisms whose genomes have been altered by the activity of cas nucleases, meganucleases, or zinc finger nucleases. An exogenous or recombinant nucleic acid molecule can be integrated into the recombinant/genetically engineered organism's genome or in other instances are not integrated into the recombinant/genetically engineered organism's genome. As used herein, "recombinant alga" or "recombinant host cell" includes progeny or derivatives of the recombinant algae of the disclosure. Because certain modifications may occur in succeeding generations due to either mutation or environmental influences, such progeny or derivatives may not, in fact, be identical to the parent cell, but are still included within the scope of the term as used herein.

The term "promoter" refers to a nucleic acid sequence capable of binding RNA polymerase in a cell and initiating transcription of a downstream (3' direction) coding sequence. A promoter includes the minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, algal, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (initiate transcription in one direction) or bidirectional (initiate transcription in either direction). A promoter may be a constitutive promoter, a repressible promoter, or an inducible promoter.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g. a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

Gene and protein Accession numbers, commonly provided herein in parenthesis after a gene or species name, are unique identifiers for a sequence record publicly available at the National Center for Biotechnology Information (NCBI) website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present disclosure, included are sequence identities of at least 40%, at least 45%, at least 50%, at least 55%, of at least 70%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 100, at least 125, at least 150 or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production", when referring to protein abundance or the abundance of active protein resulting from gene expression, protein turnover rates, protein activation states, and the like, includes an increase in the amount of polypeptide expression, in the level of the enzymatic activity of a polypeptide, or a combination of both, as compared to the native production or enzymatic activity of the polypeptide.

Some aspects of the present disclosure include the partial, substantial, or complete deletion, silencing, inactivation, or down-regulation of expression of particular polynucleotide sequences. The genes may be partially, substantially, or completely deleted, silenced, inactivated, or their expression may be down-regulated in order to affect the activity performed by the polypeptide they encode, such as the activity of an enzyme. Genes can be partially, substantially, or completely deleted, silenced, inactivated, or down-regulated by insertion of nucleic acid sequences that disrupt the function and/or expression of the gene (e.g., viral insertion, transposon mutagenesis, meganuclease engineering, homologous recombination, or other methods known in the art). The terms "eliminate," "elimination," and "knockout" can be used interchangeably with the terms "deletion," "partial deletion," "substantial deletion," or "complete deletion." In certain embodiments, a alga of interest may be engineered by site directed homologous recombination to knockout a particular gene of interest. In still other embodiments, RNAi or antisense DNA (asDNA) constructs may be used to partially, substantially, or completely silence, inactivate, or down-regulate a particular gene of interest.

These insertions, deletions, or other modifications of certain nucleic acid molecules or particular polynucleotide sequences may be understood to encompass "genetic modification(s)" or "transformation(s)" such that the resulting strains of the algas or host cells may be understood to be "genetically modified", "genetically engineered" or "transformed."

As used herein, "up-regulated" or "up-regulation" includes an increase in expression of a gene or nucleic acid molecule of interest or the activity of an enzyme, e.g., an increase in gene expression or enzymatic activity as compared to the expression or activity in an otherwise identical gene or enzyme that has not been up-regulated.

As used herein, "down-regulated" or "down-regulation" includes a decrease in expression of a gene or nucleic acid molecule of interest or the activity of an enzyme, e.g., a decrease in gene expression or enzymatic activity as compared to the expression or activity in an otherwise identical gene or enzyme that has not been down-regulated.

As used herein, "mutant" refers to an organism that has a mutation in a gene that is the result of classical mutagenesis, for example, using gamma irradiation, UV, or chemical mutagens. "Mutant" as used herein also refers to a recombinant cell that has altered structure or expression of a gene as a result of genetic engineering that many include, as non-limiting examples, overexpression, including expression of a gene under different temporal, biological, or environmental regulation and/or to a different degree than occurs naturally and/or expression of a gene that is not naturally expressed in the recombinant cell; homologous recombination, including knock-outs and knock-ins (for example, gene replacement with genes encoding polypeptides having greater or lesser activity than the wild type polypeptide, and/or dominant negative polypeptides); gene attenuation via RNAi, antisense RNA, or ribozymes, or the like; and genome engineering using meganucleases, TALENs, and/or CRISPR technologies, and the like.

The term "Pfam" refers to a large collection of protein domains and protein families maintained by the Pfam Consortium and available at several sponsored world wide web sites, including: pfam.sanger.ac.uk/ (Welcome Trust, Sanger Institute); pfam.sbc.su.se/(Stockholm Bioinformatics Center); pfam.janelia.org/ (Janelia Farm, Howard Hughes Medical Institute); pfam.jouy.inra.fr/ (Institut national de la Recherche Agronomique); and pfam.ccbb.re.kr. The latest release of Pfam is Pfam 28.0 (May 2015) based on the UniProt protein database release 2015_09, a composite of Swiss-Prot release 2015_09 and TrEMBL release 2015_09 (Finn et al, 2014, Nucleic Acids Res. 2014 January; 42; The Uniprot Consortium, 2015). Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) Nucleic Acids Research 26, 320-322; Bateman (2000) Nucleic Acids Research 26, 263-266; Bateman (2004) Nucleic Acids Research 32, Database Issue, D138-D141; Finn (2006) Nucleic Acids Research Database Issue 34, D247-251; Finn (2010) Nucleic Acids Research Database Issue 38, D211-222; Finn et al, 2014, Nucleic Acids Res. 2014 January; 42). By accessing the Pfam database, for example, using any of the above-reference websites, protein sequences can be queried against the HMMs using HMMER homology search software (e.g., HMMER2, HMMER3, or a higher version, hmmer.janelia.org/). Significant matches that identify a queried protein as being in a pfam family (or as having a particular Pfam domain) are those in which the bit score is greater than or equal to the gathering threshold for the Pfam domain Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

The term "conserved domain" refers to a conserved part of a given protein or DNA sequence that can evolve, function, and/or exist independently of the rest of the protein or DNA chain. In the case of protein domains, each domain forms a compact three-dimensional structure and often can be independently stable and folded. Many proteins consist of several structural domains. One domain may appear in a variety of different proteins. One way to search for protein or nucleic acid domains is to use the Conserved Domain Database (CDD) search function through NCBI (Marchler-Bauer et al, 2015, Nucleic Acids Res. January; 43). CDD is a protein annotation resource that consists of a collection of well-annotated multiple sequence alignment models for ancient domains and full-length proteins. These are available as position-specific score matrices (PSSMs) for fast identification of conserved domains in protein sequences via RPS-BLAST. CDD content includes NCBI-curated domains, which use 3D-structure information to explicitly define domain boundaries and provide insights into sequence/structure/function relationships, as well as domain models imported from a number of external source databases (Pfam, SMART, COG, PRK, TIGRFAM). Conserved domains are those that are identified using the above mentioned databases that have an E value of 1e-2 or lower. For example, as disclosed herein *Nannochloropsis* VCP1 (SEQ ID NO:1) comprises a PLN00120 domain with an E-value of 3.75e-37 and a Pfam PF00504 domain with an E-value of 9.34e-27.

When referring to a photosynthetic organism, such as an algal, the term "acclimated to low light" means having the increased chlorophyll and photosynthetic properties of the photosynthetic organism after being exposed to a low light intensity for a period of time that is sufficient for changes in chlorophyll and photosynthetic properties to stabilize at the low light condition. Low light can be for example, less than 200 μE·m-2·s-1 and preferably about 100 μE·m-2·s-1 or less or 50 μE·m-2·s-1 or less, and the period of time for acclimation can be for at least about four hours, at least about six hours, at least about eight hours, or at least about twelve hours, at least 24 hours, or at least 48 hours.

A "cDNA" is a DNA molecule that comprises at least a portion the nucleotide sequence of an mRNA molecule, with the exception that the DNA molecule substitutes the nucleobase thymine, or T, in place of uridine, or U, occurring in the mRNA sequence. A cDNA can be double stranded or single stranded and can be, for example, the complement of the mRNA sequence. In preferred examples, a cDNA does not include one or more intron sequences that occur in the naturally-occurring gene that the cDNA corresponds to (i.e., the gene as it occurs in the genome of an organism). For example, a cDNA can have sequences from upstream of an intron of a naturally-occurring gene juxtaposed to sequences downstream of the intron of the naturally-occurring gene, where the upstream and downstream sequences are not juxtaposed in a DNA molecule in nature (i.e., the sequences are not juxtaposed in the naturally occurring gene). A cDNA can be produced by reverse transcription of mRNA molecules, or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences or compiled from the sequences multiple partial cDNAs.

"Photosynthetic properties", "photosynthetic properties", "photophysiological properties", or photophysiological parameters" include, without limitation, maximal photosynthetic rate, Pmax (calculated on a per cell or per mg chlorophyll basis), the intensity at which photosynthesis saturates, Ek, as measured by oxygen evolution, and a ("alpha") the initial slope of the photosynthesis (oxygen evolution) versus irradiance intensity (P/I) curve. Additional photosynthetic properties include various parameters that can be measured using fluorescence detection, including, for example, photosynthetic efficiency, Fv/Fm; the photosynthetic quantum yield of photosystem II (PSII), ΦPSII; photochemical quenching, or the proportion of open PSII centers, qP; nonphotochemical quenching, NPQ; PSII electron transport rate, ETRPSII; PSI electron transport rate, ETRPSI; cross-sectional size of PSI, and cross-sectional size of PSII. The listing here is not exhaustive, and the terms do not exclude other parameters that measure various aspects of photosynthesis.

The term "ETR" or "ETR(II)" or "electron transport rate" as used herein, refers to the apparent ETR(II) measurement from a Dual-PAM fluorometer (Walz, Germany). Apparent electron transfer efficiency in PS II in light is calculated according to $ETR(II)=PAR\times0.84\times0.5\times Y(II)$, and is used to measure electron transfer of carbon fixation resulted from photochemical reactions. ETR(II) is considered to be a relative measure of the rate of electron transport or the rate of charge separation at PSII reaction centers.

References to properties that are "substantially the same" are intended to mean the properties are within 25%, and preferably within 20%, within 10%, or within 5% of the reference value. Unless otherwise specified, "significant" or "significantly" refers to statistical significance.

VCP and FCP Mutants

Provided herein are algal mutants that have attenuated expression of one or more violaxanthin and chlorophyll a binding protein (VCP) genes. Further provided herein are algal mutants that have attenuated expression of one or more fucoxanthin-chlorophyll a/c binding protein (FCP) genes. An algal mutant with attenuated expression of VCP genes can be a eukaryotic microalga, for example, of a marine or freshwater eukaryotic microalgal species, such as, for example, a species of heterokont algae such as a eustigmatophyte species. An algal mutant with attenuated expression of FCP genes can be a heterokont alga, for example, of a diatom. An algal VCP mutant as provided herein can be a genetically engineered algal mutant in which one or more VCP genes, as described herein, have been targeted by insertional gene disruption or gene replacement (for example with mutated form of the gene that may encode a polypeptide having reduced function with respect to the wild type polypeptide). Included herein are aspects of engineering a alga in which the introduction, addition, integration, or incorporation of certain nucleic acid molecules or particular polynucleotide sequences into algal or host cells in order to affect the expression of a gene in the alga. For example, an alga of interest may be engineered by site directed homologous recombination or non-homologous end joining repair to insert a particular gene of interest with or without an expression control sequence such as a promoter, into a particular genomic locus, or to insert a promoter into a genetic locus of the host alga to affect the expression of a particular gene or set of genes at the locus.

Alternatively or in addition, a genetically engineered VCP or FCP mutant can be engineered to include a construct for attenuating gene expression by reducing the amount, stability, or translatability of mRNA of a VCP or FCP gene. For example, an alga can be transformed with an antisense RNA, RNAi, or ribozyme construct targeting an mRNA of a VCP gene or FCP gene using methods known in the art. For example, an antisense RNA construct that includes all or a portion of the transcribed region of a gene can be introduced into a microalga to decrease gene expression (Shroda et al. (1999) The Plant Cell 11:1165-78; Ngiam et al. (2000) Appl. Environ. Microbiol. 66: 775-782; Ohnuma et al. (2009) Protoplasma 236: 107-112; Lavaud et al. (2012) PLoS One 7:e36806, all incorporated by reference herein). Alternatively or in addition, an RNAi construct (for example, a construct encoding a short hairpin RNA) targeting a VCP gene can be introduced into an alga for reducing expression of the regulator (see, for example, Cerruti et al. (2011) Eukaryotic Cell (2011) 10: 1164-1172; Shroda et al. (2006) Curr. Genet. 49:69-84, each of which is incorporated herein by reference). Other genetic engineering strategies for generating VCP mutants include TALEN or zinc finger nuclease genome engineering (Perez-Pinera et al. (2012) Curr. Opin. Chem. Biol. 16: 268-277) or CRISPR technology (e.g., DiCarlo et al. (2013) Nucl Acids Res 41:doi:10.1093/nar/gtk135), both of which are incorporated by reference herein.

Alternatively, a VCP or FCP mutant can be a mutant generated by any feasible method, including but not limited to UV irradiation, gamma irradiation, or chemical mutagenesis. Methods for generating mutants of microbial strains by classical mutagenesis methods are well-known in the art.

A VCP or FCP mutant in some examples can be generated through targeting of a gene encoding a VCP or FCP. A VCP or FCP gene can encode a protein comprising a PF00504 pfam domain and preferably, a PLN00120 domain Pfam PF00504 designates a chlorophyll a-b binding protein. PLN is a subset of the Entrez database and PLN00120 designates a fucoxanthin-chlorophyll a-c binding protein, a type of light harvesting complex (LHC) protein found in diatoms that is closely related to the VCPs. VCPs (e.g., the VCPs whose sequences are provided herein, SEQ ID NO:1, SEQ ID NO:2, and SEQ ID NO:3) include the PLN00120 domain characteristic of FCPs. Thus FCP genes which occur in diatoms and are structurally related to the VCP genes of the eustigmatophytes are considered, along with VCP genes, as genes whose attenuated expression can result in reduced chlorophyll and higher productivity with respect to control or wild type strains. For example, a gene whose expression is attenuated in a mutant as provided herein can be a gene encoding an FCP or a VCP, and can include a chlorophyll a-b binding protein domain (e.g., Pfam PF00504 and/or c102879), and can also include a PLN00120 fucoxanthin-chlorophyll a-c binding protein domain.

A mutant alga as provided herein can be a species of heterokont alga (ochrophytes), for example, a species of the bacillariophytes (diatoms), eustigmatophytes, phaeophytes, xanthophytes, raphidophytes, or chrysophytes, As nonlimiting examples, a mutant alga as provided herein can be a diatom species that has attenuated expression of at least one FCP gene, for example a species of any of, without limitation, *Achnanthes, Achnanthidium, Actinocyclus, Actinoptychus, Amphora, Anaulus, Astartiella, Asterionella, Aulacoseira, Bacillaria, Berkeleya, Biremis, Brachysira, Brockmanniella, Campylodiscus, Catenula, Cavinula, Cerataulina, Cocconeis, Coscinodiscus, Ctenophora, Cyclostephanos, Cyclotella, Cymatosira, Cymbella, Delphineis, Diatoma, Dickieia, Dimeregramma, Diploneis, Encyonema, Encyonopsis, Entomoneis, Epithemia, Eunotia, Fallacia, Fragilaria, Fragilariforma, Fragilariopsis, Frustulia, Glyphodesmis, Gomphonemopsis, Grammatophora, Gyrosigma, Haslea, Hyalodiscus, Karayevia, Martyana, Mastogloia, Melosira, Minidiscus, Navicula, Nitzschia, Odontella, Opephora, Paralia, Pauliella, Petroneis, Phaeodactylum, Pinnularia, Plagiogramma, Plagiogrammopsis, Plagiotropis, Planothidium, Pleurosigma, Porosira, Psammothidium, Pseudo-Nitzschia, Pseudostaurosira, Reimeria, Rhabdonema, Rhaphoneis, Rhoicosphenia, Rhopalodia, Stauroneis, Staurosira, Staurosirella, Stephanodiscus, Surirella, Tabellaria, Tabularia, Thalassionema, Thalassiosira, Trachyneis*, and *Tryblionella*. Alternatively, a mutant alga as provided herein can be a eustigmatophyte species that has attenuated expression of at least one VCP gene, for example a species of any of, without limitation, *Chloridella, Chlorobptrys, Ellipsoidion, Eustigmatos, Goniochloris, Monodopsis, Monodus, Nannochloropsis, Pseudocharaciopsis, Pseudostaruastrum, Pseudotetraedriella*, and *Vischeria*. In some examples, the mutant also can be a *Nannochloropsis* species, for example, *N. gaditana, N. granulata, N. limnetica, N. oculata, N. oceanica*, or *N. salina*. The mutants can have reduced chlorophyll and increased productivity, e.g., biomass or lipid productivity, with respect to a control or wild type alga.

A VCP mutant can be an alga, such as a eustigmatophyte alga, engineered to have attenuated expression of a VCP gene, where the VCP gene is characterized by the presence, in the encoded polypeptide, of the protein domains PF00504 and PLN00120 that are characteristic of VCP and FCP polypeptides. Alternatively, an FCP mutant can be an alga, such as a bacillariophyte alga, engineered to have attenuated expression of an FCP gene, where the FCP gene is characterized by the presence, in the encoded polypeptide, of the protein domains PF00504 and PLN00120. For example, a VCP mutant can be mutated in a gene encoding a VCP protein of a *Nannochloropsis* species.

The three VCP genes in *Nannochloropsis gaditana* (SEQ ID NO:7, SEQ ID NO:8, SEQ ID NO:9), are herein referred to as VCP1, VCP2a, and VCP2b respectively. While the coding sequences (SEQ ID NO:4) and the protein sequences of VCP2a and VCP2b (SEQ ID NO:2) are believed to be identical.

The VCP proteins of *Nannochloropsis gaditana* (SEQ ID NO:1 and SEQ ID NO:2) comprise a chlorophyll a-b binding protein domain (pfam domain PF00504, SEQ ID NO:12 (VCP1) and SEQ IS NO:13 (VCP2a and VCP2b)), a domain commonly found in light harvesting complex (LHC) proteins, corresponding to amino acids 66-200 of SEQ ID NO:1, and amino acids 59-193 of SEQ ID NO:2. The VCP proteins of *Nannochloropsis gaditana* (SEQ ID NO:1 or SEQ ID NO:2) also comprise a fucoxanthin-chlorophyll a-c binding protein domain (PLN domain PLN00120, SEQ ID NO:10 (VCP1) and SEQ ID NO:11 (VCP2a, VCP2b, and VCP2c), a domain commonly found in light harvesting complex (LHC) proteins known as fucoxanthin chlorophyll binding protein (FCPs) that bind the violaxanthin derivative, fucoxanthin, in addition to binding chlorophyll. This domain is also found in the VCPs. The PLN00120 domain comprises amino acids 13-208 of SEQ ID NO:1 (*Nannochloropsis* VCP1), amino acids 1-201 of SEQ ID NO:2 (*Nannochloropsis* VCP2a, 2b, and 2c).

A VCP mutant can be mutated in a gene encoding a VCP protein of *Nannochloropsis gaditana*, for which there are four genes (SEQ ID NO:5, SEQ ID NO:6, SEQ ID NO:7) comprising two coding sequences respectively (SEQ ID NO:3, SEQ ID NO:4) or any orthologs or homologs of the VCP proteins having at least 50% identity to SEQ ID NO:1 or SEQ ID NO:32 and having a PLN00120 domain, in any algal species, such as heterokont algal species. For example, a VCP or FCP mutant can be mutated in a gene encoding the polypeptide of SEQ ID NO:1, SEQ ID NO:2, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or combinations thereof, or can be mutated in a naturally-occurring gene encoding a polypeptide having at least 35%, at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with SEQ ID NO:1, SEQ ID NO:2, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or combinations thereof, where the polypeptide preferably includes a PLN00120 domain. The polypeptide encoded by the VCP gene or FCP gene can include at least one chlorophyll a-b binding protein domain and can recruit to pfam PF00504, e.g., with a bit score greater than the gathering cutoff (21.0), and an E value of less than 1.00E-2 or less than 1.00E-10. The polypeptide encoded by the VCP gene or FCP gene can further include at least one fucoxanthin-chlorophyll a-c binding protein domain (PLN domain PLN00120). Further, the encoded polypeptide that is at least 30% identical to SEQ ID NO:1, or SEQ ID NO:2, or is at least 80% or at least 85% identical to SEQ ID NO:1, SEQ ID NO:2, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or combinations thereof, can optionally include an amino acid sequence having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:10, SEQ ID NO:11, SEQ ID NO:12, SEQ ID NO:13, or combinations thereof.

For example, a VCP or FCP mutant can be mutated in a gene encoding a polypeptide having at least 50% identity to SEQ ID NO:1, or SEQ ID NO:2, and the polypeptide can in some examples include an amino acid sequence encoding a PLN00120 domain and/or a PF00504 domain, in which the amino acid sequence has at least 80%, or at least 85%, for example at least 86%, at least 87%, at least 88%, at least 89%, at least 90%, at least 91%, at least 92%, at least 93%, at least 94%, at least 95% identity with the amino acid sequence of SEQ ID NO:10, SEQ ID NO:11, SEQ ID NO:12, SEQ ID NO:13, or combinations thereof.

The disclosure also provides VCP mutants or FCP mutants that are mutated in genes comprising a nucleotide sequence having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:5, or SEQ ID NO:6, in which the gene encodes a polypeptide that includes an amino acid sequence having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of SEQ ID NO:10, SEQ ID NO:11, SEQ ID NO:12, or SEQ ID NO:13. Alternatively or in addition, the polypeptide encoded by the gene can recruit to pfam PF00504. Further, the polypeptide encoded by the gene can have at least 40%, at least 45%, at least 50%, at least 55%, having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:1, or SEQ ID NO:2.

Further, the disclosure provides VCP mutants or FCP mutants that are mutated in genes comprising a nucleotide sequence having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:5, SEQ ID NO:6, SEQ ID NO:7, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, or a portion or combination thereof. The gene that is mutated in the FCP or VCP mutant can encode, in a wild type alga, a polypeptide that includes a PLN00120 domain and/or PF00504 domain, and can include, for example, an amino acid sequence having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:10, SEQ ID NO:11, SEQ ID NO:12, SEQ ID NO:13, or combinations thereof.

A VCP or FCP mutant as provided herein can gave at least one of the following properties: reduced chlorophyll, increased electron transport rate (ETR), decreased non-photochemical quenching (NPQ), and increased productivity.

For example, total chlorophyll or chlorophyll a can be reduced by at least 5%, at least 10%, at least 15%, at least 20%, at least 25%, at least 30%, at least 35%, at least 40%, at least 45%, at least 50%, at least 55%, at least 60%, at least 65%, at least 75%, at least 80%, or at least 85%. Total chlorophyll or chlorophyll a can alternatively or additionally be reduced by at least 5% but not more than 85%, at least 5% but not more than 75%, at least 5% but not more than 65%, at least 5% but not more than 55%, at least 5% but not more than 45%, at least 5% but not more than 35%, at least 5% but not more than 25%, or at least 10% but not more than 50%. Chlorophyll reduction can be assessed on cultures grown under a broad range of light intensities, for example, less than 50 μE, less than 100 μE, less than 200 μE, less than 300

μE, less than 400 μE, less than 500 μE, less than 600 μE, less than 700 μE, less than 800 μE, less than 900 μE, less than 1000 μE, less than 1250 μE, less than 1500 μE, less than 1750 μE, less than 2000 μE, less than 2500 μE, less than 3000 μE, or any combination thereof. In some examples chlorophyll reduction with respect to a wild type or control cell is exhibited at light intensities of less than less than 500 μE, for example, less than 300 μE.

Alternatively or in addition, electron transport rate (ETR) can be increased (referring to the apparent ETR(II) measurement from a Dual-PAM fluorometer (Walz, Germany)), with respect to a control or wild type cell, from about 5% to about 300%, from about 10% to about 300%, from about 15% to about 300%, from about 20% to about 300%, from about 25% to about 300%, from about 30% to about 300%, from about 40% to about 300%, from about 50% to about 300%, from about 60% to about 300%, from about 70% to about 300%, from about 80% to about 300%, from about 90% to about 300%, from about 100% to about 300%, from about 125% to about 300%, from about 150% to about 300%, from about 175% to about 300%, from about 200% to about 300%, or from about 250% to about 300%. ETR can alternatively or additionally be increased from about 5% to about 250%, from about 5% to about 200%, from about 5% to about 175%, from about 5% to about 150%, from about 5% to about 125%, from about 5% to about 100%, from about 5% to about 90%, from about 5% to about 80%, from about 5% to about 70%, from about 5% to about 60%, from about 5% to about 50%, from about 5% to about 40%, from about 5% to about 30%, from about 5% to about 20%, or from about 5% to about 10%. ETR can be assessed under a single or a range of multiple light intensities, for example, from about 50 μE to about 3000 μE, and any combination of light intensities thereof. For examples, ETR can be increased by at least 10% at all irradiances between 200 μE and 2000 μE, or by at least 20% at all irradiances between 300 μE and 2000 μE, or by at least 30% at all irradiances between 500 μE and 2000 μE. Additionally or alternatively, ETR can be increased by at least 10%, at least 20%, or at least 30% at the light intensity at which photosynthesis saturates for the control alga.

Alternatively or in addition, non-photochemical quenching (NPQ) can be decreased, with respect to a wild type or control cell from about 5% to about 100%, from about 10% to about 100%, from about 15% to about 100%, from about 20% to about 100%, from about 25% to about 100%, from about 30% to about 100%, from about 40% to about 100%, from about 50% to about 100%, from about 60% to about 100%, from about 70% to about 100%, from about 80% to about 100%, or from about 90% to about 100%. NPQ can alternatively or additionally be decreased from about 5% to about 100%, from about 5% to about 90%, from about 5% to about 80%, from about 5% to about 70%, from about 5% to about 60%, from about 5% to about 50%, from about 5% to about 40%, from about 5% to about 30%, from about 5% to about 20%, or from about 5% to about 10%. NPQ can be assessed under a single or a range of multiple light intensities ranging, for example, from about 50 μE to about 3000 μE, and including any combination of light intensities thereof. For example, NPQ can be decreased by at least 10% at all irradiances between 200 μE and 2000 μE, or by at least 30% at all irradiances between 300 μE and 2000 μE, or by at least 50% at all irradiances between 500 μE and 2000 μE. Alternatively or additionally, NPQ can be decreased by at least 10%, 30%, or 50% at the light intensity at which photosynthesis is saturated for the control alga.

An algal mutant having attenuated expression of at least one VCP gene or at least one FCP gene can demonstrate increased productivity with respect to a wild type or control cell. For example, productivity can be increased from about 5% to about 300%, from about 8% to about 300%, from about 10% to about 300%, from about 12% to about 300%, from about 13% to about 300%, from about 15% to about 300%, from about 20% to about 300%, from about 25% to about 300%, from about 30% to about 300%, from about 40% to about 300%, from about 50% to about 300%, from about 60% to about 300%, from about 70% to about 300%, from about 80% to about 300%, from about 90% to about 300%, from about 100% to about 300%, from about 125% to about 300%, from about 150% to about 300%, from about 175% to about 300%, from about 200% to about 300%, or from about 250% to about 300%. Productivity can alternatively or additionally be increased from about 5% to about 250%, from about 5% to about 200%, from about 5% to about 175%, from about 5% to about 150%, from about 5% to about 125%, from about 5% to about 100%, from about 5% to about 90%, from about 5% to about 80%, from about 5% to about 70%, from about 5% to about 60%, from about 5% to about 50%, from about 5% to about 40%, from about 5% to about 30%, from about 5% to about 20%, or from about 5% to about 10% with respect to a wild type and/or control cell. Productivity may be, for example, biomass productivity (e.g., dry weight, AFDW, or TOC) or may be lipid productivity, as nonlimiting examples. Productivity may be measured in a batch, semi-continuous, continuous culturing system, or combinations thereof, while the culture is being grown under autotrophic, heterotrophic, phototrophic conditions, or combinations thereof. For example, biomass productivity can be increased by at least 5%, at least 8%, at least 12% with respect to a control alga. Alternatively or additionally, biomass productivity can be increased between 5% and 500% or between 10% and 100% with respect to a control alga. Biomass productivity increase can be over a period of at least 5, 7, 10, or 14 days of semi-continuous or continuous growth.

A recombinant or classically-mutagenized algal mutant having attenuated expression of at least one VCP gene or at least one FCP gene can demonstrate increased productivity with respect to a wild type or control cell cultured under the same conditions. In some examples, an algal VCP or FCP mutant as provided herein can be cultured under a diel light cycle in which the light intensity changes throughout the light period, which can be natural sunlight or artificial light that mimics exposure to natural light, or a combination thereof. Additionally or alternatively, an algal VCP or FCP mutant as disclosed herein can demonstrate higher productivity, such as but not limited to higher biomass productivity, in a culture that experiences constant (24 hour per day) light or that experiences light on a diel cycle, where the light period may be, as nonlimiting examples, from 6 to 23 hours per 24 hour cycle and is typically from about 8 to about 16 hours per 24 hour cycle. Light provided during the light period of a diel cycle can be provided at a constant intensity or can be provided at an intensity that varies during the light period, for example, to mimic natural daylight such that the intensity increases from the beginning of the light period to peak in intensity at solar noon, after which the intensity declines to the end of the light period. In some examples, an algal VCP or FCP mutant as provided herein can have greater productivity, e.g., greater biomass productivity, under one or more of a constant light regime or a diel light regime that provides light of a constant or variable intensity. In some examples, an algal VCP or FCP mutant as provided herein can have greater productivity, e.g., greater biomass productivity, under a constant light regime as well as under a diel light regime that provides light of either a constant or variable intensity. In some examples, an algal VCP or FCP mutant as provided herein can have greater productivity, e.g., greater biomass productivity, under a diel light regime that provides peak light intensity of at least 1900 μmol photons m-2 sec-1. For example, an algal VCP or FCP mutant as provided herein can accumulate at least 5%, at least 8%, at least 10%, at least 12%, at least 13%, at least 15%, or at least 20% more biomass on a daily basis under a diel light regime that provides light of a variable intensity that peaks at between about 1900 μmol photons m-2 sec-1 and about 2000 μmol photons m-2 sec-1. In some examples, an algal VCP or FCP mutant as provided herein can have greater productivity, e.g., greater biomass productivity, under a diel light regime that mimics the intensity pattern of natural daylight, where the light profile follows a sinusoidal curve and provides peak light intensity of at least about 1900 μmol photons m-2 sec-1 and 2000 μmol photons m-2 sec-1 at the middle of the light period. In some examples, the light is natural sunlight or artificial light designed to mimic the changing intensity of natural sunlight.

Alternatively, a recombinant or classically-mutagenized mutant alga as provided herein can exhibit greater productivity, for example, greater biomass productivity, for at least 5, 6, 7, 10, or 14 days of semi-continuous or continuous growth in a culture system that experiences constant light, for example, constant light of greater than about 100, 200, 400, 500, 600, 800, 1000, 1200, 1400, 1600, 1800, or 2000 μE.

Gene Attenuation

A mutant alga having attenuated expression of a gene that encodes a VCP or FCP can be a mutant generated by any feasible method, including but not limited to UV irradiation, gamma irradiation, or chemical mutagenesis, and screening for mutants having decreased chlorophyll. Methods for generating mutants of microbial strains are well-known.

A mutant as provided herein that produces at least 10% more biomass than the progenitor cell can also be a genetically engineered mutant, for example, a mutant in which a VCP gene or FCP gene (e.g., a gene encoding a polypeptide having a PLN00120 domain or PF00504 domain, or, for example, a gene encoding a polypeptide having at least 55%, at least 60%, at least 65%, at least 70%, at least 75%, at least 80%, at least 85%, at least 90%, or at least 95% identity to SEQ ID NO:1, or SEQ ID NO:2) has been targeted by homologous recombination for knock-out or gene replacement (for example with mutated form of the gene that may encode a polypeptide having reduced activity with respect to the wild type polypeptide). For example, a microbial strain of interest may be engineered by site directed homologous recombination to insert a sequence into a genomic locus and thereby alter a gene and/or its expression, or to insert a promoter into a genetic locus of the host alga to affect the expression of a particular gene or set of genes at the locus.

For example, gene knockout or replacement by homologous recombination can be by transformation of a nucleic acid (e.g., DNA) fragment that includes a sequence homologous to the region of the genome to be altered, where the homologous sequence is interrupted by a foreign sequence, typically a selectable marker gene that allows selection for the integrated construct. The genome-homologous flanking sequences on either side of the foreign sequence or mutated gene sequence can be for example, at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides in length. A gene knockout or gene "knock in" construct in which a foreign sequence is flanked by target gene sequences, can be provided in a vector that can optionally be linearized, for example, outside of the region that is to undergo homologous recombination, or can be provided as a linear fragment that is not in the context of a vector, for example, the knock-out or knock-in construct can be an isolated or synthesized fragment, including but not limited to a PCR product. In some instances, a split marker system can be used to generate gene knock-outs by homologous recombination, where two DNA fragments can be introduced that can regenerate a selectable marker and disrupt the gene locus of interest via three crossover events (Jeong et al. (2007) *FEMS Microbiol Lett* 273: 157-163).

In some aspects the disclosure provides genetically modified organisms, e.g. algas having one or more genetic modifications for attenuating expression of a VCP gene, such as a gene having at least 55% identity to any of SEQ ID NO:5, SEQ ID NO:6, or SEQ ID NO:7. As used herein "attenuating expression of a VCP gene" means reducing or eliminating expression of the gene in any manner that reduces production of the fully functional protein. Means for attenuating a VCP gene or FCP gene include, for example, homologous recombination constructs; CRISPR systems, including guide RNAs, cas9 enzymes, and optionally, donor fragments for insertion into the targeted site; other RNA-guided nucleases along with their targeting and activating RNAs; RNAi constructs, including shRNAs; antisense RNA constructs; ribozyme constructs; TALENS, Zinc Finger nucleases; meganucleases; and combinations thereof.

For example, a recombinant alga engineered to have attenuated expression of a VCP gene or FCP gene can have a VCP gene or FCP gene that includes as least one insertion, mutation, or deletion that reduces or abolishes expression of the gene such that a fully functional VCP gene or FCP gene is not produced or is produced in lower amounts than is produced by a control alga that does not include a disrupted VCP or FCP gene. The disrupted VCP or FCP gene can be disrupted by, for example, an insertion or gene replacement mediated by homologous recombination and/or by the activity of a meganuclease, zinc finger nuclease (Perez-Pinera et al. (2012) Curr. Opin. Chem. Biol. 16: 268-277), TALEN (WO 2014/207043; WO 2014/076571, all of which are incorporated by reference), or a Cas protein (e.g., a cas9 protein) of a CRISPR system. CRISPR systems, reviewed recently by Hsu et al. (Cell 157:1262-1278, 2014, incorporated by reference) include, in addition to the cas nuclease polypeptide or complex, a targeting RNA, often denoted "crRNA", that interacts with the genome target site by complementarity with a target site sequence, a trans-activating ("tracr") RNA that complexes with the cas polypeptide and also includes a region that binds (by complementarity) the targeting crRNA. In some CRISPR systems, such as those comprising the RNA-guided endonuclease Cbf1, utilize a single targeting RNA (Zetsche et al., 2015, Cell, September 25).

The disclosure contemplates the use of two RNA molecules (a "crRNA" and a "tracrRNA") that can be co-transformed into a host strain (or expressed in a host strain) that expresses or is transfected with a cas protein for genome editing, or the use of a single guide RNA that includes a sequence complementary to a target sequence as well as a sequence that interacts with a cas protein. That is, in some strategies a CRISPR system as used herein can comprise two separate RNA molecules (RNA polynucleotides: a "tracr-RNA" and a "targeter-RNA" or "crRNA", see below) and referred to herein as a "double-molecule DNA-targeting RNA" or a "two-molecule DNA-targeting RNA." Alternatively, as illustrated in the examples, the DNA-targeting RNA can also include the trans-activating sequence for interaction with the Cas protein (in addition to the target-homologous ("cr") sequences), that is, the DNA-targeting RNA can be a single RNA molecule (single RNA polynucleotide) and is referred to herein as a "chimeric guide RNA," a "single-guide RNA," or an "sgRNA." The terms "DNA-targeting RNA" and "gRNA" are inclusive, referring both to double-molecule DNA-targeting RNAs and to single-molecule DNA-targeting RNAs (i.e., sgRNAs). Both single-molecule guide RNAs and two RNA systems have been described in detail in the literature and for example, in U.S. Patent Application Publication No. US 2014/0068797, incorporated by reference herein in its entirety.

Any cas protein can be used in the methods herein, e.g., Cast, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cbf1, homologs thereof, or modified versions thereof. The Cas protein can be a cas9 protein, such as a cas9 protein of *Staphylococcus pyogenes, S. thermophilus, S. pneumonia, S. aureus*, or *Neisseria meningitidis*, as nonlimiting examples. Also considered are the cas9 proteins provided as SEQ ID NOs:1-256 and 795-1346 in U.S. Patent Application Publication No. US 2014/0068797, incorporated by reference herein in its entirety, and chimeric cas9 proteins that may combine domains from more than one cas9 protein, as well variants and mutants of identified cas9 proteins.

Cas nuclease activity cleaves target DNA to produce double strand breaks. These breaks are then repaired by the cell in one of two ways: non-homologous end joining or homology-directed repair. In non-homologous end joining (NHEJ), the double-strand breaks are repaired by direct ligation of the break ends to one another. In this case, no new nucleic acid material is inserted into the site, although some nucleic acid material may be lost, resulting in a deletion, or altered, often resulting in mutation. In homology-directed repair, a donor polynucleotide (sometimes referred to as a "donor DNA" or "editing DNA") which may have homology to the cleaved target DNA sequence is used as a template for repair of the cleaved target DNA sequence, resulting in the transfer of genetic information from the donor polynucleotide to the target DNA. As such, new nucleic acid material may be inserted or copied into the site. The modifications of the target DNA due to NHEJ and/or homology-directed repair (for example using a donor DNA molecule) can lead to, for example, gene correction, gene replacement, gene tagging, transgene insertion, nucleotide deletion, gene disruption, gene mutation, etc.

In some instances, cleavage of DNA by a site-directed modifying polypeptide (e.g., a cas nuclease, zinc finger nuclease, meganuclease, TALEN, or combinations thereof) may be used to delete nucleic acid material from a target DNA sequence by cleaving the target DNA sequence and allowing the cell to repair the sequence in the absence of an exogenously provided donor polynucleotide. Such NHEJ events can result in mutations ("mis-repair") at the site of rejoining of the cleaved ends that can resulting in gene disruption.

Alternatively, if a DNA-targeting RNA is co-administered to cells that express a cas nuclease along with a donor DNA, the subject methods may be used to add, i.e. insert or replace, nucleic acid material to a target DNA sequence (e.g. "knock out" by insertional mutagenesis, or "knock in" a nucleic acid that encodes a protein (e.g., a selectable marker and/or any protein of interest), an siRNA, an miRNA, etc., to modify a nucleic acid sequence (e.g., introduce a mutation), and the like.

A donor DNA can in particular embodiments include a gene regulatory sequence (e.g., a promoter) that can, using CRISPR targeting, be inserted upstream of the coding regions of the gene and upstream of the presumed proximal promoter region of the gene, for example, at least 50 bp, at least 100 bp, at least 120 bp, at least 150 bp, at least 200 bp, at least 250 bp, at least 300 bp, at least 350 bp, at least 400 bp, at least 450 bp, or at least 500 bp upstream of the initiating ATG of the coding region of the VCP or FCP gene. The donor DNA can include a sequence, such as for example a selectable marker or any convenient sequence, that may interfere with the native promoter. The additional sequence inserted upstream of the initiating ATG of the VCP or FCP open reading frame (e.g., in the 5'UTR or upstream of the transcriptional start site of VCP gene) can decrease or even eliminate expression of the endogenous VCP gene. Alternatively or in addition, the native VCP gene or FCP gene can have its endogenous promoter wholly or partially replaced by a weaker or differently regulated promoter, or a non-promoter sequence.

In some examples, a nucleic acid molecule introduced into a host cell for generating a high efficiency genome editing cell line encodes a cas9 enzyme that is mutated to with respect to the corresponding wild-type enzyme such that the mutated cas9 enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (an enzyme that cleaves a single strand). Other examples of mutations that render Cas9 a nickase include, without limitation, H840A, N854A, and N863A. In some embodiments, a Cas9 nickase may be used in combination with guide sequence(s), e.g., two guide sequences, which target respectively sense and antisense strands of the DNA target. This combination allows both strands to be nicked and used to induce NHEJ. Two nickase targets (within close proximity but targeting different strands of the DNA) can be used to inducing mutagenic NHEJ. Such targeting of a locus using enzymes that cleave opposite strains at staggered positions can also reduce nontarget cleavage, as both strands must be accurately and specifically cleaved to achieve genome mutation.

In additional examples, a mutant cas9 enzyme that is impaired in its ability to cleave DNA can be expressed in the cell, where one or more guide RNAs that target a sequence upstream of the transcriptional or translational start site of the targeted gene are also introduced. In this case, the cas enzyme may bind the target sequence and block transcription of the targeted gene (Qi et al. (2013) Cell 152:1173-1183, incorporated herein by reference). This CRISPR interference of gene expression can be referred to as RNAi and is also described in detail in Larson et al. (2013) Nat. Protoc. 8: 2180-2196, herein incorporated by reference.

In some cases, a cas polypeptide such as a Cas9 polypeptide is a fusion polypeptide, comprising, e.g.: i) a Cas9 polypeptide (which can optionally be variant Cas9 polypeptide as described above); and b) a covalently linked heterologous polypeptide (also referred to as a "fusion partner"). A heterologous nucleic acid sequence may be linked to another nucleic acid sequence (e.g., by genetic engineering)

to generate a chimeric nucleotide sequence encoding a chimeric polypeptide. In some embodiments, a Cas9 fusion polypeptide is generated by fusing a Cas9 polypeptide with a heterologous sequence that provides for subcellular localization (i.e., the heterologous sequence is a subcellular localization sequence, e.g., a nuclear localization signal (NLS) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a hemagglutinin (HA) tag; a FLAG tag; a Myc tag; and the like).

Host cells can be genetically engineered (e.g. transduced or transformed or transfected) with, for example, a vector construct that can be, for example, a vector for homologous recombination that includes nucleic acid sequences homologous to a portion of a VCP gene locus of the host cell or to regions adjacent thereto, or can be an expression vector for the expression of any or a combination of: a cas protein (e.g., a cas9 protein), a CRISPR chimeric guide RNA, a crRNA, and/or a tracrRNA, an RNAi construct (e.g., a shRNA), an antisense RNA, or a ribozyme. The vector can be, for example, in the form of a plasmid, a viral particle, a phage, etc. A vector for expression of a polypeptide or RNA for genome editing can also be designed for integration into the host, e.g., by homologous recombination. A vector containing a polynucleotide sequence as described herein, e.g., sequences having homology to host VCP or FCP gene sequences (including sequences that are upstream and downstream of the VCP-encoding sequences), as well as, optionally, a selectable marker or reporter gene, can be employed to transform an appropriate host to cause attenuation of a VCP or FCP gene.

The recombinant alga in some examples can have reduced but not abolished expression of the VCP or FCP gene, and the recombinant alga can have an increase in biomass production of from about 5% to about 500% or more, for example. A genetically modified alga as provided herein can in some examples include a nucleic acid construct for attenuating the expression of a VCP gene or FCP gene, such as, for example, a gene encoding a polypeptide having at least 55%, at least 60%, at least 65%, at least 70%, at least 75%, at least 80%, at least 85%, at least 90%, or at least 95% identity to SEQ ID NO:1, SEQ ID NO:2. For example, a host alga can include a construct for expressing an RNAi molecule, ribozyme, or antisense molecule that reduces expression of a VCP gene or FCP gene encoding a polypeptide having at least 55% identity to SEQ ID NO:1, or SEQ ID NO:2. In some examples, a recombinant alga as provided herein can include at least one introduced (exogenous or non-native) construct for reducing expression of a VCP or FCP gene.

In some examples, engineered strains can be selected for expression of a VCP or FCP gene that is decreased with respect to a control cell that does not include a genetic modification for attenuating VCP or FCP gene expression, but not eliminated, using methods known in the art, such as, for example, RNA-Seq or quantitative reverse transcription-PCR (qRT-PCR).

A genetically engineered strain as provided herein can be engineered to include a construct for attenuating gene expression by reducing the amount, stability, or translatability of mRNA of a gene encoding a VCP or FCP. For example, a alga such as an algal or heterokont strain can be transformed with an antisense RNA, RNAi, or ribozyme construct targeting an mRNA of a VCP or FCP gene using methods known in the art. For example, an antisense RNA construct that includes all or a portion of the transcribed region of a gene can be introduced into a alga to decrease gene expression (Shroda et al. (1999) The Plant Cell 11:1165-78; Ngiam et al. (2000) Appl. Environ. Microbiol. 66: 775-782; Ohnuma et al. (2009) Protoplasma 236: 107-112; Lavaud et al. (2012) PLoS One 7:e36806, all incorporated by reference herein). Alternatively or in addition, an RNAi construct (for example, a construct encoding a short hairpin RNA) targeting a gene having a PLN00120 domain or Pfam PF00504 domain can be introduced into a alga such as an alga or heterokont for reducing expression of the VCP or FCP gene (see, for example, Cerruti et al. (2011) Eukaryotic Cell (2011) 10: 1164-1172; Shroda et al. (2006) Curr. Genet. 49:69-84, all of which are incorporated by reference herein).

Ribozymes are RNA-protein complexes that cleave nucleic acids in a site-specific fashion. Ribozymes have specific catalytic domains that possess endonuclease activity. For example, U.S. Pat. No. 5,354,855, incorporated herein by reference, reports that certain ribozymes can act as endonucleases with a sequence specificity greater than that of known ribonucleases and approaching that of the DNA restriction enzymes. Catalytic RNA constructs (ribozymes) can be designed to base pair with an mRNA encoding a gene as provided herein to cleave the mRNA target. In some examples, ribozyme sequences can be integrated within an antisense RNA construct to mediate cleavage of the target. Various types of ribozymes can be considered, their design and use is known in the art and described, for example, in Haseloff et al. (1988) Nature 334:585-591, incorporated by reference herein.

Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A, C, or U) (Thompson et al., (1995) Nucl Acids Res 23:2250-68, incorporated by reference). The frequency of this dinucleotide occurring in any given RNA is statistically 3 out of 16. Therefore, for a given target messenger RNA of 1,000 bases, 187 dinucleotide cleavage sites are statistically possible.

The general design and optimization of ribozyme directed RNA cleavage activity has been discussed in detail (Haseloff and Gerlach (1988) *Nature* 334:585-591; Symons (1992) *Ann Rev Biochem* 61: 641-71; Chowrira et al. (1994) *J Biol Chem* 269:25856-64; Thompson et al. (1995) supra), all incorporated by reference in their entireties. Designing and testing ribozymes for efficient cleavage of a target RNA is a process well known to those skilled in the art. Examples of scientific methods for designing and testing ribozymes are described by Chowrira et al., (1994) supra and Lieber and Strauss (1995) *Mol Cell Biol.* 15: 540-51, each incorporated by reference. The identification of operative and preferred sequences for use in down regulating a given gene is a matter of preparing and testing a given sequence, and is a routinely practiced "screening" method known to those of skill in the art.

The use of RNAi constructs is described in literature cited above as well as in US2005/0166289 and WO 2013/016267, for example, which are herein incorporated by reference. A double stranded RNA with homology to the target gene is delivered to the cell or produced in the cell by expression of an RNAi construct, for example, an RNAi short hairpin (sh) construct. The construct can include a sequence that is identical to the target gene, or at least 70%, 80%, 90%, 95%, or between 95% and 100% identical to a sequence of the target gene. The construct can have at least 20, at least 30, at least 40, at least 50, at least 100, at least 200, at least 300, at least 400, at least 500, at least 600, at least 700, at least 800, at least 900, or at least 1 kb of sequence homologous to the target gene. Expression vectors can be engineered using promoters selected for continuous or inducible expression of an RNAi construct, such as a construct that produces an shRNA.

A nucleic acid construct for gene attenuation, e.g., a ribozyme, RNAi, or antisense construct can include at least fifteen, at least twenty, at least thirty, at least forty, at least fifty, or at least sixty nucleotides having at least 80% identity, such as at least 85%, at least 90%, at least 95%, or at least 99% or complementarity to at least a portion of the sequence of an endogenous VCP or FCP gene of the alga to be engineered. A nucleic acid construct for gene attenuation, e.g., a ribozyme, RNAi, or antisense construct can include at least fifteen, at least twenty, at least thirty, at least forty, at least fifty, or at least sixty nucleotides having at least 80%, such as at least 95% or about 100%, identity or complementarity to the sequence of a naturally-occurring gene, such as a gene having encoding a polypeptide having at least 50%, at least 55%, at least 60%, at least 65%, at least 70%, at least 75%, at least 80% or at least 85%, at least 90%, or at least 95% sequence identity to an endogenous VCP or FCP gene. For example, a nucleic acid construct for gene attenuation, e.g., a ribozyme, RNAi, or antisense construct can include at least fifteen, at least twenty, at least thirty, at least forty, at least fifty, or at least sixty nucleotides having at least 80% identity or complementarity to the sequence of a naturally-occurring VCP or FCP gene, such as any provided herein. The nucleotide sequence can be, for example, from about 30 nucleotides to about 3 kilobases or greater, for example, from 30-50 nucleotides in length, from 50 to 100 nucleotides in length, from 100 to 500 nucleotides in length, from 500 nucleotides to 1 kb in length, from 1 kb to 2 kb in length, or from 2 to 5 kb. For example, an antisense sequence can be from about 100 nucleotides to about 1 kb in length. For example, a nucleic acid construct for gene attenuation, e.g., a ribozyme, RNAi, or antisense construct can include at least fifteen, at least twenty, at least thirty, at least forty, at least fifty, at least sixty, or at least 100 nucleotides having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity or complementarity to an endogenous VCP or FCP gene or a portion thereof.

Promoters used in antisense, RNAi, or ribozyme constructs can be any that are functional in the host organism and that are suitable for the levels of expression required for reducing expression of the target gene to a desired amount. Promoters functional in algae and heterokonts are known in the art and disclosed herein. The construct can be transformed into algae using any feasible method, include any disclosed herein. A recombinant organism or alga transformed with a nucleic acid molecule for attenuating VCP or FCP gene expression, such as but not limited to an antisense, RNAi, or ribozyme construct, can have the properties of a VCP mutant or FCP mutant as described herein, including, for example, reduced chlorophyll, increased photosynthetic efficiency, and increased productivity in culture, with respect to a host organism or alga that does not include the exogenous nucleic acid molecule that results in attenuated gene expression.

Nucleic Acid Molecules

The present disclosure also includes isolated nucleic acid molecules encoding violaxanthin-chlorophyll a binding proteins (VCP) or fucoxanthin-chlorophyll a/c binding proteins (FCP). The nucleic acid molecules provided herein can be used, for example, to generate gene targeting constructs as described herein, and for RNAi, and ribozyme constructs as well as for expression constructs. The nucleic acid molecules can also encode variant polypeptide fragments that act as dominant negative proteins that can be produced in an algal cell to produce a mutant phenotype, and may also be used in strategies for obtaining additional genes encoding polypeptides that function in the same pathway as the VCP or FCP proteins.

In some examples, an isolated nucleic acid molecule as provided herein comprises a nucleic acid sequence encoding a polypeptide comprising an amino acid sequence encoding at least one PLN00120 or PF00504 domain. The polypeptide encoded by the gene can recruit to pfam PF00504 or PLN00120 with a bit score at least as high as the gathering cutoff for pfam PF00504 or PLN00120 respectively (e.g., 21.0) when queried against the Pfam or Entrez database respectively. In some examples an isolated nucleic acid molecule as provided herein comprises a nucleic acid sequence encoding a polypeptide comprising an amino acid sequence encoding at least one PLN00120 or PF00504 domain having at least 40%, at least 45%, at least 50%, at least 55%, at least 60%, at least 65%, at least 70%, at least 75%, or at least 80% identity to SEQ ID NO:10, SEQ ID NO:11, SEQ ID NO:12, SEQ ID NO:13, or combinations thereof. The nucleic acid molecule can encode a polypeptide having a mutation, with respect to a wild type gene, e.g., a the gene can encode a polypeptide having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of any of SEQ ID NO:1, SEQ ID NO:2, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or combinations thereof, in which the polypeptide has at least one mutation with respect to a wild type gene. The mutation can optionally be in a PLN00120 or PF00504 domain (e.g., in a sequence having at least 50%, at least 65%, at least 70%, at least 75%, or at least 80% identity to SEQ ID NO:10, SEQ ID NO:11, SEQ ID NO:12, SEQ ID NO:13, or combinations thereof). Further, the polypeptide encoded by the gene can have at least 30%, at least 35%, at least 40%, at least 45%, at least 50%, at least 55%, having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:1, or SEQ ID NO:2. The nucleic acid molecule in some embodiments can encode a polypeptide having a mutation, with respect to a wild type gene, in a PLN00120 or PF00504 domain (e.g., in a sequence having at least 50%, at least 65%, at least 70%, at least 75%, or at least 80% identity to SEQ ID NO:10, SEQ ID NO:11, SEQ ID NO:12, SEQ ID NO:13, or combinations thereof). Alternatively or in addition, the nucleic acid molecule in some embodiments can encode a truncated, frameshifted, or internally deleted polypeptide.

The disclosure provides, in various examples, nucleic acid molecules encoding polypeptides having at least at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of SEQ ID NO:1, SEQ ID NO:2, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or combinations thereof, in which the polypeptides include a PLN00120 or PF00504 domain, for example, a PLN00120 or PF00504 domain having an amino acid sequence with at least 40% identity to SEQ ID NO:10, SEQ ID NO:11, SEQ ID NO:12, SEQ ID NO:13, or combinations thereof. The polypeptides can have, for example, at least 85%, at least 90%, or at least 95%, sequence identity with the amino acid sequence of SEQ ID NO:1, SEQ ID NO:2, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or combinations thereof, in which the polypeptides include a PLN00120 or PF00504 domain having an amino acid sequence with at least 40% identity to SEQ ID NO:10, SEQ ID NO:11, SEQ ID NO:12, SEQ ID NO:13, or combinations thereof. The nucleic acid molecules in various examples are cDNAs, do not have the sequence of a naturally occurring gene, and/or are constructs for homologous recombination or gene attenuation.

The disclosure further provides isolated nucleic acid molecules comprising nucleotide sequences having at least 50%, at least 55%, at least 60%, at least 65%, at least 70%, at least 75%, at least 80%, or at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the nucleotide sequence of SEQ ID NO:3, SEQ ID NO:4, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, or combinations thereof, as well as nucleic acid molecules comprising nucleotide sequences complementary to any thereof, where the nucleotide sequence preferably is not identical to the nucleotide sequence of the naturally-occurring gene. Also included are nucleic acid molecules comprising nucleotide sequences having at least 80%, or at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with at least a portion of a naturally-occurring gene, in which the nucleic acid molecule is a construct for homologous recombination or gene attenuation (e.g., a construct for RNAi, antisense, or ribozyme expression), and in which the naturally-occurring gene encodes a polypeptide having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of any of SEQ ID NO:1, SEQ ID NO:2, SEQ ID NO:3, SEQ ID NO:27, SEQ ID NO:29, SEQ ID NO:31, SEQ ID NO:33, SEQ ID NO:35, SEQ ID NO:39, SEQ ID NO:41, SEQ ID NO:43, SEQ ID NO:45, or combinations thereof. The naturally-occurring gene that is targeted by the antisense, RNAi, or ribozyme construct can in some examples have at least 30%, at least 35%, at least 40%, at least 45%, at least 50%, at least 55%, at least 60%, at least 65%, at least 70%, at least 75%, at least 80%, or at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the nucleotide sequence of SEQ ID NO:4, SEQ ID NO:5, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, or combinations thereof.

In some exemplary embodiments, a nucleic acid provided herein encodes a polypeptide having at least 50% identity to SEQ ID NO:1, or SEQ ID NO:2 in which the polypeptide at least PLN00120 or PF00504 domain having at least 80% identity to SEQ ID NO:10, SEQ ID NO:11, SEQ ID NO:12, SEQ ID NO:13, or combinations thereof. For example, a nucleic acid as provided herein can encode a polypeptide having at least 85% identity to SEQ ID NO:1, SEQ ID NO:2, or combinations thereof, where the polypeptide includes PLN00120 or PF00504 domain having an amino acid sequence with at least 85% identity to SEQ ID NO:10, SEQ ID NO:11, SEQ ID NO:12, SEQ ID NO:13, or combinations thereof.

The disclosure also encompasses variations of the nucleotide sequences of the disclosure, such as those encoding functional fragments or variants of the polypeptides as described herein. Such variants can be naturally-occurring, or non-naturally-occurring, such as those induced by various mutagens and mutagenic processes. Intended variations include, but are not limited to, addition, deletion, and substitution of one or more nucleotides which can result in conservative or non-conservative amino acid changes, including additions and deletions. Codon-optimization of nucleotide sequences encoding polypeptides for expression in a host cell of interest is also contemplated.

The disclosure also encompasses nucleotide sequences encoding guide RNAs of a CRISPR system that target a specific target sequence within a nucleotide sequence encoding the polypeptide sequence of SEQ ID NO:1, SEQ ID NO:2, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or combinations thereof, for cleavage by an RNA-guided nuclease, such as, for example, Cas9 or Cbf1. For a Cas9/CRISPR system, the guide RNAs can be a chimeric gRNA or a set of separated crRNA and tracrRNA compatible with Cas9 protein. For a Cbf1/CRISPR system, the guide RNA can comprise or be a single gRNA compatible with Cbf1 protein.

The disclosure also provides constructs comprising a nucleic acid sequence as provided herein that can further include one or more sequences that regulate or mediate transcription, translation, or integration of nucleotide sequences into a host genome. For example, the disclosure provides expression constructs that comprise one or more "expression control elements" or sequences that regulate expression transcription of an operably linked gene, or translation of the transcribed RNA. For example, an expression control element can be a promoter that may be operably linked to a gene of interest or antisense or shRNA-encoding sequence in an expression construct or "expression cassette." Various algal promoters are disclosed in U.S. Patent Application Publication US 2013/0023035; U.S. patent application Ser. No. 13/486,930, filed Jun. 1, 2012; U.S. Ser. No. 13/693,585, filed Dec. 4, 2012; and U.S. application Ser. No. 13/915,522, filed Jun. 11, 2013, the entire contents of each of which are hereby incorporated by reference herein for their disclosure related to said algal promoters. A promoter used in a construct may in some instances be regulatable, e.g., inducible.

An inducible promoter can be responsive to, e.g., light intensity or high or low temperature, and/or can be responsive to specific compounds. The inducible promoter may be, for example, a hormone-responsive promoter (e.g., an ecdysone-responsive promoter, such as described in U.S. Pat. No. 6,379,945), a metallothionien promoter (e.g., U.S. Pat. No. 6,410,828), a pathogenesis-related (PR) promoter that can be responsive to a chemical such as, for example, salicylic acid, ethylene, thiamine, and/or BTH (U.S. Pat. No. 5,689,044), or the like, or some combination thereof. An inducible promoter can also be responsive to light or dark (U.S. Pat. No. 5,750,385, U.S. Pat. No. 5,639,952; U.S. Pat. No. 8,314,228), metals (Eukaryotic Cell 2:995-1002 (2003)) or temperature (U.S. Pat. No. 5,447,858; Abe et al. Plant Cell Physiol. 49: 625-632 (2008); Shroda et al. Plant J. 21: 121-131 (2000)). The foregoing examples are not limiting as to the types of promoters or specific promoters that may be used. The promoter sequence can be from any organism, provided that it is functional in the host organism. In certain embodiments, inducible promoters are formed by fusing one or more portions or domains from a known inducible promoter to at least a portion of a different promoter that can operate in the host cell, e.g. to confer inducibility on a promoter that operates in the host species.

In aspects where the nucleic acid construct does not contain a promoter in operable linkage with the nucleic acid sequence encoding the gene of interest (e.g., a dehydrogenase gene) the nucleic acid sequence can be transformed into the cells such that it becomes operably linked to an endogenous promoter by, e.g., homologous recombination, site specific integration, and/or vector integration. In some instances, genomic host sequences included in a nucleic acid construct for mediating homologous recombination into the host genome may include gene regulatory sequences, for example, a promoter sequence, that can regulate expression of a gene or antisense or RNAi sequence of the nucleic acid construct. In such examples, the transgene(s) of the construct can become operably linked to a promoter that is endogenous to the host alga. The endogenous promoter(s) may be regulatable, e.g., inducible.

Constructs for site-directed non-homologous end joining repair into an algal genome (e.g., for disruption or gene replacement of a regulator gene) can include a nucleotide sequence of a regulator gene, such as any provided herein, or sequences from the algal genome that are adjacent to the regulator gene in the host organism.

Constructs for expressing antisense or interfering RNA (RNAi) or ribozymes are also provided for generating LIHLA mutants. Such constructs can include one or more sequences that are complementary, or antisense, with respect to the nucleic acid sequences provided herein that encode regulator polypeptides. For example, provided herein are nucleic acid molecule constructs for expression of antisense RNA, shRNA, microRNA, or a ribozyme comprising a nucleotide sequence complementary to at least a portion of a naturally-occurring algal gene encoding an RNA Recognition Motif (RRM) domain protein, where the RRM domain protein comprises an amino acid sequence having at least 40% for example, at least 45%, at least 50%, at least 55%, at least 60%, at least 65%, at least 70%, at least 75%, at least 80%, at least 85%, at least 90%, at least 95%, or at least 99% identity to SEQ ID NO:10, SEQ ID NO:11, SEQ ID NO:12, or SEQ ID NO:13. In exemplary embodiments, the construct can include a sequence complementary to at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of SEQ ID NO:7, SEQ ID NO:8, or SEQ ID NO:9 and/or a noncoding region of an mRNA that comprises SEQ ID NO:7, SEQ ID NO:8, or SEQ ID NO:9.

Methods of Producing Algal Products

Also provided herein are methods of producing algal products by culturing algae having increased biomass productivity, such as the VCP or FCP mutants disclosed herein. The methods include culturing an algal VCP or FCP mutant in a suitable medium to provide an algal culture and recovering biomass or at least one product from the culture. The algal culture is preferably a photoautotrophic culture, and the culture medium preferably does not include a substantial amount of reduced carbon, that is, the culture does not include reduced carbon in a form or at a level that can be used by the algae for growth.

The algae may be cultured in any suitable vessel, including flasks or bioreactors, where the algae may be exposed to artificial or natural light. The culture comprising VCP or FCP mutant algae may be cultured on a light/dark cycle that may be, for example, a natural or programmed light/dark cycle, and as illustrative examples, may provide twelve hours of light to twelve hours of darkness, fourteen hours of light to ten hours of darkness, sixteen hours of light to eight hours of darkness, etc.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. As demonstrated in the examples herein, the VCP or FCP mutants provided herein exhibiting increase biomass productivity can achieve higher cell density of the culture over time, for example, over a period of a week or more, with respect to a culture wild type algal cells of the same strain that are not deregulated in low light acclimation. For example, a VCP or FCP mutant may be cultured for at least five, at least six, at least seven at least eight, at least nine, at least ten, at least eleven at least twelve, at least thirteen, at least fourteen, or at least fifteen days, or at least one, two three, four, five, six, seven, eight, nine, or ten weeks, or longer.

Non-limiting examples of selected and/or controlled conditions that can be used for culturing the recombinant alga can include the use of a defined medium (with known characteristics such as pH, ionic strength, and/or carbon source), specified temperature, oxygen tension, carbon dioxide levels, growth in a bioreactor (e.g. a photobioreactor), or the like, or combinations thereof. In some embodiments, the alga or host cell can be grown mixotrophically, using both light and a reduced carbon source. Alternatively, the alga or host cell can be cultured phototrophically. When growing phototrophically, the algal strain can advantageously use light as an energy source. An inorganic carbon source, such as CO2 or bicarbonate can be used for synthesis of biomolecules by the alga. “Inorganic carbon”, as used herein, includes carbon-containing compounds or molecules that cannot be used as a sustainable energy source by an organism. Typically “inorganic carbon” can be in the form of CO2 (carbon dioxide), carbonic acid, bicarbonate salts, carbonate salts, hydrogen carbonate salts, or the like, or combinations thereof, which cannot be further oxidized for sustainable energy nor used as a source of reducing power by organisms. Algae grown photoautotrophically can be grown on a culture medium in which inorganic carbon is substantially the sole source of carbon. For example, in a culture in which inorganic carbon is substantially the sole source of carbon, any organic (reduced) carbon molecule or organic carbon compound that may be provided in the culture medium either cannot be taken up and/or metabolized by the cell for energy and/or is not present in an amount sufficient to provide sustainable energy for the growth and proliferation of the cell culture. Cells grown photoautrophically can be grown under constant light or a diel cycle, for example a diel cycle in which the light period can be, for example, at least four hours, about five hours, about six hours, about seven hours, about eight hours, at least eight hours, about nine hours, about ten hours, about eleven hours, about twelve hours, about thirteen and a half hours, or up to about sixteen hours per day, for example, between about twelve hours and about fourteen hours, or between about fourteen hours and about sixteen hours.

Algae and host cells that can be useful in accordance with the methods of the present disclosure can be found in various locations and environments throughout the world. The particular growth medium for optimal propagation and generation of lipid and/or other products can vary and may be optimized to promote growth, propagation, or production of a product such as a lipid, protein, pigment, antioxidant, etc. In some cases, certain strains of algae may be unable to grow in a particular growth medium because of the presence of some inhibitory component or the absence of some essential nutritional requirement of the particular strain of alga or host cell.

Solid and liquid growth media are generally available from a wide variety of sources, as are instructions for the preparation of particular media suitable for a wide variety of strains of algas. For example, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as nonlimiting examples, the UTEX Culture Collection of Algae (www.sbs.utexas.edu/utex/media.aspx); Culture Collection of Algae and Protozoa (www.ccap.ac.uk); and Katedra Botaniky (botany.natur.cuni.cz/algo/caup-media.html).

The culture methods can optionally include inducing expression of one or more genes for the production of a product, such a but not limited to a protein that participates in the production of a lipid, one or more proteins, antioxidants, or pigments, and/or regulating a metabolic pathway in the alga. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present disclosure, the algae with attenuated VCP expression or attenuated FCP expression and increased biomass productivity can be cultured in a photobioreactor equipped with an artificial light source, and/or having one or more walls that is transparent enough to light, including sunlight, to enable, facilitate, and/or maintain acceptable alga growth and proliferation. For production of fatty acid products or triglycerides, photosynthetic algae or host cells can additionally or alternately be cultured in shake flasks, test tubes, vials, microtiter dishes, petri dishes, or the like, or combinations thereof.

Additionally or alternately, recombinant photosynthetic alga or host cells may be grown in ponds, canals, sea-based growth containers, trenches, raceways, channels, or the like, or combinations thereof. In such systems, the temperature may be unregulated, or various heating or cooling method or devices may be employed. As with standard bioreactors, a source of inorganic carbon (such as, but not limited to, CO2, bicarbonate, carbonate salts, and the like), including, but not limited to, air, CO2-enriched air, flue gas, or the like, or combinations thereof, can be supplied to the culture. When supplying flue gas and/or other sources of inorganic that may contain CO in addition to CO2, it may be necessary to pre-treat such sources such that the CO level introduced into the (photo) bioreactor does not constitute a dangerous and/or lethal dose with respect to the growth, proliferation, and/or survival of the algae.

The algal VCP mutants or FCP mutants can include one or more non-native genes encoding a polypeptide for the production of a product, such as, but limited to, a lipid, a colorant or pigment, an antioxidant, a vitamin, a nucleotide, an nucleic acid, an amino acid, a hormone, a cytokine, a peptide, a protein, a polymer, or combinations thereof. For example, the encoded polypeptide can be an enzyme, metabolic regulator, cofactor, carrier protein, transporter, or combinations thereof.

The methods include culturing a VCP mutant or FCP mutant that includes at least one non-native gene encoding a polypeptide that participates in the production of a product, to produce biomass or at least one algal product. Products such as lipids and proteins can be recovered from culture by recovery means known to those of ordinary skill in the art, such as by whole culture extraction, for example, using organic solvents. In some cases, recovery of fatty acid products can be enhanced by homogenization of the cells. For example, lipids such as fatty acids, fatty acid derivatives, and/or triglycerides can be isolated from algae by extraction of the algae with a solvent at elevated temperature and/or pressure, as described in the co-pending, commonly-assigned U.S. patent application Ser. No. 13/407,817 entitled “Solvent Extraction of Products from Algae”, filed on Feb. 29, 2012, which is incorporated herein by reference in its entirety.

Biomass can be harvested, for example, by centrifugation or filtering. The biomass may be dried and/or frozen. Further products may be isolated from biomass, such as, for example, lipids or one or more proteins.

Also included in the disclosure is an algal biomass comprising biomass of an algal VCP mutant or FCP mutant, such as any disclosed herein, for example, an algal VCP or FCP mutant that includes a mutation in a gene encoding a polypeptide having at least 40% identity to SEQ ID NO:1, SEQ ID NO:2. Also included in the disclosure is an algal biomass comprising biomass of an algal VCP or FCP mutant, such as any disclosed herein, for example, an algal VCP or FCP mutant wherein expression of a gene encoding a polypeptide having at least 40% identity to SEQ ID NO:1, SEQ ID NO:2, or SEQ ID NO:3 has been attenuated by a mutation, RNAi, or any other method disclosed herein or that is well known in the field to result in gene attenuation. Further included is an algal product produced by a VCP mutant or an FCP mutant, such as any disclosed herein, including an algal VCP or FCP mutant that includes a mutation in a gene or attenuation of the expression of a gene encoding a polypeptide having at least 40% identity to SEQ ID NO:1, SEQ ID NO:2.

Additional Embodiments

Alternatively or in addition to any of the forgoing embodiments, the disclosure provides the following embodiments:

Embodiment 1 is a recombinant or classically-mutagenized mutant alga that has attenuated expression of at least one VCP or FCP gene and produces at least 5%, at least 10%, at least 12%, or at least 13% more biomass than is produced by a control alga cultured under substantially identical conditions in which the control alga accumulates biomass, optionally wherein any one or more of the following are fulfilled:

(a) the control alga is a wild type alga;

(b) the mutant alga produces at least 5%, at least 10%, at least 12%, at least 13%, at least 15%, at least 20%, at least 22%, or at least 100%, as much biomass as the control cell, which can be average biomass (e.g., TOC) productivity per day, during a culture period of at least three, at least four, at least five, at least six, at least seven, at least eight, at least nine, at least ten, at least eleven, at least twelve, at least thirteen days, at least fourteen, at least fifteen, at least twenty, at least thirty, or at least sixty days; optionally wherein the culture conditions are under constant light or under a diel cycle, optionally wherein the light period of the diel cycle uses natural sunlight or artificial light of varying intensity to mimic natural sunlight to the culture; and (c) the alga is a heterokont alga, for example a diatom or eustigmatophyte.

Embodiment 2 is a recombinant or classically-mutagenized mutant alga according to embodiment 1 in which the mutant has attenuated expression of at least one violaxanthin chlorophyll a binding protein (VCP) gene or fucoxanthin chlorophyll a/c binding protein (FCP) gene, wherein the VCP or FCP gene encodes a polypeptide having a PLN00120 domain and a PF00504 domain; optionally wherein the VCP or FCP gene encodes a polypeptide having at least 50%, at least 55%, at least 60%, at least 65%, at least 70%, at least 75%, at least 80%, at least 85%, at least 90%, at least 95%, at least 96%, at least 97%, at least 98%, or at least 99% to SEQ ID NO:1, SEQ ID NO:2, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or combinations thereof.

Embodiment 3 is a recombinant or classically-mutagenized mutant alga according to embodiment 1 or embodiment 2, wherein the mutant is a classically-derived mutant or an engineered mutant, optionally wherein the mutant is an engineered mutants that:

(a) has a disrupted VCP or FCP gene, optionally wherein the VCP or FCP gene is disrupted in a noncoding region;

(b) is deleted in all or a portion of a VCP or FCP gene;

(c) includes an antisense construct, an RNAi construct, or a ribozyme construct that targets a VCP or FCP gene;

(d) includes an insertion in a VCP or FCP gene, optionally wherein the insertion is generated by CRISPR/cas genome editing; and/or (e) includes a mutation in a VCP or FCP gene generated by CRISPR/cas genome editing.

Embodiment 4 is a mutant alga according to any of embodiments 1-3, wherein: the mutant expression of the VCP or FCP gene is reduced by at least 50%, at least 65%, at least 80%, at least 90%, at least 95%, or to undetectable levels.

Embodiment 5 is a mutant alga according to any of embodiments 1-4, wherein:

(a) the culture conditions under which the mutant alga produces more biomass than a control cell is batch, semi-continuous, or continuous culture; and/or (b) the daily biomass productivity of the mutant alga is greater than the daily biomass productivity of the control alga throughout the culture period; and/or (c) the culture is under a diel cycle, optionally where the mutant alga and control alga are exposed to light of varying intensity during the course of the light period of the diel cycle, optionally wherein the light of varying intensity is natural sunlight or artificial light programmed to simulate natural sunlight.

Embodiment 6 is a mutant alga according to any of embodiments 1-5 in which the mutant alga comprises a mutation in a non-coding region of a gene that encodes a VCP or FCP, optionally wherein the mutation is an insertion.

Embodiment 7 is a mutant alga according to any of embodiments 1-6 in which the mutant alga comprises a construct that reduces expression of at least one VCP or FCP gene, wherein the construct encodes an RNAi, antisense transcript, or ribozyme.

Embodiment 8 is a mutant alga according to any of embodiments 1-7, wherein the expression of at least one VCP or FCP gene is:

(a) less than 50%, less than 45%, less than 40%, less than 35%, less than 30%, less than 25%, less than 20%, less than 15%, less than 10%, less than 5%, or less than 3%, of the expression level of the VCP or FCP gene in a control strain; and/or (b) undetectable or not significantly above the background of VCP or FCP transcript levels in a control strain.

Embodiment 9 is a mutant alga according to any of embodiments 1-8, wherein the mutant alga is a heterokont species, (a) optionally wherein the mutant alga is a species belonging to any of the genera *Amphiprora, Amphora, Chaetoceros, Cyclotella, Eustigmatos, Fragilaria, Fragilaropsis, Hantzschia, Monodus, Nannochloropsis, Navicula, Nitzschia, Phaeodactylum, Pseudostaurastrum, Vischeria, Phaeodactylum, Skeletonema*, or *Thalassiosira;*

(b) optionally wherein the mutant alga is a species belonging to any of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Pari-*

*etochloris, Pascheria, Pavlova, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, or *Volvox*; or wherein the mutant alga is an Eustigmatophyte algal species, and/or (c) optionally a species belonging to any of the genera *Chloridella, Chlorobptrys, Ellipsoidion, Eustigmatos, Goniochloris, Monodopsis, Monodus, Nannochloropsis, Pseudocharaciopsis, Pseudostaruastrum, Pseudotetraedriella*, or *Vischeria.*

Embodiment 10 is biomass comprising any of the mutant alga of any of embodiments 1-9.

Embodiment 11 is a nucleic acid molecule construct for attenuating expression of a gene encoding a polypeptide according to any of embodiments 1-10 having at least 60%, at least 65%, at least 70%, or at least 75%, at least 80%, at least 85%, at least 90%, or at least 95% identity to SEQ ID NO:1, SEQ ID NO:2, SEQ ID NO:3, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or combinations thereof; and a sequence encoding a guide RNA of a CRISPR system, an RNAi construct, an antisense construct, a ribozyme construct, or a construct for homologous recombination, e.g., a construct having one or more nucleotide sequences having homology to a naturally-occurring VCP or FCP gene as disclosed herein and/or sequences adjacent thereto in the native genome from which the gene is derived.

Embodiment 12 is method of engineering a cell for increased biomass production comprising attenuating expression of a gene encoding a polypeptide having at least 60%, at least 65%, at least 70%, or at least 75%, at least 80%, at least 85%, at least 90%, or at least 95% identity to SEQ ID NO:1, SEQ ID NO:2, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or combinations thereof, and/or optionally attenuating and/or disrupting a gene having a coding sequence with at least 50%, at least 55%, at least 60%, at least 65%, at least 70%, or at least 75%, at least 80%, at least 85%, at least 90%, or at least 95% identity to SEQ ID NO:4, SEQ ID NO:3, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, or combinations thereof, in a alga to produce a mutant alga having higher lipid productivity than the progenitor alga, optionally wherein attenuating expression of the gene comprises introducing a nucleic acid molecule according to embodiment 11 into the alga.

Embodiment 13 is method for producing biomass comprising culturing a mutant alga according to any of embodiments 1-10 to produce biomass, optionally including recovering biomass from the culture, optionally wherein any one or more of the following are satisfied:

(a) the culture is photoautotrophic;

(b) the culture period is at least 5, 7, 8, 9, 10, 11, 12, 13 days, or at least 15, 20, 30, 40, 50, or 60 days;

(c) the mutant alga produces at least 10% more biomass than a control alga during the culture period; and (d) the mutant alga accumulates biomass on each day of the culture period, and preferably the mutant alga accumulates more biomass than the control alga each day of at least 5, 7, 8, 9, 10, 11, 12, 13 days, or at least 15, 20, 30, 40, 50, or 60 days of the culture period.

Embodiment 14 is method for producing a bioproduct comprising culturing a mutant alga according to any of embodiments 1-10 to produce a bioproduct, optionally including recovering a bioproduct from the culture, optionally wherein any one or more of the following are satisfied:

(a) the culture is photoautotrophic;

(b) the culture period is at least 5, 7, 8, 9, 10, 11, 12, 13 days, or at least 15, 20, 30, 40, 50, or 60 days;

(c) the mutant alga produces at least 10% or at least 20% more of the bioproduct than a control alga during the culture period; and (d) the mutant alga produces biomass on each day of the culture period, and preferably the mutant alga produces more biomass than the control alga each day of at least 5, 7, 8, 9, 10, 11, 12, 13 days, or at least 15, 20, 30, 40, 50, or 60 days of the culture period.

EXAMPLES

The following examples are illustrative, and do not limit this disclosure in any way. Although methods and materials similar or equivalent to those described herein can be used in practice or testing of the present disclosure, suitable methods and materials are described below. The materials, methods and examples are illustrative only and are not intended to be limiting. Other features and advantages of the disclosure will be apparent from the detailed description and from the claims.

Media

PM074 is a nitrogen replete medium that includes nitrate as the sole nitrogen source and is 10×F/2 made by adding 1.3 ml PROLINE® F/2 Algae Feed Part A (Aquatic Eco-Systems) and 1.3 ml PROLINE® F/2 Algae Feed Part B (Aquatic Eco-Systems) to a final volume of 1 liter of a solution of Instant Ocean salts (35 g/L) (Aquatic Eco Systems, Apopka, Fla.). Proline A and Proline B together include 8.8 mM NaNO3, 0.361 mM NaH2PO4.H2O, 10×F/2 Trace metals, and 10×F/2 Vitamins (Guillard (1975) Culture of phytoplankton for feeding marine invertebrates. in "Culture of Marine Invertebrate Animals." (eds: Smith W. L. and Chanley M. H.) Plenum Press, New York, USA. pp 26-60).

PM124 medium is PM074 supplemented with 5 mM ammonium and 10 mM HEPES pH 8.0. It is made by adding 10 mls of 1 M HEPES pH 8 and 5 mls of NH4Cl to the PM074 recipe (final volume of 1 L). In some examples, additional media with controlled ammonium levels was made by adjusting the ammonium concentration of PM074 and adding additional Hepes buffer.

PM128 medium includes ammonium as the sole nitrogen source, and PM129 includes nitrate as the nitrogen source.

Example 1. Transcriptomics of High and Low Light Acclimated Wild Type *Nannochloropsis*

Commonly-owned US Patent Application Publication US 2014/0220638 (incorporated by reference) described the isolation of algal mutants LAR1, LAR2, and LAR3 having a Locked-In High Light Acclimated (LIHLA) phenotype. To explore the roles of individual proteins whose differential expression in LAR mutants might contribute to the LIHLA phenotype, the results of transcriptomics experiments that included RNA isolated from wild type (WT-3730) cells and the LAR1 mutant were analyzed.

As described in US 2014/0220638, a range of high light intensities were tested to determine the appropriate level of high light irradiance to obtain a sustained high light acclimated state in WT-3730 within the cell density range of 96 hours of logistic growth and to test the capacity of this strain to adapt to high irradiance. A light intensity of 500 μmol photons·m-2·s-1 PAR was selected because 1) this was the highest maximum irradiance the wild type cells could be cultured without stress-induced clumping at the desired starting cell density of 2×106 cells/ml, while still maintaining high-light acclimation at the final cell density following 96 h of logistic growth; and both 2) the highest maximum oxygen evolution rates per unit chlorophyll (Pmax), and 3) the greatest difference in the amount of chlorophyll per cell (Chl/cell) (from the 50 μmol photons·m-2·sec-1 PAR low light control) were determined at this intensity. Both Pmax and Chl/cell are widely accepted indicators of photosynthetic acclimation to changes in light intensity. In wild-type cells, an approximately 2-fold increase in Pmax was induced, while the amount of chlorophyll per cell (Chl/cell) decreased 2-3 fold over the course of 48 h after shifting from low to high light. These changes were consistently reproduced when *Nannochloropsis* cells were shifted from low to high light.

The WT-3730 transcriptomics-scale low to high light and high to low light shift experiments were repeated 3 times to generate biological triplicates for four time points during acclimation to high light and low light. Cultures were acclimated to high light for 48 h before the light shift. Cultures were grown in 100 mL volumes starting at approximately 2×106 cells/mL and grown to approximately 1×107 cells/mL at the time of the shift. Cells were grown axenically in Corning low profile 100 cm2 tissue culture flasks (Part#3816), sealed with previously-autoclaved rubber stoppers penetrated by red PTFE tubing 1/16" ID×1/8" OD (Cole-Parmer part #EW-96130-02) and mixed via bubbling with 0.2 μM-filtered 1% $CO_2$: air mixtures at a rate of 15 mL/min (+/−3 mL/min). For each experiment, 40 ml culture samples were pelleted and immediately frozen in liquid nitrogen at 4 time points (0 h ($T_0$), 4 h, 24 h, and 48 h). The reproducibility of a desired response to the high light and low light conditions was again validated in this experiment: $O_2$ evolution was enhanced in the high light adapted flasks, and a 2-3 fold decrease in Chl/cell was observed at 24 and 48 h post high light shift. These changes were fully reversible during the high to low light shift.

Chlorophyll content, photosynthetic rate ($P_{max}$) and Dual PAM chlorophyll fluorescence parameters (e.g., qP) were also monitored to show that physiologically successful acclimation took place. RNA was extracted from sacrificial samples removed at various time points during the light shift and submitted for genome-wide deep sequencing using HiSeq.

RNA was extracted from low and high light-adapted samples harvested at 0, 4, 24, and 48 h after the light shift from all experiments. Final RNA quality was determined by Agilent Bioanalyzer 2100 analysis. All samples had RNA integrity numbers greater than 7, with most between 8 and 9. At least 10 μg of RNA from each sample was sent to Ambry Genetics (San Diego, Calif.) for transcript sequencing. In addition to sequencing of polyA RNA, 16 of the 24 samples were also treated by RiboZero™ rRNA (Plant Leaf Kit) depletion of rRNA for total RNA sequencing. RiboZero-treated total RNA sequencing allowed for quantitation of chloroplast encoded transcripts not captured by polyA sequencing of RNA. Analysis of Ribo-Zero treated versus polyA RNA purified samples revealed similar patterns of nuclear-encoded gene transcripts, though RiboZero-treated samples allowed for additional analysis of chloroplast and mitochondrial gene transcription.

Example 2. Transcriptomics for Analysis of Genes Regulated by LAR1

In further transcriptomics experiments, the LIHLA LAR1 mutant GE5440 was grown in high light (500 μE·m-2·s-1) prior to either shifting to low light (50 μE·m-2·s-1) and culturing for two additional days, or, as a control, maintaining the high light acclimated cells in high light for an additional two days. Wild type *N. gaditana* cells were subjected to exactly the same regimen: either acclimated to high light prior to shifting to low light and culturing for two days, or maintained continuously in high light. As detailed in Example 11 of US 2014/0220638, incorporated herein by reference, the amount of chlorophyll per cell over the time course of these light shift experiments, where the high light acclimated wild type cells increased their chlorophyll content approximately two-fold over the two day period following a shift from high to low light, but decreased their chlorophyll slightly when, instead of being shifted to low light, they were maintained under high light for the additional two days. In contrast, the LAR1 mutant increased its chlorophyll only slightly over the two day period following a shift from high to low light, resulting in a chlorophyll level that was essentially the same as the chlorophyll level of wild type cells maintained in high light, consistent with the "Locked in High Light Acclimation" phenotype. Control LAR1 mutant cells that remained in high light during the experiment, maintained their low level of chlorophyll, similar to wild type.

RNA was extracted at the 0, 4 h, 24 h, and 48 h timepoints, where the 0 h timepoint was the time at which cells were shifted from high to low light and analyzed as provided in US 2014/0220638 (Example 9).

Briefly, RNA samples were depleted of rRNA by two independent methods. Samples were split into two aliquots and either polyA purified or treated using the RiboZero™ Magnetic Kit (Plant Leaf) after which both were fragmented and sequenced by Ambry Genetics (Aliso Viejo, Calif.). mRNA was sequenced using sequencing-by-synthesis (Illumina HiSeq) to generate 100 bp paired-end reads using the mRNA-Seq procedure (described in Mortazavi et al. (2008) *Nature Methods* 5:621-628. Mappable reads were aligned to the *N. gaditana* reference genome sequence using TopHat (tophat.cbcb.umd.edu/), and expression levels were computed for every annotated gene normalized for gene length and total number of mappable reads per sample using the Cuffdiff component of the Cufflinks software (cufflinks.cbcb.umd.edu). Expression levels in units of fragments per kilobase per million (FPKM) were reported for every gene in each sample using standard parameters. FPKM is a measure of relative transcriptional levels that normalizes for differences in transcript length.

Global analysis of the transcripts with significant differences (FDR less than or equal to 0.05) in their expression levels between the LAR1 mutant and wild type progenitor strain WT-3730 under the same low light conditions, demonstrated the pattern of differential expression of these genes. The edgeR software package was used to test genes for differential expression between the two strains, see Robinson et al. (2009) Bioinformatics 26: 139-140. RNA-seq was used to analyze the global transcriptional response under steady-state high light (500 μE·m-2·s-1) or the high light (500 μE·m-2·s-1) to low light (50 μE·m-2·s-1) shift conditions for the wild type and LAR1 mutant.

The light harvesting protein genes, including the VCP (annotated as FCP genes), were found to be in the TRAC I group of genes whose expression was regulated differently in the LAR1 mutant as compared with wild-type. In particular, the VCP genes, VCP1 (SEQ ID NO:5), VCP2a (SEQ ID NO:6), and VCP2b (SEQ ID NO:7), were found to be downregulated in the high light acclimation state compared to low light acclimation state, and downregulated in the LAR1 mutant in low light as compared with the wild type expression level in low light. While the precise function of these proteins and mechanism of their interaction with other components of the photosystem super-complexes are unknown, they are believed to function in the binding of auxiliary light harvesting antenna components, including violaxanthin and chlorophyll.

Example 3. Attenuation of VCP Genes in *Nannochloropsis gaditana*

In an effort to decrease the expression of VCP genes in *Nannochloropsis*, the native expression of these genes was attenuated using an RNA interference (RNAi) construct designed to simultaneously target all of the known VCP gene paralogs. When this experiment was designed, three VCP genes (VCP1, VCP2a, and VCP2b) had been identified. Subsequently, a fourth VCP gene, referred to herein as VCP2c, was found to reside proximal to VCP2a and VCP2b on chromosome 6. The sequence of the VCP2c gene is identical to that of the VCP2b gene (SEQ ID NO:7). The *Nannochloropsis gaditana* VCP2 genes, VCP2a (SEQ ID NO:6), VCP2b (SEQ ID NO:7), and VCP2c (SEQ ID NO:7), encode identical polypeptides (SEQ ID NO:2) and have coding sequences that are 100% identical (SEQ ID NO:4). The VCP1 gene (SEQ ID NO:5) is very highly homologous to the VCP2 genes (SEQ ID NOs:6 and 7), having an additional 21 nucleotide sequence at the 5' end (encoding additional amino acids at the N-terminus of this VCP) and only four additional nucleotide differences in the transcript with respect to the VCP2 coding region sequences. (The amino acid sequences of the VCP2 polypeptides (SEQ ID NO:2) are 100% identical to one another, while the VCP1 polypeptide (SEQ ID NO:1) sequence has four amino acid changes and an addition of seven amino acids at the N-terminus with respect to the VCP2 polypeptide sequence.) The highly homologous coding region of the VCP transcripts was used to design an RNAi construct designed to attenuate expression of all three *N. gaditana* VCP genes, and also targeted the fourth, later discovered, VCP2c gene. The homologous region (SEQ ID NO:69) was PCR amplified and cloned into a plasmid in direct and inverse orientation downstream of the EIF3 promoter (SEQ ID NO:8) to generate a final hairpin-forming construct (pSGE-5759, SEQ ID NO:70) for the heterologous expression of a transcript that targeted all four of the *N. gaditana* VCP transcripts.

Both *N. gaditana* wild type strain WT-3730 and LAR1 mutant strain NE-5282 (see US2014/0220638, incorporated herein by reference in its entirety) were transformed with the RNAi construct designed to knock down expression of all four VCP genes (SEQ ID NO:70) that included the "blast" gene (SEQ ID NO:62) as a selectable marker under the control of the TCTP promoter (SEQ ID NO:63) by electroporation essentially as described in U.S. Patent Application Publication US2014/0220638. As described in detail in US2014/0220638, LAR1 mutants are "locked-in high light acclimated" strains that are unable to acclimate to low light. Transformants surviving blasticidin selection were re-streaked, and then transferred to liquid culture for serial acclimation to low light conditions. Following low light acclimation, a Dual PAM fluorimeter (Walz, Effeltrich, Germany) was also used to measure electron transport rate (ETR) and Non-photochemical quenching (NPQ), over a range of light intensities according to the manufacturer's protocol.

Figure 1B:
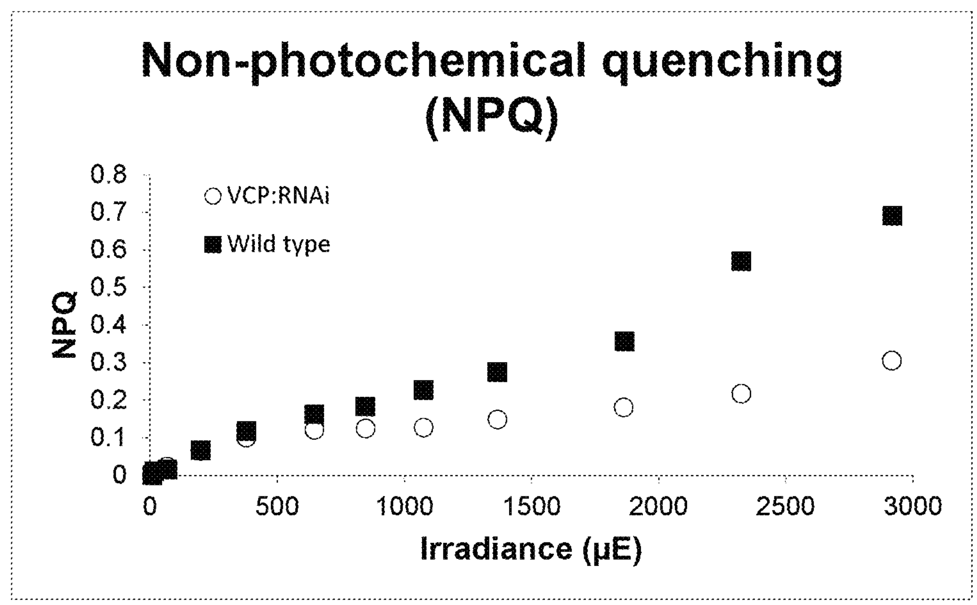
Figure 1C:
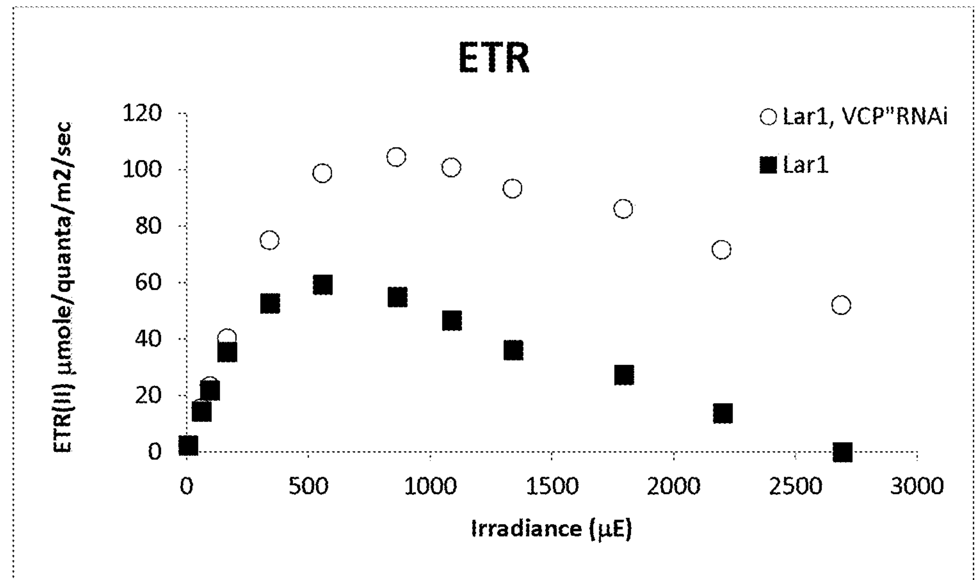
Figure 1D:
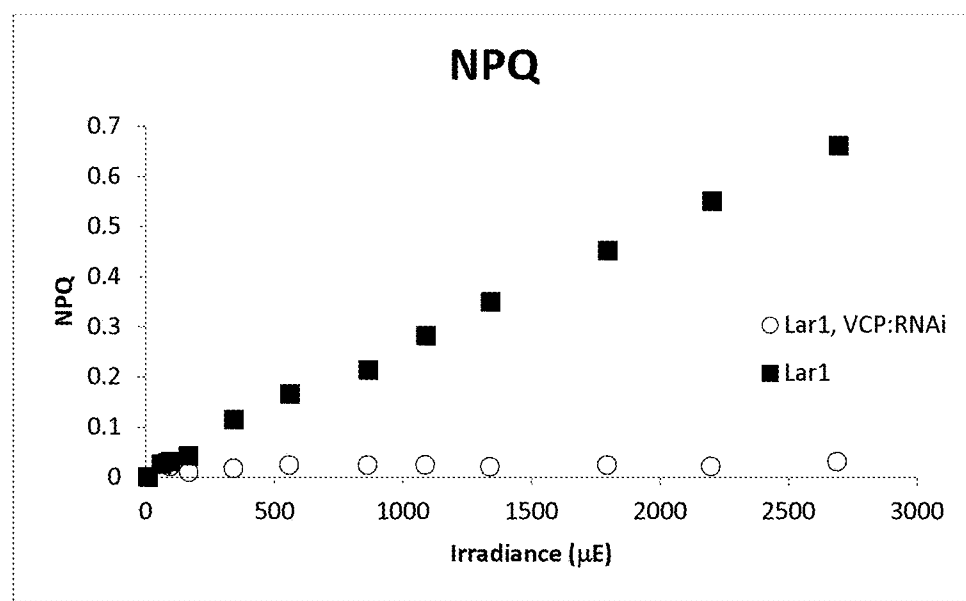

A total of 22 transformants were identified as having different photophysiological phenotypes than the respective parental strain (either wild type WT-3730 or LAR1 mutant NE-5282). As shown in FIGS. 1A-B, in which data for one representative transformant is shown, transformants having a wild type background showed increased electron transport rate (ETR) (FIG. 1A) and decreased non-photochemical quenching (NPQ) (FIG. 1B). The effect of the transgenic expression of the VCP RNAi construct in the LAR1 NE-5282 mutant background was similar but more severe (FIGS. 1C and 1D), demonstrating greater increase of ETR (II) (FIG. 1C) with respect to the parental LAR1 NE-5282 strain, along with greatly diminished NPQ (FIG. 1D), particularly at intensities of 500 μE and above.

Example 4. Knockout of VCP Genes in *Nannochloropsis gaditana*

To test the effects of reducing expression of the VCP genes individually, two guide RNAs (gRNA) were designed to target two different sequences (protospacers) (SEQ ID NO:16, and SEQ ID NO:17) found within the VCP genes in *N. gaditana* using the Cas9/CRISPR system. Because the genes have a high degree of homology, the target sequences were identical in all four VCP genes. The gRNA and a linearized hygromycin selection marker cassette (SEQ ID NO:15) were transformed into a Cas9-enabled *N. gaditana* strain GE-6791 using CRISPR technology using methods described in co-pending United States patent application U.S. Ser. No. 14/986,492 filed Dec. 31, 2015 and corresponding PCT application PCT/US15/068356, publication number WO 2016/109840, incorporated herein by reference. As described in U.S. Ser. No. 14/986,49 and WO 2016/109840, a highly efficient *Nannochloropsis* Cas9 Editor line, *N. gaditana* strain GE-6791, expressing a gene encoding the *Streptococcus pyogenes* Cas9 nuclease, was used as a host for transformation with a chimeric guide RNA and donor DNA for insertional knockout.

To produce the high efficiency *Nannochloropsis* Cas9 Editor line, a *Nannochloropsis* strain was engineered and isolated that exhibited expression of the introduced Cas9 gene in close to 100% of the cell population of a growing culture. The vector used to transform wild type *N. gaditana* strain WT-3730 included the following three elements: 1) a Cas9 expression cassette which contained a Cas9 gene from *Streptococcus pyogenes* codon optimized for *Nannochloropsis gaditana* (SEQ ID NO:56) with sequences encoding an N-terminal FLAG tag (SEQ ID NO:57), nuclear localization signal (SEQ ID NO:58), and peptide linker (SEQ ID NO:59), driven by the *N. gaditana* RPL24 promoter (SEQ ID NO:60) and terminated by *N. gaditana* bidirectional terminator 2 (SEQ ID NO:61); 2) a selectable marker expression cassette, which contained the blast gene from *Aspergillus terreus* codon optimized for *N. gaditana* (SEQ ID NO:62), driven by the *N. gaditana* TCTP promoter (SEQ ID NO:63) and followed by the EIF3 terminator (SEQ ID NO:64); and 3) a GFP reporter expression cassette, which contained the TurboGFP gene (Evrogen, Moscow, Russia)

codon optimized for *Nannochloropsis gaditana* (SEQ ID NO:65), driven by the *N. gaditana* 4A-III promoter (SEQ ID NO:66) and followed by the *N. gaditana* bidirectional terminator 5 (SEQ ID NO:67). All of these elements were combined into a single plasmid (SEQ ID NO:68) which was transformed into wildtype strain WE-3730 to generate a Cas9-enabled strain as described below. Transformation was by electroporation essentially as described in US 2014/0220638, incorporated by reference herein.

The transformation mixture was plated onto PM074 agar medium containing 100 mg/L of blasticidin. Resulting colonies were patched onto selection media for analysis and archiving. A small amount of biomass was taken from the patches and completely resuspended in 300 μl of 1× Instant Ocean Salts solution (Aquatic Eco Systems; Apopka, Fla.). Care was taken to not add too much biomass so that a light green resuspension was obtained. This suspension was directly analyzed by flow cytometry using a BD Accuri C6 flow cytometer, using a 488 nm laser and 530/10 nm filter to measure GFP fluorescence per cell. 10,000-30,000 events were recorded for each sample using the slow fluidics setting. A strain having a single fluorescence peak that was shifted to a fluorescence level higher than that demonstrated by wild-type cells and also demonstrating Cas9 protein expression by Western, designated strain GE-6791, was selected as a cas9 Editor strain and used in mutant generation by Cas9/CRISPR genome editing as described herein.

For targeting of the VCP genes for disruption, a DNA construct was made for producing a guide RNA in which the DNA molecule included the sequence of a chimeric guide engineered downstream of a T7 promoter. The chimeric guide sequence included either of the 18 bp target sequences (SEQ ID NO:16 or SEQ ID NO:17) homologous to sequence within all of the VCP genes that was upstream of an *S. pyogenes* Cas9 PAM sequence (NGG), and also included the transactivating CRISPR (tracr) sequence. The chimeric guide sequences targeting SEQ ID NO 16 or SEQ ID NO 17 were synthesized by first making a DNA template made up of complementary DNA oligonucleotides (SEQ ID NO:14 and SEQ ID NO:47, or SEQ ID NO:48 and SEQ ID NO:49, respectively) that were annealed to create a double-stranded DNA template which was used in in vitro transcription reactions using the MEGAshortscript™ T7 Kit (Life Technologies # AM1354M) according to the manufacturer's instructions to synthesize the guide RNA. The resulting RNA was purified using Zymo-Spin™ V-E columns (Zymo Research #C1024-25) according to the manufacturer's protocol.

The donor fragment (SEQ ID NO:15) for insertion into any of the three targeted VCP genes included a selectable marker cassette that included the hygromycin resistance gene (HygR) downstream of the *N. gaditana* EIF3 promoter, and followed by *N. gaditana* bidirectional terminator 2, with the entire promoter-hygromycin resistance gene-terminator sequence flanked by 27 base pair identification sequences on the 5' and 3' ends to yield the DNA fragment referred to as the "Hyg Resistance Cassette" (SEQ ID NO:15, HygR Cassette).

For targeted knockout of the VCP genes, Cas9 Editor line GE-6791 was transformed by electroporation using 5 μg of either of the purified chimeric guide RNAs targeting the respective protospacer (SEQ ID NO:16 or SEQ ID NO:17) and 1 μg of the selectable donor DNA Hyg Resistance Cassette (SEQ ID NO:15). Following electroporation, cells were plated at a concentration between 5-7×108 cells/mL on PM124 agar media containing 500 μg/mL hygromycin to select for transformants that incorporated the hygromycin resistance cassette. Plates were incubated under constant light (~80 μmol photons m-2 sec-1) until colonies appeared (about 2-3 weeks). Transformants were patched onto a fresh plate and screened by colony PCR for insertion of the donor fragment into any of the VCP genes.

For colony PCR screening, a small amount of cells from a colony to be screened was suspended into 100 μl of 5% Chelex 100 Resin (BioRad)/TE solution and the suspension was boiled for 10 minutes at 99° C., after which the tubes were briefly spun. One microliter of the lysate supernatant was added to a PCR reaction mix, in which the PCR mixture and reactions were set up and performed according to standard PCR techniques. The primers used to detect the insertion of the donor fragment and to distinguish which VCP gene was disrupted are listed in Table 1. Primers were designed to unique regions of each gene so that they could be distinguished from each other and the precise disrupted gene could be determined Although the primers were designed to detect lesions in the VCP1, VCP2a, and VCP2b genes, it was later discovered that *Nannochloropsis gaditana* has a fourth VCP gene, VCP2c. A lesion in the VCP2c gene would also be targeted by the guide RNAs based on SEQ ID NO:16 or SEQ ID NO:17 and would be detectable using same primers used to detect the donor fragment insertion into the VCP2b gene, SEQ ID NO:54 and SEQ ID NO:55 (Table 1). Strains GE-7589, GE-7587, and GE-7588 were confirmed to have a disruption in the VCP1, VCP2a, and VCP2b (and/or VCP2c) locus respectively with the insertion of the Hygromycin resistance cassette and were progressed to photophenotyping.

TABLE 1

Primers for detecting lesions in specific VCP genes

| Gene target | Primer 1 | Primer 2 |
|---|---|---|
| VCP1 | SEQ ID NO: 50 | SEQ ID NO: 51 |
| VCP2a | SEQ ID NO: 52 | SEQ ID NO: 53 |
| VCP2b, VCP2c | SEQ ID NO: 54 | SEQ ID NO: 55 |

Example 5. Physiological Assessment of Individual VCP Mutants

Chlorophyll content of mutants was determined by extracting chlorophyll from a cell pellet using a DMSO: Acetone procedure. 500 μl of culture was aliquoted into a 2 ml microcentrifuge tube and pelleted by centrifugation for 3 minutes at 12,000 rpm at room temperature. Supernatant was carefully removed and the cell pellet was resuspended in 1 ml of 1:1 DMSO:Acetone. The sample was then vortexed for 2-5 minutes at room temperature. Cell debris was pelleted by centrifugation for 3 minutes at 12,000 rpm. The supernatant absorbance was then read on a spectrophotometer blanked with a 1:1 DMSO:Acetone solution at 663 nm and 720 nm. The chlorophyll content was quantified by subtracting the 720 nm absorbance value from the 663 nm absorbance value. The resulting net absorbance value was then multiplied by the dilution factor and extinction coefficient of 20.15 to determine the μg/ml concentration or 18.01 to determine the μmol/ml concentration of chlorophyll.

Fluorescence based PSII photo-physiological parameters were used to measure electron transport rate through PSII (ETR(II)) based on apparent ETR(II) measurement from a Dual-PAM fluorometer (Walz, Effeltrich, Germany) over 12 irradiance levels. A 3 ml aliquot of cells with a cell density 1×108 cells per ml (approximately 5 mg chlorophyll per ml)

was dark adapted for five minutes, after which ETR (II) was measured on a Dual PAM fluorometer using the manufacturer's software.

Oxygen evolution was measured using a Clark-type oxygen electrode. An aliquot of cells containing 5 □g chlorophyll per ml, or 108 cells, was transferred into the oxygen electrode chamber which was illuminated with a lamp at 1500 μmol photons $m^{-2}$ $sec^{-1}$. Sodium bicarbonate (5 mM) was also added to the chamber to ensure the cells were not carbon-limited. The algal cells were exposed to increasing light intensity while oxygen concentration was continuously measured. Oxygen concentration was then plotted as a function of light intensity to provide a photosynthesis irradiance (P/I) curve demonstrating the light saturation of photosynthesis in the strains, where the light saturated rate of oxygen evolution is referred to as $P_{max}$. The $P_{max}$ value was calculated on a per mg of chlorophyll basis and on a per cell basis. Ek, the saturating irradiance for photosynthesis, was also calculated from the oxygen evolution v. light intensity curve (P/I curve) (Tailing J. (1957) *New Phytologist* 56: 29-50).

Figure 2A:
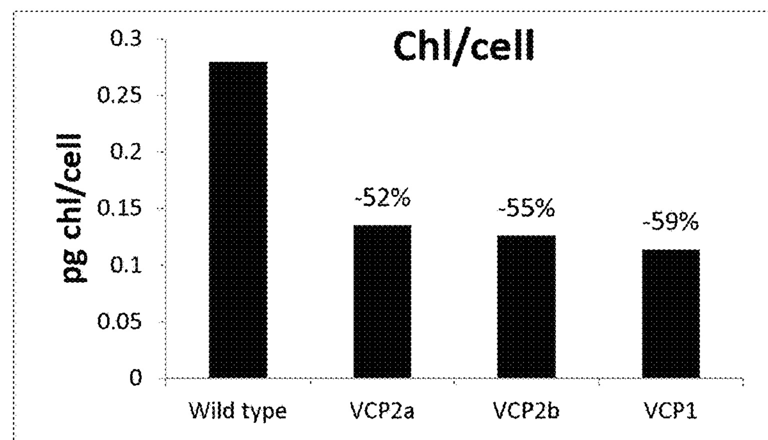
FIGS. 2A-2C. Phenotyping of single VCP knockout mutants. Graphs of (A) chlorophyll content per cell, (B) oxygen evolution Pmax per chlorophyll content, and (C) electron transport rate are displayed for wild type (WE-3730), VCP1 knockout (GE-7589), VCP2a knockout (GE-7587), and VCPb knockout (GE-7588).
Figure 2B:
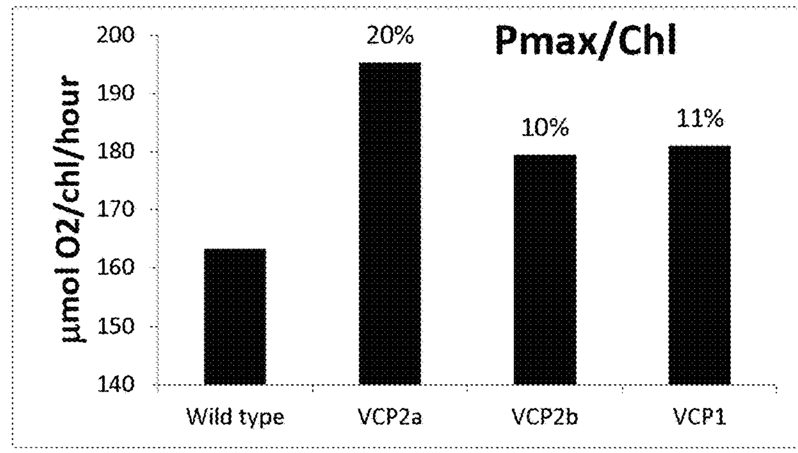

Single VCP knockout strains GE-7587, GE-7588, and GE-7589, were found to have an approximately 52%, 55%, and 59% reduction respectively in chlorophyll per cell compared to the wild type strain following low light acclimation (Table 2 and FIG. 2A). Further photo-physiological screens were implemented to verify the maintenance of balanced photosynthesis, as opposed to photosynthetic impairments that might reduce productivity. Maximal oxygen evolution per chlorophyll (Pmax) measurements were performed on low light acclimated cultures. Pmax for GE-7587, GE-7588, and GE-7589 was increased by approximately 20%, 10%, and 11% respectively on a per cell basis with respect to wild type (Table 2 and FIG. 2B).

TABLE 2

Chlorophyll content per cell and Pmax per chl

| Strain ID | Chlorophyll (pg/cell) | % change (pg/cell) | $P_{max}$/chl (μmol $O_2$ $hour^{-1}$ mg $chl^{-1}$) | % change ($P_{max}$/chl) |
|---|---|---|---|---|
| WT-3730 (WT) | 0.28 | — | 163 | — |
| GE-7587 (VCP2a KO) | 0.13 | −52% | 195 | 20% |
| GE-7588 (VCP2b KO) | 0.12 | −55% | 179 | 10% |
| GE-7589 (VCP1 KO) | 0.11 | −59% | 181 | 11% |

Figure 2C:
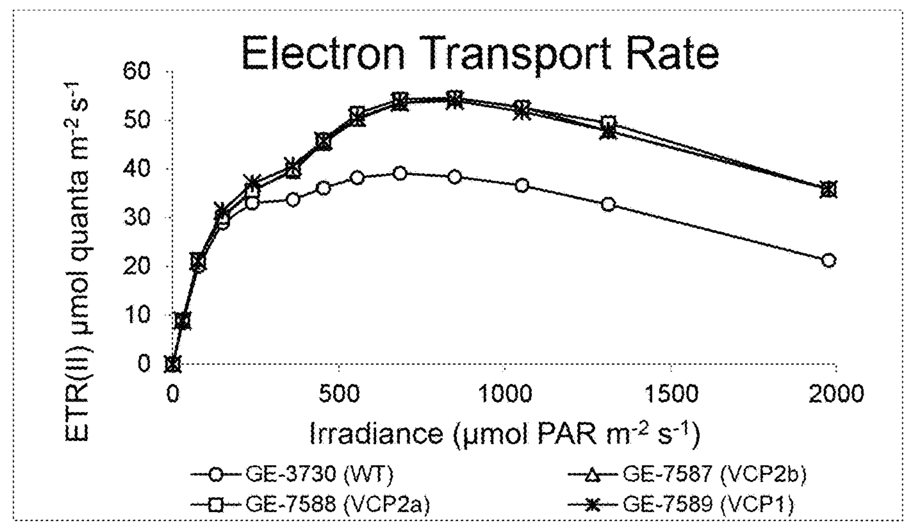

In addition to reduced chlorophyll content, these strains also demonstrated higher ETR(II) (Table 3 and FIG. 2C) than wild type strain WE-3730 at all light intensities greater than 200 μmol photons $m^{-2}$ $sec^{-1}$ that were tested. For example, the ETR(II) rate of the VCP mutants was increased by approximately 12% at 240 μE, 20% at 363 μE, 27% at 454 μE, 32% at 555 μE, 37% at 684 μE, 41% at 849 μE, 42% at 1052 μE, 46% at 1311 μE, and 69% at 1976 μE.

TABLE 3

ETR(II) rate with increasing light intensity ETR(II) μmol quanta $m^{-2}$ $s^{-1}$

| μE | WT | average single VCP knockout | percent increase |
|---|---|---|---|
| 240 | 33 | 37 | 12% |
| 363 | 33.7 | 40.6 | 20% |
| 454 | 36.1 | 45.8 | 27% |
| 555 | 38.2 | 50.5 | 32% |
| 684 | 39.1 | 53.6 | 37% |
| 849 | 38.4 | 54 | 41% |
| 1052 | 36.6 | 51.8 | 42% |
| 1311 | 32.7 | 47.8 | 46% |
| 1976 | 21.2 | 35.8 | 69% |

Example 6. Attenuation of VCP Genes in *Nannochloropsis gaditana*

To further test the effects of reducing expression of the VCP genes, the guide RNAs (gRNA) described in Example 4, (SEQ ID NO:16 and SEQ ID NO:17) found within each of the VCP genes in *N. gaditana* (SEQ ID NO:5, SEQ ID NO:6, and SEQ ID NO:7), and a linearized hygromycin selection marker cassette (SEQ ID NO:15) that further comprised an RNAi construct targeting an unrelated gene g1, were transformed into the Cas9-enabled *N. gaditana* strain GE-6791 as described in Example 4.

Following transformation and selection, colonies were screened by colony PCR as described in Example 4 using the same primers identified in Table 1. Primers were designed to unique regions of each gene so that they could be distinguished from each other and the precise disrupted gene could be determined Strain GE-9162, GE-9161, and GE-9164 were confirmed to have a disruption in the VCP1, VCP2a, and VCP2b locus respectively with insertion of the hygromycin resistance gene and gene g1 RNAi construct and were progressed to photophenotyping.

Gene sequence specific primers were used for the qRT-PCR assessment of VCP1 (SEQ ID NO:19 and SEQ ID NO:20), VCP2b and VCP2c (SEQ ID NO:21 and SEQ ID NO: 22), VCP2a (SEQ ID NO:23 and SEQ ID NO:24), and a housekeeping control gene (SEQ ID NO:25 and SEQ ID NO:26). The qRT-PCR analysis revealed that each VCP mutant had decreased transcript levels for all VCP transcripts (Table 4). This was unexpected considering that only one VCP gene was disrupted in each mutant, while the other VCP genes were left intact. The most dramatic was strain GE-9161 which was disrupted in the VCP2a gene and demonstrated less than 10% of the wild type transcript levels of VCP1 and VCP2b/VCP2c. In each of the VCP mutant strains GE-9162, GE-9161, and GE-9164, the transcript levels of g1 were approximately 50% of wild type levels. It has been observed before that a 50% reduction of g1 transcript in a wild type background results in no observable phenotype, therefore the phenotypes observed in GE-9162, GE-9161, and GE-9164 were attributable to the disruption of the respective VCP gene and not to the reduction in g1 transcript.

TABLE 4

Transcript Abundance assessed by qRT-PCR as % of wild type levels

| Strain ID | Genotype | VCP1 | VCP2a | VCP2b/ VCP2c |
|---|---|---|---|---|
| WT-3730 | WT | 100% | 100% | 100% |
| GE-9162 | VCP1: KO | KO | 21% | 10% |

TABLE 4-continued

| Transcript Abundance assessed by qRT-PCR as % of wild type levels | | | | |
|---|---|---|---|---|
| Strain ID | Genotype | VCP1 | VCP2a | VCP2b/ VCP2c |
| GE-9161 | VCP2a: KO | 2% | KO | 9% |
| GE-9164 | VCP2b: KO | 11% | 71% | KO |

Figure 3A:
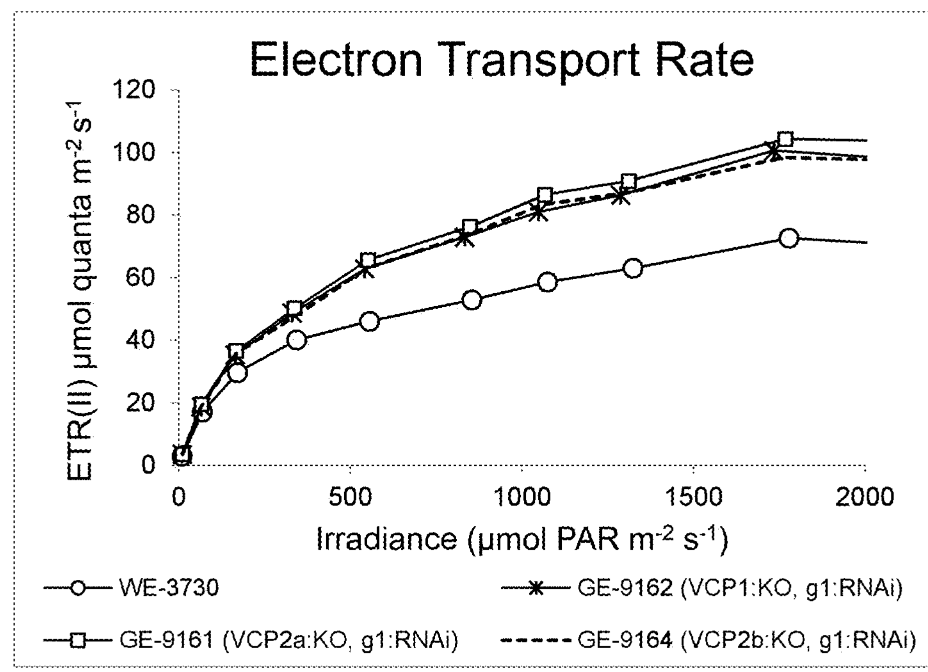
FIGS. 3A-3C. Phenotyping of single VCP knockout mutants. (A) Graph showing the electron transport rate of wild type (WT-3730) and mutant strains with individual VCP genes disrupted with g1:RNAi construct. (B) Graph showing non-photochemical quenching of VCP2a:KO,g1:RNAi strain (GE-9161) compared to wild type (WE-3730). (C) Graph of biomass (total organic carbon, TOC) on successive days of a semi-continuous culture of GE-9161 and WE-3730, wherein the light varied in intensity throughout the day to mimic natural sunlight and each point represents the TOC average of three cultures.
Figure 3B:
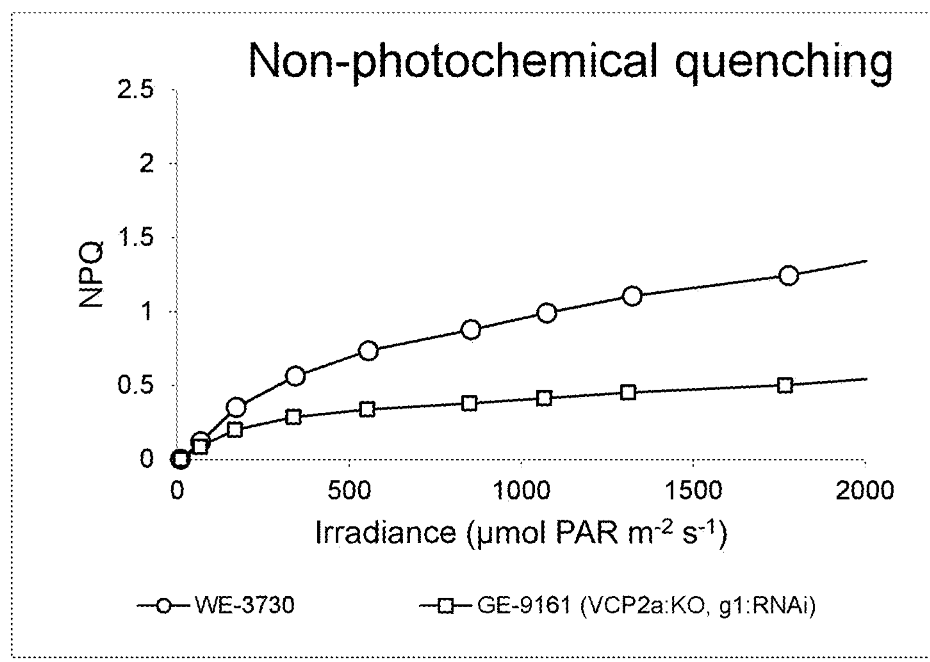

Strains GE-9162, GE-9161, and GE-9164 were all found to have increased electron transport rate (ETR) (Table 5 and FIG. 3A) compared to wild type strain WE-3730 at all light intensities greater than 200 μmol photons m-2 sec-1 that were tested. For example, the ETR(II) rate of the VCP mutant GE-9161 was increased by approximately 23% at 172 μE, 25% at 344 μE, 42% at 556 μE, 44% at 854 μE, 48% at 1074 μE, 44% at 1323 μE, 44% at 1778 μE, 48% at 2171 μE, and 44% at 2656 μE. Furthermore, NPQ was decreased in these mutants compared to wild type, as can be seen in strain GE-9161 (Table 5 and FIG. 3B). The NPQ of GE-9161 was decreased by approximately 48% at 172 μE, 45% at 344 μE, 47% at 556 μE, 46% at 854 μE, 45% at 1074 μE, 44% at 1323 μE, 43% at 1778 μE, 40% at 2171 μE, and 37% at 2656 μE compared to wild type strain WE-3730.

TABLE 5

ETR(II) rate and NPQ values of VCP-attenuated strain GE-9161

| | ETR(II) μmol quanta $m^{-2}$ $s^{-1}$ | | ETR(II) perent | NPQ | | NPQ percent |
|---|---|---|---|---|---|---|
| μE | WT | GE-9161 | increase | WT | GE-9161 | decrease |
| 10 | 3 | 4 | 20% | 0.00 | 0.00 | — |
| 69 | 17 | 20 | 15% | 0.04 | 0.02 | −44% |
| 172 | 30 | 37 | 23% | 0.15 | 0.08 | −48% |
| 344 | 40 | 50 | 25% | 0.26 | 0.14 | −45% |
| 556 | 46 | 66 | 42% | 0.34 | 0.18 | −47% |
| 854 | 53 | 76 | 44% | 0.40 | 0.22 | −46% |
| 1074 | 59 | 87 | 48% | 0.43 | 0.24 | −45% |
| 1323 | 63 | 91 | 44% | 0.47 | 0.26 | −44% |
| 1778 | 73 | 104 | 44% | 0.50 | 0.29 | −43% |
| 2171 | 70 | 104 | 48% | 0.54 | 0.32 | −40% |
| 2656 | 70 | 100 | 44% | 0.58 | 0.37 | −37% |

Figure 3C:
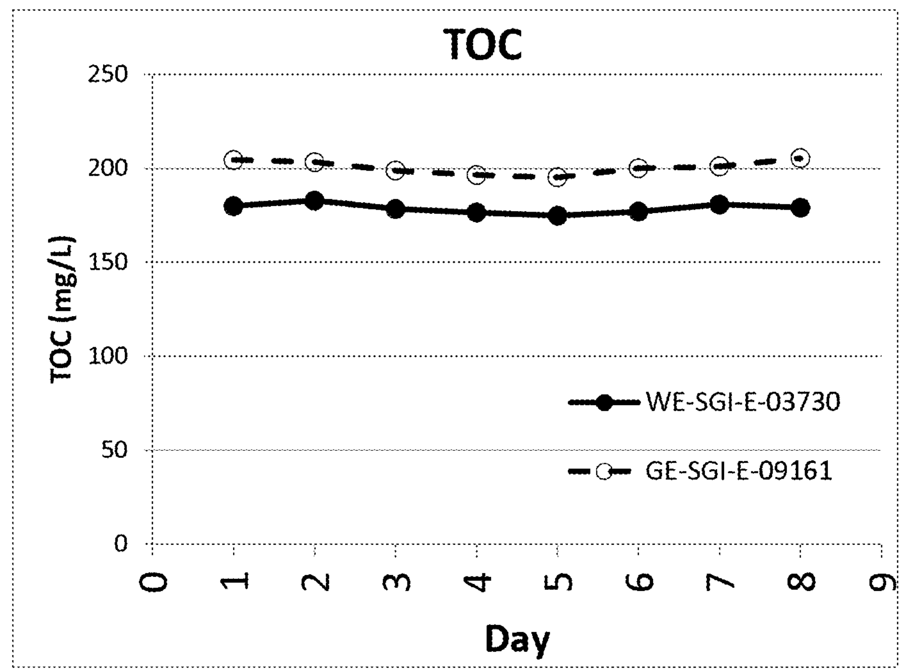

To determine the biomass productivity of GE-9161, triplicate 225 $cm^2$ flasks for each strain were inoculated with algae to provide a culture density of 0.15 OD 730 nm in a total volume of 500 mL of PM074 medium. Stir bars were added to each flask, and stoppers having a syringe filter for air/$CO_2$ delivery at a rate of 100 ml/min and a clave connector for sampling were fitted to the flasks, which were given random positions along the 16-flask rack. The stir plates beneath the rack were operated at 450 rpm. The LED light bank provided a programmed sinusoidal 13.5 light:10.5 dark diel light regime designed to steadily ramp up to a peak of 2000 $\mu E \cdot m^{-2} \cdot s^{-1}$ and back down to 0 $\mu E \cdot m^{-2} \cdot s^{-1}$ over 13.5 hours, followed by 10.5 hours of darkness. The temperature varied from 25° C. to 34° C. Cultures were diluted 30% daily to achieve semi-continuous growth and, once cultures reached a steady growth state, samples (typically 2 mLs) were removed each day over 8 days for TOC analysis. VCP mutant strain GE-9161 was found to also outperform the wild-type in TOC productivity by an average of approximately 12% (Table 6 and FIG. 3C).

TABLE 6

Semi-continuous Culture (diel) productivity of VCP-attenuated strain GE-9161

| Strain ID | Average TOC (mg/L) | % improvement |
|---|---|---|
| WT-3730 | 178 ± 2.6 | — |
| GE-9161 | 200 ± 3.7 | 12% |

Example 7. Attenuation of all VCP Genes in *Nannochloropsis gaditana*

GE-8145 was generated by designing a construct (SEQ ID NO:18) to knock out both VCP2a (SEQ ID NO:8) and VCP2b (SEQ ID NO:9). The construct, along with a gRNA targeting a sequence found within both VCP2a and VCP2b (SEQ ID NO:16), was transformed into a Cas9 enabled strain as described in Example 3. The gRNA used to generate this mutant is the same as one of the gRNAs used to generate the single VCP KO mutants described in Example 3 and was generated as described above using template oligos (SEQ ID NO:14 and SEQ ID NO:47). The transformants were plated on agar plates containing hygromycin in order to select for transformants containing the construct for insertion into the VCP locus. Isolated strains were then screened by PCR to identify strains in which VCP2a and VCP2b had been replaced by the construct. These methods were used to generate strain GE-8145, which was confirmed to be lacking VCP2a and VCP2b based on PCR results. This double knockout strain was selected for further phenotyping as described in the following examples.

Example 8. Physiological Assessment of Double VCP Knockout Mutant GE-8145

Chlorophyll content, Dual-PAM based photophysiology, and oxygen evolution Pmax of GE-8145 were determined as described in Example 5. Dual-PAM (Dual PAM fluorometer made by Walz, Effeltrich, Germany) was also used according to the manufacturer's instructions to measure the induction of non-photochemical quenching (NPQ) following low-light acclimation. NPQ measures the amount of absorbed light energy that is lost to heat dissipation instead of being used for photochemistry.

Quantitative real-time reverse transcription-PCR (qRT-PCR) was performed on RNA isolated from strains that were grown under standard nitrogen replete conditions (PM074 medium, containing nitrate as the nitrogen source) and harvested during early stationary phase. Total RNA was isolated from cells, using methods provided in Example 1, above. RNA was converted to cDNA BioRad's iScript™ Reverse Transcription Supermix kit according to the manufacturer's protocol. For PCR, Ssofast EvaGreen Supermix (Bio-Rad, Hercules, Calif.) was used along with gene-specific primers. The PCR reaction was carried out on C1000 Thermal Cycler coupled with a CFX Real-time System (BioRad). Primer and cDNA concentrations were according to the manufacturer's recommendation. Transcript levels for each sample were normalized against a housekeeping gene with consistent expression levels under different culture conditions and relative expression levels were calculated using the ddCT method using BioRad's CFX Manager software.

Figure 4A:
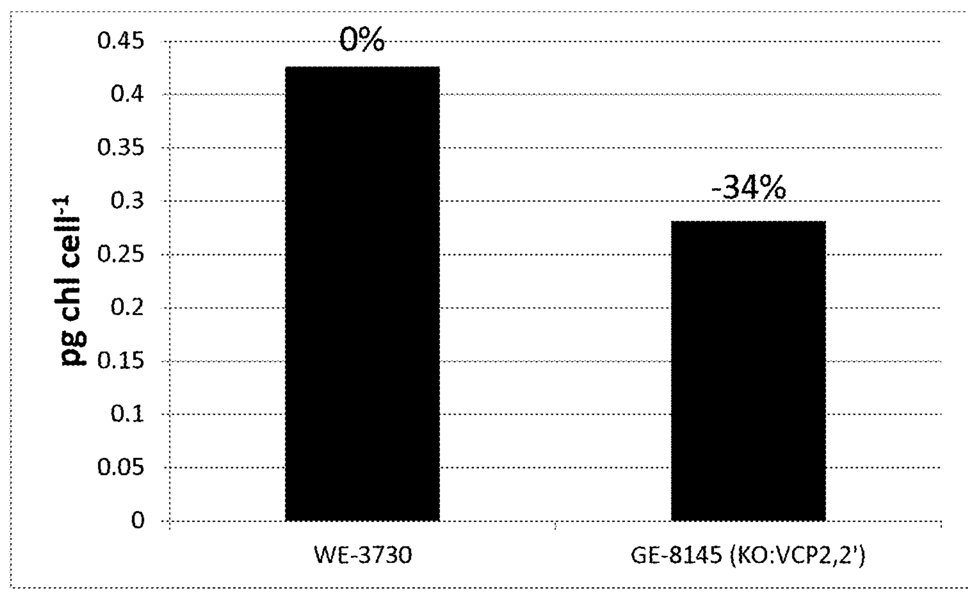
FIGS. 4A-4D. Phenotyping of VCP double knockout mutant. Graphs depicting (A) the chlorophyll content per cell, (B) chlorophyll content per biomass TOC, (C) electron transport rate, and (D) non-photochemical quenching of VCP2a:KO,VCP2b:KO strain GE-8145 compared to wild type (WT-3730).
Figure 4B:
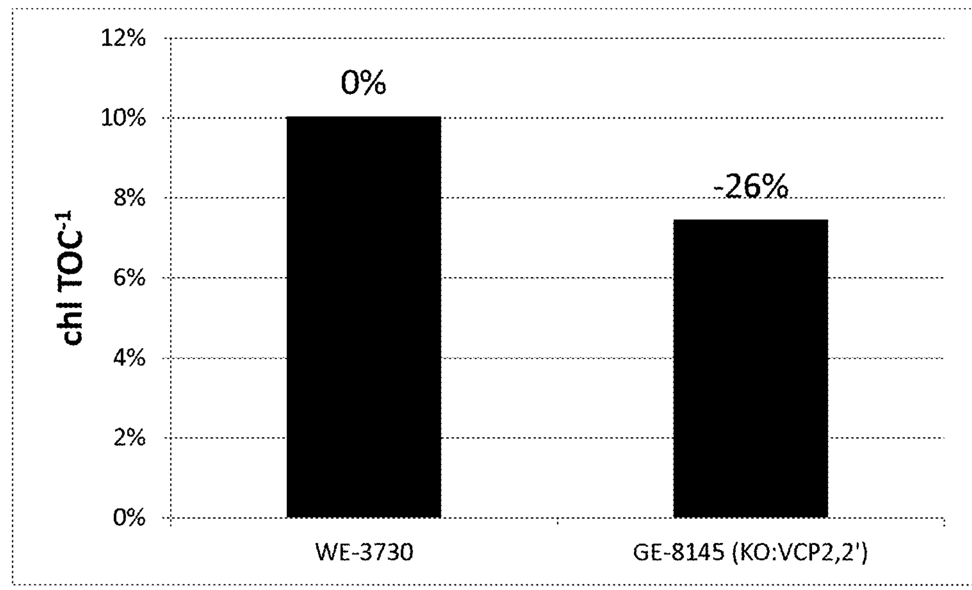

Strain GE-8145 was found to have an approximately 34% reduction in chlorophyll per cell and 26% reduction in chlorophyll per total organic carbon (TOC) content compared to wild type following low light acclimation (Table 7 and FIGS. 4A and 4B).

TABLE 7

| Chlorophyll content of Double VCP Knockout GE-8145 | | | | |
|---|---|---|---|---|
| Strain ID | Chlorophyll (pg/cell) | % change (pg/cell) | Chlorophyll (Chl/TOC) | % change (Chl/TOC) |
| WT-3730 | 0.42 | — | 10% | — |
| GE-8145 | 0.28 | −34% | 7% | −26% |

Figure 4C:
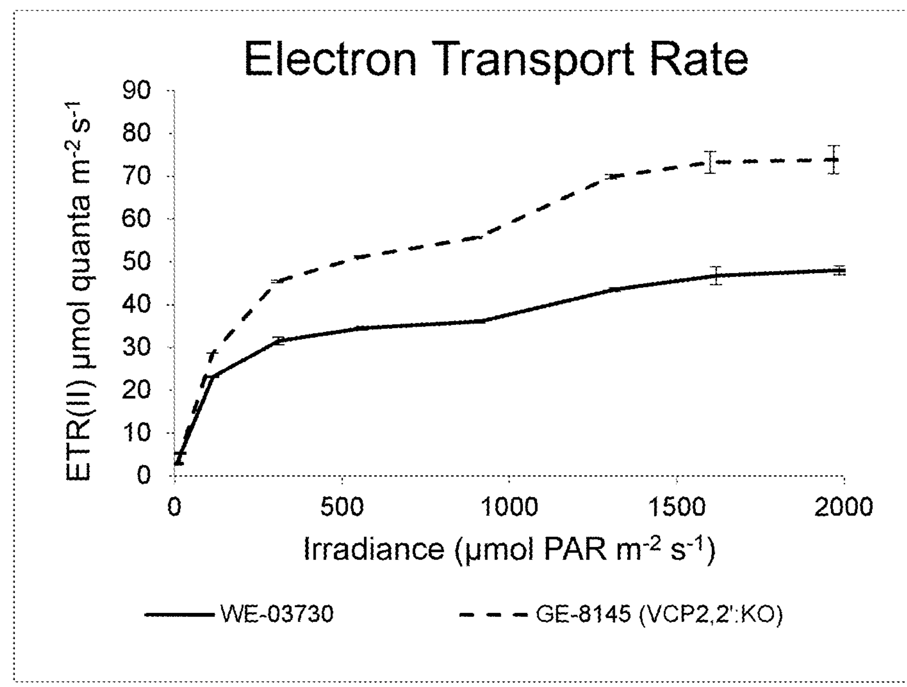
Figure 4D:
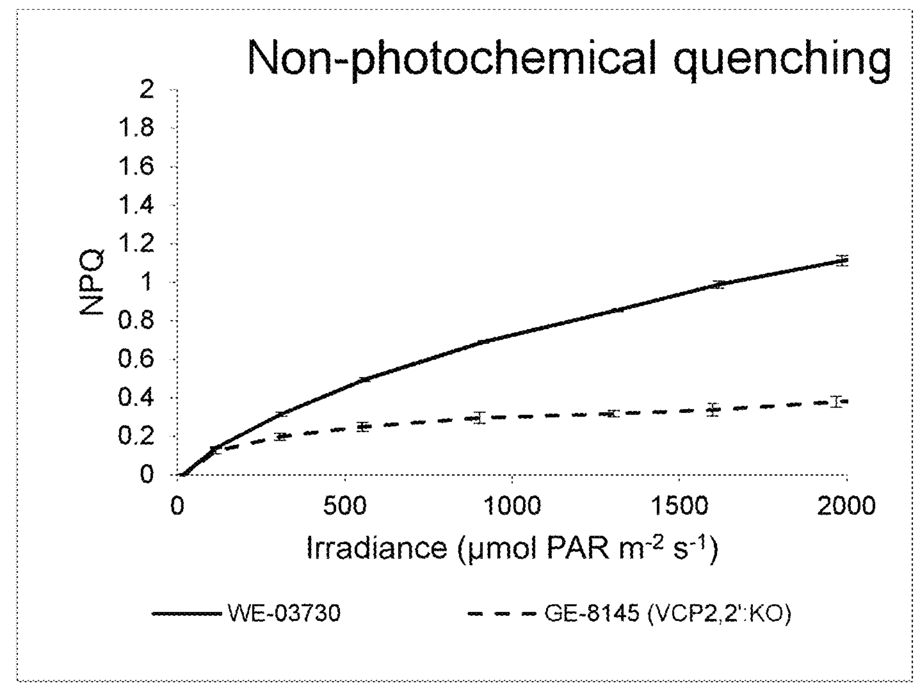

In addition to reduced chlorophyll content, this strain also demonstrated higher ETR(II) and decreased NPQ than wild type strain WE-3730 at all light intensities greater than 200 μmol photons $m^{-2}$ $sec^{-1}$ that were tested (Table 8 and FIGS. 4C and 4D). For example, the ETR(II) rate of GE-8145 was increased by approximately 44% at 310 μE, 48% at 560 μE, 54% at 913 μE, 61% at 1315 μE, 57% at 1617 μE, 54% at 1986 μE, 61% at 2462 μE, 51% at 3047 μE, and 42% at 3788 μE. Furthermore, the NPQ rate of GE-8145 was decreased by approximately 37% at 310 μE, 50% at 560 μE, 57% at 913 μE, 63% at 1315 μE, 66% at 1617 μE, 66% at 1986 μE, 66% at 2462 μE, 68% at 3047 μE, and 66% at 3788 μE.

TABLE 8

| ETR(II) rate and NPQ of Double VCP Knockout Strain GE-8145 | | | | | | |
|---|---|---|---|---|---|---|
| | ETR(II) μmol quanta $m^{-2}$ $s^{-1}$ | | ETR(II) percent | NPQ | | NPQ percent |
| μE | WT | GE-8145 | increase | WT | GE-8145 | decrease |
| 116 | 23.2 | 28.7 | 24% | 0.14 | 0.12 | −13% |
| 310 | 315 | 45.4 | 44% | 0.31 | 0.20 | −37% |
| 560 | 34.5 | 51.2 | 48% | 0.50 | 0.25 | −50% |
| 913 | 36.1 | 55.7 | 54% | 0.69 | 0.30 | −57% |
| 1315 | 43.6 | 69.9 | 61% | 0.85 | 0.32 | −63% |
| 1617 | 46.8 | 73.3 | 57% | 0.99 | 0.34 | −66% |
| 1986 | 48.1 | 73.9 | 54% | 1.11 | 0.38 | −66% |
| 2462 | 44.4 | 71.7 | 61% | 1.26 | 0.42 | −66% |
| 3047 | 42.1 | 63.6 | 51% | 1.45 | 0.47 | −68% |
| 3788 | 38.3 | 54.3 | 42% | 1.69 | 0.57 | −66% |

Figure 5A:
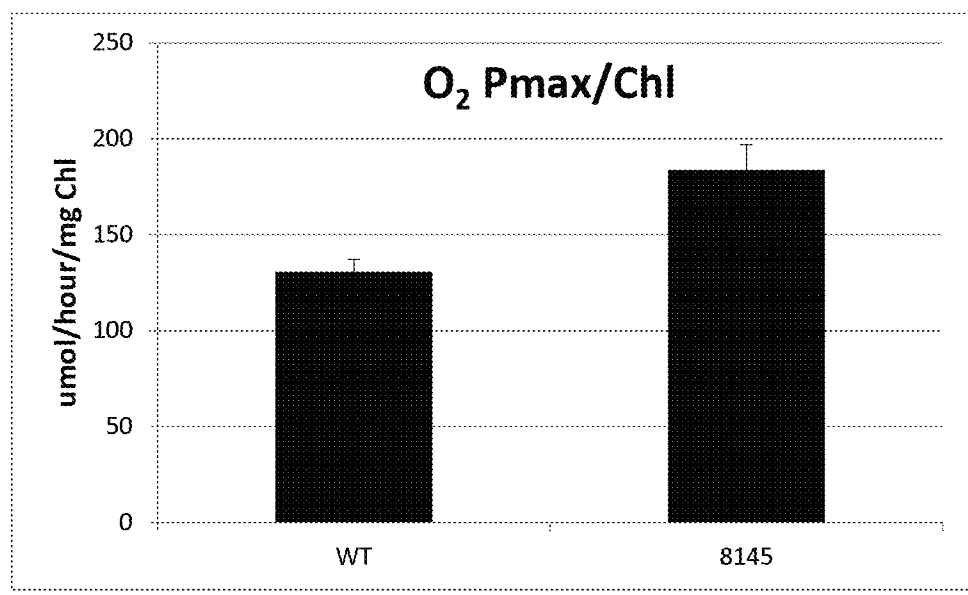
FIGS. 5A-5B. Phenotyping of VCP double knockout mutant. Graphs depicting (A) the oxygen evolution Pmax per chlorophyll content and (B) per biomass TOC of VCP2a:KO,VCP2b:KO strain GE-8145 compared to wild type (WE-3730).
Figure 5B:
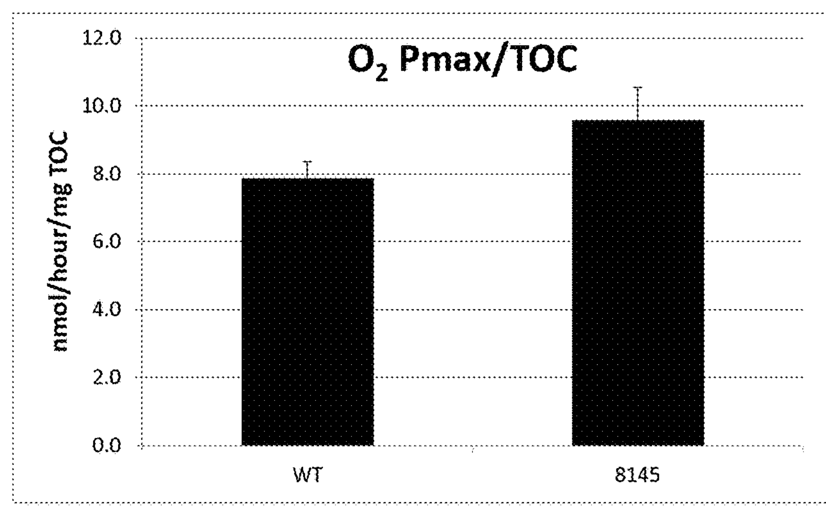

Maximal oxygen evolution per chlorophyll content and per total organic carbon content (TOC) ($P_{max}$) measurements were performed on low light acclimated cultures. $P_{max}$ for GE-8145 was increased by approximately 41% on a per mg of chlorophyll basis and by 22% on a per TOC basis with respect to wild type (Table 9 and FIGS. 5A and 5B).

TABLE 9

| Maximum oxygen evolution per cell of Double VCP Knockout Strain GE-8145 | | | | |
|---|---|---|---|---|
| Strain ID | $P_{max}$/chl (nmol $O_2$ $hour^{-1}$ mg $chl^{-1}$) | % change ($P_{max}$/chl) | $P_{max}$/TOC (nmol $O_2$ $hour^{-1}$ $\mu g^{-1}$) | % change ($P_{max}$/TOC) |
| WT-3730 | 130 ± 6 | — | 7.8 ± 0.4 | — |
| GE-8145 | 183 ± 13 | 41% | 9.6 ± 0.9 | 22% |

Other photosynthetic parameters are summarized in the table of FIG. 18B. To obtain Fv/Fm and $\sigma_{PSII}$ measurements of Fluorescence Induction and Relaxation (FIRe) kinetics were performed in the dark. Presented values for Fv/Fm and $\sigma_{PSII}$ were calculated as an average of 6 measurements (3 measurements of each of the 2 biological replicates). To determine $NPQ_{max}$ we measured FIRe kinetics over a range of ambient irradiances (20 μE to 2000 μE of blue light, 450 nm with 30 nm half bandwidth). $NPQ_{max}$ were calculated as an average of 2 measurements (1 measurement of each of the 2 biological replicates). Oxygen evolution was measured on an ALGi instrument using Clark-style oxygen electrodes. Cultures were normalized to 5 μg chl $ml^{-1}$ in media containing 0.5 g $l^{-1}$ (5.95 mM) sodium bicarbonate and assayed using at irradiances ranging from 0-2000 μE of white light. a was calculated from the production-irradiance plot by measuring the slope of the linear portion of the curve. Values in brackets are ±SD. These data are from samples obtained during steady state on the SCPA. Oxygen evolution was measured on an ALGi instrument using Clark-style oxygen electrodes. Cultures were normalized to 5 μg chl $ml^{-1}$ in media containing 0.5 g/l (5.95 mM) sodium bicarbonate and assayed using at irradiances ranging from 0-2000 μE of white light. From Table A we see that GE-8145 is characterized by reduced functional cross-section of PSII, and the initial slope of the PI curve "α" (this parameter determines the functional cross-section of oxygen evolution of the cell and is a product of the absorption cross-section of photosystem II, number of active PSII and quantum yield of photochemical energy conversion in PSII). Along with proportional reduction in chlorophyll/TOC this strongly implies that reduction in chlorophyll is primarily related to loss of antenna pigmentation and not the number of photosystems. Fv/Fm, a measure of quantum efficiency, was not found to be slightly elevated in GE-8145, while Pmax was found to be the same as in the wild type. We also observed a substantial decrease in the Non-photochemical quenching, which indicates key role of VCPs in this process.

Sequence specific primers were used for the qRT-PCR assessment of VCP1 (SEQ ID NO:19 and SEQ ID NO:20), VCP2a (SEQ ID NO:21 and SEQ ID NO:22), VCP2b and VCP2c (SEQ ID NO:23 and SEQ ID NO:24), and a housekeeping control gene (SEQ ID NO:25 and SEQ ID NO:26). The qRT-PCR analysis revealed that in addition to lacking any transcript from the VCP2 genes, GE-8145 had no detectable VCP1 transcript (Table 10). This was unexpected considering only the VCP2a and VCP2b genes were targeted for knock out in this mutant strain. Therefore, knockout of VCP2 genes in GE-8145 led to essentially complete attenuation of the VCP1 gene expression as well, meaning no VCP genes are expressed in GE-8145.

TABLE 10

| Transcript Levels of Double Knockout Strain GE-8145 by qRT-PCR (% wild type) | | | |
|---|---|---|---|
| Strain ID | VCP1 | VCP2a | VCP2b/VCP2c |
| WT-3730 | 100% | 100% | 100% |
| GE-8145 | 0% | 0% | 0% |

Example 9. GE-8145 Productivity Analysis

Figure 6A:
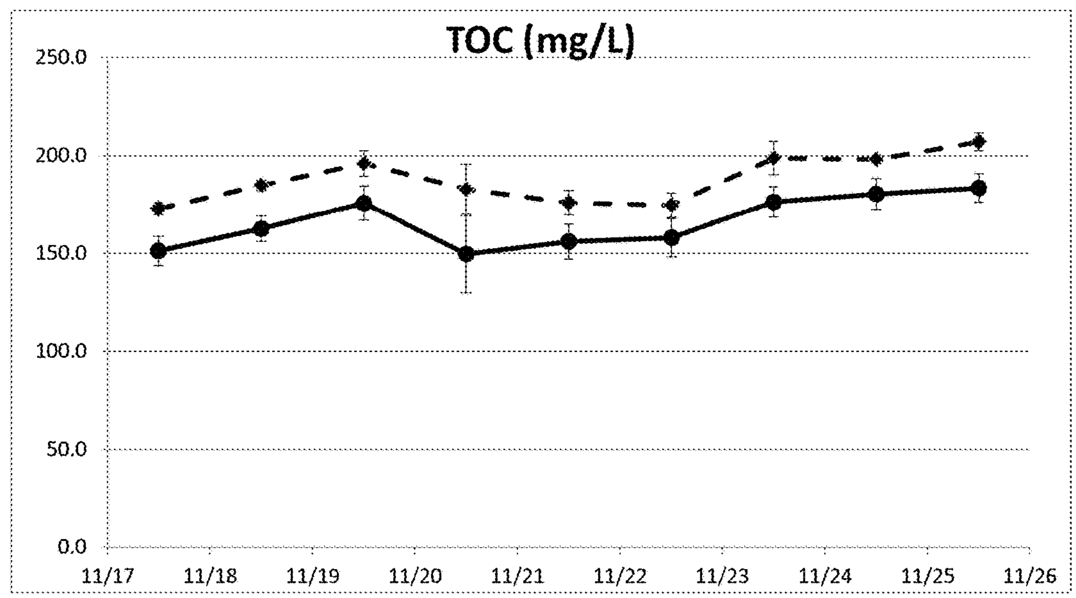
FIGS. 6A and 6B. Productivity assessment of VCP double knockout mutant. Graph of biomass (total organic carbon, TOC) on successive days of a semi-continuous culture of GE-8145 and WE-3730, wherein the light varied in intensity throughout the day to mimic natural sunlight and each point represents the TOC average of three cultures.
Figure 6B:
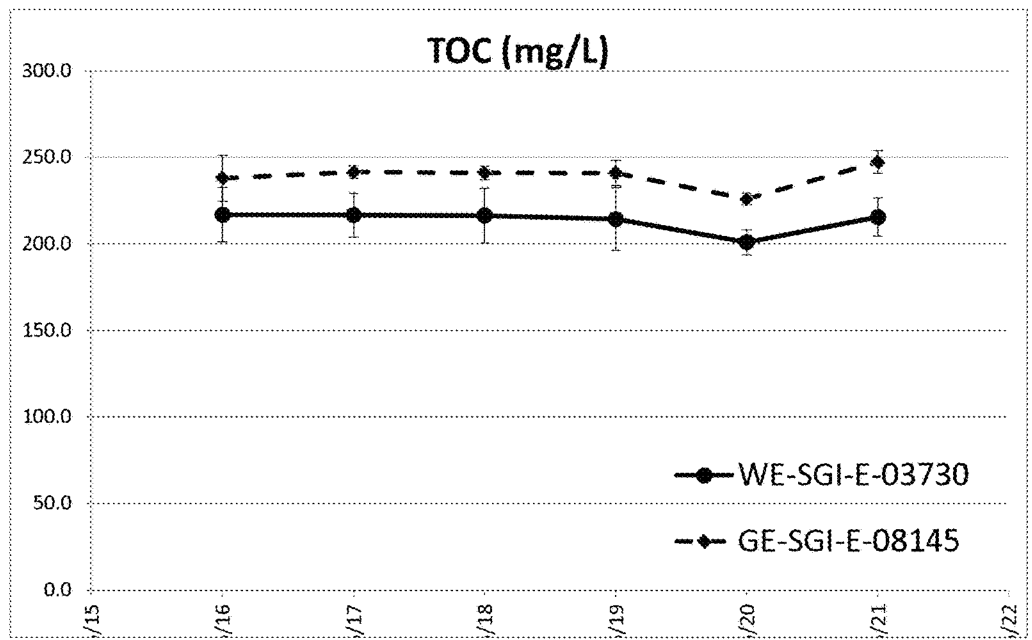

To determine the biomass productivity level of GE-8145, triplicate 225 $cm^2$ flasks for each strain were inoculated with algae to provide a culture density of 0.15 OD 730 nm in a total volume of 500 mL of PM074 medium. Stir bars were added to each flask, and stoppers having a syringe filter for air/$CO_2$ delivery at a rate of 100 ml/min and a clave connector for sampling were fitted to the flasks, which were given random positions along the 16-flask rack. The stir plates beneath the rack were operated at 450 rpm. The LED light bank provided a programmed sinusoidal 16:8 light regime designed to steadily ramp up to a peak of 2000 μE·m-2·s-1 and back down to 0 μE·m-2·s-1 over 16 hours, followed by 8 hours of darkness, i.e., a diel cycle light regime with the light intensity varying throughout the 16 hour light period. The temperature varied from 25° C. to 34° C. Cultures were diluted 30% daily to achieve semi-continuous growth and, once cultures reached a steady growth state, samples (typically 2 mLs) were removed each day over 5-6 days for TOC and FAME analysis. FIGS. 6A and 6B and Table 11 summarize the results of experiments assessing productivity levels based on total organic carbon values for GE-8145 and wildtype WT-3730, where three cultures per strain were run in each experiment, with the average values plus/minus the standard deviation shown. VCP mutant strain GE-8145 was found to also outperform the wild-type in daily TOC productivity by an average of approximately 13% (FIGS. 6A and 6B, Table 11).

TABLE 11

Semi-continuous diel cultures, productivity results from two separate experiments

| | Experiment 1 | | Experiment 2 | |
|---|---|---|---|---|
| Strain ID | Average TOC (mg/L) | % improvement | Average TOC (mg/L) | % improvement |
| WT-3730 | 166 ± 13 | — | 213 ± 6 | — |
| GE-8145 | 188 ± 12 | 13% | 239 ± 7 | 12% |

Figure 7:
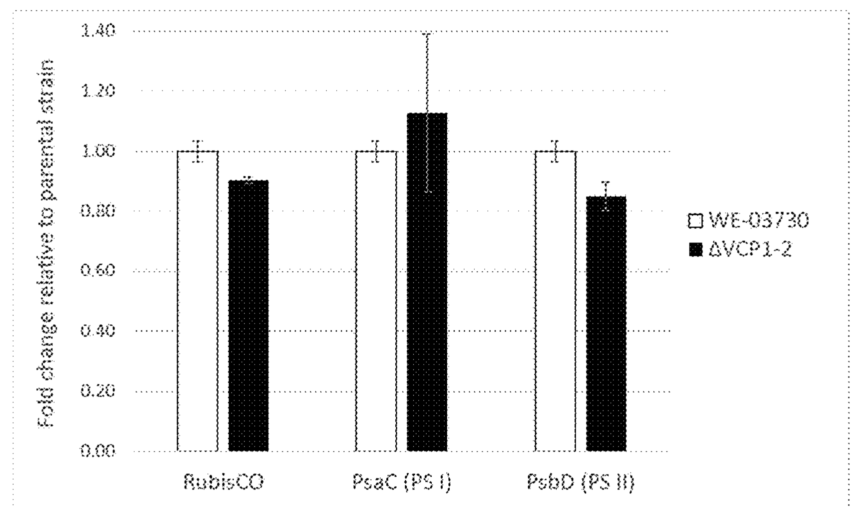
FIG. 7. Results of quantitative Westerns showing protein levels of ribulose bisphosphate carboxylase (Rubisco), PsaC, a photosystem I component, and PSbD, a photosystem II in VCP knockout strain GE-81451 as compared to wild type (WE-3730).

Quantitative Western analysis was performed to determine the impact of VCP deletion on PSI and PSII reaction center content as well as on ribulose bisphosphate carboxylase (Rubisco) abundance. Antibodies for PsaC, PsbD and the Rubisco large subunit were used for estimating PSI, PSII and Rubisco content respectively in cells cultured under the same semi-continuous diel cycle conditions. These analyses showed that the deletion of VCPs had no significant impact on reaction center or Rubisco content (FIG. 7).

Example 10. Quenching Assay from Steady State Cultures

Figure 8:
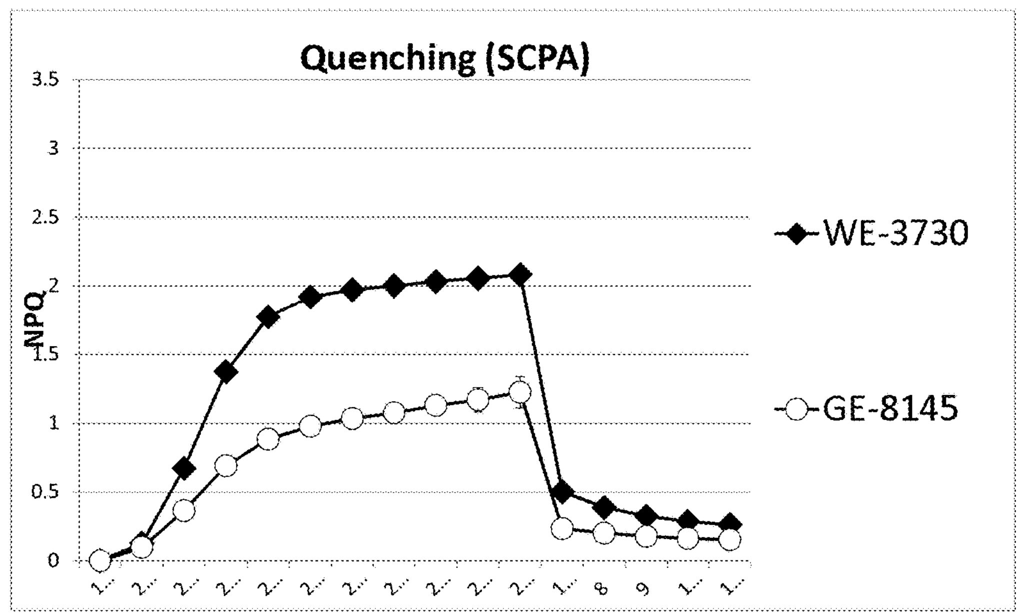
FIG. 8. Nonphotochemical quenching (NPQ) of double VCP knockout GE-8145 as compared to wild type WT-3730 in response to light.

To determine the NPQ activation response of cultures grown in the semi-continuous productivity assay (SCPA, described in Example 9), Dual-PAM measurements of NPQ were performed on wild-type and GE-8145 following 4 hours of high light exposure (Table 12 and FIG. 8). Low-light acclimated cultures from the productivity assay (described in Example 9) were diluted 1:10 in PM074 and exposed to ~1850 μE light for 4 hrs while being bubbled with 1% $CO_2$. After four hours the cultures were concentrated and normalized to 5 ug chl/ml, dark adapted for 5 min, and then assayed using the NPQ protocol of the Dual-PAM machine according to the manufactures instructions. These NPQ data indicated that VCP double mutant strain GE-8145 has significantly reduced NPQ compared to wild type. Specifically, GE-8145 had at least a 40% decrease in NPQ activation at every 2450 μE saturating flash after the first flash (Table 12 and FIG. 8).

TABLE 12

NPQ of VCP Knockout Strain GE-8145

| 2450 μE | NPQ | | NPQ percent |
|---|---|---|---|
| flash # | WT | GE-8145 | decrease |
| 1 | 0.13 | 0.10 | −23% |
| 2 | 0.67 | 0.36 | −46% |
| 3 | 1.37 | 0.69 | −50% |
| 4 | 1.77 | 0.88 | −50% |
| 5 | 1.92 | 0.98 | −49% |
| 6 | 1.97 | 1.03 | −48% |
| 7 | 2.00 | 1.07 | −47% |
| 8 | 2.03 | 1.13 | −44% |
| 9 | 2.06 | 1.17 | −43% |
| 10 | 2.08 | 1.22 | −41% |

Example 11. GE-8145 Productivity Analysis in Constant Light

Figure 9:
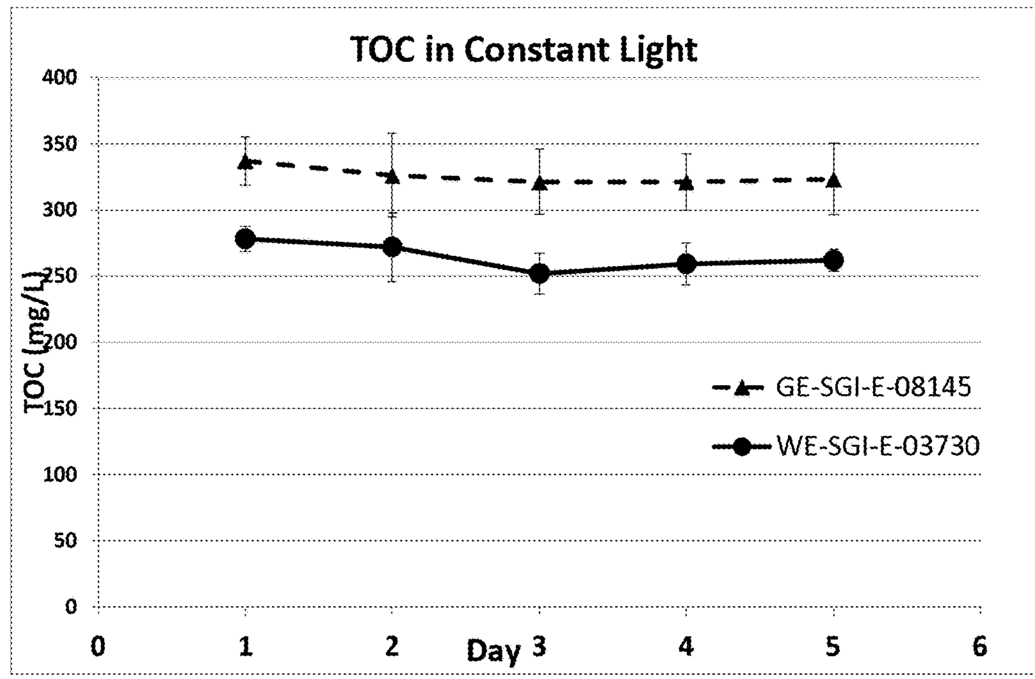
FIG. 9. Productivity assessment of VCP double knockout mutant in constant light. Graph of biomass (total organic carbon, TOC) on successive days of a semi-continuous culture of GE-8145 and WE-3730, wherein the constant light was approximately 2000 μE 24 hours a day and each point represents the TOC average of three cultures.

To determine the biomass productivity level of GE-8145 in constant light, triplicate 225 $cm^2$ flasks for each strain were inoculated with algae to provide a culture density of 0.15 OD 730 nm in a total volume of 500 mL of PM074 medium. Stir bars were added to each flask, and stoppers having a syringe filter for air/$CO_2$ delivery at a rate of 100 ml/min and a clave connector for sampling were fitted to the flasks, which were given random positions along the 16-flask rack. The stir plates beneath the rack were operated at 450 rpm. The LED light bank provided a constant light regime of approximately 2000 μE·m-2·s-1 24 hours a day. The temperature varied from 25° C. to 34° C. Cultures were diluted 45% daily to achieve semi-continuous growth and, once cultures reached a steady growth state, samples (typically 2 mLs) were removed each day over 5-6 days for TOC and FAME analysis. FIG. 9 and Table 13 summarize the results of an experiment assessing productivity level of total organic carbon values for GE-8145 and wildtype WE-3730. VCP mutant strain GE-8145 was found to also outperform the wild-type in TOC productivity by an average of approximately 23% (Table 13 and FIG. 9) under these constant high light culture conditions.

TABLE 13

Constant light semi-continuous culture daily productivity results of VCP attenuated strain.

| Strain ID | Average TOC (mg/L) | % improvement |
|---|---|---|
| WT-3730 | 264 ± 11 | — |
| GE-8145 | 326 ± 12 | 23% |

Example 12. LHC Single and Double Gene Knockouts

We identified a total of twenty-six LHC genes in *Nannochloropsis*, including 4 VCPs, and 22 LHCs, of which 3 (listed in Table 14 as genes 3431, 6477, and 7831), were hypothesized to be LHCSRs (LHCs playing a major role in NPQ), based on their sequences. In addition to the 4 VCP genes targeted in Examples 4-11, above, other non-VCP light harvesting complex (LHC) family member genes were targeted for disruption using the same Cas9-mediated knock out approach described in Example 4 using a donor fragment that included a hygromycin resistance cassette (SEQ ID NO:15). The guide sequences and primers used to identify the gene disruptions are listed in Table 14.

Double LHC knockouts were also generated. LHCs 810, 1373, 7521, 3454, and 5134 were of interest as they were found to have the most abundant transcript levels based on transcriptomics analysis. In this case, LHC-810 knockout strain GE-14700 was used as the parent which was transformed with a guide RNA targeting a second LHC gene (LHC-1317, LHC-7521, LHC-3454, or LHC-5134), and a donor fragment that included a gene conferring resistance to bleomycin. Colonies were selected on zeocin and tested for intergration of the donor fragment in to the targeted locus using the primers in Table 14.

TABLE 14

LHC genes, target sequences for Cas9-mediated knockout, and primers for confirming gene disruption

| LHC Gene target | Genome Locus | Strain | Target Sequence | Primer 1 | Primer 2 |
|---|---|---|---|---|---|
| 4250 | Naga_100168g13 | GE-14698 GE-14699 | SEQ ID NO: 77 | SEQ ID NO: 96 | SEQ ID NO: 97 |
| 810 | Naga_100017g83 | GE-14700 GE-14701 | SEQ ID NO: 78 | SEQ ID NO: 98 | SEQ ID NO: 99 |
| 1373 | Naga_100002g18 | GE-14702 GE 14703 | SEQ ID NO: 79 | SEQ ID NO: 100 | SEQ ID NO: 101 |
| 7521 | Naga_100005g99 | GE-14704 GE-14705 | SEQ ID NO: 80 | SEQ ID NO: 102 | SEQ ID NO: 103 |
| 3454 | Naga_100056g15 | GE-14706 GE 14707 | SEQ ID NO: 81 | SEQ ID NO: 104 | SEQ ID NO: 105 |
| 5134 | Naga_100018g45 | GE-14708 GE-14709 | SEQ ID NO: 82 | SEQ ID NO: 106 | SEQ ID NO: 107 |
| 9417 | | GE-15005 GE-15006 | SEQ ID NO: 83 | SEQ ID NO: 108 | SEQ ID NO: 109 |
| 554 | Naga_100173g12 | GE-15007 GE-15008 | SEQ ID NO: 84 | SEQ ID NO: 110 | SEQ ID NO: 111 |
| 3432 | Naga_100056g41 | GE-15009 GE-15010 | SEQ ID NO: 85 | SEQ ID NO: 112 | SEQ ID NO: 113 |
| 7677 | Naga_100434g4 | GE-15012 GE-15268 | SEQ ID NO: 86 | SEQ ID NO: 114 | SEQ ID NO: 115 |
| 6755 | Naga_100157g5 | GE-15216 GE-15217 | SEQ ID NO: 87 | SEQ ID NO: 116 | SEQ ID NO: 117 |
| 4249 | Naga_100168g14 | GE-15218 GE-15219 | SEQ ID NO: 88 | SEQ ID NO: 118 | SEQ ID NO: 119 |
| 9833 | Naga_100092g17 | GE-15220 GE-15221 | SEQ ID NO: 89 | SEQ ID NO: 120 | SEQ ID NO: 121 |
| 790 | Naga_100017g59 | GE-15222 GE-15223 | SEQ ID NO: 90 | SEQ ID NO: 122 | SEQ ID NO: 123 |
| 171 | Naga_100013g28 | GE-15224 GE-15225 | SEQ ID NO: 91 | SEQ ID NO: 124 | SEQ ID NO: 125 |
| 4967 | Naga_100641g3 | GE-15226 GE-15227 | SEQ ID NO: 92 | SEQ ID NO: 126 | SEQ ID NO: 127 |
| 1993 | Naga_100004g86 | GE-15228 GE 15229 | SEQ ID NO: 93 | SEQ ID NO: 128 | SEQ ID NO: 129 |
| 4422 | | GE-15266 GE-15267 | SEQ ID NO: 94 | SEQ ID NO: 130 | SEQ ID NO: 131 |
| 6329 | Naga_100027g19 | GE-15271 | SEQ ID NO: 95 | SEQ ID NO: 132 | SEQ ID NO: 133 |
| 3431 | Naga_100056g42 | | | | |
| 6477 | Naga_100967g1 | | | | |
| 7831 | Naga_100742g1 | | | | |

Mutants were screened by PCR using primers provided in Table 14 to confirm disruption of the targeted LHC gene, and two lines for each knockout were selected for further analysis, with the exception of LHC-6329, where only one line was obtained. LHC mutants were assessed for chlorophyll and carbon fixation rate.

Chlorophyll was extracted from cells grown in liquid culture under low light (50 μE·m-2·s-1) conditions as described in Example 5. Samples from the same cultures were assessed for total organic carbon (TOC) by diluting 2 mL of cell culture to a total volume of 20 mL with DI water. Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The 4 point calibration range was from 2 ppm to 200 ppm corresponding to 20-2000 ppm for non-diluted cultures with a correlation coefficient of r2>0.999.

Carbon fixation rates (C14 Pmax) were determined using cultures normalized to 5 ug chl ml-1 in media containing 0.5 g l-1 (5.95 mM) sodium bicarbonate. C14 labeled sodium bicarbonate (20.4 μCi ml-1) was added to each culture and the cultures were then exposed to 2500 μE for a duration of 10 minutes. Samples were immediately acidified with 2N HCl and allowed to off-gas overnight. The following day samples were measured using a Beckman LS6500 scintillation counter and quantified using equations from Littler and Arnold (1985) Electrodes and chemicals. Handbook of phycological methods; ecological field methods: macroalgae. Cambridge University Press, Cambridge, 349-75.

These data indicate that knocking out individual LHC genes does not always lead to decreased chlorophyll on a per biomass basis or to increased rates of carbon fixation (Table 15). The LHC genes found to have the most abundant transcript levels (LHC-810, LHC-1373, LHC-7521, LHC-3454, LHC-5134) are shown in bold in the rightmost column of the table.

TABLE 15

Chlorophyll and Carbon Fixation Rates of non-VCP LHC Knockout Strains, % Change with respect to Wild Type strain WT-3730

| LHC ID | Strain ID | Chl/TOC (% change) | $^{14}C\ P_{max}$ (% change) |
|---|---|---|---|
| 4250 | GE-14698 | **−15%** | −24% |
| 4250 | GE-14699 | **−19%** | −40% |
| **810** | GE-14700 | **−13%** | −4% |
| **810** | GE-14701 | **−2%** | **9%** |
| **1373** | GE-14702 | 3% | −5% |
| **1373** | GE-14703 | **0%** | −8% |
| **7521** | GE-14704 | 14% | −1% |
| **7521** | GE-14705 | 3% | −10% |
| **3454** | GE-14706 | 8% | 0% |
| **3454** | GE-14707 | 16% | −6% |
| **5134** | GE-14708 | **−14%** | −14% |
| **5134** | GE-14709 | 1% | −21% |
| 9417 | GE-15005 | **−1%** | −19% |
| 9417 | GE-15006 | **−7%** | −48% |
| 554 | GE-15007 | **−8%** | −1% |
| 554 | GE-15008 | **−6%** | −16% |
| 3432 | GE-15009 | 13% | **14%** |
| 3432 | GE-15010 | **−3%** | −12% |
| 7677 | GE-15012 | **−3%** | −6% |
| 7677 | GE-15268 | 8% | **24%** |
| 6755 | GE-15216 | 4% | **16%** |
| 6755 | GE-15217 | **−8%** | **12%** |
| 4249 | GE-15218 | 6% | **16%** |
| 4249 | GE-15219 | **−4%** | **6%** |
| 9833 | GE-15220 | 3% | **19%** |
| 9833 | GE-15221 | 6% | **36%** |
| 790 | GE-15222 | 14% | **23%** |
| 790 | GE-15223 | 6% | **28%** |
| 171 | GE-15224 | **−7%** | **9%** |
| 171 | GE-15225 | **−3%** | **11%** |
| 4967 | GE-15226 | **−1%** | **10%** |
| 4967 | GE-15227 | **−3%** | **1%** |
| 1993 | GE-15228 | **−8%** | **6%** |
| 1993 | GE-15229 | **−8%** | **8%** |
| 4422 | GE-15266 | 2% | **12%** |
| 4422 | GE-15267 | 3% | **21%** |
| 6329 | GE-15271 | 3% | **19%** |
| 810, 1373 | GE-15415 | −1% | −7% |

TABLE 15-continued

Chlorophyll and Carbon Fixation Rates of non-VCP LHC Knockout Strains, % Change with respect to Wild Type strain WT-3730

| LHC ID | Strain ID | Chl/TOC (% change) | $^{14}$C $P_{max}$ (% change) |
|---|---|---|---|
| 810, 7521 | GE-15416 | −6% | −5% |
| 810, 3454 | GE-15417 | −3% | 1% |
| | GE-15418 | 4% | 8% |
| 810, 5134 | GE-15419 | −1% | 8% |
| | GE-15420 | 0% | 14% |
| Wildtype | WE-3730 | YTD | YTD |
| | | CV = 20% | CV = 26% |
| | | n = 15 | n = 15 |

Moreover, the chlorophyll content of non-VCP LHC knockout strains was somewhat variable, with some strains experiencing apparent gains in chlorophyll of up to 16% and other demonstrating decreases in chlorophyll ranging from 1 to 19%. Carbon fixation rates were also variable in the non-VCP LHC single gene knockout lines, as some strains demonstrated increases in carbon fixation while others had decreased rates of carbon fixation with respect to wild type cells (Table 15). There was no clear relationship between chlorophyll decrease (or increase) and the rate of carbon fixation in these knockout lines.

Figure 10:
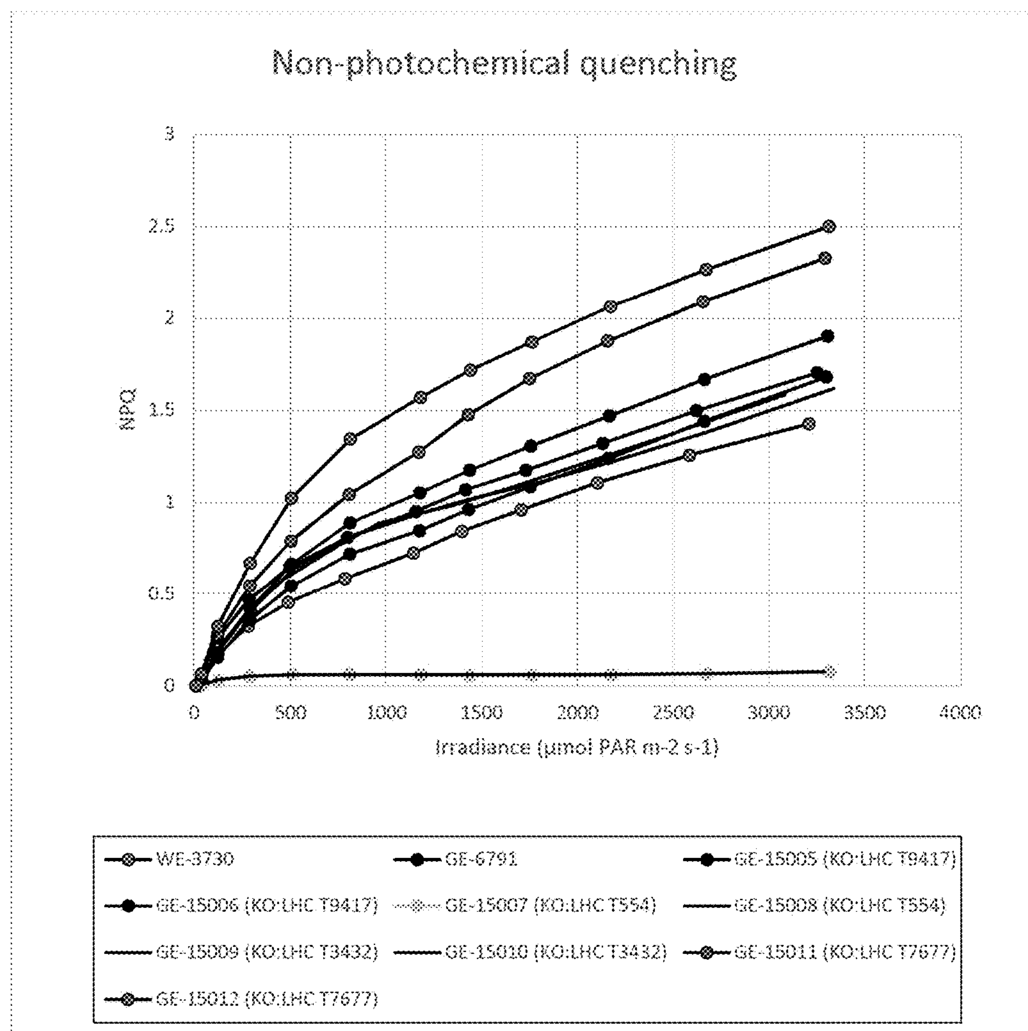
FIG. 10. Nonphotochemical quenching of several single gene LHC knockout strains. Uniquely, strain GE-15007, lacking LHC-554, has no NPQ response.

NPQ was also assessed in the single LHC knockout lines. FIG. 10 provides an example of light intensity NPQ curves for wild type strain WT-3730, the parental Cas9 Editor line GE-6791, and several non-VCP LHC single gene knockout strains. With a single striking exception, dramatic changes in NPQ were not found in the non-VCP LHC single gene knockout mutants. Mutant strains GE-15007 and GE-15008, attenuated in the same gene encoding LHC-554 (corresponding to the Naga_100173 g12 locus of the *Nannochloropsis gaditana* genome sequence described in Corteggiani Carpinelli et al., Mol Plant 7, 323-335 (2014) and available at nannochloropsis.org) using the identical guide RNA, were found to have no NPQ response (FIG. 10). This was all the more surprising as an LHC subtype, known as "LHCSR" had been previously characterized in a green alga (Bonente et al., (2010) PloS Biology 9:31000577; Toksutu and Mingawa (2013) Proc. Natl Acad. Sci. USA 10:10016-21) and a diatom (Bailleul et al. (2010) Proc. Natl Acad. Sci. USA 107:18214-18219) as being responsible for the majority of the NPQ in these species, and LHC-554 (coding sequence of the gene provided as SEQ ID NO:134, amino acid sequence of the encoded polypeptide provided as SEQ ID NO:135) was not annotated as an LHCSR polypeptide. Instead, the *Nannochloropsis* genome annotation at nannochloropsis.org provides that Naga_100005 g99 is an LHCSR. Further in-house sequence analysis indicated that three other *Nannochloropsis* LHCs corresponding to genome loci Naga_100056 g42, Naga_100967 g1, and Naga_100742 g1 (coding sequences provided as SEQ ID NO:101, SEQ ID NO:85, and SEQ ID NO:102, respectively, in US 2014/0220638, incorporated by reference herein) were likely to be LHCSRs.

Figure 11A:
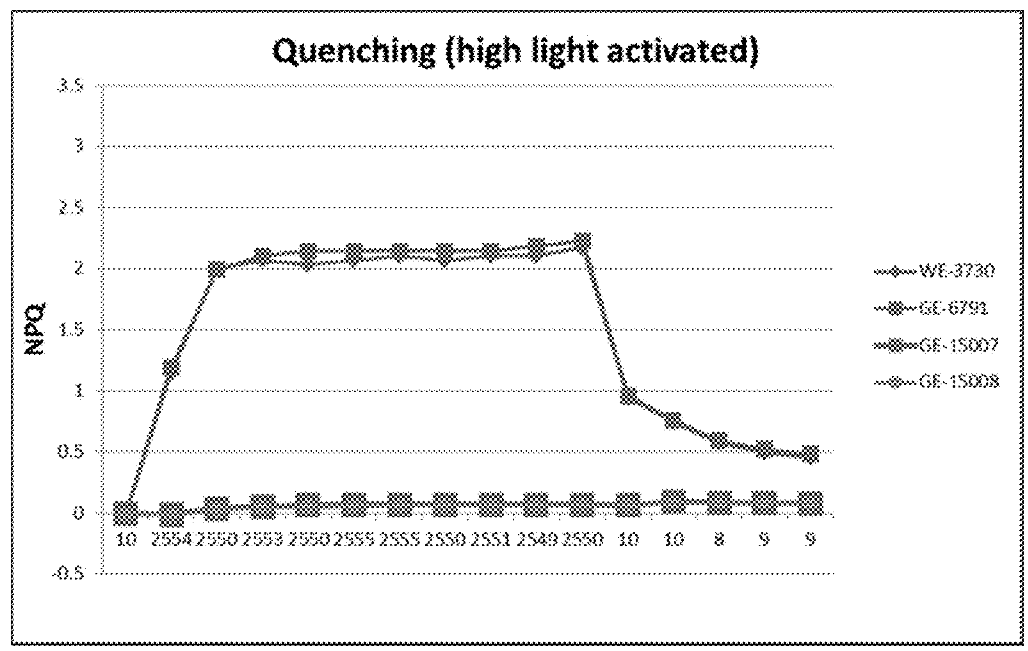
FIGS. 11A-11B. (A) high light activated NPQ of strains WT-3730 (wild type) GE-6791 (cas9 parent), and two strains, GE-15007 and GE15008 knocked out in the LHC-554 gene and demonstrating no NPQ response. (B) NPQ of WT-3730 (wild type) and GE-15007 cultured in a semi-continuous system.
Figure 11B:
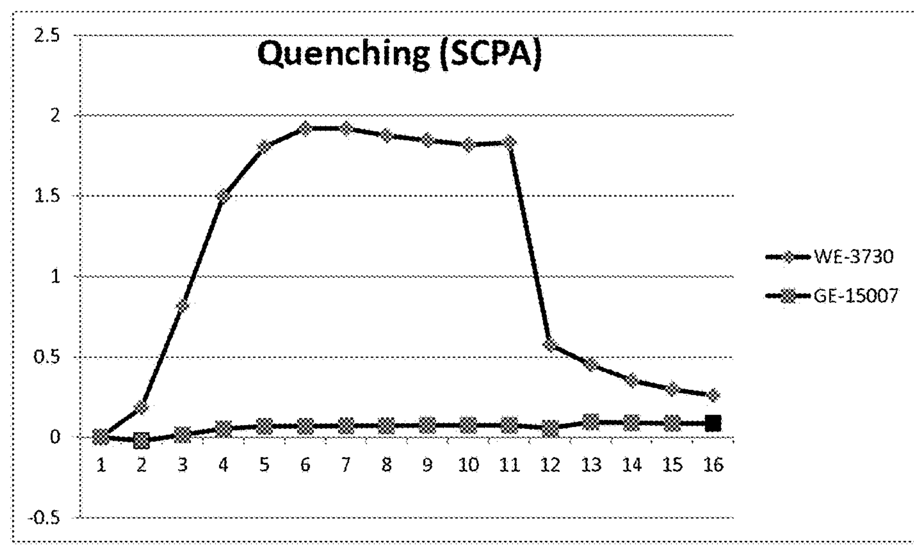

Further experiments to confirm the effect of disruption of the LHC-554 gene on NPQ were performed. In a first experiment, cultures of wild type (WT-3730) and Cas9 Editor parental strain GE-6791 and the two knockout lines GE-15007 and GE-15008 were cultured in low (50 μmol photons·m-2·sec-1) light before exposing the cells to very high (2550 μmol photons·m-2·sec-1) light. While the wild type and Cas9 Editor line demonstrated a steep increase in NPQ following the shift to high light, no NPQ response at all is seen in LHC-554 knockout strains GE-15007 and GE-15008 (FIG. 11A). Moreover, NPQ remained high in the wild type and Cas9 editor line for as long as they are exposed to high light, whereas NPQ is never activated in the LHC-554 knockout strains. A similar experiment was conducted using cells cultured in a semi-continuous diel system where the light varied in intensity during the day to mimic pond outdoor conditions. The mutants cultured under these conditions also failed to show any NPQ response (FIG. 11B). Unlike the wild type and Cas9 Editor strains, the knockout mutant strains never activated NPQ in response to bright light. Thus, LHC-554 is a critical component of the NPQ response, and the LHC-554 gene represents a promising candidate for modulating gene expression to decrease NPQ.

Example 13. Proteomics of LHC Single and Double Gene Knockouts

To characterize protein complexes present in wild type *N. gaditana* (WT-3730) photosynthetic membranes, thylakoid membranes were isolated from WT-3730 cells acclimated to low light conditions following a crude membrane preparation protocol essentially as described by Jarvi et. al. (*Biochem. J.* 439:207-214 (2011)) or by separation of cell lysate on a percoll gradient. These were analyzed by Blue Native Poly Acrylamide Gel Electrophoresis (BN-PAGE) to separate native membrane complexes (Jarvi et al., ibid). Ten distinct chlorophyll-containing complexes were observed. Chlorophyll-containing green bands were then excised from the gel and provided for mass spectrometry analysis (Michigan State University Proteomics Core Facility, East Lansing, Mich.) to determine their composition.

Results from mass spectrometry analysis of the 10 bands cut from the BN-PAGE gel enabled characterization of some of major supercomplexes present in the thylakoid membrane. Bands 1, 3, and 8 were found to be photosystem II (PSII)-LHC polypeptides supercomplexes. Band 2 was identified as including PSII, the ATP synthase, and LHCs. Band 4 included PSI, PSII, and LHCs. Band 5 was found to include PSI and the ATP synthase. Band 6 included PSI, PSII, and LHCs. Band 7 included PSII and the cytochrome $b_6f$ complex. Band 9 was made up of LHC trimers, and Band 10 was found to be LHC monomers.

TABLE 16

LHC Association with photosystems based on BN-PAGE and mass spec analyses

| LHCs (gene IDs) | Average Spectral count | Association** |
|---|---|---|
| 2787, 2788 (VCPs) | 76 | Trimer-monomer |
| 4250 | 42.5 | PS I/PS II/Trimer-monomer |
| **3454** | 28.5 | PS I-specific |
| **7521** | 27.5 | PS II/Trimer-monomer |
| **1373** | 24.5 | PS II/Trimer-monomer |
| **810** | 18.5 | PS I/Trimer-monomer |
| 2925 | 16 | PS II/Trimer-monomer |
| 1993 | 14.5 | PS II/Trimer-monomer |
| 4967 | 14 | PS I/Trimer-monomer |
| **5134** | 14 | PS II/Trimer-monomer |
| 4422 | 12.5 | PS I-specific |
| 171 | 10.5 | PS II/Trimer-monomer |
| 6329 | 9.5 | Trimer-monomer (maybe PS II as well) |
| 554* | 9 | Trimer-monomer |
| 7677 | 4 | PS I-specific |
| 4249 | 2.5 | PS II-specific |

TABLE 16-continued

| LHC Association with photosystems based on BN-PAGE and mass spec analyses | | |
|---|---|---|
| LHCs (gene IDs) | Average Spectral count | Association** |
| 6477 | 2 | Trimer-monomer |
| 3492 | 2 | PS I-specific? |

These analyses also yielded distinct profiles of the LHCs in each band, which enabled association of the different LHCs with specific photosystems (Table 16). Consistent with transcriptomics analyses, the VCP proteins were the most abundant of the LHCs from proteomics analysis. The VCPs were found to be present in monomeric and trimeric forms, predominating in bands 9 and 10 of the BN gels, indicating their localization in the thylakoids is in the light harvesting antenna, where they make up close to 50% of the spectral counts. The predominance of the VCPs in the antenna, from which they are isolated as monomers and trimers in the BN PAGE prep, was confirmed by proteomic analysis of the VCP knockout strain GE-8145 that had no detectable VCP transcripts. Thylakoid membrane preps of strain GE-8145 and wild type WT-3730 were isolated and analyzed side by side on BN PAGE gels. Bands 9 and 10 were almost completely absent from the gel lane that included thylakoid complexes of the VCP knockout mutant (GE-8145), demonstrating that the vast majority of chlorophyll bound by LHCs in the antenna region is attributable to the VCPs.

Example 14. Dynamics of Light Harvesting Complex Composition in *N. gaditana* Mutants As shown in Table 15, while we were able to obtain knock-outs for 19 non-VCP LHC genes individually, we observed only modest reductions of chlorophyll in these strains. In addition, the double LHC knockout mutants that were generated (GE-15415, GE-15416, GE-15417, GE-15418, GE-15419, and GE-15420) based on the use of the LHC-810 knockout strain GE-14700 as a parent did not demonstrate incremental further reductions in chlorophyll content with respect to GE-14700 (Table 15). These data suggested that *N. gaditana* cells have a robust system for regulating LHC expression, in which losses of some LHC proteins are compensated for by overexpression of other, possibly functionally redundant, LHCs.

To inform the next phase of our targeted LHC deletion, we compared the composition of the thylakoid membrane complexes of wild type and LHC mutant strains using BN-PAGE followed by mass spectrometry. We assessed five deletion strains (GE-08145 (VCP2a and VCP2b knockout that lacked any detectable VCP transcript), GE-14700 (LHC-810 knockout), GE-14702 (LHC-1373 knockout), GE-15417 (LHC-810 and LHC-3454 double knockout) and GE-15419 (LHC-810 and LHC-5134 double knockout), and compared them to the parental strains (GE-06791 Cas9 Editor line and WT-3730).

The chlorophyll content of the strains as well as the spectral counts resulting from mass spectrometry after BN PAGE are summarized in Table 17 and Table 18. In the VCP deletion strain GE-8145, the knock-out led to an approximately 22% reduction in total spectral counts for all LHCs consistent with the observed reduction of Chl/TOC relative to wild type in this strain (Table 17). While most of the reduction in chlorophyll could be attributed to the loss of the VCPs, four additional LHCs (LHC-4602, LHC-8038, LHC-1467 and LHC-8604) also demonstrated reduced abundances (Table 18), possibly contributing to the reduced pigment content of this strain. No known chlorophyll binding proteins showed any substantive increase in this strain. This was in contrast to the two other single deletion strains analyzed (GE-14700 and GE-14702), which showed both substantive increases and decreases in a number of other LHC proteins not specifically targeted (Table 18). All three non-VCP LHC single gene deletion strains had total spectral counts for LHCs that were substantially reduced relative to parental strain GE-06791 (Table 17).

We did not observe any consistent pattern in the altered expression of LHC proteins in response to targeted non-VCP LHC gene disruptions. In GE-14700, for example, in which a highly-abundant PSI-associated LHC (LHC-810) is knocked out, the only LHC which showed increased abundance was the PSI-associated LHC-3454, while other PSI-associated LHCs showed reduced abundance in this knockout strain (Table 18). The deletion of one non-VCP LHC resulting in the reduced abundance (or complete absence) of other LHCs not specifically targeted was a common feature of the non-VCP LHC single gene knockouts. In the double deletion strains, however, several non-targeted non-VCP LHCs increased in abundance relative to the parental strain. However, no pattern of which LHCs would be upregulated in response to which deletions was apparent.

In GE-14702, in which a highly-abundant PSII-associated LHC (LHC-1373) was knocked out, we observed the loss of the many high molecular weight bands from the blue-native gels, which are PSII-LHC supercomplexes. These positions in the gel were excised and analyzed by mass spectrometry which revealed primarily PSI-LHC supercomplexes at these positions in the gel. This observation could be explained by the reduced abundance of several PSII-associated LHCs (in addition to the deleted PSII-associated LHC-1373), while PSI-associated LHCs (LHC-4422 and LHC-3492) increased in abundance in this strain (Table 18). This suggests a possible structural role for LHC-1373 in the assembly of PS II supercomplexes.

TABLE 17

| Comparison of chlorophyll content and total observed spectral counts for all LHCs from mass spectrometry analysis. | | | | |
|---|---|---|---|---|
| Parent | KO strain | Description | Chl/TOC (% change) | Normalized spectral count of LHCs (% change over GE-6791) |
| GE-06791 | GE-08145 | Single KO (VCP 2a and 2b) | −17% | −22% |
| GE-06791 | GE-14700 | Single KO (810) | −13% | −38% |
| GE-06791 | GE-14702 | Single KO (1373) | 3% | −18% |
| GE-14700 | GE-15417 | Double KO (810 & 3454) | −3% | −13% |
| GE-14700 | GE-15419 | Double KO (810 & 5134) | −1% | 4% |
| WE-03730 | GE-06791 | Cas 9 enabled strain | 3% | 3% |

TABLE 18

Summary of mass spectrometry data highlighting changes in LHC abundance in response to genetic perturbation of LHC loci.

| Gene IDs | Single deletions[a] | | | Double deletions[b] | | Association[c] |
|---|---|---|---|---|---|---|
| | GE-8145 | GE-14700 | GE-14702 | GE-15417 | GE-15419 | |
| 2787, 2788 ** | * | | UP | | UP | Trimer-Monomer |
| 554 | | | | UP | UP | Trimer-Monomer |
| 4249 | | | | UP | UP | PS II |
| 6477 | | | | UP | UP | Trimer-Monomer |
| 2925 | | | | UP | | PS II/Trimer-Monomer |
| 6329 | | | | UP | | Trimer-Monomer (PS II?) |
| 1373 | | | * | UP | UP | PS II/Trimer-Monomer |
| 1993 | | DOWN | DOWN | UP | UP | PS II/Trimer-Monomer |
| 171 | DOWN | | DOWN | UP | | PS II/Trimer-Monomer |
| 5134 | DOWN | DOWN | DOWN | UP | * | PS II/Trimer-Monomer |
| 0814 | | | UP | ABSENT | | PS I |
| 3492 | | | UP | | | PS I? |
| 7677 | DOWN | | | DOWN | | PS I |
| 7521 | | | | | DOWN | PS II/Trimer-Monomer |
| 4967 | | ABSENT | | ABSENT | | PS I/Trimer-Monomer |
| 810 | | * | | * | * | PS I/Trimer-Monomer |
| 4250 | DOWN | DOWN | DOWN | UP | UP | PS I/PS II/Trimer-Monomer |
| 3454 | | UP | | * | | PS I |

(* indicates the gene is knocked out)

Taken together, these observations suggest that deletion of LHCs that are closely associated with photosystems can affect the stability of the photosystems. Deletion of these non-VCP LHCs might elicit a concerted response involving multiple non-VCP LHCs to compensate for such losses. Other the other hand, deletion of LHCs more closely associated with the light harvesting antenna such as the VCPs (e.g., in strain GE-8145) did not elicit any major compensatory response from the cell and thus genetic manipulations that target one or more VCP genes are likely to be more useful for altering antenna size and increasing photosynthetic efficiency and/or productivity.

Example 15. Impact of Acclimation State on LHC Composition in *N. gaditana*

Unicellular algae employ various strategies to photo-acclimate to changes in light intensity. At the most general level, acclimation to decreased irradiance is observed as an increase in cellular pigment content (principally chlorophyll). Two contrasting strategies have been well documented. The first entails increase in the size of the light harvesting antenna, or more specifically increasing the functional absorption cross-section (σPSII), termed σ-type acclimation. The second is photo-acclimation by increasing the number of photosynthetic units per cell, or n-type acclimation. These two types of photo-acclimation are not mutually exclusive and many algae likely use a combination of these strategies.

Figure 12:
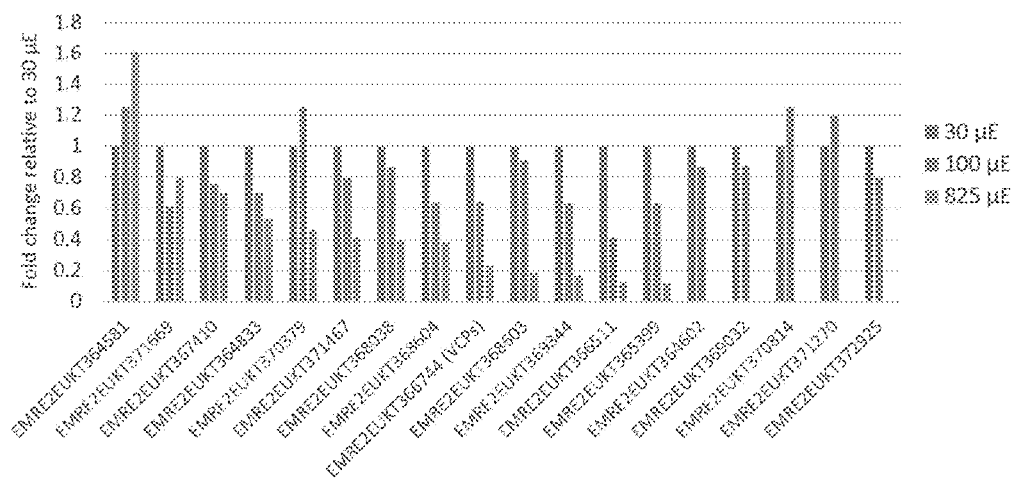
FIG. 12. Abundance of various LHC proteins in the wild type strain under different light conditions.

To assess the impact of acclimation state on LHC composition proteomics analysis of thylakoid preps obtained from WT-3730 cultures acclimated to 30, 100 or 825 μE were conducted. Most of the LHC proteins showed significant reductions in abundance at high irradiance (825 μE), consistent with the reduced pigment under this condition (FIG. 12). However, one of the LHCs, LHC-554, showed a significant increase in abundance (~1.6 fold) at high radiance. This might indicate a role for this LHC in response to high light stress, consistent with its critical role in NPQ as demonstrated in Example 12 and shown in FIGS. 11A and 11B.

Example 16. Generation of a Markerless, Cre-Enabled Cas9 Editor Line in *N. gaditana*

Figure 13:
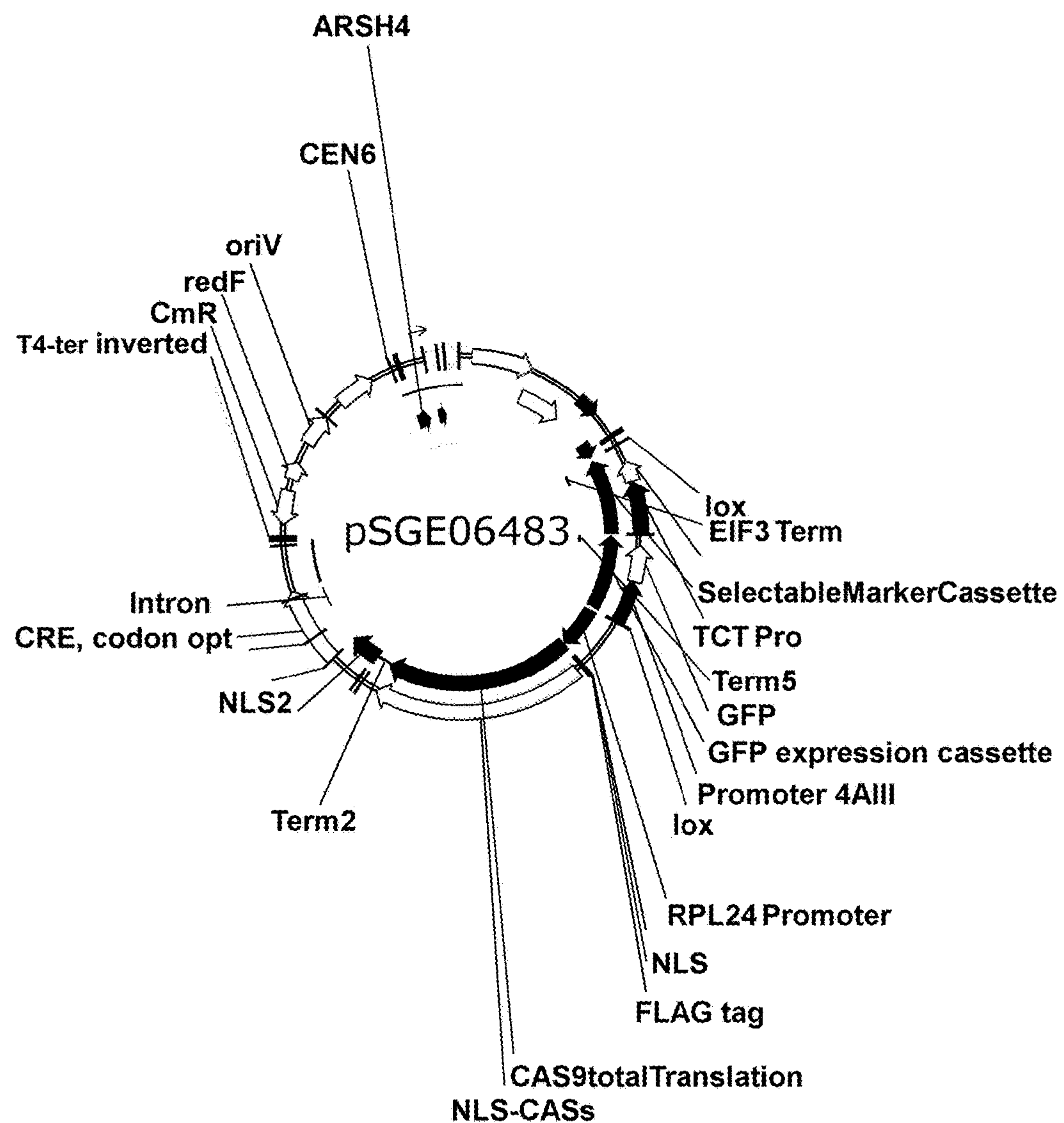
FIG. 13. Construct pSG-06483, designed for the expression of Cas9 and cre recombinase.
Figures 14A, 14B, 14C, 14D, 14E:
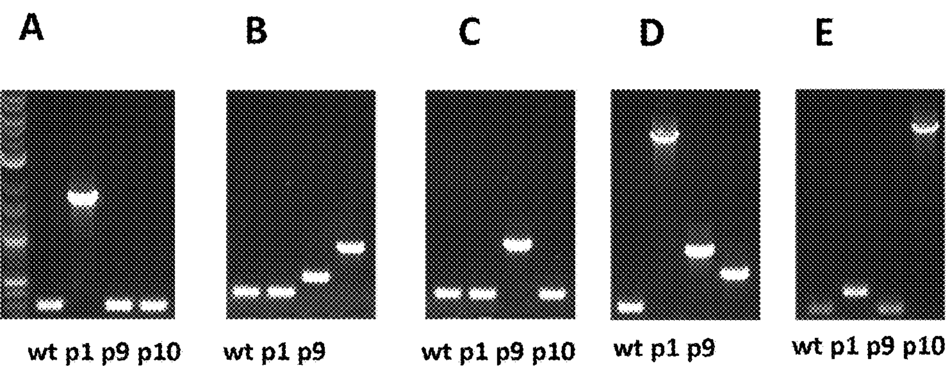
FIGS. 14A-14E. Results of PCR on genomic DNA to determine disrupted LHC gene loci. Bands larger than the wild type (WT) demonstrate disrupted genes. Each of A, B, C, D, and E represents PCR with primers to detect a different LHC gene.

The development of a markerless, reporterless Cas9 Editor strain that included a repressible cre recombinase gene is described in U.S. patent application Ser. No. 14/986,492, filed Dec. 31, 2015 and corresponding PCT application PCT/US15/068356 publication number WO 2016/109840, incorporated herein by reference. The vector pSG6483 was designed and engineered for constitutive expression of a Cas9 nuclease and repressible expression of Cre recombinase in *Nannochloropsis gaditana*. The vector contained the following four elements: 1) the Cas9 expression cassette described in Example 4, 2) the selectable marker cassette ("HygR cassette"; SEQ ID NO:15) described in Example 4, 3) the same GFP reporter cassette described previously in Example 4, and 4) a repressible CRE expression cassette containing the Cre recombinase from P1 Bacteriophage codon optimized for *Nannochloropsis gaditana*, which contains the same N-terminal NLS used for the Cas9 construct and also includes an *N. gaditana* intron inserted into the Cre coding region (engineered Cre gene provided as (SEQ ID NO:9). The *Nannochloropsis*-engineered Cre gene was operably linked to the "Ammonia repressible Nitrite/Sulfite Reductase" promoter (SEQ ID NO:149) at the 5' end of the Cre gene and the "Nitrite/Sulfite Reductase" terminator (SEQ ID NO:150) at the 3' end of the Cre gene. The BlastR selectable marker and GFP reporter cassettes are arranged in tandem in the construct, and together they are flanked by identical lox sites in the same orientation. Sequences that are flanked by loxP sites are commonly referred to as "floxed". An ammonia-repressible promoter was used so that expression of the Cre gene could be repressed on ammonium-containing media until after generating antibiotic resistant colonies and establishing full phenotypic penetrance of GFP. Additionally, cloning Cre into a vector that contains lox sites proved to be problematic, as even basal levels of Cre expression in *E. coli* looped out the floxed BlastR and GFP once Cre was cloned in. To get around this hurdle, an intron was inserted into the Cre gene disrupting the catalytic and nucleophilic domains. This resulted in the final stable vector pSGE-6483 (FIG. 13) which doesn't self-excise its floxed markers in *E. coli.*

Construct pSGE-6483 was transformed into *Nannochloropsis gaditana* and plated onto PM128 agar medium that contains ammonia but not nitrate to suppress expression of the cre recombinase, where the medium contained 100 mg/L of blasticidin. Colonies were re-patched onto the same selective PM128 media for analysis and archiving, and screened for full phenotypic penetrance of GFP by flow cytometry as described in Example 4.

A line was selected that retained GFP expression after serial culturing on ammonium-containing medium, but that lost GFP expression after serial culturing on nitrate-containing medium. Expression of both the cre recombinase and Cas9 was confirmed as assessed by Western blotting. This cre and Cas9-enabled cell line, markerless and GFP-less after culturing in the absence of ammonium, was named GE-13630.

Example 17. Knockout of Multiple LHC Genes

In the GE-13630 strain that is enabled with both Cas9 nuclease as well as cre recombinase, one or more selectable markers used in a first transformation can be deleted in the transformed strains by cre recombinase when expression of the recombinase is induced, and the same marker or markers can be re-used for subsequent transformations. This was particularly useful in efforts to knock out multiple genes. We attempted to knock out several members of the LHC protein family to see whether it would be possible to further reduce the antenna size of strains and whether antenna reduction would lead to greater productivity of the strains.

Five different guide RNAs were employed to target different five LHC genes encoding the five most abundant non-VCP LHCs in *Nannochloropsis* as assessed by transcriptomics (LHCs-810, -1373, -7521, -3454, and -5134). The target sequences of the guide RNAs for the particular LHC genes are provided in Table 14. Guide RNAs were synthesized using two annealed oligonucleotides that included a T7 promoter sequence and were used as templates for in vitro transcription as disclosed in Example 4. Guide RNAs targeting the five different LHC genes were pooled and transformed into the GE-13630 strain by electroporation along with a donor fragment encoding a zeocin resistance gene driven by the TCTP promoter (SEQ ID NO:63) and terminated by the EIF3 terminator sequence (SEQ ID NO:64); the donor fragment also included a TurboGFP gene (SEQ ID NO:65) driven by the 4AIII promoter (SEQ ID NO:66) and terminated by bidirectional terminator 5 (SEQ ID NO:67). The zeocin resistance plus GFP-containing donor fragment (SEQ ID NO:136) included flanking lox2272 sites so that the zeocin resistance gene cassette and GFP gene cassette could be excised by the cre recombinase. The electroporated cells were transferred to blasticidin-containing PM128 liquid medium in which ammonium, which represses the expression of the cre recombinase, was the sole nitrogen source.

Cells that grew in liquid culture that included zeocin were then subjected to a second transformation with the same set of five guide RNAs targeting LHCs 810, 1373, 7521, 3454, and 5134. In this case, the guide RNAs were transformed along with a donor fragment (SEQ ID NO:137) that included a blasticin resistance cassette that included a blasticin resistance gene (SEQ ID NO:6) driven by the TCTP promoter (SEQ ID NO:63) and terminated by the EIF3 terminator sequence (SEQ ID NO:64); the donor fragment also included a TurboGFP gene (SEQ ID NO:65) driven by the 4AIII promoter (SEQ ID NO:66) and terminated by bidirectional terminator 5 (SEQ ID NO:67). The blasticin resistance plus GFP-containing donor fragment (SEQ ID NO:136) included flanking loxP sites to allow cre-mediated recombination to excise the blasticidin resistance gene and GFP gene.

The cells that had been through two rounds of electroporation with the LHC-810, -1373, -7521, -3454, and -5134 guide RNAs were cultured in liquid medium containing blasticin in which ammonium, which represses the expression of the cre recombinase, was the sole nitrogen source.

Cell that grew in liquid culture that included blasticin were then subjected to a third transformation with the same set of five guide RNAs targeting LHCs 810, 1373, 7521, 3454, and 5134. In this case, the guide RNAs were transformed along with a donor fragment (SEQ ID NO:138) that included a hygromycin resistance cassette that included a hygromycin resistance gene driven by the TCTP promoter (SEQ ID NO:63) and terminated by the EIF3 terminator sequence (SEQ ID NO:64); the donor fragment also included a TurboGFP gene (SEQ ID NO:65) driven by the 4AIII promoter (SEQ ID NO:66) and terminated by bidirectional terminator 5 (SEQ ID NO:67). The donor fragment included loxN sites flanking the hygromycin resistance gene cassette plus GFP gene cassette to allow excision of these genes on de-repression of the cre recombinase.

Cells from the third and final transformation of the five non-VCP LHC guide RNA sequences were plated on PM128 (ammonium-containing medium) plates and PCR-screened for the presence of disrupted LHC-810, LHC-1373, LHC-7521, LHC-3454, and LHC-5134 genes. Primers used to screen for disrupted gene loci are provided in Table 14. An example of such a screen is shown in FIG. 14A-E, where PCR bands from amplification of knocked-out loci have a different size than bands amplified from wild type cells. Most likely because of basal or leaky levels of expression of the cre recombinase gene, in many cases the donor fragment had already excised from the PCR-screened cells. However, differences in the size of the disrupted gene loci could still be detected by PCR in most cases, as well as by sequencing.

Figure 15:
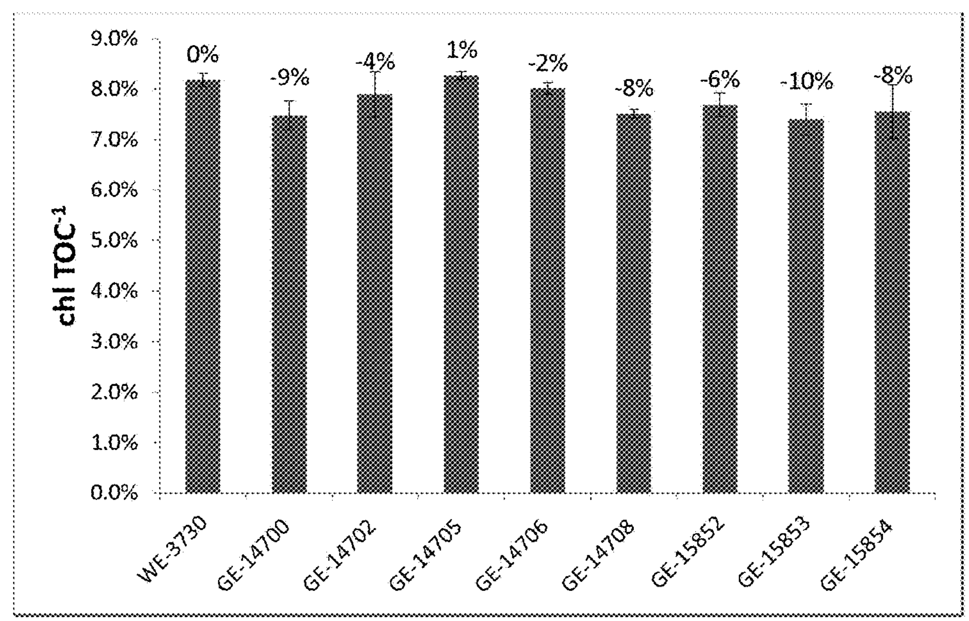
FIG. 15. Modest reduction in chlorophyll in single LHC gene knockout strains.

No significant, or only modest, reductions of chlorophyll content were observed in most double or triple LHC KO mutant strains, largely due to an increase in abundance of non-targeted, possibly functional redundant LHCs in these mutants (FIG. 15), as was found for several double LHC knockout mutants analyzed by mass spectrometry (Table 17 and Table 18). Several double or triple LHC KO mutants were selected for the further characterization: GE-15853 (with knocked out LHC-1373, LHC-7521, and LHC-3454 genes) and GE-15854 (with knocked out LHC-1373, LHC-3454, LHC-5134 genes). These two strains were also used streaked on PM129 nitrate-containing medium to de-repress expression of the cre recombinase gene and thereby remove the blasticin resistance, zeocin resistance, and hygromycin resistance genes. PCR was performed to ensure that the GE-15853 and GE-15854 used for further modifications lacked all three markers. The markerless triple LHC knockout strains GE-15853 and GE-15854, which were generated by three sequential transformations which each used a donor DNA with a unique selectable marker and five different gene-specific guide RNAs, followed by derepression of cre recombinase expression to allow excision of the markers used in the three donor DNAs, were used as the parental strains for knocking out the VCP genes.

Example 18. Knockout of Multiple VHC Genes in Triple LHC Knockout Lines

Figures 16A, 16B:
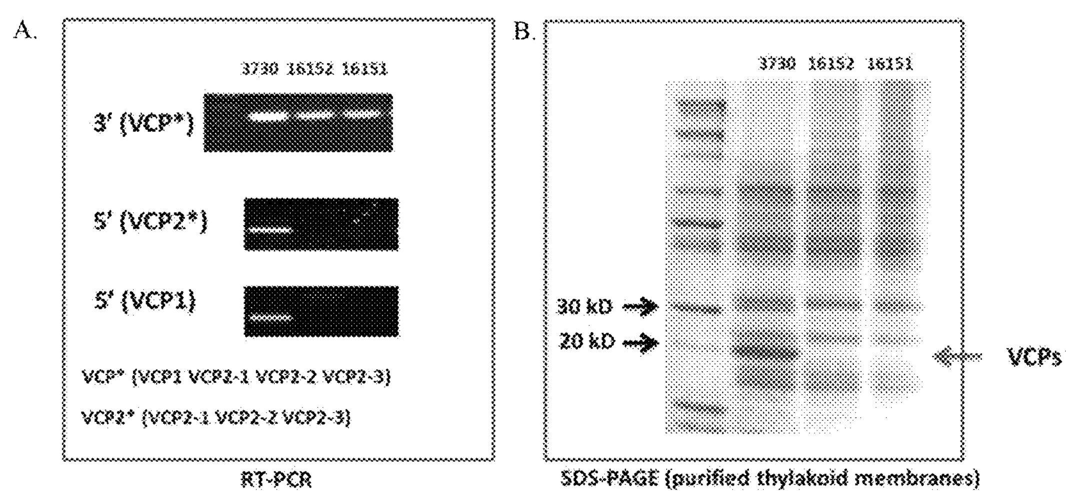
FIGS. 16A-16B. (A) Gels showing amplicons from RT-PCR to detect specific VCP transcripts; (B) protein gel showing GE-16152 and GE-16151 lack VCP proteins.

The markerless triple LHC knockout strains GE-15853 and GE-15854 were each transformed with a guide RNA having a target sequence (SEQ ID NO:16) homologous to all four *Nannochloropsis gaditana* VCP genes. Transformation of the guide RNA, along with a donor fragment that included a hygromycin resistance cassette (SEQ ID NO:15) was performed as disclosed in Example 4. The resulting hygromycin-resistant colonies were screened by colony PCR for disruption of the VCP genes using the primer sequences SEQ ID NO:50 and SEQ ID NO:51 to detect disruption of the VCP1 gene, SEQ ID NO:52 and SEQ ID NO:53 to detect disruption of the VCP2a gene, SEQ ID NO:54 and SEQ ID NO:55 to detect disruption of the VCP2b and VCP2c genes. Strains GE-16150 and GE-1652 were found to have disrupted VCP1, VCP2a, VCP2b, and VCP2c loci. To promote deletion of the selectable marker cassette, the strains were streaked on nitrate-containing medium (PM129), a medium on which expression of the cre recombinase is de-repressed. Reverse transcription PCR using VCP transcript-specific primers was performed on lines GE-16150 and GE-1652. These strains were found to produce transcripts that amplified with VCP-specific primers; however, they were larger than corresponding wild type VCP transcripts (FIG. 16A), and sequencing of the PCR products revealed the amplified transcript sequences included nonsense mutations in the 5' region of the transcripts introduced by the Cas9-mediated donor fragment and its subsequent deletion using the cre recombinase. SDS PAGE of proteins isolated from strains GE-16150 and GE-1652 revealed a complete absence of the VCP band prominent in wild type cells (FIG. 16B).

The Triple LHC knockout, Quadruple VCP knockout lines GE-16151 and GE-16152 had a chlorophyll reduction of 37-51% with respect to wild type cells, and a 40% reduction in the cross section of photosystem II (PSII).

Example 19. Knockout of Chloroplastic SRP54 Pathway Genes in *Nannochloropsis*

As described in commonly-owned, co-pending U.S. patent application Ser. No. 15/130,866 and corresponding PCT application PCT/US16/27976, published as WO 2016/168756, both filed Apr. 15, 2016 and incorporated by reference in their entireties, another strategy for antenna reduction in *Nannochloropsis* included targeting components of the chloroplastic SRP54 pathway. The *Nannochloropsis gaditana* cpSRP54 gene (cpSRP-6676, coding sequence provided as SEQ ID NO:139) was targeted for disruption by first making a DNA construct for producing a guide RNA in which the construct included the sequence of a chimeric guide engineered downstream of a T7 promoter. The chimeric guide sequence included a target sequence (SEQ ID NO:140) homologous to a sequence within the cpSRP-6676 gene sequence, and also included the transactivating CRISPR (tracr) sequence. The chimeric guide sequence was synthesized as described in Cho et al., 2013 (Nature biotechnology 31, 230-232) by first making a DNA template made up of complementary DNA oligonucleotides that were annealed to create a double-stranded DNA template which was used in in vitro transcription reactions using the MEGAshortscript™ T7 Kit (Life Technologies # AM1354M) according to the manufacturer's instructions to synthesize the guide RNA. The resulting RNA was purified using Zymo-Spin™ V-E columns (Zymo Research #C1024-25) according to manufacturer's protocol.

For targeted knockout of the cpSRP54-6676 locus, Cas9 Editor line GE-6791 was transformed by electroporation using 5 μg of purified chimeric guide RNA targeting the cpSRP54-6676 gene (target sequence SEQ ID NO:140) and 1 μg of the selectable donor DNA (Hyg Resistance Cassette; SEQ ID NO:15) essentially as described in US 2014/0220638. Following electroporation, cells were plated on PM124 agar media containing hygromycin to select for transformants that incorporated the hygromycin resistance cassette. Transformants were patched onto a fresh plate and screened by colony PCR for insertion of the donor fragment into the cpSRP54-6676 gene.

For colony PCR screening, a small amount of cells from a colony to be screened was suspended into 100 μl of 5% Chelex 100 Resin (BioRad)/TE solution and the suspension was boiled for 10 minutes at 99° C., after which the tubes were briefly spun. One microliter of the lysate supernatant was added to a PCR reaction mix, in which the PCR mixture and reactions were set up and performed according to the QIAGEN Fast Cycling PCR Master Mix Protocol from the manufacturer (Handbook available at qiagen.com). The primers used to detect the insertion of the donor fragment into the targeted locus of the cpSRP54-6676 gene were SEQ ID NO:141 and SEQ ID NO:142. Based on the PCR-based colony screening, knockout strain GE-15274 was tested for reduced chlorophyll, photosynthetic properties, and productivity.

Additional genes of the SRP54 pathway for insertion of proteins into the thylakoid membranes such as the Ftsy polypeptide (coding sequence SEQ ID NO:143) were also disrupted using synthesized guide RNAs that were introduced, along with the HygR cassette donor DNA (SEQ ID NO:15) into Cas9 Editor line GE-6791 in the same way. For disruption of the gene encoding the ALB3b polypeptide (SEQ ID NO:144, coding sequence SEQ ID NO:145), the target sequence used in making the guide RNA was SEQ ID NO:146. In addition, as a control, the gene encoding the cytosolic SRP54 polypeptide (cytoSRP54, encoded by SEQ ID NO:147) was targeted for knockout using a guide sequence that included target sequence SEQ ID NO:148). In each case the HygR cassette donor DNA (SEQ ID NO:15) was co-transformed into Cas9 Editor line GE-6791 with the guide sequence. Based on PCR-based colony screening, each of the resulting knockout strains GE-15272 (Ftsy Knockout), GE-14315 (ALB3 Knockout), and GE-14792 (Cytosolic SRP54 Knockout) was tested for chlorophyll content, photosynthetic properties, and productivity.

Figure 17A:
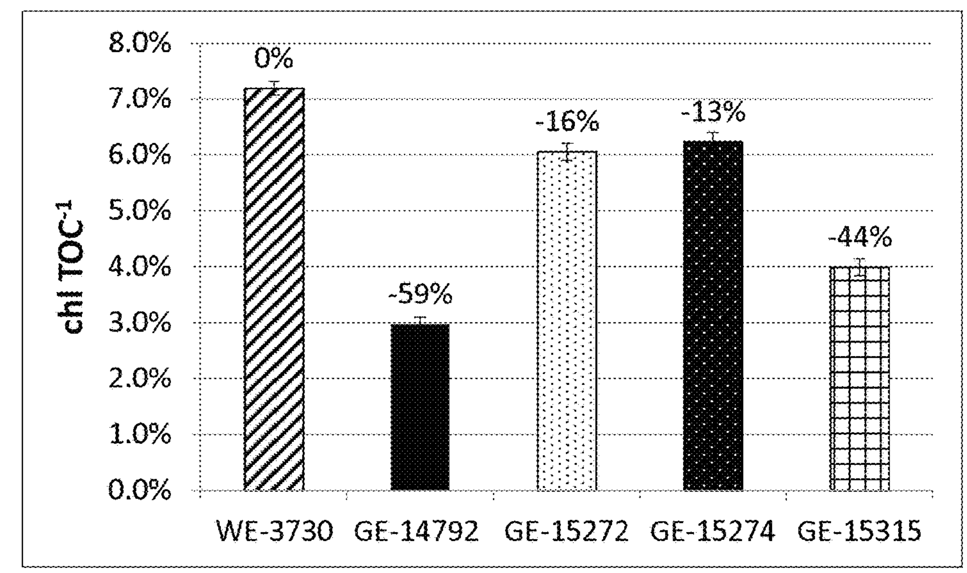
FIGS. 17A-17B. (A) chlorophyll per TOC content of chloroplastic SRP54 pathway mutants, (B) chlorophyll per cell of chloroplastic SRP54 pathway mutants.
Figure 17B:
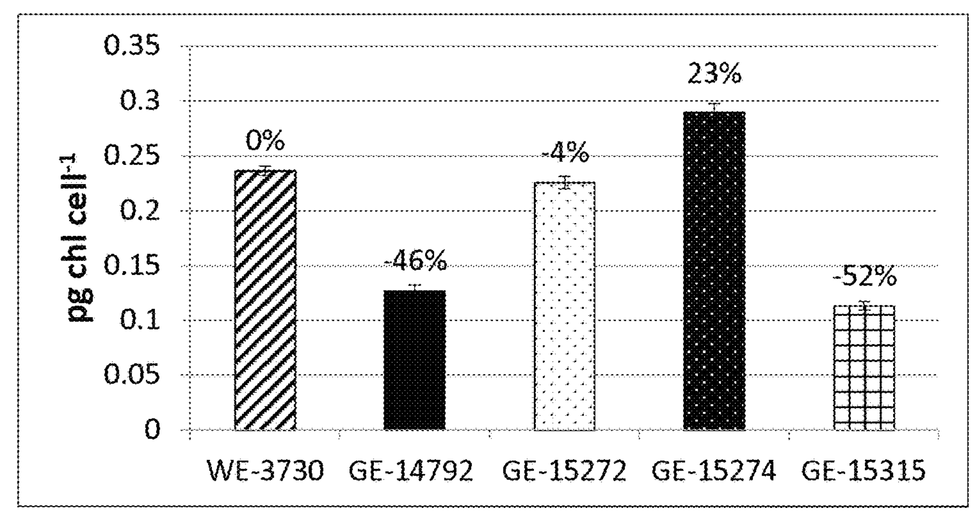
Figure 19:
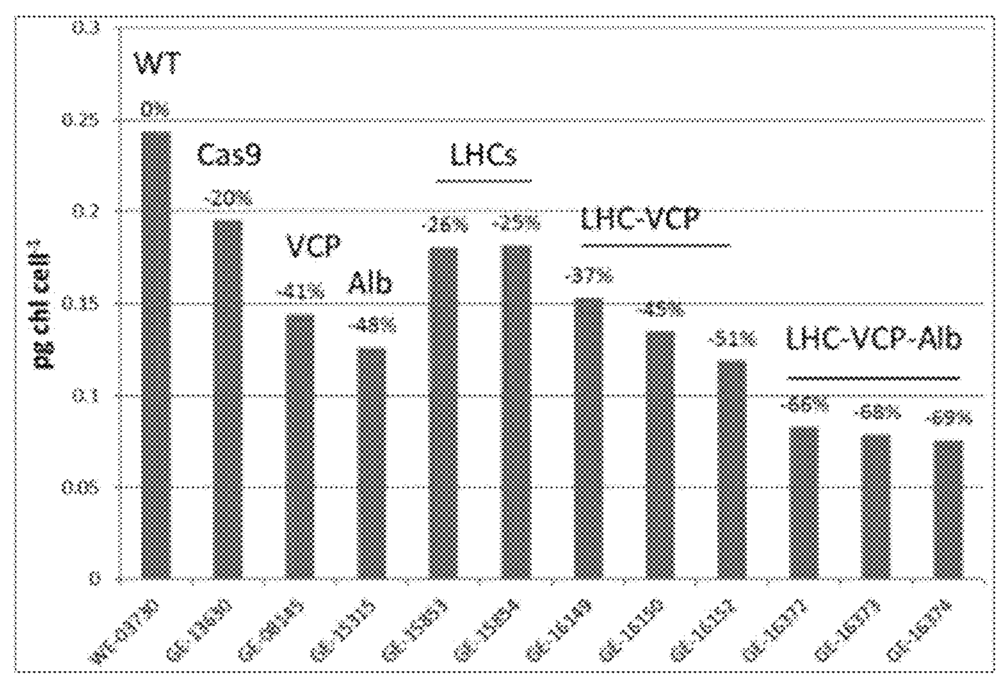
FIG. 19. Graph showing decrease in chlorophyll of various gene knockout strains compared with wild type WT-3730 and the Cas9 parental strain. "VCP" "Alb" and "LHC" labels refer to the genes knocked out in the strains shown.

All of the chloroplastic SRP54 pathway mutants demonstrated a reduction in chlorophyll relative to wild type cells, however this reduction was moderate for the cpSRP54 mutant (strain GE-15274) and the FtsY mutant strain (GE-15272) (FIGS. 17A and B). Strain GE-15315, knocked out in the ALB3 gene, later determined to be the ALB3B gene (coding sequence SEQ ID NO:145) (the ALB3A gene could not be knocked out, and is likely essential), had an approximately 40% reduction in chlorophyll. This ALB3B knockout mutant appeared to be specifically reduced in the cross section of PSII.

Example 20. Knockout of ALB3b Gene in Multiple LHC, VCP Knockout Strains

The GE-16152 triple (non-VCP) LHC knockout, quadruple VCP knockout line of Example 18 was used to knockout yet a further gene to further reduce chlorophyll and the photosynthetic antenna. The ALB3B gene (SEQ ID NO:145), disclosed in Example 19, was targeted using a guide RNA having the target sequence of SEQ ID NO:146.

Three ALB3 knockout strains in the GE-16152 background were designated GE-16372, GE-16373, and GE-16374, each having disrupted non-VCP LHC genes LHC-1373, LHC-7521, and LHC-3454, disrupted VCP genes VCP1, VCP2a, VCP2b, and VCP2c, and a disrupted ALB3B gene.

Strains GE-16372, GE-16373, and GE-16374 were analyzed for chlorophyll content and PSII antenna size as well as a number of photophysiological parameters, including Fv/Fm, Ek, τ, PSII concentration, alpha (a, the initial slope of the P/I curve), Pmax for O2 evolution, Pmax for carbon fixation, chlorophyll per TOC, and productivity in a semi-continuous constant light productivity assay. Analysis of various photosynthetic parameters was performed using the Fluorescence Induction and Relaxation (FIRe) technique developed to measure a comprehensive series of photosynthetic and physiological characteristics of photosynthetic organisms (Gorbunov and Falkowski (2005) "Fluorescence Induction and Relaxation (FIRe) Technique and Instrumentation for Monitoring Photosynthetic Processes and Primary Production in Aquatic Ecosystems" In: Photosynthesis: Fundamental Aspects to Global Perspectives, Proc. 13th International Congress of Photosynthesis, Montreal, Aug. 29-Sep. 3, 2004. (Eds: A. van der Est and D. Bruce), Allen Press, V.2, pp. 1029-1031). The FIRe technique relies on measurement and analysis of chlorophyll "variable fluorescence" profiles (reviewed by Falkowski et. al., 2004 Development and Application of Variable Chlorophyll Fluorescence Techniques in Marine Ecosystems. In: "Chlorophyll a Fluorescence: A Signature of Photosynthesis" (C. Papageorgiou and Govingjee, eds), Springer, pp. 757-778) which depend on the relationship between chlorophyll fluorescence and the efficiency of photosynthetic processes. This technique provides a set of parameters that characterize photosynthetic light-harvesting processes, the photochemistry in Photosystem II (PSII), and photosynthetic electron transport down to carbon fixation.

All measurements were taken using constant light (2000 μmol photons·m-2·sec-1) semicontinuous cultures (CL-SCPA) cultures (see Example 11). To obtain FV/FM and σPSII measurements of Fluorescence Induction and Relaxation (FIRe) kinetics were performed in the dark. Presented values for Fv/Fm and σPSII were calculated as an average of 6 measurements (3 measurements of each of the 2 biological replicates)–errors for these parameters did not exceed 5%. τ'Qa (time of electron transport on the acceptor side of PSII measured under saturating light conditions–effectively determined by the slowest step of linear photosynthetic electron transport) was measured from FIRe light curves and DIRK profiles. Relative to wild type volumetric PSII concentration was estimated as (Fv/σ530PSII). Errors for these parameters were estimated not to exceed 15%. Optical absorption cross section (averaged over emission spectrum of a light source) was estimated using the following equation:

$$a_{chl/TOC} = \frac{1}{[Chl/TOC]} \int_{400}^{700} \ln(10) \times \frac{OD(\lambda)}{\Delta l} \times \frac{I(\lambda)}{\int_{400}^{700} I(\lambda) d\lambda} d\lambda$$

where [Chl/TOC] is the chlorophyll/TOC of the sample, OD(λ) is the measured optical density of the sample at wavelength λ, Δl is the measuring beam pathlength in the cuvette (1 cm), I(λ) is the intensity of the light source used to grow algae at wavelength λ (see April 2016 quarterly report). The absorption cross-section of individual chlorophyll molecule (averaged over spectrum of white LED) was calculated assuming mass of chlorophyll molecule 1.49×10-21 g. Using both blue and green functional cross-sections of PSII and optical absorption cross-sections of individual chlorophyll molecule averaged over blue/green FIRe LED (data not shown), we estimated the number of chlorophyll molecules in photosystem 2. The number of photosystems was estimated by dividing total number of chlorophylls by the number of chlorophylls adjusting for photosynthetic efficiency (Φp); Φp was assumed to be 0.8.

The triple non-VCP LHC, quadruple VCP, ALB3B knockout strains GE-16373 and GE-16374 were analyzed alongside the wild type *Nannochloropsis* strain WT-3730, the Cas9 Editor line derived from WT-3730 and used to generate all knockout strains, VCP knockout strain GE-8145 (Examples 7-11), ALB3B knockout line GE-15315 (U.S. patent application Ser. No. 15/130,866 and corresponding PCT application PCT/US16/27976 (WO 2016/168756)), Triple non-VCP LHC knockout lines GE-15853 and GE-15854, Triple non-VCP LHC/Quadruple VCP knockout lines GE-16149, GE-16150, and GE-16152. The strains were acclimated to low light (140 μmol photons·m-2·sec-1) prior to measurement. Results for the strains GE-15853, GE-15854, GE-16152, and GE-16374 are summarized in the table of FIG. 18.

Chlorophyll per cell for the knockout strains is compared in the bar graph of FIG. 25, where the percentage difference from the wild type value for each of the strains is provide over the bars. It can be seen that triple knockout LHCs (strains GE-15853 and GE-15854) demonstrated only about a 25% drop in chlorophyll with respect to wild type cells, whereas eliminating expression of the VCPs (strain GE-8145) resulted in an approximately 40% decline in chlorophyll. A further decline in chlorophyll content was seen in the mutants having disrupted genes encoding both non-VCP LHCs (3 genes) and VCPs (4 genes): strains GE-16149, GE16150, and GE-16152 demonstrated between a 35% and an approximately 50% reduction in chlorophyll. The most severe loss of chlorophyll was experienced by the strains that had 3 disrupted non-VCP LHC genes, 4 disrupted VCP genes, and a disrupted ALB3B gene: These strains (GE-16372, GE-16373, and GE-16374) had a decline in chlorophyll of between about 65% and about 70% with respect to wild type cells.

Figure 20A:
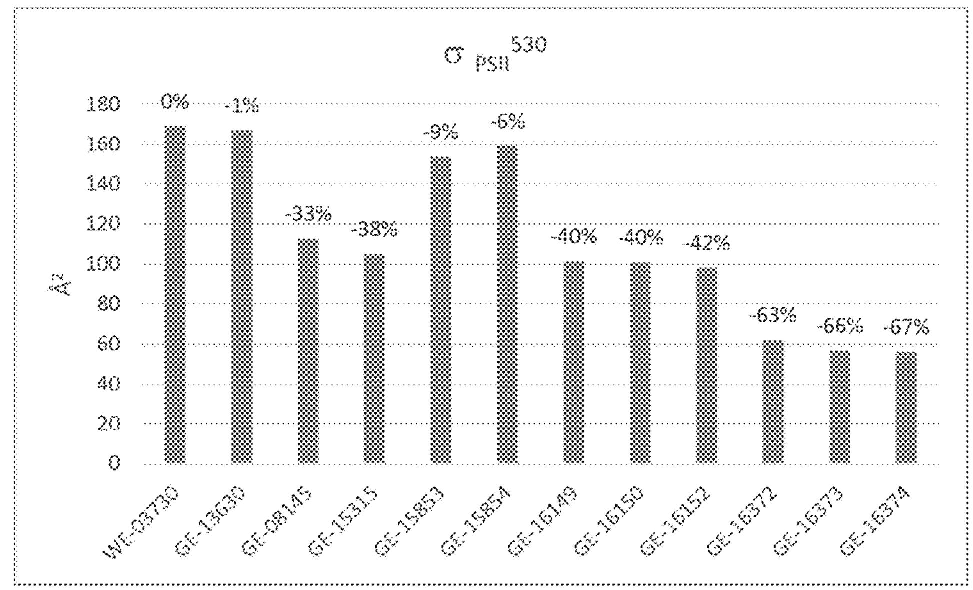
FIGS. 20A-20B. (A) The cross-sectional size of PSII and (B) maximal oxygen evolution rates for the various knockout strains shown in FIG. 19.
Figure 20B:
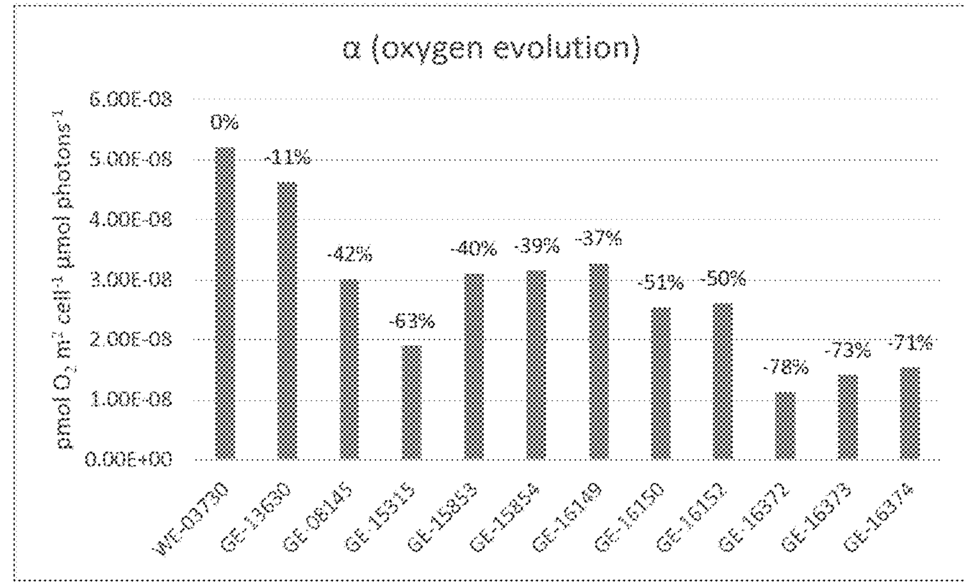
Figure 21A:
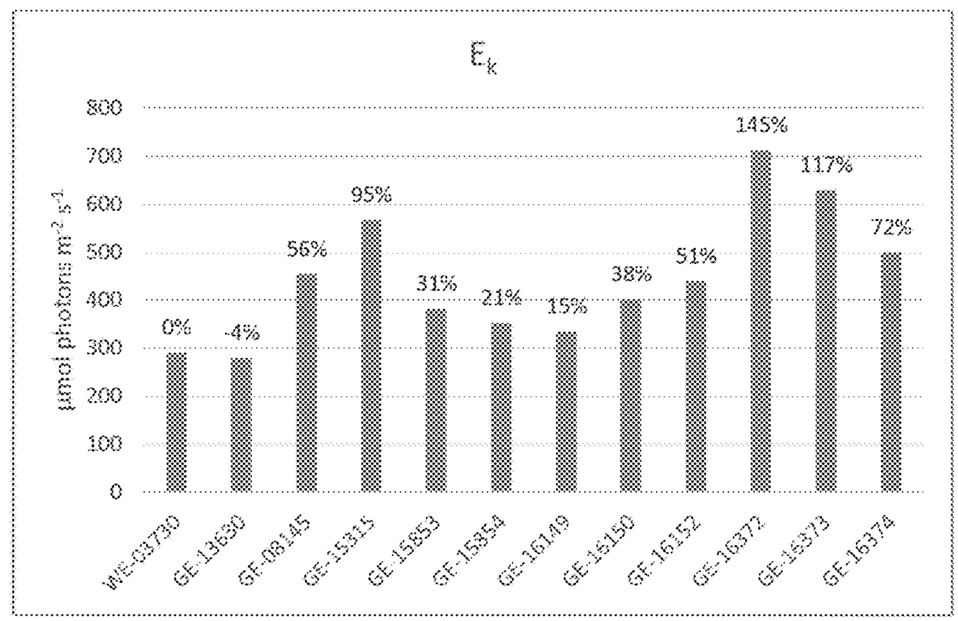
FIGS. 21A-21B. (A) Ek and (B) Fv/Fm for the various knockout strains shown in FIG. 19.
Figure 21B:
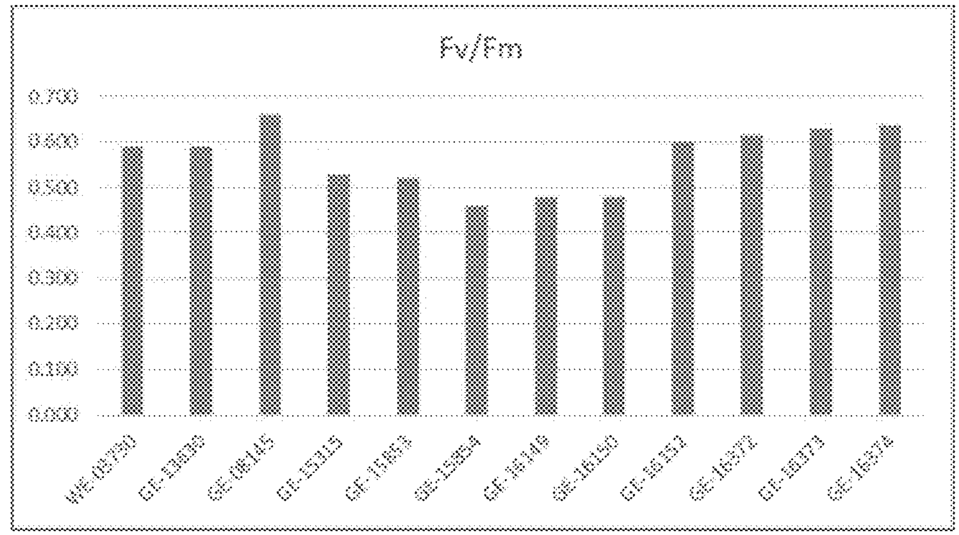

Corresponding decreases in the cross-sectional size of photosystem II (σPSII) measured at 530 nm are shown in FIG. 20A, where the decrease in σPSII follows the same general pattern as the decline in total cellular chlorophyll content, which indicates that reduction is primarily related to loss of pigments in the photosynthetic antenna and not in the number of photosystems. This is further confirmed by the behavior of the initial slope of the PI curve, "α" (this parameter determines the functional cross-section of oxygen evolution of the cell and is a product of the absorption cross-section of photosystem II, number of active PSII and quantum yield of photochemical energy conversion in PSII) varies among the knockout mutants but is significantly lower than that of the wild type strain in all of the knockout strains (FIG. 20B). Ek, on the other hand, is increased in all knockout strains and particularly in VCP attenuated strain GE-8145, ALB3B knockout strain 15315, and particularly in the triple LHC/quadruple VCP knockout/ALB3B knockout strains (GE-16372, GE-16373, and GE-16374) FIG. 21A. Fv/Fm, a measure of quantum efficiency, was not found to be significantly different in the attenuated strains FIG. 21B, suggesting that photosynthesis was not compromised in strains lacking abovementioned LHCs and VCPs.

Figures 22A, 22B:
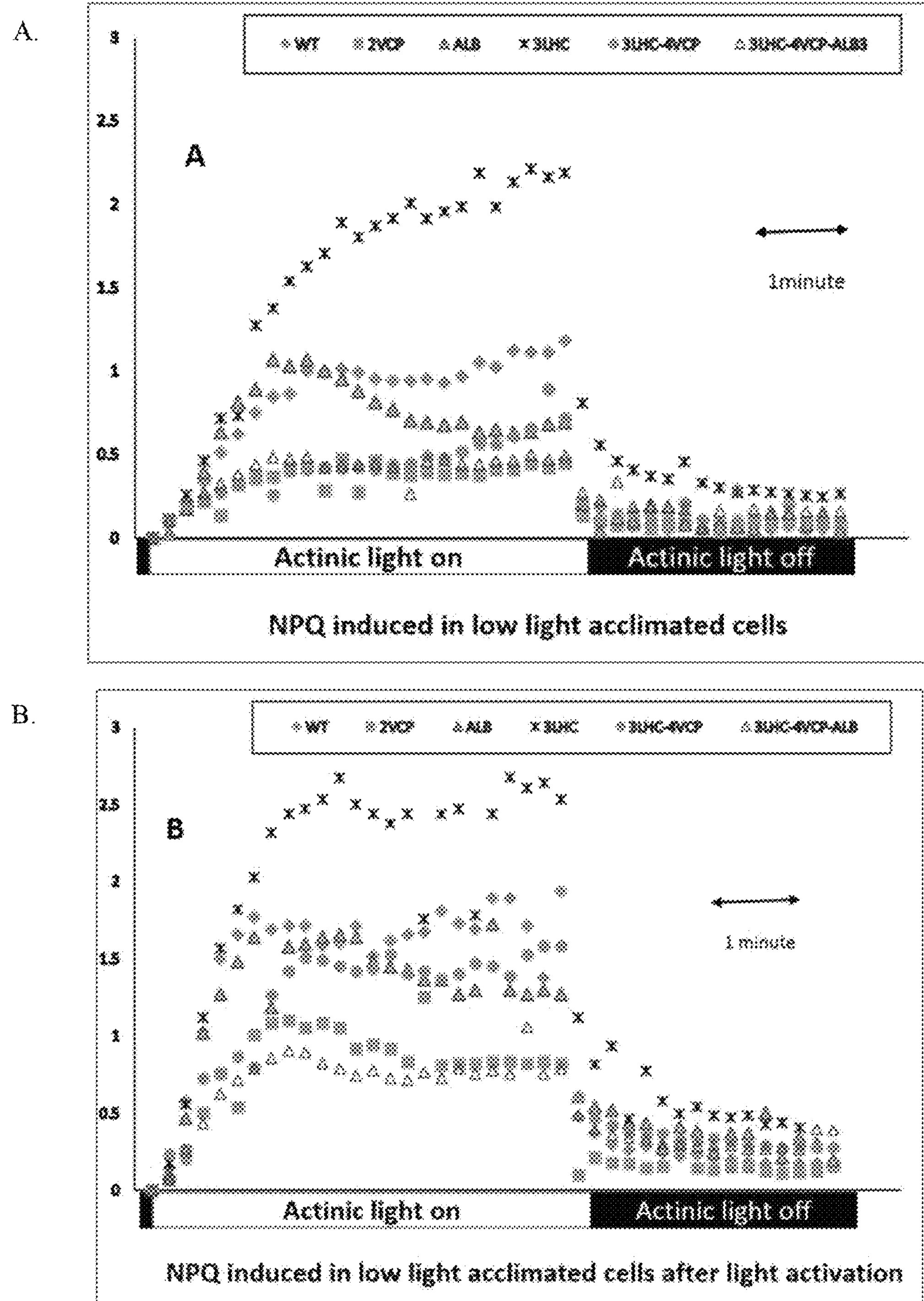
FIGS. 22A-22B.

NPQ was measured with Dual-PAM after cells dark-adapted for 30 minutes. For pre-light activation, low light acclimated cells were exposed in high light (500 μE) for 30 minutes, then dark-adapted for 30 minutes before measurement. Wild type and KO strain were acclimated to low light (100 μE) for 5 days with daily dilution to maintain a similar cell dentistry (1×108 cells ml-1). Similar NPQ kinetics of multiple strains with the same genotypes were observed, and only one reprehensive kinetics from each genotype is shown in FIGS. 22A and 22B: Parental Cas9 and cre recombinase-enabled strain GE-13630 (diamonds); Strain GE-8145 with KO of two VCP genes and no detectable expression of any VCP genes (squares), Alb3B knockout Strain GE-15315 (filled triangles); LHC triple knockout strain GE-15853 (X'x); triple LHCs/quadruple VCP knockout strain GE-16152 (circles); and triple LHCs/quadruple VCP/ALB3B knockout strain GE-16374 (open triangles).

The kinetics of nonphotochemical quenching (NPQ) of the attenuated strains did however show dramatic changes as shown in FIGS. 22A and 22B. NPQ represents a protective mechanism that quenches singlet-excited chlorophylls (Chl) through heat dissipation to remove excess excitation energy. As shown in FIG. 22A, losing VCPs, either in wild type background or in LHC knockout and ALB knockout background, causes a significant reduction in NPQ; in contrast, knockout of 3 abundant LHCs (e.g., LHC-, LHC-, and LHC-) results in a dramatic increase in NPQ. As Knocking out of LHC has previously been shown to induce increased level of VCP expression, the increased NPQ in the LHC triple KO mutants may partially be attributed to increased VCP level.

Following the initial characterization of the LHC KO strains, they were submitted for semicontinuous culture productivity testing as described in Example 9. Results are provided in the rightmost column of the table of FIG. 18 and show that the antenna reduced strains maintain the same levels of antenna reduction during semicontinuous constant light culturing where the light peaks at approximately 2000 μE·m-2·s-1 as previously observed under low light. The most antenna reduced strains (attenuated in expression of 3 LHCs, 4 VCPs, plus the ALB3B gene) showed a dramatic decrease in the number of chlorophylls per PSII, and an increase in the chlorophyll specific absorption cross-section. However, only GE-16152 (knocked out in three abundant non-VCP LHC genes as well as four VCP genes) showed improvements in productivity. Thus, further reduction of the antenna by knockout of ALB3B in this background (FIGS. 20 and 26) did not lead to increases in productivity, at least in the constant high light semicontinuous culture system.

We claim:

1. A recombinant or classically-mutagenized *Nannochloropsis* alga that has attenuated expression of at least one violaxanthin chlorophyll a-binding protein (VCP) gene.

2. The recombinant or classically-mutagenized mutant *Nannochloropsis* alga of claim 1, wherein expression of all VCP genes of the alga are attenuated.

3. The recombinant or classically-mutagenized mutant *Nannochloropsis* alga of claim 1, wherein the amount of RNA transcribed by all of the VCP genes in the mutant alga is less than 10% of the amount of RNA transcribed by all of the VCP genes in a control alga.

4. A recombinant or classically-mutagenized *Nannochloropsis* alga according to claim 1, wherein the alga has at least one disrupted VCP gene.

5. The recombinant or classically-mutagenized *Nannochloropsis* alga of claim 4, wherein all VCP genes of the alga are disrupted.

6. The recombinant or classically-mutagenized *Nannochloropsis* alga of claim 4, wherein the at least one VCP gene is disrupted by insertional mutagenesis.

7. The recombinant or classically-mutagenized *Nannochloropsis* alga of claim 4, wherein the at least one gene is disrupted by deletion of all or a portion of one or more VCP genes.

8. The recombinant or classically-mutagenized *Nannochloropsis* alga of claim 4, wherein the at least one gene is disrupted by homologous recombination.

9. The recombinant or classically-mutagenized *Nannochloropsis* alga of claim 4, wherein the at least one gene is disrupted by CRISPR RNA-guided nuclease activity.

10. The recombinant or classically-mutagenized *Nannochloropsis* alga of claim 1, wherein the mutant alga exhibits a higher Electron Transport Rate (ETR) than a control alga substantially identical to the mutant alga with the exception that the control alga does not have attenuated expression of at least one VCP gene.

11. The recombinant or classically-mutagenized *Nannochloropsis* alga of claim 1, wherein the mutant alga exhibits lower Non-Photochemical Quenching (NPQ) induction than a control alga substantially identical to the alga with the exception that the control alga does not have attenuated expression of at least one VCP gene.

12. The recombinant or classically-mutagenized *Nannochloropsis* alga of claim 1, wherein the chlorophyll content of the mutant algal is reduced by at least 15% on a per cell basis.

13. The recombinant or classically-mutagenized *Nannochloropsis* alga of claim 1, wherein the mutant alga has increased biomass productivity with respect to a control alga that does not have attenuated expression of at least one VCP gene.

* * * * *

```
SEQUENCE LISTING

<160> NUMBER OF SEQ ID NOS: 150

<210> SEQ ID NO 1
<211> LENGTH: 217
<212> TYPE: PRT
<213> ORGANISM: Nannochloropsis gaditana
<220> FEATURE:
<221> NAME/KEY: misc_feature
<223> OTHER INFORMATION: VCP1 protein 7958

<400> SEQUENCE: 1

Met Arg Phe Phe Glu Gln Asn Gly Arg Thr Ala Ala Leu Leu Thr Val
1               5                   10                  15

Ser Ser Leu Met Gly Ala Ser Ala Phe Val Ala Pro Ala Pro Lys Phe
            20                  25                  30

Ser Arg Thr Arg Gly Val Ala Arg Met Ser Phe Glu Gly Glu Ala Gly
        35                  40                  45

Val Thr Ala Pro Leu Gly Tyr Trp Asp Pro Leu Gly Phe Ser Ala Asp
    50                  55                  60

Gly Asp Val Glu Lys Phe Asn Arg Tyr Arg Ala Ile Glu Ile Lys His
65                  70                  75                  80

Gly Arg Val Ala Met Leu Ala Met Leu His Thr Leu Val Thr Gly Leu
                85                  90                  95

Gly Val Lys Leu Pro Gly Leu Val Ala Ala Gly Asp Gly Ile Pro Ala
            100                 105                 110

Ser Met Pro Ala Gly Ile Asn Ala Ile Thr Ser Gly Ala Trp Ala Ala
        115                 120                 125

Gln Gly Trp Ala Gln Val Leu Leu Phe Cys Ser Ala Leu Glu Val Leu
    130                 135                 140

Ala Pro Gln Lys Glu Asp Lys Ile Pro Gly Asp Val Gln Pro Asp Thr
145                 150                 155                 160

Ser Ala Phe Ala Lys Phe Glu Asp Lys Thr Glu Glu Glu Ala Leu Ala
                165                 170                 175
```

```
Tyr Gln Asn Lys Glu Ile Asn Asn Gly Arg Leu Ala Met Val Ala Trp
            180                 185                 190

Thr Gly Ala Thr Val Gly Ala Leu Leu Thr Asn Gly Glu Asp Pro Ile
        195                 200                 205

Thr Thr Leu Leu Ala Lys Leu Gly Asn
    210                 215


<210> SEQ ID NO 2
<211> LENGTH: 210
<212> TYPE: PRT
<213> ORGANISM: Nannochloropsis gaditana
<220> FEATURE:
<221> NAME/KEY: misc_feature
<223> OTHER INFORMATION: VCP2a, VCP2b, and VCP2c proteins

<400> SEQUENCE: 2

Met Lys Thr Ala Ala Leu Leu Thr Val Ser Ser Leu Met Gly Ala Ser
1               5                   10                  15

Ala Phe Val Ala Pro Ala Pro Lys Phe Ser Arg Thr Arg Gly Val Ala
            20                  25                  30

Arg Met Ser Phe Glu Asp Glu Ala Gly Val Thr Ala Pro Leu Gly Tyr
        35                  40                  45

Trp Asp Pro Leu Gly Phe Ser Ala Asp Gly Asp Val Glu Lys Phe Asn
    50                  55                  60

Arg Tyr Arg Ala Ile Glu Ile Lys His Gly Arg Val Ala Met Leu Ala
65                  70                  75                  80

Met Leu His Thr Leu Val Thr Gly Leu Gly Val Lys Leu Pro Gly Leu
                85                  90                  95

Val Ala Ala Gly Asp Gly Ile Pro Ala Ser Met Pro Ala Gly Ile Asn
            100                 105                 110

Ala Ile Thr Ser Gly Ala Trp Ala Ala Gln Gly Trp Ala Gln Val Leu
        115                 120                 125

Leu Phe Cys Ser Ala Leu Glu Val Leu Ala Pro Gln Lys Glu Asp Lys
    130                 135                 140

Ile Pro Gly Asp Val Gln Pro Asp Thr Ser Ala Phe Ala Lys Leu Glu
145                 150                 155                 160

Asp Lys Thr Glu Glu Glu Ala Leu Ala Tyr Gln Asn Lys Glu Ile Asn
                165                 170                 175

Asn Gly Arg Leu Ala Met Val Ala Trp Thr Gly Ala Thr Val Gly Ala
            180                 185                 190

Leu Leu Thr Asn Gly Glu Asp Pro Ile Thr Thr Leu Leu Ser Lys Leu
        195                 200                 205

Gly Asn
    210


<210> SEQ ID NO 3
<211> LENGTH: 654
<212> TYPE: DNA
<213> ORGANISM: Nannochloropsis gaditana
<220> FEATURE:
<221> NAME/KEY: misc_feature
<223> OTHER INFORMATION: VCP1 coding sequence

<400> SEQUENCE: 3

atgcgttttt tcgaacaaaa tggaaggacc gccgctctgc tcaccgtctc ctccctcatg      60

ggagcctctg cctttgtggc ccccgccccc aagttcagcc gcacccgcgg tgttgcccgc     120

atgtccttcg agggcgaggc cggcgtgacc gcccccccttg gctactggga ccccccttggc    180
```

```
ttctccgccg atggtgatgt cgagaagttc aaccgttacc gcgccatcga gatcaagcac    240

ggccgagtgg ccatgcttgc catgctccac accctggtga ccggcctcgg cgtgaagctc    300

cccggccttg tggctgccgg tgacggcatc cccgcctcca tgcccgcggg catcaacgcc    360

atcacctccg gcgcttgggc cgcacaggga tgggcgcagg tgctcctctt ctgctccgcc    420

ctcgaggtcc tggcccccca gaaggaggac aagatccccg ggatgtgca gcccgacacc     480

tctgccttcg ccaagttcga ggacaagacc gaggaggagg cactcgccta ccagaacaag    540

gagatcaaca acggccgcct ggccatggtt gcctggaccg gagccactgt gggcgccctc    600

ctcaccaacg gcgaggaccc catcaccacc ctcctggcca agctcggcaa ctaa          654
```

```
<210> SEQ ID NO 4
<211> LENGTH: 633
<212> TYPE: DNA
<213> ORGANISM: Nannochloropsis gaditana
<220> FEATURE:
<221> NAME/KEY: misc_feature
<223> OTHER INFORMATION: VCP2a, VCP2b, and VCP2c coding sequence

<400> SEQUENCE: 4

atgaagaccg ccgctctgct caccgtctcc tccctcatgg gcgcctccgc ctttgtggcc     60

cccgccccca agttcagccg cacccgcggt gttgcccgca tgtccttcga ggacgaggcc    120

ggcgtgaccg ccccccctggg ctactgggac ccgcttggct tctccgccga tggtgatgtc   180

gagaaattca accgttaccg cgccatcgag atcaagcacg gccgagtggc catgcttgcc    240

atgctccaca ccctggtgac cggcctcggc gtgaagctcc ccggccttgt ggctgccggt    300

gacggcatcc ccgcctccat gcccgcgggc atcaacgcca tcacctccgg cgcttgggcc    360

gcacagggat gggcgcaggt gctcctcttc tgctccgccc tcgaggtcct ggcccccccag   420

aaggaggaca agatccccgg ggatgtgcag cccgacacct ctgccttcgc caagctcgag    480

gacaagaccg aggaggaggc gctcgcctac cagaacaagg agatcaacaa cggccgcctg    540

gccatggttg cctggaccgg agccactgtg ggcgccctcc tcaccaacgg cgaggacccc    600

atcaccaccc ttctctccaa gctcggcaac taa                                 633
```

```
<210> SEQ ID NO 5
<211> LENGTH: 924
<212> TYPE: DNA
<213> ORGANISM: Nannochloropsis gaditana
<220> FEATURE:
<221> NAME/KEY: misc_feature
<223> OTHER INFORMATION: VCP1 gene 7958

<400> SEQUENCE: 5

atgcgttttt tcgaacaaaa tggagtggcg tgtgtatgtt atagagtgat aagtctttct     60

ggctggactt gcctcctcac tggtctgtct cttcccccac acctcaactc cgagcagagg    120

accgccgctc tgctcaccgt ctcctccctc atgggagcct ctgcctttgt ggcccccgcc    180

cccaagttca gccgcacccg cggtgttgcc cgcatgtcct tcgagggcga ggccggcgtg    240

accgcccccc ttggctactg ggtacgtgaa tcatcactct tcactcgatc tttggcctcc    300

ccgcgtcgta ccatgatgtc acattctcta acacttcgtc cttgaatagg acccccttgg    360

cttctccgcc gatggtgatg tcgagaagtt caaccgttac cgcgccatcg agatcaagca    420

cggccgaggt aggcgattcg agagagatct tatcccatcg gccctggagg tactcactcg    480

ctcctttccc ccttttgttc cgcctcatct cccgcagtgg ccatgcttgc catgctccac    540

accctggtga ccggcctcgg cgtgaagctc cccggccttg tggctgccgg tgacggcatc    600
```

```
cccgcctcca tgcccgcggg catcaacgcc atcacctccg gcgcttgggc cgcacaggga    660

tgggcgcagg tgctcctctt ctgctccgcc ctcgaggtcc tggcccccca gaaggaggac    720

aagatccccg ggatgtgca gcccgacacc tctgccttcg ccaagttcga ggacaagacc     780

gaggaggagg cactcgccta ccagaacaag gagatcaaca acggccgcct ggccatggtt    840

gcctggaccg gagccactgt gggcgccctc ctcaccaacg gcgaggaccc catcaccacc    900

ctcctggcca agctcggcaa ctaa                                           924
```

```
<210> SEQ ID NO 6
<211> LENGTH: 867
<212> TYPE: DNA
<213> ORGANISM: Nannochloropsis gaditana
<220> FEATURE:
<221> NAME/KEY: misc_feature
<223> OTHER INFORMATION: VCP2a gene

<400> SEQUENCE: 6

atgaagaccg ccgctctgct caccgtctcc tccctcatgg gcgcctccgc ctttgtggcc     60

cccgccccca agttcagccg cacccgcggt gttgcccgca tgtccttcga ggacgaggcc    120

ggcgtgaccg ccccccctgggg ctactgggtg agtctcatgg aacacgttag gtttcgtaat  180

gtgcatgtga cgctcaagcc agtccaccca ccctctcctc cgtaaatctc acaggacccg    240

cttggcttct ccgccgatgg tgatgtcgag aaattcaacc gttaccgcgc catcgagatc    300

aagcacggcc gaggtaagag atggctaggt gcatggtcga gggtgacgtg attgcgaaga    360

actgtccctg ctgatctcga gacgatacct gaagtagagt ttggatccaa gcatgaactg    420

acttcacctc acccatgtca cattcatatc tgtccggcag tggccatgct tgccatgctc    480

cacaccctgg tgaccggcct cggcgtgaag ctccccggcc ttgtggctgc cggtgacggc    540

atccccgcct ccatgcccgc gggcatcaac gccatcacct ccggcgcttg ggccgcacag    600

ggatgggcgc aggtgctcct cttctgctcc gccctcgagg tcctggcccc ccagaaggag    660

gacaagatcc ccggggatgt gcagcccgac acctctgcct tcgccaagct cgaggacaag    720

accgaggagg aggcgctcgc ctaccagaac aaggagatca acaacggccg cctggccatg    780

gttgcctgga ccggagccac tgtgggcgcc ctcctcacca acggcgagga ccccatcacc    840

acccttctct ccaagctcgg caactaa                                        867
```

```
<210> SEQ ID NO 7
<211> LENGTH: 867
<212> TYPE: DNA
<213> ORGANISM: Nannochloropsis gaditana
<220> FEATURE:
<221> NAME/KEY: misc_feature
<223> OTHER INFORMATION: VCP2b, VCP2c genes

<400> SEQUENCE: 7

atgaagaccg ccgctctgct caccgtctcc tccctcatgg gcgcctccgc ctttgtggcc     60

cccgccccca agttcagccg cacccgcggt gttgcccgca tgtccttcga ggacgaggcc    120

ggcgtgaccg ccccccctgggg ctactgggtg agtctcatga aacacgttag gtttcgtaat  180

gtgcatgtga cgctcaagcc agtccaccca ccctctcctc cgtaaatctc acaggacccg    240

cttggcttct ccgccgatgg tgatgtcgag aaattcaacc gttaccgcgc catcgagatc    300

aagcacggcc gaggtaagag atggctaggt gcatggtcga gggtgacgtg attgcgaaga    360

actgtccctg ctgatctcga gacgatacct gaagtagagt ttggatccaa gcatgaactg    420
```

```
acttcacctc acccatgtca cattcatatc tgtccggcag tggccatgct tgccatgctc    480

cacaccctgg tgaccggcct cggcgtgaag ctccccggcc ttgtggctgc cggtgacggc    540

atccccgcct ccatgcccgc gggcatcaac gccatcacct ccggcgcttg ggccgcacag    600

ggatgggcgc aggtgctcct cttctgctcc gccctcgagg tcctggcccc ccagaaggag    660

gacaagatcc ccggggatgt gcagcccgac acctctgcct tcgccaagct cgaggacaag    720

accgaggagg aggcgctcgc ctaccagaac aaggagatca acaacggccg cctggccatg    780

gttgcctgga ccggagccac tgtgggcgcc ctcctcacca acggcgagga ccccatcacc    840

acccttctct ccaagctcgg caactaa                                        867
```

```
<210> SEQ ID NO 8
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: EIF3 promoter

<400> SEQUENCE: 8

tcataatcaa agatgagcca gccacgaagc taccggagaa ttctgtaaga aaaatgttta     60

aagttgaaaa tgctaacagt gaagtgatat cctttttttaa tggagtgttg aggtgaagtc   120

tagcatcgta ggggaaaaca ggattctgtg tcttccattc tactccttga taaagcgaag    180

aaatccgaca aaaccaaaga gattgttcaa gtttaagatt tgtaagcgta caactatgaa    240

cttcttctct ttgtaggcct gagtggtcgt atgcatacga ttcatgaagt gaatcagtat    300

cgctggattt tgcttaggag taaagcacaa ctaagaaaat atgctgcctg gcaggcatcc    360

tgagacatga ggcaagcgac gtagcaattg aatcctaatt taagccaggg catctgtatg    420

actctgttag ttaattgatg aaccaatgag ctttaaaaaa aaatcgttgc gcgtaatgta    480

gttttaattc tccgccttga ggtgcggggc catttcggac aaggttcttt ggacggagat    540

ggcagcatgt gtcccttctc caaattggtc cgtgtggtag ttgagatgct gccttaaaat    600

tctgctcggt catcctgcct tcgcattcac tcctttcgag ctgtcgggtt cctcacgagg    660

cctccgggag cggattgcgc agaaaggcga cccggagaca cagagaccat acaccgacta    720

aattgcactg gacgatacgg catggcgacg acgatggcca agcattgcta cgtgattatt    780

cgccttgtca ttcagggaga aatgatgaca tgtgtgggac ggtctttaca tgggaagagg    840

gcatgaaaat aacatggcct ggcgggatgg agcgtcacac ctgtgtatgc gttcgatcca    900

caagcaactc accatttgcg tcggggcctg tctccaatct gctttaggct acttttctct    960

aatttagcct attctataca gacagagaca cacagggatc                         1000
```

```
<210> SEQ ID NO 9
<211> LENGTH: 1511
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic cre gene codon optimized for
      Nannochloropsis with nuclear localization sequence and intron

<400> SEQUENCE: 9

atgccgaaaa agaaacgcaa ggtggggtcc aacctgttga cggtgcatca gaacttgcct     60

gccttgcctg tggatgccac atccgatgaa gtgcggaaga acctgatgga catgttccga    120
```

```
gacagacaag ccttcagcga gcacacctgg aagatgctgc tgtccgtgtg tagatcttgg    180

gcagcatggt gcaagctcaa taaccggaag tggttcccag ccgaacctga ggacgtgaga    240

gactacctgc tgtacctgca agccagagga ttggcagtga aaaccatcca gcagcacttg    300

ggccagctga acatgttgca tcgacgatcc gggttgccta gacctagcga ctctaatgcc    360

gtgtctctgg tgatgcgccg aatcagaaag gagaacgtgg atgccggaga acgggccaaa    420

caagcattgg cctttgagcg aaccgacttc gaccaagtga gatccttgat ggagaactcc    480

gaccggtgcc aagacatccg gaatctggcg ttcttgggaa tcgcctacaa cacgttgttg    540

agaatagccg agatcgcccg gatccgcgtg aaagacatct ccagaacaga cggaggacgg    600

atgttgatcc atatcggacg gacgaagacc ctggtgtcta cagctggagt ggaaaaggcc    660

ctgtccttgg gagtgacgaa attggtggag cgatggatct ccgtgtctgg agtggccgat    720

gatcccaaca actacctgtt ctgcagagtg cggaagaatg gagtggcagc ccctagtgcc    780

acgtcccaat tgtccacaag agccttagag ggaatcttcg aagccacaca tcgcctgatc    840

tacggcgcca aggacgattc cggacaacgg tatttggcct ggtctggaca ttctgcaaga    900

gtgggagcag cccgagatat ggtaagtgtt tgcaagaggt cgtgcggagg atgaagaggt    960

gcctgagaac gatagatgga aagggtcggg tggccttggt gatggcattc ttttcagagc   1020

tttccgaaca cagtcttgta tctgcagtat taattgatgt atgcagtgtg tatgatccca   1080

cccagtgcct ttatgcagca tggattgtt aaatagatat gaaagcataa ccggtagaaa    1140

agaaagagag atgagacgct tggtagaacg ccataatcta tgcgttatat gaggagatac   1200

aagcataggc tgtcactcaa tatgtaaatg ggagaagaag cgtatgttac ttgtagatca   1260

gggagacgtg tggataaagc gcgcagcgat ttgtcttccc ctctccgtct cgataccttt   1320

ctgctcggta acaaactgac atggactcta tcttatataa atcacaacgt ttgtaggcgc   1380

gcgctggagt gtccattccc gagatcatgc aagctggagg atggaccaac gtgaacatcg   1440

tgatgaacta catccggaac ctggactccg agacgggagc aatggtgcgg ctgttggaag   1500

atggagatta a                                                         1511
```

```
<210> SEQ ID NO 10
<211> LENGTH: 196
<212> TYPE: PRT
<213> ORGANISM: Nannochloropsis gaditana
<220> FEATURE:
<221> NAME/KEY: misc_feature
<223> OTHER INFORMATION: VCP1 PLN00120 domain

<400> SEQUENCE: 10

Leu Leu Thr Val Ser Ser Leu Met Gly Ala Ser Ala Phe Val Ala Pro
1               5                   10                  15

Ala Pro Lys Phe Ser Arg Thr Arg Gly Val Ala Arg Met Ser Phe Glu
            20                  25                  30

Gly Glu Ala Gly Val Thr Ala Pro Leu Gly Tyr Trp Asp Pro Leu Gly
        35                  40                  45

Phe Ser Ala Asp Gly Asp Val Glu Lys Phe Asn Arg Tyr Arg Ala Ile
    50                  55                  60

Glu Ile Lys His Gly Arg Val Ala Met Leu Ala Met Leu His Thr Leu
65                  70                  75                  80

Val Thr Gly Leu Gly Val Lys Leu Pro Gly Leu Val Ala Ala Gly Asp
                85                  90                  95

Gly Ile Pro Ala Ser Met Pro Ala Gly Ile Asn Ala Ile Thr Ser Gly
            100                 105                 110
```

```
Ala Trp Ala Ala Gln Gly Trp Ala Gln Val Leu Leu Phe Cys Ser Ala
        115                 120                 125

Leu Glu Val Leu Ala Pro Gln Lys Glu Asp Lys Ile Pro Gly Asp Val
    130                 135                 140

Gln Pro Asp Thr Ser Ala Phe Ala Lys Phe Glu Asp Lys Thr Glu Glu
145                 150                 155                 160

Glu Ala Leu Ala Tyr Gln Asn Lys Glu Ile Asn Asn Gly Arg Leu Ala
                165                 170                 175

Met Val Ala Trp Thr Gly Ala Thr Val Gly Ala Leu Leu Thr Asn Gly
            180                 185                 190

Glu Asp Pro Ile
        195


<210> SEQ ID NO 11
<211> LENGTH: 201
<212> TYPE: PRT
<213> ORGANISM: Nannochloropsis gaditana
<220> FEATURE:
<221> NAME/KEY: misc_feature
<223> OTHER INFORMATION: VCP2a/b PLN00120 domain

<400> SEQUENCE: 11

Met Lys Thr Ala Ala Leu Leu Thr Val Ser Ser Leu Met Gly Ala Ser
1               5                   10                  15

Ala Phe Val Ala Pro Ala Pro Lys Phe Ser Arg Thr Arg Gly Val Ala
            20                  25                  30

Arg Met Ser Phe Glu Asp Glu Ala Gly Val Thr Ala Pro Leu Gly Tyr
        35                  40                  45

Trp Asp Pro Leu Gly Phe Ser Ala Asp Gly Asp Val Glu Lys Phe Asn
    50                  55                  60

Arg Tyr Arg Ala Ile Glu Ile Lys His Gly Arg Val Ala Met Leu Ala
65                  70                  75                  80

Met Leu His Thr Leu Val Thr Gly Leu Gly Val Lys Leu Pro Gly Leu
                85                  90                  95

Val Ala Ala Gly Asp Gly Ile Pro Ala Ser Met Pro Ala Gly Ile Asn
            100                 105                 110

Ala Ile Thr Ser Gly Ala Trp Ala Ala Gln Gly Trp Ala Gln Val Leu
        115                 120                 125

Leu Phe Cys Ser Ala Leu Glu Val Leu Ala Pro Gln Lys Glu Asp Lys
    130                 135                 140

Ile Pro Gly Asp Val Gln Pro Asp Thr Ser Ala Phe Ala Lys Leu Glu
145                 150                 155                 160

Asp Lys Thr Glu Glu Glu Ala Leu Ala Tyr Gln Asn Lys Glu Ile Asn
                165                 170                 175

Asn Gly Arg Leu Ala Met Val Ala Trp Thr Gly Ala Thr Val Gly Ala
            180                 185                 190

Leu Leu Thr Asn Gly Glu Asp Pro Ile
        195                 200


<210> SEQ ID NO 12
<211> LENGTH: 135
<212> TYPE: PRT
<213> ORGANISM: Nannochloropsis gaditana
<220> FEATURE:
<221> NAME/KEY: misc_feature
<223> OTHER INFORMATION: VCP1 PF00504 domain

<400> SEQUENCE: 12
```

```
Asp Val Glu Lys Phe Asn Arg Tyr Arg Ala Ile Glu Ile Lys His Gly
1               5                   10                  15

Arg Val Ala Met Leu Ala Met Leu His Thr Leu Val Thr Gly Leu Gly
            20                  25                  30

Val Lys Leu Pro Gly Leu Val Ala Ala Gly Asp Gly Ile Pro Ala Ser
        35                  40                  45

Met Pro Ala Gly Ile Asn Ala Ile Thr Ser Gly Ala Trp Ala Ala Gln
    50                  55                  60

Gly Trp Ala Gln Val Leu Leu Phe Cys Ser Ala Leu Glu Val Leu Ala
65                  70                  75                  80

Pro Gln Lys Glu Asp Lys Ile Pro Gly Asp Val Gln Pro Asp Thr Ser
                85                  90                  95

Ala Phe Ala Lys Phe Glu Asp Lys Thr Glu Glu Glu Ala Leu Ala Tyr
            100                 105                 110

Gln Asn Lys Glu Ile Asn Asn Gly Arg Leu Ala Met Val Ala Trp Thr
        115                 120                 125

Gly Ala Thr Val Gly Ala Leu
    130                 135
```

<210> SEQ ID NO 13
<211> LENGTH: 135
<212> TYPE: PRT
<213> ORGANISM: Nannochloropsis gaditana
<220> FEATURE:
<221> NAME/KEY: misc_feature
<223> OTHER INFORMATION: VCP2/2' PF00504 domain

<400> SEQUENCE: 13

```
Asp Val Glu Lys Phe Asn Arg Tyr Arg Ala Ile Glu Ile Lys His Gly
1               5                   10                  15

Arg Val Ala Met Leu Ala Met Leu His Thr Leu Val Thr Gly Leu Gly
            20                  25                  30

Val Lys Leu Pro Gly Leu Val Ala Ala Gly Asp Gly Ile Pro Ala Ser
        35                  40                  45

Met Pro Ala Gly Ile Asn Ala Ile Thr Ser Gly Ala Trp Ala Ala Gln
    50                  55                  60

Gly Trp Ala Gln Val Leu Leu Phe Cys Ser Ala Leu Glu Val Leu Ala
65                  70                  75                  80

Pro Gln Lys Glu Asp Lys Ile Pro Gly Asp Val Gln Pro Asp Thr Ser
                85                  90                  95

Ala Phe Ala Lys Leu Glu Asp Lys Thr Glu Glu Glu Ala Leu Ala Tyr
            100                 105                 110

Gln Asn Lys Glu Ile Asn Asn Gly Arg Leu Ala Met Val Ala Trp Thr
        115                 120                 125

Gly Ala Thr Val Gly Ala Leu
    130                 135
```

<210> SEQ ID NO 14
<211> LENGTH: 122
<212> TYPE: DNA
<213> ORGANISM: Nannochloropsis gaditana
<220> FEATURE:
<221> NAME/KEY: misc_feature
<223> OTHER INFORMATION: gRNA forward template

<400> SEQUENCE: 14

```
taatacgact cactataggg gagacggtga gcagagcggg ttttagagct agaaatagca     60
```

agttaaaata aggctagtcc gttatcaact tgaaaaagtg gcaccgagtc ggtgcttttt 120
tt 122

<210> SEQ ID NO 15
<211> LENGTH: 2400
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Hyg resistance cassette with flanking ID sequnces

<400> SEQUENCE: 15
tccacagccc gaacccatga gagagaatca taatcaaaga tgagccagcc acgaagctac 60
cggagaattc tgtaagaaaa atgtttaaag ttgaaaatgc taacagtgaa gtgatatcct 120
tttttaatgg agtgttgagg tgaagtctag catcgtaggg gaaaacagga ttctgtgtct 180
tccattctac tccttgataa agcgaagaaa tccgacaaaa ccaaagagat tgttcaagtt 240
taagatttgt aagcgtacaa ctatgaactt cttctctttg taggcctgag tggtcgtatg 300
catacgattc atgaagtgaa tcagtatcgc tggattttgc ttaggagtaa agcacaacta 360
agaaaatatg ctgcctggca ggcatcctga gacatgaggc aagcgacgta gcaattgaat 420
cctaatttaa gccagggcat ctgtatgact ctgttagtta attgatgaac caatgagctt 480
taaaaaaaaa tcgttgcgcg taatgtagtt ttaattctcc gccttgaggt gcggggccat 540
ttcggacaag gttctttgga cggagatggc agcatgtgtc ccttctccaa attggtccgt 600
gtggtagttg agatgctgcc ttaaaattct gctcggtcat cctgccttcg cattcactcc 660
tttcgagctg tcgggttcct cacgaggcct ccgggagcgg attgcgcaga aaggcgaccc 720
ggagacacag agaccataca ccgactaaat tgcactggac gatacggcat ggcgacgacg 780
atggccaagc attgctacgt gattattcgc cttgtcattc agggagaaat gatgacatgt 840
gtgggacggt ctttacatgg gaagagggca tgaaaataac atggcctggc gggatggagc 900
gtcacacctg tgtatgcgtt cgatccacaa gcaactcacc atttgcgtcg gggcctgtct 960
ccaatctgct ttaggctact tttctctaat ttagcctatt ctatacagac agagacacac 1020
agggatcatg gggaagaaac cggaactgac cgctacgtcc gtggagaaat tccttattga 1080
gaagttcgac tctgtctccg acttgatgca actgagcgag ggagaggaga gtagggcgtt 1140
ctcgtttgac gtagggggtc ggggatacgt gttgagggtt aatagttgtg cggacgggtt 1200
ctacaaggat cggtatgtct accgtcattt cgcctccgcc gctctcccca taccagaggt 1260
actggacatt ggggagttta gcgaatctct cacgtactgc atctcgcgcc gagcccaggg 1320
agtgacgttg caagatctgc ccgaaactga attgcctgcc gttttgcaac ccgtggccga 1380
ggccatggac gcgatcgctg ccgcagatct gtctcagacg tccggctttg gaccttttgg 1440
gccccagggc atcgggcagt acacgacctg gcgagacttc atctgcgcca ttgccgatcc 1500
tcacgtctat cattggcaga cagtcatgga tgacaccgtg tctgcatccg tggcccaagc 1560
actggacgaa ctcatgttgt gggccgagga ttgccctgag gtcaggcacc tggtgcacgc 1620
ggatttcggc agcaataacg tacttacaga caatggtcgg attactgctg tcatcgactg 1680
gtccgaagcg atgtttggtg atagccaata cgaagtggcg aacatattct tctggcgtcc 1740
ctggttggcg tgcatggagc agcagacacg ctactttgaa cggaggcacc cggagctggc 1800
cggctcccca cgactccgcg cctatatgtt gcgtatcgga ctcgatcagc tttaccagtc 1860
tctcgtcgac ggcaacttcg acgacgccgc gtgggcgcag ggccgctgcg acgcgatagt 1920
ccgcagcggg gctgggacgg tgggtcggac ccaaatcgca cgccggtcgg ctgcggtgtg 1980
gacagacggc tgtgttgagg tgcttgcgga ctcgggcaac cgtaggccga gcacccgacc 2040
gcgtgcaaag gagtgattga atcattgaat gaaccattgt gtgcagaatc gatttcggga 2100
gtgttgccaa cacaagaaat atgcccaggg ttgtgtagaa gtttgcgtga atgtgatgaa 2160
gggaagccat acgctgaatt atcgtgacgt gtgtgagacg aagtgtcaca tcatacaccc 2220
aatttgagaa gctgtaccta ttagaagaat ttgtgagata cattaaaccc cttttggtac 2280
gtggtataat tgttatttgg gaagctgtaa acacgcagat cgttcctgag attgtcaatt 2340
acttttgtgg tgtttcctaa aggccgcatc actgcccgaa tcgagttgat ggcccgcaaa 2400

<210> SEQ ID NO 16
<211> LENGTH: 20
<212> TYPE: DNA
<213> ORGANISM: Nannochloropsis gaditana
<220> FEATURE:
<221> NAME/KEY: misc_feature
<223> OTHER INFORMATION: single VCP KO gRNA target 1
<220> FEATURE:
<221> NAME/KEY: misc_feature
<223> OTHER INFORMATION: Single VCP KO gRNA target 1

<400> SEQUENCE: 16
ggagacggtg agcagagcgg 20

<210> SEQ ID NO 17
<211> LENGTH: 20
<212> TYPE: DNA
<213> ORGANISM: Nannochloropsis gaditana
<220> FEATURE:
<221> NAME/KEY: misc_feature
<223> OTHER INFORMATION: single VCP KO gRNA target 2
<220> FEATURE:
<221> NAME/KEY: misc_feature
<223> OTHER INFORMATION: Single VCP KO gRNA target 2

<400> SEQUENCE: 17
ggtcaccagg gtgtggagca 20

<210> SEQ ID NO 18
<211> LENGTH: 8814
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VCP2a/2b knockout construct

<400> SEQUENCE: 18
gacgaaaggg cctcgtgata cgcctatttt tataggttaa tgtcatgata ataatggttt 60
cttagacgtc aggtggcact tttcggggaa atgtgcgcgg aacccctatt tgtttatttt 120
tctaaataca ttcaaatatg tatccgctca tgagacaata accctgataa atgcttcaat 180
aatattgaaa aaggaagagt atgagtattc aacatttccg tgtcgccctt attccctttt 240
ttgcggcatt ttgccttcct gtttttgctc acccagaaac gctggtgaaa gtaaaagatg 300
ctgaagatca gttgggtgca cgagtgggtt acatcgaact ggatctcaac agcggtaaga 360
tccttgagag ttttcgcccc gaagaacgtt ttccaatgat gagcactttt aaagttctgc 420
tatgtggcgc ggtattatcc cgtattgacg ccgggcaaga gcaactcggt cgccgcatac 480

```
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagtttaaac aaatagcggg atagttctgc gtattggtgt   2040
ataagtttag tggtaacatc attagatttg tttttgtact tttgtaccg  aaacagttgc   2100
agagtctaca gttctgacct ttcctgtccc cttgctcttt gccgtcacgg cgatgatgcg   2160
aggagggtca tcgtggccat agagccttaa tatgaggtgt tcttgttcgc gccacatgag   2220
tttagaagta gttgatagca aactcagagc tattgtgggc ttgcgagata attgaatgag   2280
aagcacgatg aatctttaca tttacgaggg taacaagctt ttcatgagtt tttgtacgca   2340
caacacagtc atgaccttgt gcaccgataa atacaagtgt ccggacgact taggaatgtt   2400
ttggcacgaa aagatatata taagtacacg tgcgtatacc ttttcgatag taaaatgtga   2460
cgtaatgcga ggctgctctc gctgtgaacc ctcatagtca ctcctgcaac attctgggga   2520
aaagctcctg tcgtccacac gcgtggatgc aattgaagca gtacttggta aaataggcga   2580
tatcgaagtc gatgaaaagg ttttcgtatc ctgcttcttt cgtttctcag aaaagagtgg   2640
ctttggaaac gttgtttgac gggaaaagct gacagcttga cggagcgatg tacgtgatgc   2700
agccttgcga ggtgcaggtt gccgcgtgac tgtcgaatcg ctcgccttaa acaatcccat   2760
gagacgtata ggacattaaa aaaaatatat atcggtcaat gagcccgtaa atgaacgggt   2820
```

-continued

```
ttttatagtg aaagcttacc cggccagagt cagatctgtt tgtgctgtca ctcaaagata   2880

aagctgaaga tagacgtcga atgcgctcca ctttccatga aacgtgtggg atcgccaacg   2940

cgaaagtttt caatttgtcc aaagacacta ctttgtcttc gtttacttca aattttctca   3000

caagaaggcc gacatcagtc ttccgcacat gtaaggcata aaaaatgtag ttaaggctga   3060

gaaagaatcc cgcgaaacaa tccatgattg acaagtggaa atgtgttgac atcacagaag   3120

atgaaatata atacttccac ccctgccgca aaaaatggca gatagcagaa attgttttgc   3180

ctccgcgtac ctccgtcagg cagaaaatat ccggactgag tttcctcagg gcagctacga   3240

aggcttttga tgaaatagtg ctggtgactt catgtttaag acagaatttt ttaaaaatat   3300

catcataagt catgccagac tctttcgcac gaatgaatat ttcttgcagt ttcgacgtac   3360

aatctgtgga ggtgtggcat gctgctttat ttcgcaatat tatcgagcga ataccattaa   3420

aaaatatagc atcattacct tcctcatgct ctagataact tttgttgatg gaaactccat   3480

taattgcgtc actgtatgat ttatttaggc tcatggctgc catgacccta agcgattgtc   3540

ggcgacgatc ttcgaggcgg tcttcagtgc ttgtaacggc ggtttgccca ttcgacgagc   3600

catttgatga gtcagaatac tgggaagcta atcgatacgc cttgggcctg tgttgtgaaa   3660

gtgaagaatt tgcagatgag agatatttcg gcttttaaaa ttttgggcgg tcacttacct   3720

gctaatgtga atgtcctcca tatgcctgcg gatgcttatc tgttgctcaa cacgagattg   3780

aacgagatgt gaaaagaatg aggagatttc tgtaaaacaa gtaatatgct ttatacgtgc   3840

aataccgcgt gactttgaca ggggatcaca aggccggtcg ccgccgctat ttccgaggtg   3900

gtgaaagtcc gagagtccac ccgggcgcct tgccgaggtc ggaccaagat aagagtggcc   3960

gctcaatcta caagttaaac gacgtaaggc gtgcaatcaa gcgtagtcga ggggaacttt   4020

tcactccaac agaaaattgt aaataaagaa aactacaaaa tagtcaataa aagcagcaac   4080

tcacaaagga atgcggccgc tccacagccc gaacccatga gagagaatca taatcaaaga   4140

tgagccagcc acgaagctac cggagaattc tgtaagaaaa atgtttaaag ttgaaaatgc   4200

taacagtgaa gtgatatcct tttttaatgg agtgttgagg tgaagtctag catcgtaggg   4260

gaaaacagga ttctgtgtct tccattctac tccttgataa agcgaagaaa tccgacaaaa   4320

ccaaagagat tgttcaagtt taagatttgt aagcgtacaa ctatgaactt cttctctttg   4380

taggcctgag tggtcgtatg catacgattc atgaagtgaa tcagtatcgc tggattttgc   4440

ttaggagtaa agcacaacta agaaaatatg ctgcctggca ggcatcctga gacatgaggc   4500

aagcgacgta gcaattgaat cctaatttaa gccagggcat ctgtatgact ctgttagtta   4560

attgatgaac caatgagctt taaaaaaaaa tcgttgcgcg taatgtagtt ttaattctcc   4620

gccttgaggt gcggggccat ttcggacaag gttctttgga cggagatggc agcatgtgtc   4680

ccttctccaa attggtccgt gtggtagttg agatgctgcc ttaaaattct gctcggtcat   4740

cctgccttcg cattcactcc tttcgagctg tcgggttcct cacgaggcct ccgggagcgg   4800

attgcgcaga aaggcgaccc ggagacacag agaccataca ccgactaaat tgcactggac   4860

gatacggcat ggcgacgacg atggccaagc attgctacgt gattattcgc cttgtcattc   4920

agggagaaat gatgacatgt gtgggacggt ctttacatgg gaagagggca tgaaaataac   4980

atggcctggc gggatggagc gtcacacctg tgtatgcgtt cgatccacaa gcaactcacc   5040

atttgcgtcg gggcctgtct ccaatctgct ttaggctact tttctctaat ttagcctatt   5100

ctatacagac agagacacac agggatcatg gggaagaaac cggaactgac cgctacgtcc   5160

gtggagaaat tccttattga gaagttcgac tctgtctccg acttgatgca actgagcgag   5220
```

```
ggagaggaga gtagggcgtt ctcgtttgac gtagggggtc ggggatacgt gttgagggtt   5280
aatagttgtg cggacgggtt ctacaaggat cggtatgtct accgtcattt cgcctccgcc   5340
gctctcccca taccagaggt actggacatt ggggagttta gcgaatctct cacgtactgc   5400
atctcgcgcc gagcccaggg agtgacgttg caagatctgc ccgaaactga attgcctgcc   5460
gttttgcaac ccgtggccga ggccatggac gcgatcgctg ccgcagatct gtctcagacg   5520
tccggctttg gaccttttgg gccccagggc atcgggcagt acacgacctg gcgagacttc   5580
atctgcgcca ttgccgatcc tcacgtctat cattggcaga cagtcatgga tgacaccgtg   5640
tctgcatccg tggcccaagc actggacgaa ctcatgttgt gggccgagga ttgccctgag   5700
gtcaggcacc tggtgcacgc ggatttcggc agcaataacg tacttacaga caatggtcgg   5760
attactgctg tcatcgactg gtccgaagcg atgtttggtg atagccaata cgaagtggcg   5820
aacatattct tctggcgtcc ctggttggcg tgcatggagc agcagacacg ctactttgaa   5880
cggaggcacc cggagctggc cggctcccca cgactccgcg cctatatgtt gcgtatcgga   5940
ctcgatcagc tttaccagtc tctcgtcgac ggcaacttcg acgacgccgc gtgggcgcag   6000
ggccgctgcg acgcgatagt ccgcagcggg gctgggacgg tgggtcggac ccaaatcgca   6060
cgccggtcgg ctgcggtgtg gacagacggc tgtgttgagg tgcttgcgga ctcgggcaac   6120
cgtaggccga gcacccgacc gcgtgcaaag gagtgattga atcattgaat gaaccattgt   6180
gtgcagaatc gatttcggga gtgttgccaa cacaagaaat atgcccaggg ttgtgtagaa   6240
gtttgcgtga atgtgatgaa gggaagccat acgctgaatt atcgtgacgt gtgtgagacg   6300
aagtgtcaca tcatacaccc aatttgagaa gctgtaccta ttagaagaat ttgtgagata   6360
cattaaaccc cttttggtac gtggtataat tgttatttgg gaagctgtaa acacgcagat   6420
cgttcctgag attgtcaatt acttttgtgg tgtttcctaa aggccgcatc actgcccgaa   6480
tcgagttgat ggcccgcaaa ggcgcgcccc tccaatgcat tttttccacc gatgaccgtg   6540
cctttgtgtt atttacattc caactggact atggagagca gcttgatgcc tgccagtttg   6600
ctagtttcgt gatggacgac attgatttgc gaaagtgttc acgctcttgt gtggggagaa   6660
caagtgcttt gcattcctgc atttggtctt catttcgcat cacacccagg ttttctttag   6720
caagattttt tggaagcaat gaacccgtgt caggtgctga ggaagggtaa gggagtagat   6780
tgtgaacaag taatatgtga aactaactcc agccgcaaac accgaaagcg ttgttcgcga   6840
ccattacttt caatttcact gtcgcccgac agactgacca ctgaaatgac gcagctctgt   6900
aagcagcgca tttccttcct atgttttatg ccttattcag aatatctccg cgttcgcata   6960
tctttatcta ctccttctcg acactcttca cgtgacccct tcctcttaca cgggaaatct   7020
ctctcgcctt atctctacag cctcatgcga cgcatcacgt aaagtcctct cgaatcactg   7080
tggctcaacc aacaatgtac gagtcaggag agagaagttt ggtcaagcta taaggtatgg   7140
gtgcagagcc gtcttccaag ccattcacgg ccgttacatt gacgtcggcg tacaagattt   7200
gtgaggagaa agacacaata atggggaaaa agacttgcgc gtctcggcct gccacgacaa   7260
attccagcgc ccccgaagaa ttcgatgcat ccacgagatc catgtgccaa attaggcgtt   7320
gctcgcgagg atcatgccga tatgtaccat cgatggatgc aacctcgggc ggctcggccg   7380
ttcccaaagg gatagagaca ttaacgttgt gcagctcttg gctctgccca ttcatctggt   7440
actcaatgct gatgttcatc ttcccctgcc cctcctcttc gggccaacaa ttgagggtaa   7500
tggggaccac gctatcgtcc gtggaggagt agctccaccg gagcacgccg accgcccttc   7560
```

```
ccactgggaa acctttgctt gtgtctttca gcaccaacac ccggttggag tcgtactcct   7620

gcttattcac cttgggatga gtctggaaat tgagccctgc aggcaccggt cttgcacccc   7680

ctgccgccag tgctaccttg gatagggcgg ctgcctctgt cgttgccgtc agcgttagag   7740

agccctttac ctcgaaagcg tcaaccgcgc catcgcgggt caagtgtgcg acgattttct   7800

cctccacagc cagctggatc ggttgatgct ggatcacagg ggcggataga gcctcctcgc   7860

ccgaacccgc tcccgcactg agaggcggcg cacgtgtcgc cgcgatgttg ctcaagttgt   7920

cctcctgcac gagcgagtcc agcatgctgg cggccttgct gggggcgcca agcttcatgc   7980

ctttggagac cgtcttgacc gtctcagtct tgctgacagt aaagctgtcc accgtgctag   8040

gcgcgtacac ggatggcgtg gaggccccga aggcgtcctg tccaatgcca gcctggccat   8100

cgaaagctcc actcccgccc acgtagtcca tccctccccc gccaatgcct tggtatgccc   8160

cgcccagccc cgatcgagtc gctcccaacc ggtctcgcgc gagctcccgc tgtcgctctt   8220

tgatggcttt agcctgtcga gcggcctggt ccttggcgga gtccatctta ctctgtttga   8280

tcatgagagc cagcttctcc tcatgggagt ccatctccat gttggttttg atttgctgca   8340

gtgtcacgct ttctcggtac ccgcccgtgg tcaagacctc gtcgaaggcg aacacgagct   8400

caaagcattt gtcactgaca cgctcttcgg tgacgccgcc cgccacgtct ggcacgatct   8460

ttgacaggag ccgaagggtc tccaaatctt ctacgatatt tgaagccttg ttcgtgatga   8520

gtaagaggaa aaggttgtcg attggttgat acacgtatcg caccgtgtca gtttcgataa   8580

acgtgtgctg cttctcttcc ccagagccga gtagcttcgg aaacgcagcc agaagaccct   8640

cgatacggat gcgactcatc tctacaaatt gtctcgataa taatgctttc ccatttttgg   8700

tgcagatggc acctgatagg acgacctgga tgaacacgag ttgaacagga aagagaaaga   8760

atttcaaagc gtgcagaagc tcaggcgcta tacttgactt ggaacagtgg agga         8814
```

<210> SEQ ID NO 19
<211> LENGTH: 18
<212> TYPE: DNA
<213> ORGANISM: Nannochloropsis gaditana
<220> FEATURE:
<221> NAME/KEY: misc_feature
<223> OTHER INFORMATION: qRTPCR primer 1 VCP1 gene

<400> SEQUENCE: 19

```
gttgcccgca tgtccttc                                                   18
```

<210> SEQ ID NO 20
<211> LENGTH: 20
<212> TYPE: DNA
<213> ORGANISM: Nannochloropsis gaditana
<220> FEATURE:
<221> NAME/KEY: misc_feature
<223> OTHER INFORMATION: qRTPCR primer 2 VCP1 gene

<400> SEQUENCE: 20

```
gcggtaacgg ttgaacttct                                                 20
```

<210> SEQ ID NO 21
<211> LENGTH: 20
<212> TYPE: DNA
<213> ORGANISM: Nannochloropsis gaditana
<220> FEATURE:
<221> NAME/KEY: misc_feature
<223> OTHER INFORMATION: qRTPCR primer 1 VCP2a gene

<400> SEQUENCE: 21
ctgtttcatc catcgacgtt 20

<210> SEQ ID NO 22
<211> LENGTH: 23
<212> TYPE: DNA
<213> ORGANISM: Nannochloropsis gaditana
<220> FEATURE:
<221> NAME/KEY: misc_feature
<223> OTHER INFORMATION: qRTPCR primer 2 VCP2a gene

<400> SEQUENCE: 22
tgtctttgat atcgaaccag ctt 23

<210> SEQ ID NO 23
<211> LENGTH: 20
<212> TYPE: DNA
<213> ORGANISM: Nannochloropsis gaditana
<220> FEATURE:
<221> NAME/KEY: misc_feature
<223> OTHER INFORMATION: qRTPCR primer 1 VCP2b gene

<400> SEQUENCE: 23
atcgctccac ttcctccaat 20

<210> SEQ ID NO 24
<211> LENGTH: 21
<212> TYPE: DNA
<213> ORGANISM: Nannochloropsis gaditana
<220> FEATURE:
<221> NAME/KEY: misc_feature
<223> OTHER INFORMATION: qRTPCR primer 2 VCP2b gene

<400> SEQUENCE: 24
aagctgctct ccatagtcca g 21

<210> SEQ ID NO 25
<211> LENGTH: 19
<212> TYPE: DNA
<213> ORGANISM: Nannochloropsis gaditana
<220> FEATURE:
<221> NAME/KEY: misc_feature
<223> OTHER INFORMATION: qRTPCR primer 1 housekeeping gene

<400> SEQUENCE: 25
gaggaagcgg aagaggatg 19

<210> SEQ ID NO 26
<211> LENGTH: 20
<212> TYPE: DNA
<213> ORGANISM: Nannochloropsis gaditana
<220> FEATURE:
<221> NAME/KEY: misc_feature
<223> OTHER INFORMATION: qRTPCR primer 2 housekeeping gene

<400> SEQUENCE: 26
tcaagtacca gttccacacg 20

<210> SEQ ID NO 27
<211> LENGTH: 217
<212> TYPE: PRT
<213> ORGANISM: Thalassiosira oceanica
<220> FEATURE:
<221> NAME/KEY: misc_feature
<223> OTHER INFORMATION: gb-EJK62959.1 protein

<400> SEQUENCE: 27

Met Lys Thr Ser Ala Leu Leu Ala Ser Ser Leu Val Cys Gly Ala Ser

```
1               5                   10                  15

Ala Phe Ala Pro Ala Pro Gln Ser His Ala Arg Ser Thr Glu Met Ser
            20                  25                  30

Ala Ala Leu Pro Arg Glu Thr Val Leu Ala Glu Pro Asp Ser Ile Glu
        35                  40                  45

Phe Gly Ser Val Trp Asp Pro Leu Gly Leu Ser Glu Met Gly Ser Asp
    50                  55                  60

Glu Thr Ile Ala Trp Phe Arg His Ala Glu Val Lys His Gly Arg Val
65                  70                  75                  80

Ala Met Ala Ala Phe Thr Gly Trp Trp Ala Val Gly Ala Gly Val Arg
                85                  90                  95

Leu Pro Gly Glu Ile Ser His Gly Leu Asp Phe Ala Ser Leu Pro Ser
            100                 105                 110

Lys Gly Leu Glu Ala Trp Asp Ala Val Pro Gly Trp Gly Lys Ala Gln
        115                 120                 125

Met Leu Leu Phe Ala Gly Leu Ile Glu Phe His Asp Glu Leu Phe Phe
    130                 135                 140

Ser Arg Arg Gly Thr His Tyr Met Lys Gly Gly Val Pro Gly Lys Asn
145                 150                 155                 160

Met Val Pro Gly Leu Phe Asp Pro Phe Gly Ile Ser Lys Gly Lys Ser
                165                 170                 175

Glu Glu Ala Leu Ala Arg Gly Arg Ser Ser Glu Ile Lys Asn Gly Arg
            180                 185                 190

Leu Ala Met Ile Gly Ile Ala Gly Met Trp Ala Ala Ala Thr Leu Pro
        195                 200                 205

Gly Ser Val Pro Leu Gln Pro Pro Cys
    210                 215
```

<210> SEQ ID NO 28
<211> LENGTH: 654
<212> TYPE: DNA
<213> ORGANISM: Thalassiosira oceanica
<220> FEATURE:
<221> NAME/KEY: misc_feature
<223> OTHER INFORMATION: coding sequence for SEQ ID NO:27

<400> SEQUENCE: 28

```
atgaagacct ccgccctcct agcctcgtcc cttgtttgcg gtgcgtccgc attcgccccg     60

gcgccccaga gccatgctcg ctcgaccgag atgagcgccg ccctccctcg cgagacggtt    120

ctcgccgagc ccgactccat cgagttcgga tcggtttggg accctctggg tctttctgag    180

atgggttccg acgagaccat cgcctggttc cgccatgccg aggttaagca cggacgcgtc    240

gccatggctg cattcaccgg ctggtgggct gttggagccg gagtgcgtct tcctggagag    300

atctcccacg gacttgactt cgcctccctt ccctccaagg gacttgaggc ctgggatgcc    360

gtcccgggat ggggaaaggc ccagatgctt ctttttgcgg gacttatcga gttccatgac    420

gagctctttt tctctagacg cggcacacac tacatgaagg gtggtgttcc gggaaagaac    480

atggtgcctg gacttttcga tccctttggc atttcgaagg gaaagagcga ggaagcgttg    540

gcgcgaggac gttcgtccga gatcaagaac ggcaggctcg cgatgatcgg tattgccggt    600

atgtgggccg ccgcgactct gccgggatca gttccgcttc agccccgtg ctaa           654
```

<210> SEQ ID NO 29
<211> LENGTH: 215
<212> TYPE: PRT
<213> ORGANISM: Thalassiosira pseudonana

```
<220> FEATURE:
<221> NAME/KEY: misc_feature
<223> OTHER INFORMATION: Genbank Accession XP-002291432

<400> SEQUENCE: 29

Met Lys Thr Ala Ala Leu Leu Leu Ser Ala Leu Ser Met Ala Ser Ala
1               5                   10                  15

Phe Ala Pro Ala Ser Val Ser Lys Arg Thr Thr Ser Leu Asn Ala Cys
            20                  25                  30

Ile Ser Arg Glu Thr Val Leu Ser Glu Pro Asp Thr Val Glu Phe Gly
        35                  40                  45

Gln Lys Trp Asp Pro Leu Gly Leu Ser Asp Leu Gly Ser Asp Glu Thr
    50                  55                  60

Ile Ala Trp Phe Arg His Ser Glu Ile Lys His Gly Arg Val Ala Met
65                  70                  75                  80

Ala Ala Phe Val Gly Trp Trp Ala Val Gly Ala Gly Trp Arg Leu Pro
                85                  90                  95

Gly Glu Leu Ser Tyr Gly Leu Asp Phe Ala Ser Ile Pro Ser Lys Gly
            100                 105                 110

Leu Asp Ala Trp Glu Ala Val Pro Gly Trp Gly Lys Val Gln Met Leu
        115                 120                 125

Leu Phe Ala Gly Leu Ile Glu Phe His Asp Glu Ile Phe Phe Ser Lys
    130                 135                 140

Arg Gly Thr His Tyr Met Lys Gly Gly Ile Pro Gly Lys Asn Met Val
145                 150                 155                 160

Pro Gly Leu Tyr Asp Pro Leu Gly Phe Ser Lys Gly Arg Ser Glu Glu
                165                 170                 175

Ala Lys Ala Arg Gly Arg Ala Ser Glu Ile Lys Asn Gly Arg Leu Ala
            180                 185                 190

Met Ile Gly Val Ala Gly Met Tyr Ala Ala Ala Thr Ile Asp Gly Ser
        195                 200                 205

Val Pro Leu Gln Pro Pro Cys
    210                 215


<210> SEQ ID NO 30
<211> LENGTH: 849
<212> TYPE: DNA
<213> ORGANISM: Thalassiosira pseudonana
<220> FEATURE:
<221> NAME/KEY: misc_feature
<223> OTHER INFORMATION: Genbank Accession NC_012069.1 coding sequence

<400> SEQUENCE: 30

atgaagactg ccgctctcct cctctctgca ctcagcatgg cctcggcctt cgcacctgca      60

tctgtctcaa agcgcactac ttccttgaac gcttgcatct ctcgtgaaac cgtcctctct     120

gagccagaca ctgttgagtt tggacaaaaa tgggatcctc tcggtctctc agacctcggc     180

tccgatgaaa ccatcgcttg gttccgtcac tccgaaatca aacacggacg tgttgccatg     240

gctgcctttg tgggatggtg ggccgttggt gctggttggc gtcttcctgg tgaactttcg     300

tatggacttg actttgcttc tattccgagt aaggggttgg atgcatggga ggctgtgcct     360

ggatggggaa aggttcaaat gcttctcttt gctggtctta ttgaattcca cgatgagatt     420

ttctttagca agaggggtac tcactacatg aagggaggta ttccaggaaa ggtcagtaca     480

gaacagtgtg aatgtctttt tgtctgcaat gctgttgacg gcaccaatgc tttgctttgg     540

tactgccagc tgacatcaat caattttctc actatttcaa cagaacatgg ttccagggct     600
```

```
gtatgatccc cttggttttt caaagggacg atcggaagag gccaaagcaa gaggacgcgc    660

atcagagatc aagaacggac gtcttgccag tgagtatcac gtttcatttg tgtatcttca    720

tatcttgtgt ctcatctttt cgttgctaac attcattctt tttgtcattt cggaacagtg    780

attggagttg ctggcatgta cgcagctgcc acaattgacg gatcagttcc tcttcagcca    840

ccgtgctaa                                                            849
```

```
<210> SEQ ID NO 31
<211> LENGTH: 206
<212> TYPE: PRT
<213> ORGANISM: Phaeodactylum tricornutum
<220> FEATURE:
<221> NAME/KEY: misc_feature
<223> OTHER INFORMATION: Genbank Accession XP_002178860

<400> SEQUENCE: 31

Met Lys Ser Val Ala Ala Ile Leu Ala Ile Ala Ser Thr Ala Ala Ala
1               5                   10                  15

Phe Ala Pro Ser Ser Lys Ser Lys Ala Pro Thr Thr Val Thr Arg Val
            20                  25                  30

Ala Leu Asp Asp Leu Ala Gly Ser Thr Ala Pro Leu Lys Arg Phe Asp
        35                  40                  45

Pro Leu Gly Leu Ala Gln Val Gly Ser Glu Gln Thr Phe Ala Trp Phe
    50                  55                  60

Gln Ala Ala Glu Leu Lys His Ser Arg Ala Ala Met Leu Ala Thr Thr
65                  70                  75                  80

Gly Phe Ile Val Gln Ala Ala Gly Ile His Phe Pro Gly Met Leu Ser
                85                  90                  95

Lys Asp Ile Ser Phe Glu Ser Leu Ser Gly Met Asn Pro Val Glu Gln
            100                 105                 110

Trp Ala Gly Val Pro Asp Ala Gly Lys Trp Gln Ile Ile Leu Thr Ile
        115                 120                 125

Phe Ile Ala Glu Ile Ala Thr Glu Ala Lys Lys Pro His Tyr Met Met
    130                 135                 140

Gly Gly Asp Leu Pro Thr Met Val Phe Pro Pro Ile Asp Phe Ser Lys
145                 150                 155                 160

Val Asp Ala Ala Thr Leu Lys Thr Lys Arg Ser Arg Glu Leu Asn Asn
                165                 170                 175

Gly Arg Leu Ala Met Ile Gly Ile Met Ser Phe Ile Ser Glu Tyr Asn
            180                 185                 190

Ile Pro Gly Ser Val Pro Val Leu Ser Gly Leu Asp Ala Phe
        195                 200                 205
```

```
<210> SEQ ID NO 32
<211> LENGTH: 1064
<212> TYPE: DNA
<213> ORGANISM: Phaeodactylum tricornutum
<220> FEATURE:
<221> NAME/KEY: misc_feature
<223> OTHER INFORMATION: Genbank Accession NC_011673.1 coding sequence

<400> SEQUENCE: 32

atgaagtctg tcgctgccat tctcgctatc gctagcactg ccgctgcctt tgctccgtct     60

tccaagtcca aggtgcgctc atcgcggaaa ttcttgttaa gcgaccgcgt gccgatcccc    120

tccgtttcgt agatgtgttg attgacagcg acaaatggcg acggatacca ttccatggaa    180

gggtatcgat ggtatccgtc gctatccgtc cctgtcaatc aacagatctt caaagtttgt    240
```

```
ttggcactgg cgatgattcg agaaagtagc gcgtcggctt tttcccactt tcaaggatga    300

tgttccccgg cacccacggc ctctttttcc gtcccgcgtc cctctaacat tgtgcgtcgt    360

tgaatcatcc acaggctccc accaccgtta cccgtgtagc gctcgatgac cttgcgggta    420

gcacggctcc gttgaaacgg ttcgaccccc tcggcttggc acaagtcggc agcgagcaga    480

cctttgcctg gttccaagcc gccgagctga agcacagccg tgccgccatg ttggccacca    540

ccgggtttat cgtccaggcc gccggaatcc actttcccgg tatgctcagc aaggatatct    600

ccttcgaatc cctttccggc atgaaccctg tggaacagtg ggccggtgtg cctgatgctg    660

gtacgtgaac acggttgcaa taaagtcgga cgtgctccgt ttccgtcatc tgcaacgacg    720

cgccgatcaa ctagctttct cgtccgtacg gcgaatcttg aagtctcact catacgacac    780

cttctttttc cgttttgaca ggtaagtggc agatcatcct cacgatcttt attgctgaaa    840

tcgccaccga agccaagaag ccgcattaca tgatgggcgg tgatctaccg accatggtat    900

tccccccgat tgacttttcc aaagttgacg ccgccactct caagaccaag cgaagccgcg    960

aactgaacaa tggacgtctc gcaatgatcg gcatcatgtc cttcatcagt gaatacaaca   1020

tccccggatc ggtcccggtc cttagtgggc tggatgcctt ttaa                    1064
```

<210> SEQ ID NO 33
<211> LENGTH: 204
<212> TYPE: PRT
<213> ORGANISM: Thalassiosira pseudonana
<220> FEATURE:
<221> NAME/KEY: misc_feature
<223> OTHER INFORMATION: Genbank Accession XP_002292206

<400> SEQUENCE: 33

```
Met Lys Thr Tyr Ala Ala Ile Cys Leu Ser Leu Val Ser Ala Thr Ala
1               5                   10                  15

Ala Phe Ser Pro Val Pro Thr Lys Pro Val Asn Thr Gln Ile Ser Leu
            20                  25                  30

Thr Leu Asp Asp Ile Gly Gly Ala Ser Ala Pro Leu Lys Asn Phe Asp
        35                  40                  45

Pro Leu Asn Leu Ala Thr Leu Gly Ser Asp Glu Thr Leu Leu Trp Phe
    50                  55                  60

Arg Ala Ala Glu Leu Lys Asn Gly Arg Cys Ala Met Val Ala Cys Val
65                  70                  75                  80

Gly Tyr Leu Thr Asn Val Ala Gly Ile His Phe Pro Gly Gln Leu Ser
                85                  90                  95

Ser Asp Ile Ser Phe Glu Ser Leu Ser Thr Met Asn Pro Phe Asp Ala
            100                 105                 110

Trp Gly Ala Val Pro Val Ala Gly Lys Thr Gln Ile Leu Ala Thr Ile
        115                 120                 125

Phe Ile Ala Glu Met Ile Thr Glu Ser Lys Glu Val His Tyr Thr Lys
    130                 135                 140

Gly Gly Pro Leu Pro Gly Met Val Phe Pro Ala Ile Asp Phe Ser Gly
145                 150                 155                 160

Val Ser Glu Glu Thr Met Lys Arg Lys Arg Thr Ser Glu Leu Asn Asn
                165                 170                 175

Gly Arg Leu Ala Met Ile Gly Met Met Ser Phe Ile Ala Ala His Asn
            180                 185                 190

Ile Pro Gly Ser Val Pro Val Leu Gly Ser Asn Phe
        195                 200
```

<210> SEQ ID NO 34
<211> LENGTH: 965
<212> TYPE: DNA
<213> ORGANISM: Thalassiosira pseudonana
<220> FEATURE:
<221> NAME/KEY: misc_feature
<223> OTHER INFORMATION: Genbank Accession NC_012072.1 coding sequence

<400> SEQUENCE: 34

```
atgaagactt atgccgccat ttgcctttca ctcgtcagcg ctactgctgc tttttcgccc     60

gtgcctacaa aggtgtgtta gattcgtggt ttgggagaag ctaggacatg agatgtgtgt    120

ttatggtgct gatgattcat gaaccgtcgc aaagttgtga tgctaggatt gaggtatcat    180

cggcttcaaa cacctctttc attcatacgc tgtccgcctt tatgagaaca tgatatgaac    240

ttctctttac caaacactga ctgctgtttt ctcaaacaat caactcctct acacctttcc    300

aacatacaca gcccgtcaac acccaaattt cactcactct tgacgatatc ggtggtgctt    360

ccgctcctct aaaaaacttt gaccctttga accttgctac tctcggaagt gacgagactc    420

ttctttggtt cagagctgct gagttgaaga acggaagatg tgccatggtt gcctgtgttg    480

gtaagcttgt tgttaccttt ggtacatctc ttttgcaaat caatacgtca aagaataaca    540

acctcactct ctaacataca aactatcttc attatgcaac cactctacca ggatacctca    600

ccaacgttgc tggaatccac tttcctggcc aactctctag cgacattagc tttgaatccc    660

tctccacaat gaaccccttc gacgcatggg gcgccgttcc agttgcagga aagactcaaa    720

tccttgccac aatctttatt gcagaaatga ttaccgagtc aaaggaagtt cattacacca    780

agggaggtcc gcttccaggt atggttttcc ctgccattga cttttctggg gttagtgagg    840

agactatgaa gaggaagaga acgagtgagc tgaacaatgg aaggttggca atgattggta    900

tgatgtcgtt tattgcggca cacaacattc ctggatcggt gcctgttctt ggaagcaact    960

tctaa                                                                 965
```

<210> SEQ ID NO 35
<211> LENGTH: 204
<212> TYPE: PRT
<213> ORGANISM: Thalassiosira pseudonana
<220> FEATURE:
<221> NAME/KEY: misc_feature
<223> OTHER INFORMATION: Genbank Accession EJK70084.1

<400> SEQUENCE: 35

```
Met Lys Thr Ala Ala Leu Ile Ser Ala Cys Val Gly Ile Ala Ser Ala
1               5                   10                  15

Phe Ala Pro Ala Lys Asn Val Asn Arg Gly Thr Ala Leu Ser Ala Leu
            20                  25                  30

Glu Asp Met Ala Gly Ala Thr Met Pro Phe Lys Ala Tyr Asp Pro Leu
        35                  40                  45

Asn Leu Ala Ser Ile Gly Ser Asp Ser Thr Leu Ala Trp Phe Arg Ala
    50                  55                  60

Ala Glu Leu Lys His Gly Arg Val Ala Met Leu Ala Thr Thr Gly Tyr
65                  70                  75                  80

Ile Val Gln Ala Ala Gly Tyr His Phe Pro Gly Met Leu Ser Ser Asp
                85                  90                  95

Val Ser Phe Glu Ser Leu Ser Ala Met Lys Pro Phe Asp Ala Trp Asp
            100                 105                 110

Ala Val Pro Asp Leu Gly Lys Ala Gln Ile Tyr Phe Thr Ile Phe Phe
        115                 120                 125
```

```
Ala Glu Ile Val Ser Glu Ser Lys Gly Thr His Tyr Thr Lys Gly Gly
    130                 135                 140

Asp Leu Pro Thr Ile Val Phe Pro Asn Val Asn Phe Ala Pro Glu Asp
145                 150                 155                 160

Pro Ala Ala Met Lys Val Gln Gln Ser Lys Glu Leu Asn Asn Gly Arg
                165                 170                 175

Leu Ala Met Ile Ala Val Met Ser Phe Ala Ala Ala Ala Asn Ile Pro
            180                 185                 190

Gly Ser Val Pro Val Leu Ala Asp Asn Pro Met Phe
        195                 200


<210> SEQ ID NO 36
<211> LENGTH: 615
<212> TYPE: DNA
<213> ORGANISM: Thalassiosira oceanica
<220> FEATURE:
<221> NAME/KEY: misc_feature
<223> OTHER INFORMATION: THAOC_08587 coding sequence

<400> SEQUENCE: 36

atgaagactg ctgctttgat ctctgcttgc gttggcattg ccagcgcctt cgccccggcg     60

aagaatgtca acaggggaac ggccctctct gccctcgagg acatggccgg tgccaccatg    120

ccctttaagg catacgaccc gctgaacctt gcgtcgatcg gatcggacag cacccttgcc    180

tggttccgag ctgctgagct gaagcacgga cgcgttgcca tgctcgccac gacgggatac    240

atcgtccagg cggctggcta ccacttccct ggaatgcttt cgtcggatgt cagttttgag    300

agcctctcgg ccatgaagcc tttcgatgcg tgggatgccg tacctgacct tggaaaggcc    360

caaatttatt tcaccatctt ctttgctgag attgtttcgg agtcgaaagg cacacattac    420

acgaagggag gagacctgcc gacaattgtg ttccctaatg tcaactttgc gccagaggat    480

ccggcggcga tgaaggttca gcaatcgaag gaacttaaca atggacgact ggctatgatt    540

gcagttatgt cattcgctgc cgcggccaac atcccaggaa gcgttcctgt ccttgctgac    600

aacccgatgt tctaa                                                     615


<210> SEQ ID NO 37
<211> LENGTH: 207
<212> TYPE: PRT
<213> ORGANISM: Thalassiosira pseudonana
<220> FEATURE:
<221> NAME/KEY: misc_feature
<223> OTHER INFORMATION: Genbank Accesssion XP_002288721

<400> SEQUENCE: 37

Met Lys Thr Thr Ala Ile Leu Ser Cys Ile Gly Ile Ala Ser Val Ser
1               5                   10                  15

Ala Phe Ala Pro Val Gln Asn Ala Asn Lys Val Thr Ser Leu Gly Ala
            20                  25                  30

Thr Asn Ile Gln Asp Leu Pro Gly Ala Thr Ala Pro Leu Lys Gly Phe
        35                  40                  45

Asp Pro Leu Asn Leu Ala Thr Leu Gly Ser Glu Ser Thr Leu Ala Trp
    50                  55                  60

Phe Arg Ala Ala Glu Leu Lys His Ser Arg Val Ala Met Leu Ala Thr
65                  70                  75                  80

Thr Gly Tyr Ile Val Gln Ala Ala Gly Ile His Phe Pro Gly Met Leu
                85                  90                  95

Ser Ser Asp Val Ser Phe Glu Ser Leu Ser Ala Met Lys Pro Leu Asp
            100                 105                 110
```

```
Ala Trp Asp Ala Val Pro Asp Leu Gly Lys Ala Gln Ile Tyr Phe Thr
        115                 120                 125

Ile Phe Phe Ala Glu Phe Val Ser Glu Phe Ser Gly Thr His Tyr Met
    130                 135                 140

Lys Gly Gly Asp Phe Pro Thr Ile Val Phe Pro Pro Ile Asn Phe Ala
145                 150                 155                 160

Ser Ser Asp Ala Glu Lys Glu Lys Leu Gln Met Ser Arg Glu Leu Asn
                165                 170                 175

Asn Gly Arg Leu Ala Met Ile Ser Ile Met Ser Phe Val Ala Ala Ala
            180                 185                 190

Asn Ile Pro Gly Ser Val Pro Ala Leu Ala Gly Asn Pro His Phe
        195                 200                 205


<210> SEQ ID NO 38
<211> LENGTH: 1076
<212> TYPE: DNA
<213> ORGANISM: Thalassiosira pseudonana
<220> FEATURE:
<221> NAME/KEY: misc_feature
<223> OTHER INFORMATION: Genbank Accesssion NC_012066.1 coding sequence

<400> SEQUENCE: 38

cgcaacacat caaacacgcc atcaacatga agacaaccgc tatcctctcc tgtattggta      60

ttgccagtgt atctgccttt gctcccgtgc aaaacgtgag tatgcgacaa tatggtttct     120

tcgttatgca actcgtcggc gtcctctctc tctcacctcg tcatgccgtc attcaggcga     180

acaaagtcac ctccttgggt gccacaaaca ttcaagacct ccctggagcc actgctccat     240

tgaaggggtt tgatccactc aatctcgcca cgcttggatc tgagagcact ctcgcttggt     300

tccgtgctgc cgagctcaaa cattctcgtg ttgccatgtt ggcgactacg ggctacattg     360

ttcaggctgc tggtatccac ttccccggca tgctctcgtc ggatgttagt ttcgagagtc     420

tttcggcgat gaaacctctt gatgcttggg atgcagtgcc tgatcttggt acgtctgttg     480

tgatcatcgt attgtactgt acgtgatatc atatctcatc atcaaactct ctacccaaag     540

gcaaggccca aatctacttc accatcttct ttgctgagtt tgtgtctgag ttcagtggaa     600

cacattacat gaagggagga gactttccca caatcgtttt ccctcctatt aactttgcct     660

cgtcagacgc cgagaaagag aagcttcaaa tgagcagaga gttgaacaac ggacgtttgg     720

ctatgatttc catcatgagc ttcgttgctg ctgcaaacat tccagggtct gtgccggctt     780

tggcaggaaa ccctcacttc taatgatcag agtctatcat tacttgtttg tgaacttgta     840

catcttttct gtaaattgtg ggtcttcggc tggtgtacgg tgctatcgag tacctcaatt     900

ctactccatc gggttttgta tgaactgaac caacgagatg caacaaagcg tgacttggga     960

agtgaagagc acgagcggag tcagagtatg atacaacgtt tgagggactg tcatgggtgc    1020

cgttggtgcc aagtattgta aaaagtccaa agaaataact ttatatttac ttctct        1076


<210> SEQ ID NO 39
<211> LENGTH: 210
<212> TYPE: PRT
<213> ORGANISM: Cyclotella sp.
<220> FEATURE:
<221> NAME/KEY: misc_feature
<223> OTHER INFORMATION: FCP 1 protein

<400> SEQUENCE: 39

Met Met Lys Leu Ala Leu Leu Ser Ala Leu Ala Gly Ser Ala Ala Ala
1               5                   10                  15
```

```
Phe Ala Pro Ala Ala Thr Arg Ala Ser Ser Ser Ala Leu Asn Ala Phe
            20                  25                  30

Ser Ala Ala Asp Leu Pro Gly Ala Leu Pro Pro Val Gly Phe Phe Asp
        35                  40                  45

Pro Leu Gly Phe Ala Glu Lys Ala Asp Glu Lys Thr Leu Lys Arg Tyr
    50                  55                  60

Arg Glu Ala Glu Val Thr His Gly Arg Val Ala Met Leu Ala Val Ile
65                  70                  75                  80

Gly Phe Leu Val Gly Glu Ala Val Glu Gly Ser Ser Phe Leu Phe Asp
                85                  90                  95

Ala Gln Ile Ser Gly Pro Ala Ile Thr His Phe Thr Gln Val Pro Asp
            100                 105                 110

Gly Trp Asp Ala Leu Ile Val Thr Phe Ile Gly Ala Ala Glu Ala Gln
        115                 120                 125

Arg Ala Gln Ile Gly Trp Val Asp Pro Ala Asp Ala Ser Tyr Asp Gln
    130                 135                 140

Pro Gly Leu Leu Arg Asp Asn Tyr Tyr Pro Gly Asp Ile Gly Phe Asp
145                 150                 155                 160

Pro Leu Gly Leu Lys Pro Glu Asp Pro Glu Glu Leu Asn Ile Met Ile
                165                 170                 175

Thr Lys Glu Leu Gln Asn Gly Arg Leu Ala Met Leu Ala Ala Ala Gly
            180                 185                 190

Phe Leu Ala Gln Glu Ala Val Asp Gly Lys Gly Ile Leu Glu His Phe
        195                 200                 205

Ser Ser
    210
```

<210> SEQ ID NO 40
<211> LENGTH: 633
<212> TYPE: DNA
<213> ORGANISM: Cyclotella sp.
<220> FEATURE:
<221> NAME/KEY: misc_feature
<223> OTHER INFORMATION: FCP 1 coding sequence

<400> SEQUENCE: 40

```
atgatgaagc tcgccctcct ctctgctctt gccggctccg ccgccgcgtt cgcccctgcc      60

gccacccgtg cttcttcttc ggcgctcaac gctttctctg cagcggatct tccaggagct     120

cttcctcccg ttgggttttt cgatcccctc ggatttgcgg agaaggccga cgagaaaact     180

ctcaagcgtt accgtgaggc tgaggtcacc catggacgtg tcgccatgct cgctgtcatc     240

ggattcctcg taggagaagc agttgaggga agctccttcc ttttcgatgc tcagatctct     300

ggacccgcca taacccactt cacccaggtt cctgacgggt gggatgcact tattgtgacc     360

ttcattggtg ctgctgaggc ccaacgtgca cagattggat gggtcgatcc tgctgatgct     420

tcgtacgacc aaccgggttt gttgagggat aactattacc ccggagacat tggattcgat     480

cctttgggct tgaagccgga ggatcccgag gagttgaaca tcatgatcac gaaggagctg     540

cagaatggac gcctggcaat gcttgctgct gctgggttct tggcacaaga ggccgttgat     600

ggaaagggaa tcctcgaaca cttctcttcg taa                                  633
```

<210> SEQ ID NO 41
<211> LENGTH: 210
<212> TYPE: PRT
<213> ORGANISM: Cyclotella sp.
<220> FEATURE:

<221> NAME/KEY: misc_feature
<223> OTHER INFORMATION: FCP 2 protein

<400> SEQUENCE: 41

```
Met Met Lys Leu Ala Leu Leu Ser Ala Leu Ala Gly Ser Ala Ala Ala
1               5                   10                  15

Phe Ala Pro Ala Ala Thr Arg Ala Ser Ser Ser Ala Leu Asn Ala Phe
            20                  25                  30

Ser Ala Ala Asp Leu Pro Gly Ala Leu Pro Pro Val Gly Phe Phe Asp
        35                  40                  45

Pro Leu Gly Phe Ala Glu Lys Ala Asp Glu Lys Thr Leu Lys Arg Tyr
    50                  55                  60

Arg Glu Ala Glu Val Thr His Gly Arg Val Ala Met Leu Ala Val Ile
65                  70                  75                  80

Gly Phe Leu Val Gly Glu Ala Val Glu Gly Ser Ser Phe Leu Phe Asp
                85                  90                  95

Ala Gln Ile Ser Gly Pro Ala Ile Thr His Phe Thr Gln Val Pro Asp
            100                 105                 110

Gly Trp Asp Ala Leu Ile Val Thr Phe Ile Gly Ala Ala Glu Ala Gln
        115                 120                 125

Arg Ala Gln Ile Gly Trp Val Asp Pro Ala Asp Ala Ser Tyr Asp Gln
    130                 135                 140

Pro Gly Leu Leu Arg Asp Asn Tyr Tyr Pro Gly Asp Ile Gly Phe Asp
145                 150                 155                 160

Pro Leu Gly Leu Lys Pro Glu Asp Pro Glu Glu Leu Asn Ile Met Ile
                165                 170                 175

Thr Lys Glu Leu Gln Asn Gly Arg Leu Ala Met Leu Ala Ala Ala Gly
            180                 185                 190

Phe Leu Ala Gln Glu Ala Val Asp Gly Lys Gly Ile Leu Glu His Phe
        195                 200                 205

Ser Ser
    210
```

<210> SEQ ID NO 42
<211> LENGTH: 633
<212> TYPE: DNA
<213> ORGANISM: Cyclotella sp.
<220> FEATURE:
<221> NAME/KEY: misc_feature
<223> OTHER INFORMATION: FCP 2 coding sequence

<400> SEQUENCE: 42

```
atgatgaagc tcgccctcct ctctgctctt gccggctccg ccgccgcgtt cgcccctgcc     60

gccacccgtg cttcttcttc ggcgctcaac gctttctctg cagcggatct tccaggagct    120

cttcctcccg ttgggttttt cgatcccctc ggatttgcgg agaaggccga cgagaaaact    180

ctcaagcgtt accgtgaggc tgaggtcacc catggacgtg tcgccatgct cgctgtcatc    240

ggattcctcg taggagaagc agttgaggga agctccttcc ttttcgatgc tcagatctct    300

ggacccgcca taacccactt cacccaggtt cctgacgggt gggatgcact tattgtgacc    360

ttcattggtg ctgctgaggc ccaacgtgca cagattggat gggtcgatcc tgctgatgct    420

tcgtacgacc aaccgggttt gttgagggat aactattacc ccggagacat tggattcgat    480

cctttgggct tgaagccgga ggatcccgag gagttgaaca tcatgatcac gaaggagctg    540

cagaatggac gcctggcaat gcttgctgct gctgggttct tggcacaaga ggccgttgat    600

ggaaagggaa tcctcgaaca cttctcttcg taa                                 633
```

<210> SEQ ID NO 43
<211> LENGTH: 210
<212> TYPE: PRT
<213> ORGANISM: Cyclotella sp.
<220> FEATURE:
<221> NAME/KEY: misc_feature
<223> OTHER INFORMATION: FCP 3 protein

<400> SEQUENCE: 43

```
Met Met Lys Leu Ala Leu Leu Ser Ala Leu Ala Gly Ser Ala Ala Ala
1               5                   10                  15

Phe Ala Pro Ala Ala Thr Arg Ala Ser Ser Ser Ala Leu Asn Ala Phe
            20                  25                  30

Ser Ala Ala Asp Leu Pro Gly Ala Leu Pro Pro Val Gly Phe Phe Asp
        35                  40                  45

Pro Leu Gly Phe Ala Glu Lys Ala Asp Glu Lys Thr Leu Lys Arg Tyr
    50                  55                  60

Arg Glu Ala Glu Val Thr His Gly Arg Val Ala Met Leu Ala Val Ile
65                  70                  75                  80

Gly Phe Leu Val Gly Glu Ala Val Glu Gly Ser Ser Phe Leu Phe Asp
                85                  90                  95

Ala Gln Ile Ser Gly Pro Ala Ile Thr His Phe Thr Gln Val Pro Asp
            100                 105                 110

Gly Trp Asp Ala Leu Ile Val Thr Phe Ile Gly Ala Ala Glu Ala Gln
        115                 120                 125

Arg Ala Gln Ile Gly Trp Val Asp Pro Ala Asp Ala Ser Tyr Asp Gln
    130                 135                 140

Pro Gly Leu Leu Arg Asp Asn Tyr Tyr Pro Gly Asp Ile Gly Phe Asp
145                 150                 155                 160

Pro Leu Gly Leu Lys Pro Glu Asp Pro Glu Glu Leu Asn Ile Met Ile
                165                 170                 175

Thr Lys Glu Leu Gln Asn Gly Arg Leu Ala Met Leu Ala Ala Ala Gly
            180                 185                 190

Phe Leu Ala Gln Glu Ala Val Asp Gly Lys Gly Ile Leu Glu His Phe
        195                 200                 205

Ser Ser
    210
```

<210> SEQ ID NO 44
<211> LENGTH: 633
<212> TYPE: DNA
<213> ORGANISM: Cyclotella sp.
<220> FEATURE:
<221> NAME/KEY: misc_feature
<223> OTHER INFORMATION: FCP 3 coding sequence

<400> SEQUENCE: 44

```
atgatgaagc tcgccctcct ctctgctctt gccggctccg ccgccgcgtt cgcccctgcc      60

gccacccgtg cttcttcttc ggcgctcaac gctttctctg cagcggatct tccaggagct     120

cttcctcccg ttgggttttt cgatcccctc ggatttgcgg agaaggccga cgagaaaact     180

ctcaagcgtt accgtgaggc tgaggtcacc catggacgtg tcgccatgct cgctgtcatc     240

ggattcctcg taggagaagc agttgaggga agctccttcc ttttcgatgc tcagatctct     300

ggacccgcca taacccactt cacccaggtt cctgacgggt gggatgcact tattgtgacc     360

ttcattggtg ctgctgaggc ccaacgtgca cagattggat gggtcgatcc tgctgatgct     420
```

```
tcgtacgacc aaccgggttt gttgagggat aactactacc ccggagacat tggattcgat    480

cctttgggct tgaagccgga ggatcccgag gagttgaaca tcatgatcac gaaggagctg    540

cagaatggac gcctggcaat gcttgctgct gctgggttct tggcacaaga ggccgttgat    600

ggaaagggaa tcctcgaaca cttctcttcg taa                                 633
```

<210> SEQ ID NO 45
<211> LENGTH: 210
<212> TYPE: PRT
<213> ORGANISM: Cyclotella sp.
<220> FEATURE:
<221> NAME/KEY: misc_feature
<223> OTHER INFORMATION: FCP 4 protein

<400> SEQUENCE: 45

```
Met Met Lys Leu Ala Leu Leu Ser Ala Leu Ala Gly Ser Ala Ala Ala
1               5                   10                  15

Phe Ala Pro Ala Ala Thr Arg Ala Ser Ser Ser Ala Leu Asn Ala Phe
            20                  25                  30

Ser Ala Ala Asp Leu Pro Gly Ala Leu Pro Pro Val Gly Phe Phe Asp
        35                  40                  45

Pro Leu Gly Phe Ala Glu Lys Ala Asp Glu Lys Thr Leu Lys Arg Tyr
    50                  55                  60

Arg Glu Ala Glu Val Thr His Gly Arg Val Ala Met Leu Ala Val Ile
65                  70                  75                  80

Gly Phe Leu Val Gly Glu Ala Val Glu Gly Ser Ser Phe Leu Phe Asp
                85                  90                  95

Ala Gln Ile Ser Gly Pro Ala Ile Thr His Phe Thr Gln Val Pro Asp
            100                 105                 110

Gly Trp Asp Ala Leu Ile Val Thr Phe Ile Gly Ala Ala Glu Ala Gln
        115                 120                 125

Arg Ala Gln Ile Gly Trp Val Asp Pro Ala Asp Ala Ser Tyr Asp Gln
    130                 135                 140

Pro Gly Leu Leu Arg Asp Asn Tyr Tyr Pro Gly Asp Ile Gly Phe Asp
145                 150                 155                 160

Pro Leu Gly Leu Lys Pro Glu Asp Pro Glu Glu Leu Asn Ile Met Ile
                165                 170                 175

Thr Lys Glu Leu Gln Asn Gly Arg Leu Ala Met Leu Ala Ala Ala Gly
            180                 185                 190

Phe Leu Ala Gln Glu Ala Val Asp Gly Lys Gly Ile Leu Glu His Phe
        195                 200                 205

Ser Ser
    210
```

<210> SEQ ID NO 46
<211> LENGTH: 633
<212> TYPE: DNA
<213> ORGANISM: Cyclotella sp.
<220> FEATURE:
<221> NAME/KEY: misc_feature
<223> OTHER INFORMATION: FCP 4 coding sequence

<400> SEQUENCE: 46

```
atgatgaagc tcgccctcct ctctgctctt gccggctccg ccgccgcgtt cgcccctgcc     60

gccacccgtg cttcttcttc ggcgctcaac gctttctctg cagcggatct tccaggagct    120

cttcctcccg ttgggttttt cgatcccctc ggatttgcgg agaaggccga cgagaaaact    180

ctcaagcgtt accgtgaggc tgaggtcacc catggacgtg tcgccatgct cgctgtcatc    240
```

ggattcctcg taggagaagc agttgaggga agctccttcc ttttcgatgc tcagatctct 300
ggacccgcca taacccactt cacccaggtt cctgacgggt gggatgcact tattgtgacc 360
ttcattggtg ctgctgaggc ccaacgtgca cagattggat gggtcgatcc tgctgatgct 420
tcgtacgacc aaccgggttt gttgagggat aactattacc ccggagacat tggattcgat 480
cctttgggct tgaagccgga ggatcccgag gagttgaaca tcatgatcac gaaggagctg 540
cagaatggac gcctggcaat gcttgctgct gctgggttct tggcacaaga ggccgttgat 600
ggaaagggaa tcctcgaaca cttctcttcg taa 633

<210> SEQ ID NO 47
<211> LENGTH: 122
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VCP gRNA reverse template

<400> SEQUENCE: 47
aaaaaaagca ccgactcggt gccacttttt caagttgata acggactagc cttattttaa 60
cttgctattt ctagctctaa aacccgctct gctcaccgtc tcccctatag tgagtcgtat 120
ta 122

<210> SEQ ID NO 48
<211> LENGTH: 122
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VCP gRNA forward template

<400> SEQUENCE: 48
taatacgact cactataggg gtcaccaggg tgtggagcag ttttagagct agaaatagca 60
agttaaaata aggctagtcc gttatcaact tgaaaaagtg gcaccgagtc ggtgcttttt 120
tt 122

<210> SEQ ID NO 49
<211> LENGTH: 122
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: single VCP gRNA reverse template

<400> SEQUENCE: 49
aaaaaaagca ccgactcggt gccacttttt caagttgata acggactagc cttattttaa 60
cttgctattt ctagctctaa aactgctcca caccctggtg acccctatag tgagtcgtat 120
ta 122

<210> SEQ ID NO 50
<211> LENGTH: 20
<212> TYPE: DNA
<213> ORGANISM: Nannochloropsis gaditana
<220> FEATURE:
<221> NAME/KEY: misc_feature
<223> OTHER INFORMATION: PCR primer 1 for VCP1 gene locus

<400> SEQUENCE: 50
tcggtcttgt cctcgaactt 20

<210> SEQ ID NO 51
<211> LENGTH: 20
<212> TYPE: DNA
<213> ORGANISM: Nannochloropsis gaditana
<220> FEATURE:
<221> NAME/KEY: misc_feature
<223> OTHER INFORMATION: PCR primer 2 for VCP1 gene locus

<400> SEQUENCE: 51
gtctttctgg ctggacttgc 20

<210> SEQ ID NO 52
<211> LENGTH: 20
<212> TYPE: DNA
<213> ORGANISM: Nannochloropsis gaditana
<220> FEATURE:
<221> NAME/KEY: misc_feature
<223> OTHER INFORMATION: PCR primer 1 for VCP2a gene locus

<400> SEQUENCE: 52
ggggatcttg tcctccttct 20

<210> SEQ ID NO 53
<211> LENGTH: 20
<212> TYPE: DNA
<213> ORGANISM: Nannochloropsis gaditana
<220> FEATURE:
<221> NAME/KEY: misc_feature
<223> OTHER INFORMATION: PCR primer 2 for VCP2a gene locus

<400> SEQUENCE: 53
gaccccggag gatcttagac 20

<210> SEQ ID NO 54
<211> LENGTH: 20
<212> TYPE: DNA
<213> ORGANISM: Nannochloropsis gaditana
<220> FEATURE:
<221> NAME/KEY: misc_feature
<223> OTHER INFORMATION: PCR primer 1 for VCP2b gene locus

<400> SEQUENCE: 54
ctacttcgtg gcattcagca 20

<210> SEQ ID NO 55
<211> LENGTH: 20
<212> TYPE: DNA
<213> ORGANISM: Nannochloropsis gaditana
<220> FEATURE:
<221> NAME/KEY: misc_feature
<223> OTHER INFORMATION: PCR primer 2 for VCP2b gene locus

<400> SEQUENCE: 55
gccgttgttg atctccttgt 20

<210> SEQ ID NO 56
<211> LENGTH: 4104
<212> TYPE: DNA
<213> ORGANISM: Artificial Sequence
<220> FEATURE:
<223> OTHER INFORMATION: Synthetic
<220> FEATURE:

<221> NAME/KEY: misc_feature
<223> OTHER INFORMATION: cas9 gene from Streptococcus pyogenes codon
      optimized for Nannochloropsis gaditana

<400> SEQUENCE: 56

```
gacaagaagt actccatcgg gctggacatc gggacgaact ccgtgggatg ggccgtgatc     60

acagacgaat acaaggtgcc ttccaagaag ttcaaggtgc tggggaacac ggacagacac    120

tccatcaaga agaacctcat cggggccttg ctcttcgact ccggagaaac cgccgaagca    180

acgcgattga aaagaaccgc cagaagacga tacacacgac ggaagaaccg catctgctac    240

ctccaggaga tcttcagcaa cgagatggcc aaggtggacg actcgttctt tcatcgcctg    300

gaggagagct tcctggtgga ggaagacaag aaacatgagc gccacccgat cttcgggaac    360

atcgtggacg aagtggccta ccacgagaaa taccccacga tctaccactt gcgcaagaaa    420

ctcgtggact ccacggacaa agcggacttg cggttgatct acttggcctt ggcccacatg    480

atcaaatttc ggggccactt cctgatcgag ggcgacttga atcccgacaa ttccgacgtg    540

gacaagctct tcatccagct ggtgcagacc tacaaccagc tcttcgagga gaaccccatc    600

aatgcctccg gagtggacgc caaagccatc ttgtccgccc gattgtccaa atccagacgc    660

ttggagaact tgatcgcaca acttcctggc gagaagaaga acggcctctt cggcaacttg    720

atcgcgctgt cgctgggatt gacgcctaac ttcaagtcca acttcgactt ggccgaggac    780

gccaagttgc aactgtccaa ggacacctac gacgacgacc tcgacaacct gctggcccaa    840

attggcgacc aatacgcgga cttgtttttg gcggccaaga acttgagcga cgccatcttg    900

ttgagcgaca tcttgcgcgt gaatacggag atcaccaaag ccccttttgtc cgcctctatg    960

atcaagcggt acgacgagca ccaccaagac ttgaccctgt tgaaagccct cgtgcggcaa   1020

caattgcccg agaagtacaa ggagatcttc ttcgaccagt ccaagaacgg gtacgccggc   1080

tacatcgacg gaggagcctc ccaagaagag ttctacaagt tcatcaagcc catcctggag   1140

aagatggacg gcaccgagga gttgctcgtg aagctgaacc gcgaagactt gttgcgaaaa   1200

cagcggacgt tcgacaatgg cagcatcccc caccaaatcc atttgggaga gttgcacgcc   1260

atcttgcgac ggcaagagga cttctacccg ttcctgaagg acaaccgcga gaaaatcgag   1320

aagatcctga cgttcagaat cccctactac gtgggaccct tggcccgagg caattcccgg   1380

tttgcatgga tgacgcgcaa aagcgaagag acgatcaccc cctggaactt cgaagaagtg   1440

gtcgacaaag gagcatccgc acagagcttc atcgagcgaa tgacgaactt cgacaagaac   1500

ctgcccaacg agaaggtgtt gcccaagcat tcgctgctgt acgagtactt cacggtgtac   1560

aacgagctga ccaaggtgaa gtacgtgacc gagggcatgc gcaaacccgc gttcctgtcg   1620

ggagagcaaa agaaggccat tgtggacctg ctgttcaaga ccaaccggaa ggtgaccgtg   1680

aaacagctga aagaggacta cttcaagaag atcgagtgct tcgactccgt ggagatctcc   1740

ggcgtggagg accgattcaa tgcctccttg ggaacctacc atgacctcct gaagatcatc   1800

aaggacaagg acttcctgga caacgaggag aacgaggaca tcctggagga catcgtgctg   1860

accctgaccc tgttcgagga ccgagagatg atcgaggaac ggttgaaaac gtacgcccac   1920

ttgttcgacg acaaggtgat gaagcagctg aaacgccgcc gctacaccgg atggggacga   1980

ttgagccgca aactgattaa tggaattcgc gacaagcaat ccggaaagac catcctggac   2040

ttcctgaagt ccgacgggtt cgccaaccgc aacttcatgc agctcatcca cgacgactcc   2100

ttgaccttca aggaggacat ccagaaggcc caagtgtccg gacaaggaga ctccttgcac   2160

gagcacatcg ccaatttggc cggatccccc gcaatcaaaa aaggcatctt gcaaaccgtg   2220
```

```
aaagtggtcg acgaactggt gaaggtgatg ggacggcaca agcccgagaa catcgtgatc   2280

gaaatggccc gcgagaacca aaccacccaa aaaggacaga agaactcccg agagcgcatg   2340

aagcggatcg aagagggcat caaggagttg ggctcccaga tcctgaagga gcatcccgtg   2400

gagaataccc aattgcaaaa cgagaagctc tacctctact acctccagaa cgggcgggac   2460

atgtacgtcg accaagagct ggacatcaac cgcctctccg actacgatgt ggatcatatt   2520

gtgccccaga gcttcctcaa ggacgacagc atcgacaaca aggtcctgac gcgcagcgac   2580

aagaaccggg gcaagtctga caatgtgcct tccgaagaag tcgtgaagaa gatgaagaac   2640

tactggcggc agctgctcaa cgccaagctc atcacccaac ggaagttcga caacctgacc   2700

aaggccgaga gaggaggatt gtccgagttg gacaaagccg gcttcattaa acgccaactc   2760

gtggagaccc gccagatcac gaagcacgtg gcccaaatct tggactcccg gatgaacacg   2820

aaatacgacg agaatgacaa gctgatccgc gaggtgaagg tgatcacgct gaagtccaag   2880

ctggtgagcg acttccggaa ggacttccag ttctacaagg tgcgggagat caacaactac   2940

catcacgccc atgacgccta cctgaacgcc gtggtcggaa ccgccctgat caagaaatac   3000

cccaagctgg agtccgaatt cgtgtacgga gattacaagg tctacgacgt gcggaagatg   3060

atcgcgaagt ccgagcagga gatcggcaaa gccaccgcca agtacttctt ttactccaac   3120

atcatgaact tcttcaagac cgagatcacg ctcgccaacg gcgagatccg caagcgcccc   3180

ctgatcgaga ccaacggcga gacgggagag attgtgtggg acaaaggaag agattttgcc   3240

acagtgcgca aggtgctgtc catgcctcag gtgaacatcg tgaagaagac cgaggtgcaa   3300

acaggagggt tttccaaaga gtccattttg cctaagagga attccgacaa gctcatcgcc   3360

cgcaagaagg actgggaccc caagaagtac gggggcttcg actcccccac ggtggcctac   3420

tccgtgttgg tggtggccaa agtggagaaa gggaagagca agaagctgaa atccgtgaag   3480

gagttgctcg gaatcacgat catggaacga tcgtcgttcg agaaaaaccc catcgacttc   3540

ctcgaagcca aagggtacaa agaggtgaag aaggacctga tcatcaagct gcccaagtac   3600

tccctgttcg agctggagaa cggccgcaag cggatgctgg cctccgccgg ggaactgcag   3660

aaagggaacg aattggcctt gccctccaaa tacgtgaact tcctctactt ggcctcccat   3720

tacgaaaagc tcaaaggatc ccctgaggac aatgagcaga agcaactctt cgtggaacaa   3780

cacaagcact acctggacga gatcatcgag cagatcagcg agttctccaa gcgcgtgatc   3840

ctcgccgacg ccaacctgga caaggtgctc tccgcctaca acaagcaccg cgacaagcct   3900

atccgcgagc aagccgagaa tatcattcac ctgtttaccc tgacgaattt gggagcccct   3960

gccgccttta aatactttga caccaccatc gaccgcaaaa gatacacctc caccaaggaa   4020

gtcttggacg ccaccctcat ccaccagtcc atcacgggcc tctacgagac gcgcatcgac   4080

ctctcccaat tgggcggcga ctaa                                          4104
```

<210> SEQ ID NO 57
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: encodes N-terminal FLAG tag

<400> SEQUENCE: 57

```
gactacaagg atgacgatga caag                                            24
```

<210> SEQ ID NO 58
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: encodes nuclear localization signal

<400> SEQUENCE: 58
cccaagaaaa agcggaaggt cggc 24

<210> SEQ ID NO 59
<211> LENGTH: 96
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Encodes peptide linker

<400> SEQUENCE: 59
ttggagcctg gagagaagcc ctacaaatgc cctgagtgcg gaaagagctt cagccaatct 60
ggagccttga cccggcatca acgaacgcat acacga 96

<210> SEQ ID NO 60
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: RPL24 promoter

<400> SEQUENCE: 60
aataagcata catcatatga atacaattca gcttaaattt atcatacaaa gatgtaagtg 60
cagcgtgggt ctgtaacgat cgggcgtaat ttaagataat gcgagggacc gggggaggtt 120
ttggaacgga atgaggaatg ggtcatggcc cataataata atatgggttt ggtcgcctcg 180
cacagcaacc gtacgtgcga aaaaggaaca gatccattta ataagttgaa cgttattctt 240
tcctatgcaa tgcgtgtatc ggaggcgaga gcaagtcata ggtggctgcg cacaataatt 300
gagtctcagc tgagcgccgt ccgcgggtgg tgtgagtggt catcctcctc ccggcctatc 360
gctcacatcg cctctcaatg gtggtggtgg ggcctgatat gacctcaatg ccgacccata 420
ttaaaaccca gtaaagcatt caccaacgaa cgaggggctc ttttgtgtgt gttttgagta 480
tgattttaca cctctttgtg catctctctg gtcttccttg gttcccgtag tttgggcatc 540
atcactcacg cttccctcga ccttcgttct tcctttacaa ccccgacaca ggtcagagtt 600
ggagtaatca aaaaaggggt gcacgaatga gatacattag attttgacag atatcctttt 660
actggagagg gttcaaggga tcaaatgaac agcgggcgtt ggcaatctag ggagggatcg 720
gaggttggca gcgagcgaaa gcgtgtccat ccttttggct gtcacacctc acgaaccaac 780
tgttagcagg ccagcacaga tgacatacga gaatctttat tatatcgtag accttatgtg 840
gatgaccttt ggtgctgtgt gtctggcaat gaacctgaag gcttgatagg gaggtggctc 900
ccgtaaaccc tttgtccttt ccacgctgag tctcccccgc actgtccttt atacaaattg 960
ttacagtcat ctgcaggcgg tttttctttg gcaggcaaag 1000

```
<210> SEQ ID NO 61
<211> LENGTH: 317
<212> TYPE: DNA
<213> ORGANISM: Nannochloropsis gaditana
<220> FEATURE:
<221> NAME/KEY: misc_feature
<223> OTHER INFORMATION: bidirectional terminator 2

<400> SEQUENCE: 61

agtgatgcgg cctttaggaa acaccacaaa agtaattgac aatctcagga acgatctgcg     60

tgtttacagc ttcccaaata acaattatac cacgtaccaa aaggggttta atgtatctca    120

caaattcttc taataggtac agcttctcaa attgggtgta tgatgtgaca cttcgtctca    180

cacacgtcac gataattcag cgtatggctt cccttcatca cattcacgca aacttctaca    240

caaccctggg catatttctt gtgttggcaa cactcccgaa atcgattctg cacacaatgg    300

ttcattcaat gattcaa                                                   317


<210> SEQ ID NO 62
<211> LENGTH: 399
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: blast gene from Aspergillus terreus codon
      optimized for N. gaditana

<400> SEQUENCE: 62

atggccaagc ctttatccca agaggaatcc acgctgatcg aacgtgcaac tgcgaccatc     60

aacagcatac ctattagcga ggactactcg gtggccagtg cagccctctc gtccgacggt    120

cggatcttta ccggcgtgaa tgtatatcat ttcaccggag ggccatgcgc ggagctcgtg    180

gtcctcggaa cggccgctgc ggctgctgcc ggaaatctga cgtgcatagt ggccatcggg    240

aacgaaaacc gcggcattct gtctccgtgc gggcgatgtc ggcaggtgct gcttgacttg    300

cacccgggga tcaaggcaat tgtcaaagat tccgatgggc agcccacagc ggttggcatc    360

agggagttgc ttccctctgg ctacgtctgg gagggttga                            399


<210> SEQ ID NO 63
<211> LENGTH: 1002
<212> TYPE: DNA
<213> ORGANISM: Nannochloropsis gaditana
<220> FEATURE:
<221> NAME/KEY: misc_feature
<223> OTHER INFORMATION: TCTP promoter

<400> SEQUENCE: 63

cgtgcaggtg tacagattga aggaaacaat ggagatatct ttggcagttg aaaaccgtgt     60

tcgaatcatg cttttctact ctccaactga gacgaaattt atagcgccat gtcgcttctg    120

actaccaggc ttaggaaggc ctcatcacaa gctggatcgg ttcgaattaa gcaggcactg    180

aagccaagct tgcaagacag ccacctttta attccctcaa aacactttct caattcagcc    240

cggtaaatat gccgattcac agcggccaag atagagggga ggttagcaag aatgttgcga    300

tccctcccca gtcgttgcct cgcacacaac ctaggccttc acctttccat ggaaaattga    360

gaagtgaata ttggttttct tacggcatat cagatgaaat catgacccct aaacatgaag    420

agctgcaggc aaaacacctg ctctggacga gcacgatgaa atctcgagaa cccgccgtac    480

ttcagttgat cccgcatgat gacggccgcc attgaaataa gccacctcac tttattctag    540
```

caccgatttc caccgttgtg agggccgaac gaggacaatt tcgtgcgaaa caagcacgaa 600
cacgcacacg attagtagta cagacgagca gatcgatggc atgcggcacg gtctcgcgtt 660
ctcggcgacc aggacaacgg agcagaggga ggcctgccga gttccgaggg gcattttagt 720
ccaaaattgt gttgacacgt gaacaagtgg cttgaaaaga ggaaggaaat gcctgggttt 780
cccttcgaga gcgggaactc gcttgtgcgt catcctagct acccatggtc cctttgtggg 840
ggaggctgtt tcgtcctacc gaatgtgtgg cgctccatgc atcttctgcc tcccaaacca 900
ccaacatgag cacgcgaagg aaggagaaaa aagtggccgc aacgttctct tctcatattt 960
attgtctcat cacaaacata ggtacataat acaacaatca tg 1002

<210> SEQ ID NO 64
<211> LENGTH: 318
<212> TYPE: DNA
<213> ORGANISM: Nannochloropsis gaditana
<220> FEATURE:
<221> NAME/KEY: misc_feature
<223> OTHER INFORMATION: EIF3 terminator

<400> SEQUENCE: 64
ggcactgtaa ccccggttcc gctcgacgaa ggctgggagc gccctttcgg tgggataaaa 60
tggatgcttt accgctgcgc ttcggctgag gaagagagaa atgcgagcgg ggatcggggt 120
cctagaaacg aagaaaggag aacaagttcc tggccaaaga aaaacaagac aaataccctc 180
tccaggcctg ggcccattac tttttttgc tgtttcttat acctgcactc gtgcttctct 240
agtctgtcga gaccttacct gatcttcctc cctccatcgc tccccgcccc ccccatccga 300
gcaaccgtcg accatacg 318

<210> SEQ ID NO 65
<211> LENGTH: 702
<212> TYPE: DNA
<213> ORGANISM: Artificial Sequence
<220> FEATURE:
<223> OTHER INFORMATION: TurboGFP gene codon optimized for Nannochloropsis gaditana

<400> SEQUENCE: 65
atgttggaga gcgacgagag cggcctgccc gccatggaga tcgagtgccg catcaccggc 60
accctgaacg gcgtggagtt cgagctggtg ggcggcggag agggcacccc cgagcagggc 120
cgcatgacca acaagatgaa gagcaccaaa ggcgccctga ccttcagccc ctacctgctg 180
agccacgtga tgggctacgg cttctaccac ttcggcacct accccagcgg ctacgagaac 240
cccttcctgc acgccatcaa caacggcggc tacaccaaca cccgcatcga gaagtacgag 300
gacggcggcg tgctgcacgt gagcttcagc taccgctacg aggccggccg cgtgatcggc 360
gacttcaagg tgatgggcac cggcttcccc gaggacagcg tgatcttcac cgacaagatc 420
atccgcagca acgccaccgt ggagcacctg caccccatgg gcgataacga tctggatggc 480
agcttcaccc gcaccttcag cctgcgcgac ggcggctact acagctccgt ggtggacagc 540
cacatgcact tcaagagcgc catccacccc agcatcctgc agaacggggg ccccatgttc 600
gccttccgcc gcgtggagga ggatcacagc aacaccgagc tgggcatcgt ggagtaccag 660
cacgccttca agaccccgga tgcagatgcc ggtgaagaat aa 702

<210> SEQ ID NO 66
<211> LENGTH: 822
<212> TYPE: DNA
<213> ORGANISM: Nannochloropsis gaditana

```
<220> FEATURE:
<221> NAME/KEY: misc_feature
<223> OTHER INFORMATION: 4A-III promoter

<400> SEQUENCE: 66

ggcataaagg acggcaagga aagaaaagaa agaaagaaaa ggacacttat agcatagttt     60

gaagttataa gtagtcgcaa tctgtgtgca gccgacagat gcttttttt tccgtttggc    120

aggaggtgta gggatgtcga agaccagtcc agctagtatc tatcctacaa gtcaatcatg    180

ctgcgacaaa aatttctcgc acgaggcctc tcgataaaca aaactttaaa agcacacttc    240

attgtcatgc agagtaataa ctcttccgcg tcgatcaatt tatcaatctc tatcatttcc    300

gcccctttcc ttgcatagag caagaaaagc gacccggatg aggataacat gtcctgcgcc    360

agtagtgtgg cattgcctgt ctctcattta cacgtactga aagcataatg cacgcgcata    420

ccaatatttt tcgtgtacgg agatgaagag acgcgacacg taagatcacg agaaggcgag    480

cacggttgcc aatggcagac gcgctagtct ccattatcgc gttgttcggt agcttgctgc    540

atgtcttcag tggcactata tccactctgc ctcgtcttct acacgagggc cacatcggtg    600

caagttcgaa aaatcatatc tcaatcttca gatcctttcc agaaacggtg ctcaggcggg    660

aaagtgaagg ttttctactc tagtggctac cccaattctc tccgactgtc gcagacggtc    720

cttcgttgcg cacgcaccgc gcactacctc tgaaattcga caaccgaagt tcaattttac    780

atctaacttc tttcccattc tctcaccaaa agcctagctt ac                        822


<210> SEQ ID NO 67
<211> LENGTH: 200
<212> TYPE: DNA
<213> ORGANISM: Nannochloropsis gaditana
<220> FEATURE:
<221> NAME/KEY: misc_feature
<223> OTHER INFORMATION: bidirectional terminator 5

<400> SEQUENCE: 67

gggtgggaag gagtcgggga gggtcctggc agagcggcgt cctcatgatg tgttggagac     60

ctggagagtc gagagcttcc tcgtcacctg attgtcatgt gtgtataggt taagggggcc    120

cactcaaagc cataaagacg aacacaaaca ctaatctcaa caaagtctac tagcatgccg    180

tctgtccatc tttatttcct                                                 200


<210> SEQ ID NO 68
<211> LENGTH: 11263
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Construct used to generate GE-6791

<400> SEQUENCE: 68

gcggccgccg tatggtcgac ggttgctcgg atgggggggg cggggagcga tggagggagg     60

aagatcaggt aaggtctcga cagactagag aagcacgagt gcaggtataa gaaacagcaa    120

aaaaaagtaa tgggcccagg cctggagagg gtatttgtct tgtttttctt tggccaggaa    180

cttgttctcc tttcttcgtt tctaggaccc cgatccccgc tcgcatttct ctcttcctca    240

gccgaagcgc agcggtaaag catccatttt atcccaccga aagggcgctc ccagccttcg    300

tcgagcggaa ccggggttac agtgcctcaa ccctcccaga cgtagccaga gggaagcaac    360

tccctgatgc caaccgctgt gggctgccca tcggaatctt tgacaattgc cttgatcccc    420
```

```
gggtgcaagt caagcagcac ctgccgacat cgcccgcacg gagacagaat gccgcggttt    480
tcgttcccga tggccactat gcacgtcaga tttccggcag cagccgcagc ggccgttccg    540
aggaccacga gctccgcgca tggccctccg gtgaaatgat atacattcac gccggtaaag    600
atccgaccgt cggacgagag ggctgcactg gccaccgagt agtcctcgct aataggtatg    660
ctgttgatgg tcgcagttgc acgttcgatc agcgtggatt cctcttggga taaaggcttg    720
gccatcgagc tcggtacccg gggatccatg attgttgtat tatgtaccta tgtttgtgat    780
gagacaataa atatgagaag agaacgttgc ggccactttt ttctccttcc ttcgcgtgct    840
catgttggtg gtttgggagg cagaagatgc atggagcgcc acacattcgg taggacgaaa    900
cagcctcccc cacaaaggga ccatgggtag ctaggatgac gcacaagcga gttcccgctc    960
tcgaagggaa acccaggcat ttccttcctc ttttcaagcc acttgttcac gtgtcaacac   1020
aattttggac taaaatgccc ctcggaactc ggcaggcctc cctctgctcc gttgtcctgg   1080
tcgccgagaa cgcgagaccg tgccgcatgc catcgatctg ctcgtctgta ctactaatcg   1140
tgtgcgtgtt cgtgcttgtt tcgcacgaaa ttgtcctcgt tcggccctca caacggtgga   1200
aatcggtgct agaataaagt gaggtggctt atttcaatgg cggccgtcat catgcgggat   1260
caactgaagt acggcgggtt ctcgagattt catcgtgctc gtccagagca ggtgttttgc   1320
ctgcagctct tcatgtttag ggtcatgat ttcatctgat atgccgtaag aaaaccaata   1380
ttcacttctc aattttccat ggaaaggtga aggcctaggt tgtgtgcgag gcaacgactg   1440
gggagggatc gcaacattct tgctaacctc ccctctatct tggccgctgt gaatcggcat   1500
atttaccggg ctgaattgag aaagtgtttt gagggaatta aaaggtggct gtcttgcaag   1560
cttggcttca gtgcctgctt aattcgaacc gatccagctt gtgatgaggc cttcctaagc   1620
ctggtagtca gaagcgacat ggcgctataa atttcgtctc agttggagag tagaaaagca   1680
tgattcgaac acggttttca actgccaaag atatctccat tgtttccttc aatctgtaca   1740
cctgcacggt gcaccagttg gtacggcata ttatggttta ataagcatac atcatatgaa   1800
tacaattcag cttaaattta tcatacaaag atgtaagtgc agcgtgggtc tgtaacgatc   1860
gggcgtaatt taagataatg cgagggaccg ggggaggttt tggaacggaa tgaggaatgg   1920
gtcatggccc ataataataa tatgggtttg gtcgcctcgc acagcaaccg tacgtgcgaa   1980
aaaggaacag atccatttaa taagttgaac gttattcttt cctatgcaat gcgtgtatcg   2040
gaggcgagag caagtcatag gtggctgcgc acaataattg agtctcagct gagcgccgtc   2100
cgcgggtggt gtgagtggtc atcctcctcc cggcctatcg ctcacatcgc ctctcaatgg   2160
tggtggtggg gcctgatatg acctcaatgc cgacccatat taaaacccag taaagcattc   2220
accaacgaac gaggggctct tttgtgtgtg ttttgagtat gattttacac ctctttgtgc   2280
atctctctgg tcttccttgg ttcccgtagt ttgggcatca tcactcacgc ttccctcgac   2340
cttcgttctt cctttacaac cccgacacag gtcagagttg gagtaatcaa aaaaggggtg   2400
cacgaatgag atacattaga ttttgacaga tatcctttta ctggagaggg ttcaagggat   2460
caaatgaaca gcgggcgttg gcaatctagg gagggatcgg aggttggcag cgagcgaaag   2520
cgtgtccatc cttttggctg tcacacctca cgaaccaact gttagcaggc cagcacagat   2580
gacatacgag aatctttatt atatcgtaga ccttatgtgg atgacctttg gtgctgtgtg   2640
tctggcaatg aacctgaagg cttgataggg aggtggctcc cgtaaaccct ttgtcctttc   2700
cacgctgagt ctcccccgca ctgtccttta tacaaattgt tacagtcatc tgcaggcggt   2760
```

-continued

```
ttttctttgg caggcaaaga tgcccaagaa aaagcggaag gtcggcgact acaaggatga   2820
cgatgacaag ttggagcctg gagagaagcc ctacaaatgc cctgagtgcg gaaagagctt   2880
cagccaatct ggagccttga cccggcatca acgaacgcat acacgagaca agaagtactc   2940
catcgggctg gacatcggga cgaactccgt gggatgggcc gtgatcacag acgaatacaa   3000
ggtgccttcc aagaagttca aggtgctggg gaacacggac agacactcca tcaagaagaa   3060
cctcatcggg gccttgctct tcgactccgg agaaaccgcc gaagcaacgc gattgaaaag   3120
aaccgccaga agacgataca cacgacggaa gaaccgcatc tgctacctcc aggagatctt   3180
cagcaacgag atggccaagg tggacgactc gttctttcat cgcctggagg agagcttcct   3240
ggtggaggaa gacaagaaac atgagcgcca cccgatcttc gggaacatcg tggacgaagt   3300
ggcctaccac gagaaatacc ccacgatcta ccacttgcgc aagaaactcg tggactccac   3360
ggacaaagcg gacttgcggt tgatctactt ggccttggcc cacatgatca aatttcgggg   3420
ccacttcctg atcgagggcg acttgaatcc cgacaattcc gacgtggaca agctcttcat   3480
ccagctggtg cagacctaca accagctctt cgaggagaac cccatcaatg cctccggagt   3540
ggacgccaaa gccatcttgt ccgcccgatt gtccaaatcc agacgcttgg agaacttgat   3600
cgcacaactt cctggcgaga agaagaacgg cctcttcggc aacttgatcg cgctgtcgct   3660
gggattgacg cctaacttca agtccaactt cgacttggcc gaggacgcca agttgcaact   3720
gtccaaggac acctacgacg acgacctcga caacctgctg gcccaaattg gcgaccaata   3780
cgcggacttg tttttggcgg ccaagaactt gagcgacgcc atcttgttga gcgacatctt   3840
gcgcgtgaat acggagatca ccaaagcccc tttgtccgcc tctatgatca agcggtacga   3900
cgagcaccac caagacttga ccctgttgaa agccctcgtg cggcaacaat tgcccgagaa   3960
gtacaaggag atcttcttcg accagtccaa gaacgggtac gccggctaca tcgacggagg   4020
agcctcccaa gaagagttct acaagttcat caagcccatc ctggagaaga tggacggcac   4080
cgaggagttg ctcgtgaagc tgaaccgcga agacttgttg cgaaaacagc ggacgttcga   4140
caatggcagc atcccccacc aaatccattt gggagagttg cacgccatct tgcgacggca   4200
agaggacttc tacccgttcc tgaaggacaa ccgcgagaaa atcgagaaga tcctgacgtt   4260
cagaatcccc tactacgtgg gacccttggc ccgaggcaat tcccggtttg catggatgac   4320
gcgcaaaagc gaagagacga tcaccccctg gaacttcgaa gaagtggtcg acaaaggagc   4380
atccgcacag agcttcatcg agcgaatgac gaacttcgac aagaacctgc ccaacgagaa   4440
ggtgttgccc aagcattcgc tgctgtacga gtacttcacg gtgtacaacg agctgaccaa   4500
ggtgaagtac gtgaccgagg gcatgcgcaa acccgcgttc ctgtcgggag agcaaaagaa   4560
ggccattgtg gacctgctgt tcaagaccaa ccggaaggtg accgtgaaac agctgaaaga   4620
ggactacttc aagaagatcg agtgcttcga ctccgtggag atctccggcg tggaggaccg   4680
attcaatgcc tccttgggaa cctaccatga cctcctgaag atcatcaagg acaaggactt   4740
cctggacaac gaggagaacg aggacatcct ggaggacatc gtgctgaccc tgaccctgtt   4800
cgaggaccga gagatgatcg aggaacggtt gaaaacgtac gcccacttgt tcgacgacaa   4860
ggtgatgaag cagctgaaac gccgccgcta caccggatgg ggacgattga gccgcaaact   4920
gattaatgga attcgcgaca agcaatccgg aaagaccatc ctggacttcc tgaagtccga   4980
cgggttcgcc aaccgcaact tcatgcagct catccacgac gactccttga ccttcaagga   5040
ggacatccag aaggcccaag tgtccggaca aggagactcc ttgcacgagc acatcgccaa   5100
tttggccgga tcccccgcaa tcaaaaaagg catcttgcaa accgtgaaag tggtcgacga   5160
```

```
actggtgaag gtgatgggac ggcacaagcc cgagaacatc gtgatcgaaa tggcccgcga   5220
gaaccaaacc acccaaaaag gacagaagaa ctcccgagag cgcatgaagc ggatcgaaga   5280
gggcatcaag gagttgggct cccagatcct gaaggagcat cccgtggaga atacccaatt   5340
gcaaaacgag aagctctacc tctactacct ccagaacggg cgggacatgt acgtcgacca   5400
agagctggac atcaaccgcc tctccgacta cgatgtggat catattgtgc cccagagctt   5460
cctcaaggac gacagcatcg acaacaaggt cctgacgcgc agcgacaaga accggggcaa   5520
gtctgacaat gtgccttccg aagaagtcgt gaagaagatg aagaactact ggcggcagct   5580
gctcaacgcc aagctcatca cccaacggaa gttcgacaac ctgaccaagg ccgagagagg   5640
aggattgtcc gagttggaca aagccggctt cattaaacgc caactcgtgg agacccgcca   5700
gatcacgaag cacgtggccc aaatcttgga ctcccggatg aacacgaaat acgacgagaa   5760
tgacaagctg atccgcgagg tgaaggtgat cacgctgaag tccaagctgg tgagcgactt   5820
ccggaaggac ttccagttct acaaggtgcg ggagatcaac aactaccatc acgcccatga   5880
cgcctacctg aacgccgtgg tcggaaccgc cctgatcaag aaatacccca agctggagtc   5940
cgaattcgtg tacggagatt acaaggtcta cgacgtgcgg aagatgatcg cgaagtccga   6000
gcaggagatc ggcaaagcca ccgccaagta cttcttttac tccaacatca tgaacttctt   6060
caagaccgag atcacgctcg ccaacggcga gatccgcaag cgcccccctga tcgagaccaa   6120
cggcgagacg ggagagattg tgtgggacaa aggaagagat tttgccacag tgcgcaaggt   6180
gctgtccatg cctcaggtga acatcgtgaa gaagaccgag gtgcaaacag gagggttttc   6240
caaagagtcc attttgccta agaggaattc cgacaagctc atcgcccgca agaaggactg   6300
ggaccccaag aagtacgggg gcttcgactc ccccacggtg gcctactccg tgttggtggt   6360
ggccaaagtg gagaaaggga agagcaagaa gctgaaatcc gtgaaggagt tgctcggaat   6420
cacgatcatg gaacgatcgt cgttcgagaa aaaccccatc gacttcctcg aagccaaagg   6480
gtacaaagag gtgaagaagg acctgatcat caagctgccc aagtactccc tgttcgagct   6540
ggagaacggc cgcaagcgga tgctggcctc cgccggggaa ctgcagaaag ggaacgaatt   6600
ggccttgccc tccaaatacg tgaacttcct ctacttggcc tcccattacg aaaagctcaa   6660
aggatcccct gaggacaatg agcagaagca actcttcgtg gaacaacaca agcactacct   6720
ggacgagatc atcgagcaga tcagcgagtt ctccaagcgc gtgatcctcg ccgacgccaa   6780
cctggacaag gtgctctccg cctacaacaa gcaccgcgac aagcctatcc gcgagcaagc   6840
cgagaatatc attcacctgt ttaccctgac gaatttggga gcccctgccg cctttaaata   6900
ctttgacacc accatcgacc gcaaaagata cacctccacc aaggaagtct tggacgccac   6960
cctcatccac cagtccatca cgggcctcta cgagacgcgc atcgacctct cccaattggg   7020
cggcgactaa agtgatgcgg cctttaggaa acaccacaaa agtaattgac aatctcagga   7080
acgatctgcg tgtttacagc ttcccaaata acaattatac cacgtaccaa aaggggttta   7140
atgtatctca caaattcttc taataggtac agcttctcaa attgggtgta tgatgtgaca   7200
cttcgtctca cacacgtcac gataattcag cgtatggctt cccttcatca cattcacgca   7260
aacttctaca caaccctggg catatttctt gtgttggcaa cactcccgaa atcgattctg   7320
cacacaatgg ttcattcaat gattcaagta cgttttagac ggactaggca gtttaattaa   7380
aaacatctat cctccagatc accagggcca gtgaggccgg cataaaggac ggcaaggaaa   7440
gaaaagaaag aaagaaaagg acacttatag catagtttga agttataagt agtcgcaatc   7500
```

-continued

```
tgtgtgcagc cgacagatgc ttttttttc cgtttggcag gaggtgtagg gatgtcgaag   7560
accagtccag ctagtatcta tcctacaagt caatcatgct gcgacaaaaa tttctcgcac   7620
gaggcctctc gataaacaaa actttaaaag cacacttcat tgtcatgcag agtaataact   7680
cttccgcgtc gatcaattta tcaatctcta tcatttccgc ccctttcctt gcatagagca   7740
agaaaagcga cccggatgag gataacatgt cctgcgccag tagtgtggca ttgcctgtct   7800
ctcatttaca cgtactgaaa gcataatgca cgcgcatacc aatatttttc gtgtacggag   7860
atgaagagac gcgacacgta agatcacgag aaggcgagca cggttgccaa tggcagacgc   7920
gctagtctcc attatcgcgt tgttcggtag cttgctgcat gtcttcagtg gcactatatc   7980
cactctgcct cgtcttctac acgagggcca catcggtgca agttcgaaaa atcatatctc   8040
aatcttcaga tcctttccag aaacggtgct caggcgggaa agtgaaggtt ttctactcta   8100
gtggctaccc caattctctc cgactgtcgc agacggtcct tcgttgcgca cgcaccgcgc   8160
actacctctg aaattcgaca accgaagttc aattttacat ctaacttctt tcccattctc   8220
tcaccaaaag cctagcttac atgttggaga gcgacgagag cggcctgccc gccatggaga   8280
tcgagtgccg catcaccggc accctgaacg gcgtggagtt cgagctggtg ggcggcggag   8340
agggcacccc cgagcagggc cgcatgacca acaagatgaa gagcaccaaa ggcgccctga   8400
ccttcagccc ctacctgctg agccacgtga tgggctacgg cttctaccac ttcggcacct   8460
accccagcgg ctacgagaac cccttcctgc acgccatcaa caacggcggc tacaccaaca   8520
cccgcatcga gaagtacgag gacggcggcg tgctgcacgt gagcttcagc taccgctacg   8580
aggccggccg cgtgatcggc gacttcaagg tgatgggcac cggcttcccc gaggacagcg   8640
tgatcttcac cgacaagatc atccgcagca acgccaccgt ggagcacctg caccccatgg   8700
gcgataacga tctggatggc agcttcaccc gcaccttcag cctgcgcgac ggcggctact   8760
acagctccgt ggtggacagc cacatgcact tcaagagcgc catccacccc agcatcctgc   8820
agaacggggg ccccatgttc gccttccgcc gcgtggagga ggatcacagc aacaccgagc   8880
tgggcatcgt ggagtaccag cacgccttca agaccccgga tgcagatgcc ggtgaagaat   8940
aagggtggga aggagtcggg gagggtcctg gcagagcggc gtcctcatga tgtgttggag   9000
acctggagag tcgagagctt cctcgtcacc tgattgtcat gtgtgtatag gttaaggggg   9060
cccactcaaa gccataaaga cgaacacaaa cactaatctc aacaaagtct actagcatgc   9120
cgtctgtcca tctttatttc ctggcgcgcc tatgcttgta aaccgttttg tgaaaaaatt   9180
tttaaaataa aaaaggggac ctctagggtc cccaattaat tagtaatata atctattaaa   9240
ggtcattcaa aaggtcatcc agacgaaagg gcctcgtgat acgcctattt ttataggtta   9300
atgtcatgat aataatggtt tcttagacgt caggtggcac ttttcgggga aatgtgcgcg   9360
gaacccctat ttgtttattt ttctaaatac attcaaatat gtatccgctc atgagacaat   9420
aaccctgata aatgcttcaa taatattgaa aaaggaagag tatgagtatt caacatttcc   9480
gtgtcgccct tattcccttt tttgcggcat tttgccttcc tgtttttgct cacccagaaa   9540
cgctggtgaa agtaaaagat gctgaagatc agttgggtgc acgagtgggt tacatcgaac   9600
tggatctcaa cagcggtaag atccttgaga gttttcgccc cgaagaacgt tttccaatga   9660
tgagcacttt taaagttctg ctatgtggcg cggtattatc ccgtattgac gccgggcaag   9720
agcaactcgg tcgccgcata cactattctc agaatgactt ggttgagtac tcaccagtca   9780
cagaaaagca tcttacggat ggcatgacag taagagaatt atgcagtgct gccataacca   9840
tgagtgataa cactgcggcc aacttacttc tgacaacgat cggaggaccg aaggagctaa   9900
```

```
ccgctttttt gcacaacatg ggggatcatg taactcgcct tgatcgttgg gaaccggagc   9960

tgaatgaagc cataccaaac gacgagcgtg acaccacgat gcctgtagca atggcaacaa  10020

cgttgcgcaa actattaact ggcgaactac ttactctagc ttcccggcaa caattaatag  10080

actggatgga ggcggataaa gttgcaggac cacttctgcg ctcggccctt ccggctggct  10140

ggtttattgc tgataaatct ggagccggtg agcgtgggtc tcgcggtatc attgcagcac  10200

tggggccaga tggtaagccc tcccgtatcg tagttatcta cacgacgggg agtcaggcaa  10260

ctatggatga acgaaataga cagatcgctg agataggtgc ctcactgatt aagcattggt  10320

aactgtcaga ccaagtttac tcatatatac tttagattga tttaaaactt catttttaat  10380

ttaaaaggat ctaggtgaag atcctttttg ataatctcat gaccaaaatc ccttaacgtg  10440

agttttcgtt ccactgagcg tcagaccccg tagaaaagat caaaggatct tcttgagatc  10500

cttttttct gcgcgtaatc tgctgcttgc aaacaaaaaa accaccgcta ccagcggtgg  10560

tttgtttgcc ggatcaagag ctaccaactc tttttccgaa ggtaactggc ttcagcagag  10620

cgcagatacc aaatactgtc cttctagtgt agccgtagtt aggccaccac ttcaagaact  10680

ctgtagcacc gcctacatac ctcgctctgc taatcctgtt accagtggct gctgccagtg  10740

gcgataagtc gtgtcttacc gggttggact caagacgata gttaccggat aaggcgcagc  10800

ggtcgggctg aacggggggt tcgtgcacac agcccagctt ggagcgaacg acctacaccg  10860

aactgagata cctacagcgt gagctatgag aaagcgccac gcttcccgaa gggagaaagg  10920

cggacaggta tccggtaagc ggcagggtcg gaacaggaga gcgcacgagg gagcttccag  10980

ggggaaacgc ctggtatctt tatagtcctg tcgggtttcg ccacctctga cttgagcgtc  11040

gatttttgtg atgctcgtca ggggggcgga gcctatggaa aaacgccagc aacgcggcct  11100

ttttacggtt cctggccttt tgctggcctt ttgctcacat gttctttcct gcgttatccc  11160

ctgattctgt ggataaccgt attaccgcct ttgagtgagc tgataccgct cgccgcagcc  11220

gaacgaccga gcgcagcgag tcagtgagcg aggaagcgga aga                    11263
```

<210> SEQ ID NO 69
<211> LENGTH: 400
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VCP RNAi fragment

<400> SEQUENCE: 69

```
gcctttgtgg cccccgcccc caagttcagc cgcacccgcg gtgttgcccg catgtccttc     60

gaggacgagg ccggcgtgac cgcccccctg ggctactggg acccgcttgg cttctccgcc    120

gatggtgatg tcgagaaatt caaccgttac cgcgccatcg agatcaagca cggccgagtg    180

gccatgcttg ccatgctcca caccctggtg accggcctcg gcgtgaagct ccccggcctt    240

gtggctgccg gtgacggcat ccccgcctcc atgcccgcgg gcatcaacgc catcacctcc    300

ggcgcttggg ccgcacaggg atgggcgcag gtgctcctct tctgctccgc cctcgaggtc    360

ctggcccccc agaaggagga caagatcccc ggggatgtgc                          400
```

<210> SEQ ID NO 70
<211> LENGTH: 6459
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VCP RNAi plasmid

<400> SEQUENCE: 70

```
cctgcaggtc gactctagag aggattgatt tccgagtcaa agattcgtat agctgcaaat     60
gcactcattg atgagatacc tgaagaggag gatgacaaac agtacttggc aagtgaatct    120
tttcgggaat tcatacggta ttttgatgga ctggatgcac taatggagtc ggcttcacgg    180
ccgttcggtg gaggagaaga tccaaggatg aatgcattga ctttgttggg agaggtggag    240
gaatcattga ggatgtttgt caagattgcg aagtgatgat tgcatgcatc gcgctgatga    300
aagaaatgtg ctcaatgtcg acgaaccata ggcattgata ctggagagaa tgaagacata    360
gtaacgcagg agacgtcaac tgaatccaaa actcgatgga tttccaatac aaattatgta    420
aacttatcat tctttatccc agccaaggca gcctaaactc gtacccccaa agtagtggcg    480
ccaacagcgc gacagagtga ggatcttcaa ccctcccaga cgtagccaga gggaagcaac    540
tccctgatgc caaccgctgt gggctgccca tcggaatctt tgacaattgc cttgatcccc    600
gggtgcaagt caagcagcac ctgccgacat cgcccgcacg gagacagaat gccgcggttt    660
tcgttcccga tggccactat gcacgtcaga tttccggcag cagccgcagc ggccgttccg    720
aggaccacga gctccgcgca tggccctccg gtgaaatgat atacattcac gccggtaaag    780
atccgaccgt cggacgagag ggctgcactg gccaccgagt agtcctcgct aataggtatg    840
ctgttgatgg tcgcagttgc acgttcgatc agcgtggatt cctcttggga caaaggcttg    900
gccatggcat gattgttgta ttatgtacct atgtttgtga tgagacaata aatatgagaa    960
gagaacgttg cggccacttt tttctccttc cttcgcgtgc tcatgttggt ggtttgggag   1020
gcagaagatg catggagcgc cacacattcg gtaggacgaa acagcctccc ccacaaaggg   1080
accatgggta gctaggatga cgcacaagcg agttcccgct ctcgaaggga aacccaggca   1140
tttccttcct cttttcaagc cacttgttca cgtgtcaaca caattttgga ctaaaatgcc   1200
cctcggaact cggcaggcct ccctctgctc cgttgtcctg gtcgccgaga acgcgagacc   1260
gtgccgcatg ccatcgatct gctcgtctgt actactaatc gtgtgcgtgt tcgtgcttgt   1320
ttcgcacgaa attgtcctcg ttcggccctc acaacggtgg aaatcggtgc tagaataaag   1380
tgaggtggct tatttcaatg gcggccgtca tcatgcggga tcaactgaag tacggcgggt   1440
tctcgagatt tcatcgtgct cgtccagagc aggtgttttg cctgcagctc ttcatgttta   1500
ggggtcatga tttcatctga tatgccgtaa gaaaaccaat attcacttct caattttcca   1560
tggaaaggtg aaggcctagg ttgtgtgcga ggcaacgact ggggagggat cgcaacattc   1620
ttgctaacct cccctctatc ttggccgctg tgaatcggca tatttaccgg gctgaattga   1680
gaaagtgttt tgagggaatt aaaaggtggc tgtcttgcaa gcttggcttc agtgcctgct   1740
taattcgaac cgatccagct tgtgatgagg ccttcctaag cctggtagtc agaagcgaca   1800
tggcgctata aatttcgtct cagttggaga gtagaaaagc atgattcgaa cacggttttc   1860
aactgccaaa gatatctcca ttgtttcctt caatctgtac acctgcacgg gtaccgagct   1920
cgcttccatt caggtcgagg tggcccggct ccatgcaccg cgacgcaacg cggggaggca   1980
gacaaggtat agggcggcgc ctcataatca aagatgagcc agccacgaag ctaccggaga   2040
attctgtaag aaaaatgttt aaagttgaaa atgctaacag tgaagtgata tcctttttta   2100
atggagtgtt gaggtgaagt ctagcatcgt aggggaaaac aggattctgt gtcttccatt   2160
```

```
ctactccttg ataaagcgaa gaaatccgac aaaaccaaag agattgttca agtttaagat   2220
ttgtaagcgt acaactatga acttcttctc tttgtaggcc tgagtggtcg tatgcatacg   2280
attcatgaag tgaatcagta tcgctggatt ttgcttagga gtaaagcaca actaagaaaa   2340
tatgctgcct ggcaggcatc ctgagacatg aggcaagcga cgtagcaatt gaatcctaat   2400
ttaagccagg gcatctgtat gactctgtta gttaattgat gaaccaatga gctttaaaaa   2460
aaaatcgttg cgcgtaatgt agttttaatt ctccgccttg aggtgcgggg ccatttcgga   2520
caaggttctt tggacggaga tggcagcatg tgtcccttct ccaaattggt ccgtgtggta   2580
gttgagatgc tgccttaaaa ttctgctcgg tcatcctgcc ttcgcattca ctcctttcga   2640
gctgtcgggt tcctcacgag gcctccggga gcggattgcg cagaaaggcg acccggagac   2700
acagagacca tacaccgact aaattgcact ggacgatacg gcatggcgac gacgatggcc   2760
aagcattgct acgtgattat tcgccttgtc attcagggag aaatgatgac atgtgtggga   2820
cggtctttat atgggaagag ggcatgaaaa taacatggcc tggcgggatg gagcgtcaca   2880
cctgtgtatg cgttcgatcc acaagcaact caccatttgc gtcggggcct gtctccaatc   2940
tgctttaggc tacttttctc taatttagcc tattctatac agacagagac acacagggat   3000
cggcctttgt ggcccccgcc cccaagttca gccgcacccg cggtgttgcc cgcatgtcct   3060
tcgaggacga ggccggcgtg accgcccccc tgggctactg ggacccgctt ggcttctccg   3120
ccgatggtga tgtcgagaaa ttcaaccgtt accgcgccat cgagatcaag cacggccgag   3180
tggccatgct tgccatgctc cacaccctgg tgaccggcct cggcgtgaag ctccccggcc   3240
ttgtggctgc cggtgacggc atccccgcct ccatgcccgc gggcatcaac gccatcacct   3300
ccggcgcttg ggccgcacag ggatgggcgc aggtgctcct cttctgctcc gccctcgagg   3360
tcctggcccc ccagaaggag gacaagatcc ccggggatgt gcagcccgac acctctgcct   3420
tcgccaagct cgaggacaag accgaggagg aggcgctcgc ctaccagaac aaggagatca   3480
acaacggccg cctggccatg gtgggcccgc acatccccgg ggatcttgtc ctccttctgg   3540
ggggccagga cctcgagggc ggagcagaag aggagcacct gcgcccatcc ctgtgcggcc   3600
caagcgccgg aggtgatggc gttgatgccc gcgggcatgg aggcggggat gccgtcaccg   3660
gcagccacaa ggccggggag cttcacgccg aggccggtca ccagggtgtg gagcatggca   3720
agcatggcca ctcggccgtg cttgatctcg atggcgcggt aacggttgaa tttctcgaca   3780
tcaccatcgg cggagaagcc aagcgggtcc cagtagccca ggggggcggt cacgccggcc   3840
tcgtcctcga aggacatgcg ggcaacaccg cgggtgcggc tgaacttggg ggcgggggcc   3900
acaaaggcga tccggcactg tctttgcctt tctctccaca ggtgtccact cccaggttca   3960
atacagctct taagcggccg caagcttgcc gccaacatgt cactcagagg tacgtcggtc   4020
gcaactgcgt gcacttcgtg gccgaggagc aggactaaag atcttctaga gtcggggcgg   4080
ccggccgctt cgagcagaca tgataagata cattgatgag tttggacaaa ccacaactag   4140
aatgcagtga aaaaaatgct ttatttgtga aatttgtgat gctattgctt tatttgtaac   4200
cattataagc tgcaataaac aagttaacaa caacaattgc attcatttta tgtttcaggt   4260
tcagggggag gtgtgggagg ttttttaaag caagtaaaac ctctacaaat gtggtaaaat   4320
cgataaggat ctgaacgatg gagcggagaa tgggcggaac tgggcggagt taggggcggg   4380
atgggcggag ttaggggcgg gactatggtt gctgactaat tgagatgcat gctttgcata   4440
cttctgcctg ctggggagcc tggggacttt ccacacctgg ttgctgacta attgagatgc   4500
```

```
atgctttgca tacttctgcc tgctggggag cctggggact ttccacaccc taactgacac   4560

acattccaca gccatatgca cgtgaagggc gaattcgttt aaacctgcag gactagtcgt   4620

catgataata atggtttctt agacgtcagg tggcactttt cggggaaatg tgcgcggaac   4680

ccctatttgt ttatttttct aaatacattc aaatatgtat ccgctcatga gacaataacc   4740

ctgataaatg cttcaataat attgaaaaag gaagagtatg agtattcaac atttccgtgt   4800

cgcccttatt cccttttttg cggcattttg ccttcctgtt tttgctcacc cagaaacgct   4860

ggtgaaagta aaagatgctg aagatcagtt gggtgcacga gtgggttaca tcgaactgga   4920

tctcaacagc ggtaagatcc ttgagagttt tcgccccgaa gaacgttttc caatgatgag   4980

cacttttaaa gttctgctat gtggcgcggt attatcccgt attgacgccg ggcaagagca   5040

actcggtcgc cgcatacact attctcagaa tgacttggtt gagtactcac cagtcacaga   5100

aaagcatctt acggatggca tgacagtaag agaattatgc agtgctgcca taaccatgag   5160

tgataacact gcggccaact tacttctgac aacgatcgga ggaccgaagg agctaaccgc   5220

ttttttgcac aacatggggg atcatgtaac tcgccttgat cgttgggaac cggagctgaa   5280

tgaagccata ccaaacgacg agcgtgacac cacgatgcct gtagcaatgg caacaacgtt   5340

gcgcaaacta ttaactggcg aactacttac tctagcttcc cggcaacaat taatagactg   5400

gatggaggcg gataaagttg caggaccact tctgcgctcg gcccttccgg ctggctggtt   5460

tattgctgat aaatctggag ccggtgagcg tgggtctcgc ggtatcattg cagcactggg   5520

gccagatggt aagccctccc gtatcgtagt tatctacacg acggggagtc aggcaactat   5580

ggatgaacga aatagacaga tcgctgagat aggtgcctca ctgattaagc attggtaact   5640

gtcagaccaa gtttactcat atatacttta gattgattta aaacttcatt tttaatttaa   5700

aaggatctag gtgaagatcc tttttgataa tctcatgacc aaaatccctt aacgtgagtt   5760

ttcgttccac tgagcgtcag accccgtaga aaagatcaaa ggatcttctt gagatccttt   5820

ttttctgcgc gtaatctgct gcttgcaaac aaaaaaacca ccgctaccag cggtggtttg   5880

tttgccggat caagagctac caactctttt tccgaaggta actggcttca gcagagcgca   5940

gataccaaat actgttcttc tagtgtagcc gtagttaggc caccacttca agaactctgt   6000

agcaccgcct acatacctcg ctctgctaat cctgttacca gtggctgctg ccagtggcga   6060

taagtcgtgt cttaccgggt tggactcaag acgatagtta ccggataagg cgcagcggtc   6120

gggctgaacg gggggttcgt gcacacagcc cagcttggag cgaacgacct acaccgaact   6180

gagataccta cagcgtgagc tatgagaaag cgccacgctt cccgaaggga gaaaggcgga   6240

caggtatccg gtaagcggca gggtcggaac aggagagcgc acgagggagc ttccaggggg   6300

aaacgcctgg tatctttata gtcctgtcgg gtttcgccac ctctgacttg agcgtcgatt   6360

tttgtgatgc tcgtcagggg ggcggagcct atggaaaaac gccagcaacg cggccttttt   6420

acggttcctg gccttttgct ggccttttgc tctacgtat                          6459
```

```
<210> SEQ ID NO 71
<211> LENGTH: 210
<212> TYPE: PRT
<213> ORGANISM: Nannochloropsis gaditana
<220> FEATURE:
<221> NAME/KEY: misc_feature
<223> OTHER INFORMATION: Genbank Accession EWM21572.1

<400> SEQUENCE: 71

Met Lys Thr Ala Ala Leu Leu Thr Val Ser Ser Leu Met Gly Ala Ser
1               5                   10                  15
```

```
Ala Phe Val Ala Pro Ala Pro Lys Phe Ser Arg Thr Arg Gly Val Ala
            20                  25                  30

Arg Met Ser Phe Glu Gly Glu Ala Gly Val Thr Ala Pro Leu Gly Tyr
        35                  40                  45

Trp Asp Pro Leu Gly Phe Ser Ala Asp Gly Asp Val Glu Lys Phe Asn
    50                  55                  60

Arg Tyr Arg Ala Ile Glu Ile Lys His Gly Arg Val Ala Met Leu Ala
65                  70                  75                  80

Met Leu His Thr Leu Val Thr Gly Leu Gly Val Lys Leu Pro Gly Leu
                85                  90                  95

Val Ala Ala Gly Asp Gly Ile Pro Ala Ser Met Pro Ala Gly Ile Asn
            100                 105                 110

Ala Ile Thr Ser Gly Ala Trp Ala Ala Gln Gly Trp Ala Gln Val Leu
        115                 120                 125

Leu Phe Cys Ser Ala Leu Glu Val Leu Ala Pro Gln Lys Glu Asp Lys
    130                 135                 140

Ile Pro Gly Asp Val Gln Pro Asp Thr Ser Ala Phe Ala Lys Leu Glu
145                 150                 155                 160

Asp Lys Thr Glu Glu Glu Ala Leu Ala Tyr Gln Asn Lys Glu Ile Asn
                165                 170                 175

Asn Gly Arg Leu Ala Met Val Ala Trp Thr Gly Ala Thr Val Gly Ala
            180                 185                 190

Leu Leu Thr Asn Gly Glu Asp Pro Ile Thr Thr Leu Leu Ala Lys Leu
        195                 200                 205

Gly Asn
    210


<210> SEQ ID NO 72
<211> LENGTH: 209
<212> TYPE: PRT
<213> ORGANISM: Nannochloropsis sp.
<220> FEATURE:
<221> NAME/KEY: misc_feature
<223> OTHER INFORMATION: Genbank Accession AET85085.1

<400> SEQUENCE: 72

Met Lys Thr Ala Ala Leu Leu Thr Val Ser Thr Leu Met Gly Ala Gln
1               5                   10                  15

Ala Phe Met Ala Pro Ala Pro Lys Phe Ser Arg Thr Arg Gly Val Ala
            20                  25                  30

Arg Met Ser Phe Glu Asn Glu Ala Gly Val Thr Ala Pro Leu Gly Tyr
        35                  40                  45

Trp Asp Pro Leu Gly Leu Ser Ala Asp Gly Asp Val Asp Lys Phe Asn
    50                  55                  60

Arg Tyr Arg Ala Ile Glu Ile Lys His Gly Arg Val Ala Met Leu Ala
65                  70                  75                  80

Met Leu His Thr Leu Ile Thr Gly Ala Gly Val Thr Leu Pro Gly Leu
                85                  90                  95

Val Thr Ala Gly Asp Gly Ile Pro Gln Ser Met Pro Tyr Gly Ile Gly
            100                 105                 110

Ala Ile Thr Ser Gly Ala Trp Ala Ala Gln Gly Trp Ala Gln Val Leu
        115                 120                 125

Ile Phe Cys Ser Ala Leu Glu Val Leu Ala Pro Gln Lys Glu Asp Lys
    130                 135                 140

Ile Pro Gly Asp Val Gln Pro Asp Thr Ser Ala Phe Ala Lys Leu Asp
```

```
145                 150                 155                 160

Asp Lys Thr Glu Glu Glu Ala Leu Lys Tyr Gln Asn Thr Glu Ile Asn
                165                 170                 175

Asn Gly Arg Leu Ala Met Val Ala Trp Thr Gly Ala Thr Val Gly Ala
            180                 185                 190

Leu Leu Thr Asn Gly Glu His Pro Val Thr Thr Leu Leu Asn Lys Leu
        195                 200                 205

Gly


<210> SEQ ID NO 73
<211> LENGTH: 207
<212> TYPE: PRT
<213> ORGANISM: Nannochloropsis sp.
<220> FEATURE:
<221> NAME/KEY: misc_feature
<223> OTHER INFORMATION: Genbank Accession AAB94637.1

<400> SEQUENCE: 73

Met Lys Thr Ala Ala Leu Leu Thr Val Ser Thr Leu Met Gly Ala Gln
1               5                   10                  15

Ala Phe Met Ala Pro Ala Pro Lys Phe Ser Arg Thr Arg Gly Val Ala
            20                  25                  30

Arg Met Ser Phe Glu Asn Glu Ala Gly Val Thr Ala Pro Leu Gly Tyr
        35                  40                  45

Trp Asp Pro Leu Gly Leu Ser Ala Asp Gly Asp Val Asp Lys Phe Asn
    50                  55                  60

Arg Tyr Arg Ala Ile Glu Ile Lys His Gly Arg Val Ala Met Leu Ala
65                  70                  75                  80

Met Leu His Thr Leu Ile Thr Gly Ala Gly Val Thr Leu Pro Gly Leu
                85                  90                  95

Val Thr Ala Gly Asp Gly Ile Pro Gln Ser Met Pro Thr Ala Leu Ala
            100                 105                 110

Pro Tyr Ser Gly Ala Trp Ala Gln Gly Trp Ala Gln Val Leu Ile Phe
        115                 120                 125

Cys Ser Ala Leu Glu Val Leu Ala Pro Gln Lys Glu Asp Lys Ile Pro
    130                 135                 140

Gly Asp Val Gln Pro Asp Thr Ser Ala Phe Ala Lys Leu Asp Asp Lys
145                 150                 155                 160

Thr Glu Glu Glu Ala Leu Lys Tyr Gln Asn Thr Glu Ile Asn Asn Gly
                165                 170                 175

Arg Leu Ala Met Val Ala Trp Thr Gly Ala Thr Val Gly Ala Leu Leu
            180                 185                 190

Thr Asn Gly Glu His Pro Val Thr Thr Leu Leu Asn Lys Leu Gly
        195                 200                 205


<210> SEQ ID NO 74
<211> LENGTH: 263
<212> TYPE: PRT
<213> ORGANISM: Nannochloropsis oceanica
<220> FEATURE:
<221> NAME/KEY: misc_feature
<223> OTHER INFORMATION: FCP-1

<400> SEQUENCE: 74

Met Ala Gln Tyr Arg Arg Arg Ala Glu Ala Val Arg Tyr Gly Gly Gly
1               5                   10                  15

Ala Val His Leu Ser Ala Val Met Arg Lys Phe Val Pro Ala Val Met
            20                  25                  30
```

```
Met Val Gly Gly Cys Phe Val Arg Gln Trp Val Phe Gly Ser Ile Phe
        35                  40                  45

Val Lys Ile Gln Phe Lys Gln Lys Thr Ala Ala Leu Leu Thr Val Ser
    50                  55                  60

Thr Leu Met Gly Ala Gln Ala Phe Met Ala Pro Ala Pro Lys Phe Ser
65                  70                  75                  80

Arg Thr Arg Gly Val Ala Arg Met Ser Phe Glu Asn Glu Ala Gly Val
                85                  90                  95

Thr Ala Pro Leu Gly Tyr Trp Asp Pro Leu Gly Leu Ser Ala Asp Gly
            100                 105                 110

Asp Val Asp Lys Phe Asn Arg Tyr Arg Ala Ile Glu Ile Lys His Gly
        115                 120                 125

Arg Val Ala Met Leu Ala Met Leu His Thr Leu Ile Thr Gly Ala Gly
    130                 135                 140

Val Thr Leu Pro Gly Leu Val Thr Ala Gly Asp Gly Ile Pro Gln Ser
145                 150                 155                 160

Met Pro Tyr Gly Ile Gly Ala Ile Thr Ser Gly Ala Trp Ala Ala Gln
                165                 170                 175

Gly Trp Ala Gln Val Leu Ile Phe Cys Ser Ala Leu Glu Val Leu Ala
            180                 185                 190

Pro Gln Lys Glu Asp Lys Ile Pro Gly Asp Val Gln Pro Asp Thr Ser
        195                 200                 205

Ala Phe Ala Lys Leu Asp Asp Lys Thr Glu Glu Glu Ala Leu Lys Tyr
    210                 215                 220

Gln Asn Thr Glu Ile Asn Asn Gly Arg Leu Ala Met Val Ala Trp Thr
225                 230                 235                 240

Gly Ala Thr Val Gly Ala Leu Leu Thr Asn Gly Glu His Pro Val Thr
                245                 250                 255

Thr Leu Leu Asn Lys Leu Gly
            260
```

<210> SEQ ID NO 75
<211> LENGTH: 226
<212> TYPE: PRT
<213> ORGANISM: Nannochloropsis oceanica
<220> FEATURE:
<221> NAME/KEY: misc_feature
<223> OTHER INFORMATION: FCP-2

<400> SEQUENCE: 75

```
Met Pro Tyr Pro Leu Gln Gln Gln His His His His His Phe Leu Ser
1               5                   10                  15

Met Lys Thr Ala Ala Leu Leu Thr Val Ser Thr Leu Met Gly Ala Gln
            20                  25                  30

Ala Phe Met Ala Pro Ala Pro Lys Phe Ser Arg Thr Arg Gly Val Ala
        35                  40                  45

Arg Met Ser Phe Glu Asp Glu Ala Gly Val Thr Gly Pro Leu Gly Tyr
    50                  55                  60

Trp Asp Pro Leu Gly Phe Ser Ala Asp Gly Asp Val Glu Lys Phe Asn
65                  70                  75                  80

Lys Tyr Arg Ala Ala Glu Ile Lys His Gly Arg Val Ala Met Leu Ala
                85                  90                  95

Met Leu His Thr Leu Val Thr Gly Leu Gly Val Lys Leu Pro Gly Leu
            100                 105                 110

Val Ala Ala Gly Asp Gly Ile Pro Gln Ser Met Pro Tyr Gly Ile Gly
```

```
        115                 120                 125

Ala Val Thr Ser Gly Ala Trp Ala Ala Gln Gly Trp Ala Gln Val Leu
    130                 135                 140

Leu Phe Ala Ala Ala Leu Glu Val Leu Ala Pro Gln Lys Glu Asp Lys
145                 150                 155                 160

Ile Pro Gly Asp Val Gln Pro Asp Thr Ser Ala Phe Ala Lys Leu Asp
                165                 170                 175

Glu Lys Ser Glu Glu Glu Ala Leu Ala Tyr Gln Asn Lys Glu Leu Asn
            180                 185                 190

Asn Gly Arg Leu Ala Met Val Ser Trp Leu Gly Ala Val Val Gly Ala
        195                 200                 205

Ser Leu Thr Gly Gly Glu Asp Pro Val Ala Thr Leu Leu His Lys Leu
    210                 215                 220

Gly Asn
225


<210> SEQ ID NO 76
<211> LENGTH: 252
<212> TYPE: PRT
<213> ORGANISM: Nannochloropsis oceanica
<220> FEATURE:
<221> NAME/KEY: misc_feature
<223> OTHER INFORMATION: 6 FCP-3

<400> SEQUENCE: 76

Met Asp Arg Thr Ala Ser His Leu His Pro Cys Pro Leu Val Lys Pro
1               5                   10                  15

Pro Ile Ser Ser Ala Arg Gly Thr Met Lys Gly Trp Gln Gly Arg Ser
            20                  25                  30

Cys Phe Val Asn Ser Thr Thr Leu Ser Ser Met Lys Thr Ala Ala Leu
        35                  40                  45

Leu Thr Val Ser Thr Leu Met Gly Ala Gln Ala Phe Met Ala Pro Ala
    50                  55                  60

Pro Lys Phe Ser Arg Thr Arg Gly Val Ala Arg Met Ser Phe Glu Asp
65                  70                  75                  80

Glu Ala Gly Val Thr Gly Pro Leu Gly Tyr Trp Asp Pro Leu Gly Leu
                85                  90                  95

Ser Ala Asp Gly Asp Val Glu Lys Phe Asn Lys Tyr Arg Ala Ala Glu
            100                 105                 110

Ile Lys His Gly Arg Val Ala Met Leu Ala Met Leu His Thr Leu Val
        115                 120                 125

Thr Gly Leu Gly Val Lys Leu Pro Gly Leu Val Ala Ala Gly Asp Gly
    130                 135                 140

Ile Pro Gln Ser Met Pro Tyr Gly Ile Gly Ala Val Thr Ser Gly Ala
145                 150                 155                 160

Trp Ala Ala Gln Gly Trp Ala Gln Val Leu Leu Phe Ala Ala Ala Leu
                165                 170                 175

Glu Val Leu Ala Pro Gln Lys Glu Asp Lys Ile Pro Gly Asp Val Gln
            180                 185                 190

Pro Asp Thr Ser Ala Phe Ala Lys Leu Asp Glu Lys Ser Glu Glu Glu
        195                 200                 205

Ala Leu Ala Tyr Gln Asn Lys Glu Leu Asn Asn Gly Arg Leu Ala Met
    210                 215                 220

Val Ser Trp Leu Gly Ala Val Val Gly Ala Ser Leu Thr Gly Gly Glu
225                 230                 235                 240
```

```
Asp Pro Val Ala Thr Leu Leu His Lys Leu Gly Asn
                245                 250


<210> SEQ ID NO 77
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-4250 gene

<400> SEQUENCE: 77

gggtcacacg gcccgagatc                                                 20


<210> SEQ ID NO 78
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-810

<400> SEQUENCE: 78

gggggcttcc aggaaaggga                                                 20


<210> SEQ ID NO 79
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-1373

<400> SEQUENCE: 79

ggcgagcttg ctggggatgt                                                 20


<210> SEQ ID NO 80
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-7521

<400> SEQUENCE: 80

ggtctctatc cccaaacccg                                                 20


<210> SEQ ID NO 81
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-3454

<400> SEQUENCE: 81

ggcccttctc tgctcctccg                                                 20


<210> SEQ ID NO 82
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-5134

<400> SEQUENCE: 82
```

ggcccgtcgt gccaccggcg 20

<210> SEQ ID NO 83
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-9417

<400> SEQUENCE: 83
gggagggcag tgcaggagga 20

<210> SEQ ID NO 84
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-554

<400> SEQUENCE: 84
ggaatcatgc atgcaaggaa 20

<210> SEQ ID NO 85
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-3432

<400> SEQUENCE: 85
ggatgccacc ttggacggta 20

<210> SEQ ID NO 86
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-7677

<400> SEQUENCE: 86
ggcactgccc cgggagacgt 20

<210> SEQ ID NO 87
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-6755

<400> SEQUENCE: 87
ggaattcgac cccctgggcc 20

<210> SEQ ID NO 88
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-4249

<400> SEQUENCE: 88
ggacttcatt ttgaagaagg 20

<210> SEQ ID NO 89
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-9833

<400> SEQUENCE: 89
ggaaaaaaaa tatgaagcca 20

<210> SEQ ID NO 90
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-790

<400> SEQUENCE: 90
ggcaggcgag catcgccact 20

<210> SEQ ID NO 91
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-171

<400> SEQUENCE: 91
ggggaataca aggtaggaga 20

<210> SEQ ID NO 92
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-4967

<400> SEQUENCE: 92
ggccggcatt ctcttcgtgg 20

<210> SEQ ID NO 93
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-1993

<400> SEQUENCE: 93
gggcgtgatc gagttcacgg 20

<210> SEQ ID NO 94
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-4422

<400> SEQUENCE: 94
gggacccgct gggcttcgcc 20

<210> SEQ ID NO 95
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, LHC-6329

<400> SEQUENCE: 95 gggggggcg acggaagggg 20

<210> SEQ ID NO 96
<211> LENGTH: 19
<212> TYPE: DNA
<213> ORGANISM: Nannochloropsis gaditana
<220> FEATURE:
<221> NAME/KEY: misc_feature
<223> OTHER INFORMATION: Forward primer, LHC-4250

<400> SEQUENCE: 96
aagatggagg ccatcaagg 19

<210> SEQ ID NO 97
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Reverse primer, LHC-4250

<400> SEQUENCE: 97
caaaaggatc gaaaccgaag 20

<210> SEQ ID NO 98
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-810

<400> SEQUENCE: 98
actcgtccca cttggtaggc 20

<210> SEQ ID NO 99
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Reverse primer, LHC-810

<400> SEQUENCE: 99
cccttactcc atccccagat 20

<210> SEQ ID NO 100
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-1373

<400> SEQUENCE: 100
tggctatgct tctcgttcct 20

<210> SEQ ID NO 101
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Reverse primer, LHC-1373

<400> SEQUENCE: 101
attccccaca cgacatctct 20

<210> SEQ ID NO 102
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-7521

<400> SEQUENCE: 102
cttcatgggc aagaacttcg 20

<210> SEQ ID NO 103
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Reverse primer, LHC-7521

<400> SEQUENCE: 103
gcgaaatcag ggttggatag 20

<210> SEQ ID NO 104
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-3454

<400> SEQUENCE: 104
ctcttccctc ccgaaaaact 20

<210> SEQ ID NO 105
<211> LENGTH: 19
<212> TYPE: DNA
<213> ORGANISM: Nannochloropsis gaditana
<220> FEATURE:
<221> NAME/KEY: misc_feature
<223> OTHER INFORMATION: Reverse primer, LHC-3454

<400> SEQUENCE: 105
gcaccgactt cgagaacac 19

<210> SEQ ID NO 106
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-5134

<400> SEQUENCE: 106
tcttcctcca ccagcttttt 20

<210> SEQ ID NO 107

<211> LENGTH: 19
<212> TYPE: DNA
<213> ORGANISM: Nannochloropsis gaditana
<220> FEATURE:
<221> NAME/KEY: misc_feature
<223> OTHER INFORMATION: Reverse primer, LHC-5134

<400> SEQUENCE: 107
ggagggttgt tcgagaagc 19

<210> SEQ ID NO 108
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-9417

<400> SEQUENCE: 108
atagggccct tccctctctc 20

<210> SEQ ID NO 109
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Reverse primer, LHC-9417

<400> SEQUENCE: 109
gattctgagt cgggcttgaa 20

<210> SEQ ID NO 110
<211> LENGTH: 21
<212> TYPE: DNA
<213> ORGANISM: Nannochloropsis gaditana
<220> FEATURE:
<221> NAME/KEY: misc_feature
<223> OTHER INFORMATION: Forward primer, LHC-554

<400> SEQUENCE: 110
ccatgcgtgt actctctttc c 21

<210> SEQ ID NO 111
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Reverse primer, LHC-554

<400> SEQUENCE: 111
acgcctaagt ccaaacccta 20

<210> SEQ ID NO 112
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-3432

<400> SEQUENCE: 112
aaatatcgaa ccacggcttg 20

<210> SEQ ID NO 113
<211> LENGTH: 20

<212> TYPE: DNA
<213> ORGANISM: Nannochloropsis gaditana
<220> FEATURE:
<221> NAME/KEY: misc_feature
<223> OTHER INFORMATION: Reverse primer, LHC-3432

<400> SEQUENCE: 113
gtaagtgact gcgctcagga 20

<210> SEQ ID NO 114
<211> LENGTH: 21
<212> TYPE: DNA
<213> ORGANISM: Nannochloropsis gaditana
<220> FEATURE:
<221> NAME/KEY: misc_feature
<223> OTHER INFORMATION: Forward primer, LHC-7677

<400> SEQUENCE: 114
gaagctcttg tctttcgctt g 21

<210> SEQ ID NO 115
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Reverse primer, LHC-7677

<400> SEQUENCE: 115
accagggagg tggacaaaat 20

<210> SEQ ID NO 116
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-6755

<400> SEQUENCE: 116
cttccctcct cctcctcctt 20

<210> SEQ ID NO 117
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Reverse primer, LHC-6755

<400> SEQUENCE: 117
cgttcgcttg agaccttgag 20

<210> SEQ ID NO 118
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-4249

<400> SEQUENCE: 118
tcatcgcaaa gtgctaggtg 20

<210> SEQ ID NO 119
<211> LENGTH: 20
<212> TYPE: DNA

<213> ORGANISM: Nannochloropsis gaditana
<220> FEATURE:
<221> NAME/KEY: misc_feature
<223> OTHER INFORMATION: Reverse primer, LHC-4249

<400> SEQUENCE: 119
gcgaggagaa gtttttggtg 20

<210> SEQ ID NO 120
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-9833

<400> SEQUENCE: 120
acccagccta ggaaaccaag 20

<210> SEQ ID NO 121
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Reverse primer, LHC-9833

<400> SEQUENCE: 121
gtggtctcca tggtccaatc 20

<210> SEQ ID NO 122
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-790

<400> SEQUENCE: 122
atgacgatct ggaggattgc 20

<210> SEQ ID NO 123
<211> LENGTH: 19
<212> TYPE: DNA
<213> ORGANISM: Nannochloropsis gaditana
<220> FEATURE:
<221> NAME/KEY: misc_feature
<223> OTHER INFORMATION: Reverse primer, LHC-790

<400> SEQUENCE: 123
atcggacatg atcgggatt 19

<210> SEQ ID NO 124
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-171

<400> SEQUENCE: 124
acatccgagc caatcatctc 20

<210> SEQ ID NO 125
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Reverse primer, LHC-171

<400> SEQUENCE: 125
tgttcctcat cccttttgc 20

<210> SEQ ID NO 126
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-4967

<400> SEQUENCE: 126
gatccaagtc ccttcccttc 20

<210> SEQ ID NO 127
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Reverse primer, LHC-4967

<400> SEQUENCE: 127
acccgagatc acttccaaaa 20

<210> SEQ ID NO 128
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-1993

<400> SEQUENCE: 128
gccatgctcg gtatctttgt 20

<210> SEQ ID NO 129
<211> LENGTH: 19
<212> TYPE: DNA
<213> ORGANISM: Nannochloropsis gaditana
<220> FEATURE:
<221> NAME/KEY: misc_feature
<223> OTHER INFORMATION: Reverse primer, LHC-1993

<400> SEQUENCE: 129
ccctggcctg tcaggtatt 19

<210> SEQ ID NO 130
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-4422

<400> SEQUENCE: 130
tcttctcctc cctccctctt 20

<210> SEQ ID NO 131
<211> LENGTH: 20
<212> TYPE: DNA
<213> ORGANISM: Nannochloropsis gaditana
<220> FEATURE:

<221> NAME/KEY: misc_feature
<223> OTHER INFORMATION: Reverse primer, LHC-4422

<400> SEQUENCE: 131
cccttatccg cctttttctt 20

<210> SEQ ID NO 132
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Forward primer, LHC-6329

<400> SEQUENCE: 132
ggtgtagaag tgctgcacga 20

<210> SEQ ID NO 133
<211> LENGTH: 21
<212> TYPE: DNA
<213> ORGANISM: Nannochloropsis gaditana
<220> FEATURE:
<221> NAME/KEY: misc_feature
<223> OTHER INFORMATION: Reverse primer, LHC-6329

<400> SEQUENCE: 133
cgcgtctcat tatctttttg c 21

<210> SEQ ID NO 134
<211> LENGTH: 729
<212> TYPE: DNA
<213> ORGANISM: Nannochloropsis gaditana
<220> FEATURE:
<221> NAME/KEY: misc_feature
<223> OTHER INFORMATION: LHC-554 gene coding sequence

<400> SEQUENCE: 134
atgcgtgtac tctctttcct tgctattatc ggcactgccg ctgccttcgt caagcccacc 60
ctccctgctg ctgggtctcg cactcgtgcc ggcgctctcc gcatgaacct cgccgagatc 120
gagctggagg cgggcaagac ctctcctttc cccgatggct tcgatcctct cggtctgtcc 180
aaggataagt cattcaagga gctcaagaag tggcgcgagg cggagctcaa gcacggccgc 240
gttgccatgc ttgccgtcct gggcacggcc gtgcaagaga acttccaccc cctgtggggc 300
ttcaacgaga aggagatgga tggtgccatc tttcacttcc aggagatcca aaacgtctac 360
ccccttttct ggaccgccct ccttttcatc atcggcatca ttgaggctcg caccatctcc 420
accggatggg atgagaacat ggccggatct tcccagatcg ccggcgtgaa ggaggactac 480
atctgcggga acctgggcct ggacccccctc aagatcatcg aaaatgacga cgaggaggct 540
ttcctgtcct accgcaacaa gtctcaccgg ttcttgccct acctcatctt tcaggagctc 600
aacaacggcc gtctggctat gatcgcagcc gctgggatca ccgtccagga gaagttcgtc 660
accaacggcc tccccgagtt cgagttccac cgattcgccc tctcggacgt ctacaacttc 720
ttcttctaa 729

<210> SEQ ID NO 135
<211> LENGTH: 242
<212> TYPE: PRT
<213> ORGANISM: Nannochloropsis gaditana
<220> FEATURE:
<221> NAME/KEY: misc_feature
<223> OTHER INFORMATION: LHC-554 polypeptide

<400> SEQUENCE: 135

```
Met Arg Val Leu Ser Phe Leu Ala Ile Ile Gly Thr Ala Ala Ala Phe
1               5                   10                  15

Val Lys Pro Thr Leu Pro Ala Ala Gly Ser Arg Thr Arg Ala Gly Ala
            20                  25                  30

Leu Arg Met Asn Leu Ala Glu Ile Glu Leu Glu Ala Gly Lys Thr Ser
        35                  40                  45

Pro Phe Pro Asp Gly Phe Asp Pro Leu Gly Leu Ser Lys Asp Lys Ser
    50                  55                  60

Phe Lys Glu Leu Lys Lys Trp Arg Glu Ala Glu Leu Lys His Gly Arg
65                  70                  75                  80

Val Ala Met Leu Ala Val Leu Gly Thr Ala Val Gln Glu Asn Phe His
                85                  90                  95

Pro Leu Trp Gly Phe Asn Glu Lys Glu Met Asp Gly Ala Ile Phe His
            100                 105                 110

Phe Gln Glu Ile Gln Asn Val Tyr Pro Leu Phe Trp Thr Ala Leu Leu
        115                 120                 125

Phe Ile Ile Gly Ile Ile Glu Ala Arg Thr Ile Ser Thr Gly Trp Asp
    130                 135                 140

Glu Asn Met Ala Gly Ser Ser Gln Ile Ala Gly Val Lys Glu Asp Tyr
145                 150                 155                 160

Ile Cys Gly Asn Leu Gly Leu Asp Pro Leu Lys Ile Ile Glu Asn Asp
                165                 170                 175

Asp Glu Glu Ala Phe Leu Ser Tyr Arg Asn Lys Ser His Arg Phe Leu
            180                 185                 190

Pro Tyr Leu Ile Phe Gln Glu Leu Asn Asn Gly Arg Leu Ala Met Ile
        195                 200                 205

Ala Ala Ala Gly Ile Thr Val Gln Glu Lys Phe Val Thr Asn Gly Leu
    210                 215                 220

Pro Glu Phe Glu Phe His Arg Phe Ala Leu Ser Asp Val Tyr Asn Phe
225                 230                 235                 240

Phe Phe
```

<210> SEQ ID NO 136
<211> LENGTH: 3897
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: zeocin resistance cassette plus GFP cassette flanked by lox2272 sites

<400> SEQUENCE: 136

```
cgttatcccc tgattctgtg gataaccgta ttaccgcctt tgagtgagct gataccgctc      60

gccgcagccg aacgaccgag cgcagcgagt cagtgagcga ggaagcggaa gagcggccgc     120

ataacttcgt ataggatact ttatacgaag ttatcgtatg gtcgacggtt gctcggatgg     180

ggggggcggg gagcgatgga gggaggaaga tcaggtaagg tctcgacaga ctagagaagc     240

acgagtgcag gtataagaaa cagcaaaaaa aagtaatggg cccaggcctg gagagggtat     300

ttgtcttgtt tttctttggc caggaacttg ttctcctttc ttcgtttcta ggaccccgat     360

ccccgctcgc atttctctct tcctcagccg aagcgcagcg gtaaagcatc cattttatcc     420

caccgaaagg gcgctcccag ccttcgtcga gcggaaccgg ggttacagtg ccttagtcct     480
```

gctcctcggc cacgaagtgc acgcagttgc cggccgggtc gcgcagggcg aactcccgcc 540
cccacggctg ctcgccgatc tcggtcatgg ccggcccgga ggcgtcccgg aagttcgtgg 600
acacgacctc cgaccactcg gcgtacagct cgtccaggcc gcgcacccac acccaggcca 660
gggtgttgtc cggcaccacc tggtcctgga ccgcgctgat gaacagggtc acgtcgtccc 720
ggaccacacc ggcgaagtcg tcctccacga agtcccggga gaacccgagc cggtcggtcc 780
agaactcgac cgctccggcg acgtcgcgcg cggtgagcac cggaacggcg ctggtcagct 840
tggccatcga gctcggtacc cggggatcca tgattgttgt attatgtacc tatgtttgtg 900
atgagacaat aaatatgaga agagaacgtt gcggccactt ttttctcctt ccttcgcgtg 960
ctcatgttgg tggtttggga ggcagaagat gcatggagcg ccacacattc ggtaggacga 1020
aacagcctcc cccacaaagg gaccatgggt agctaggatg acgcacaagc gagttcccgc 1080
tctcgaaggg aaacccaggc atttccttcc tcttttcaag ccacttgttc acgtgtcaac 1140
acaattttgg actaaaatgc cctcggaac tcggcaggcc tccctctgct ccgttgtcct 1200
ggtcgccgag aacgcgagac cgtgccgcat gccatcgatc tgctcgtctg tactactaat 1260
cgtgtgcgtg ttcgtgcttg tttcgcacga aattgtcctc gttcggccct cacaacggtg 1320
gaaatcggtg ctagaataaa gtgaggtggc ttatttcaat ggcggccgtc atcatgcggg 1380
atcaactgaa gtacggcggg ttctcgagat ttcatcgtgc tcgtccagag caggtgtttt 1440
gcctgcagct cttcatgttt aggggtcatg atttcatctg atatgccgta agaaaaccaa 1500
tattcacttc tcaattttcc atggaaaggt gaaggcctag gttgtgtgcg aggcaacgac 1560
tggggaggga tcgcaacatt cttgctaacc tcccctctat cttggccgct gtgaatcggc 1620
atatttaccg ggctgaattg agaaagtgtt ttgagggaat taaaaggtgg ctgtcttgca 1680
agcttggctt cagtgcctgc ttaattcgaa ccgatccagc ttgtgatgag gccttcctaa 1740
gcctggtagt cagaagcgac atggcgctat aaatttcgtc tcagttggag agtagaaaag 1800
catgattcga acacggtttt caactgccaa agatatctcc attgtttcct tcaatctgta 1860
cacctgcacg ggccagtgag gccaggaaat aaagatggac agacggcatg ctagtagact 1920
ttgttgagat tagtgtttgt gttcgtcttt atggctttga gtgggccccc ttaacctata 1980
cacacatgac aatcaggtga cgaggaagct ctcgactctc caggtctcca acacatcatg 2040
aggacgccgc tctgccagga ccctccccga ctccttccca cccttattct tcaccggcat 2100
ctgcatccgg ggtcttgaag gcgtgctggt actccacgat gcccagctcg gtgttgctgt 2160
gatcctcctc cacgcggcgg aaggcgaaca tggggccccc gttctgcagg atgctggggt 2220
ggatggcgct cttgaagtgc atgtggctgt ccaccacgga gctgtagtag ccgccgtcgc 2280
gcaggctgaa ggtgcgggtg aagctgccat ccagatcgtt atcgcccatg ggggtgcaggt 2340
gctccacggt ggcgttgctg cggatgatct tgtcggtgaa gatcacgctg tcctcgggga 2400
agccggtgcc catcaccttg aagtcgccga tcacgcggcc ggcctcgtag cggtagctga 2460
agctcacgtg cagcacgccg ccgtcctcgt acttctcgat gcgggtgttg gtgtagccgc 2520
cgttgttgat ggcgtgcagg aaggggttct cgtagccgct ggggtaggtg ccgaagtggt 2580
agaagccgta gcccatcacg tggctcagca ggtaggggct gaaggtcagg gcgcctttgg 2640
tgctcttcat cttgttggtc atgcggccct gctcgggggt gccctctccg ccgcccacca 2700
gctcgaactc cacgccgttc agggtgccgg tgatgcggca ctcgatctcc atggcgggca 2760
ggccgctctc gtcgctctcc aacatgtaag ctaggctttt ggtgagagaa tgggaaagaa 2820
gttagatgta aaattgaact tcggttgtcg aatttcagag gtagtgcgcg gtgcgtgcgc 2880

```
aacgaaggac cgtctgcgac agtcggagag aattggggta gccactagag tagaaaacct   2940

tcactttccc gcctgagcac cgtttctgga aaggatctga agattgagat atgatttttc   3000

gaacttgcac cgatgtggcc ctcgtgtaga agacgaggca gagtggatat agtgccactg   3060

aagacatgca gcaagctacc gaacaacgcg ataatggaga ctagcgcgtc tgccattggc   3120

aaccgtgctc gccttctcgt gatcttacgt gtcgcgtctc ttcatctccg tacacgaaaa   3180

atattggtat gcgcgtgcat tatgctttca gtacgtgtaa atgagagaca ggcaatgcca   3240

cactactggc gcaggacatg ttatcctcat ccgggtcgct tttcttgctc tatgcaagga   3300

aaggggcgga aatgatagag attgataaat tgatcgacgc ggaagagtta ttactctgca   3360

tgacaatgaa gtgtgctttt aaagttttgt ttatcgagag gcctcgtgcg agaaattttt   3420

gtcgcagcat gattgacttg taggatagat actagctgga ctggtcttcg acatccctac   3480

acctcctgcc aaacggaaaa aaaaagcatc tgtcggctgc acacagattg cgactactta   3540

taacttcaaa ctatgctata agtgtccttt tctttcttc ttttctttcc ttgccgtcct   3600

ttatgccata acttcgtata ggatacttta tacgaagtta tcctgcaggc agttggtacg   3660

gcatattatg gtttaaacat ctatcctcca gatcaccagg gcgcgcctat gcttgtaaac   3720

cgttttgtga aaaaattttt aaaataaaaa aggggacctc tagggtcccc aattaattag   3780

taatataatc tattaaaggt cattcaaaag gtcatccaga cgaaagggcc tcgtgatacg   3840

cctattttta taggttaatg tcatgataat aatggtttct tagacgtcag gtggcac      3897
```

<210> SEQ ID NO 137
<211> LENGTH: 3711
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: BLASTICIDIN RESISTANCE CASSETTE PLUS GFP CASSETTE FLANKED BY LOXP SITES

<400> SEQUENCE: 137

```
tccacagccc gaacccctta agctagacga acacagttag cgcggccgca taacttcgta     60

tagcatacat tatacgaagt tatgatgcta gcgtgtttaa gaagtcactt aattaacgta    120

tggtcgacgg ttgctcggat gggggggcg gggagcgatg gagggaggaa gatcaggtaa    180

ggtctcgaca gactagagaa gcacgagtgc aggtataaga aacagcaaaa aaaagtaatg    240

ggcccaggcc tggagagggt atttgtcttg tttttctttg gccaggaact tgttctcctt    300

tcttcgtttc taggaccccg atccccgctc gcatttctct cttcctcagc cgaagcgcag    360

cggtaaagca tccattttat cccaccgaaa gggcgctccc agccttcgtc gagcggaacc    420

ggggttacag tgcctcaacc ctcccagacg tagccagagg gaagcaactc cctgatgcca    480

accgctgtgg gctgcccatc ggaatctttg acaattgcct tgatccccgg gtgcaagtca    540

agcagcacct gccgacatcg cccgcacgga gacagaatgc cgcggttttc gttcccgatg    600

gccactatgc acgtcagatt tccggcagca gccgcagcgg ccgttccgag gaccacgagc    660

tccgcgcatg gccctccggt gaaatgatat acattcacgc cggtaaagat ccgaccgtcg    720

gacgagaggg ctgcactggc caccgagtag tcctcgctaa taggtatgct gttgatggtc    780

gcagttgcac gttcgatcag cgtggattcc tcttgggata aaggcttggc catcgagctc    840

ggtacccggg gatccatgat tgttgtatta tgtacctatg tttgtgatga gacaataaat    900
```

-continued

```
atgagaagag aacgttgcgg ccactttttt ctccttcctt cgcgtgctca tgttggtggt    960
ttgggaggca gaagatgcat ggagcgccac acattcggta ggacgaaaca gcctccccca   1020
caaagggacc atgggtagct aggatgacgc acaagcgagt tcccgctctc gaagggaaac   1080
ccaggcattt ccttcctctt ttcaagccac ttgttcacgt gtcaacacaa ttttggacta   1140
aaatgcccct cggaactcgg caggcctccc tctgctccgt tgtcctggtc gccgagaacg   1200
cgagaccgtg ccgcatgcca tcgatctgct cgtctgtact actaatcgtg tgcgtgttcg   1260
tgcttgtttc gcacgaaatt gtcctcgttc ggccctcaca acggtggaaa tcggtgctag   1320
aataaagtga ggtggcttat ttcaatggcg gccgtcatca tgcgggatca actgaagtac   1380
ggcgggttct cgagatttca tcgtgctcgt ccagagcagg tgttttgcct gcagctcttc   1440
atgtttaggg gtcatgattt catctgatat gccgtaagaa aaccaatatt cacttctcaa   1500
ttttccatgg aaaggtgaag gcctaggttg tgtgcgaggc aacgactggg gagggatcgc   1560
aacattcttg ctaacctccc ctctatcttg gccgctgtga atcggcatat ttaccgggct   1620
gaattgagaa agtgttttga gggaattaaa aggtggctgt cttgcaagct tggcttcagt   1680
gcctgcttaa ttcgaaccga tccagcttgt gatgaggcct tcctaagcct ggtagtcaga   1740
agcgacatgg cgctataaat ttcgtctcag ttggagagta gaaaagcatg attcgaacac   1800
ggttttcaac tgccaaagat atctccattg tttccttcaa tctgtacacc tgcacgggcc   1860
agtgaggcca ggaaataaag atggacagac ggcatgctag tagactttgt tgagattagt   1920
gtttgtgttc gtctttatgg ctttgagtgg gccccctta cctatacaca catgacaatc   1980
aggtgacgag gaagctctcg actctccagg tctccaacac atcatgagga cgccgctctg   2040
ccaggaccct ccccgactcc ttcccaccct tattcttcac cggcatctgc atccggggtc   2100
ttgaaggcgt gctggtactc cacgatgccc agctcggtgt tgctgtgatc ctcctccacg   2160
cggcggaagg cgaacatggg gccccccgttc tgcaggatgc tggggtggat ggcgctcttg   2220
aagtgcatgt ggctgtccac cacggagctg tagtagccgc cgtcgcgcag gctgaaggtg   2280
cgggtgaagc tgccatccag atcgttatcg cccatggggt gcaggtgctc cacggtggcg   2340
ttgctgcgga tgatcttgtc ggtgaagatc acgctgtcct cggggaagcc ggtgcccatc   2400
accttgaagt cgccgatcac gcggccggcc tcgtagcggt agctgaagct cacgtgcagc   2460
acgccgccgt cctcgtactt ctcgatgcgg gtgttggtgt agccgccgtt gttgatggcg   2520
tgcaggaagg ggttctcgta gccgctgggg taggtgccga agtggtagaa gccgtagccc   2580
atcacgtggc tcagcaggta ggggctgaag gtcagggcgc ctttggtgct cttcatcttg   2640
ttggtcatgc ggccctgctc gggggtgccc tctccgccgc ccaccagctc gaactccacg   2700
ccgttcaggg tgccggtgat gcggcactcg atctccatgg cgggcaggcc gctctcgtcg   2760
ctctccaaca tgtaagctag gcttttggtg agagaatggg aaagaagtta gatgtaaaat   2820
tgaacttcgg ttgtcgaatt tcagaggtag tgcgcggtgc gtgcgcaacg aaggaccgtc   2880
tgcgacagtc ggagagaatt ggggtagcca ctagagtaga aaaccttcac tttcccgcct   2940
gagcaccgtt tctggaaagg atctgaagat tgagatatga tttttcgaac ttgcaccgat   3000
gtggccctcg tgtagaagac gaggcagagt ggatatagtg ccactgaaga catgcagcaa   3060
gctaccgaac aacgcgataa tggagactag cgcgtctgcc attggcaacc gtgctcgcct   3120
tctcgtgatc ttacgtgtcg cgtctcttca tctccgtaca cgaaaaaatat tggtatgcgc   3180
gtgcattatg ctttcagtac gtgtaaatga gagacaggca atgccacact actggcgcag   3240
gacatgttat cctcatccgg gtcgcttttc ttgctctatg caaggaaagg ggcggaaatg   3300
```

```
atagagattg ataaattgat cgacgcggaa gagttattac tctgcatgac aatgaagtgt   3360

gcttttaaag ttttgtttat cgagaggcct cgtgcgagaa atttttgtcg cagcatgatt   3420

gacttgtagg atagatacta gctggactgg tcttcgacat ccctacacct cctgccaaac   3480

ggaaaaaaaa agcatctgtc ggctgcacac agattgcgac tacttataac ttcaaactat   3540

gctataagtg tccttttctt tctttctttt ctttccttgc cgtcctttat gcccctgcag   3600

ggtacgtttt agacggacta ggcagtataa cttcgtatag catacattat acgaagttat   3660

ggcgcgccag gctacgttag ttcagcagct gagaacgacc acgaacggga a            3711
```

<210> SEQ ID NO 138
<211> LENGTH: 4341
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: hygromycin resistance cassette plus GFP cassette flanked by loxN sites

<400> SEQUENCE: 138

```
tccacagccc gaacccctta agctagacga acacagttag cgcggccgca taacttcgta     60

tagtatacct tatacgaagt tatgatgcta gcgtgtttaa gaagtcactt aattaacgta    120

tggtcgacgg ttgctcggat gggggggcg gggagcgatg gagggaggaa gatcaggtaa     180

ggtctcgaca gactagagaa gcacgagtgc aggtataaga aacagcaaaa aaaagtaatg    240

ggcccaggcc tggagagggt atttgtcttg tttttctttg gccaggaact tgttctcctt    300

tcttcgtttc taggaccccg atccccgctc gcatttctct cttcctcagc cgaagcgcag    360

cggtaaagca tccattttat cccaccgaaa gggcgctccc agccttcgtc gagcggaacc    420

ggggttacag tgcctcactc ctttgcacgc ggtcgggtgc tcggcctacg gttgcccgag    480

tccgcaagca cctcaacaca gccgtctgtc cacaccgcag ccgaccggcg tgcgatttgg    540

gtccgaccca ccgtcccagc cccgctgcgg actatcgcgt cgcagcggcc ctgcgcccac    600

gcggcgtcgt cgaagttgcc gtcgacgaga gactggtaaa gctgatcgag tccgatacgc    660

aacatatagg cgcggagtcg tggggagccg gccagctccg ggtgcctccg ttcaaagtag    720

cgtgtctgct gctccatgca cgccaaccag ggacgccaga agaatatgtt cgccacttcg    780

tattggctat caccaaacat cgcttcggac cagtcgatga cagcagtaat ccgaccattg    840

tctgtaagta cgttattgct gccgaaatcc gcgtgcacca ggtgcctgac ctcagggcaa    900

tcctcggccc acaacatgag ttcgtccagt gcttgggcca cggatgcaga cacggtgtca    960

tccatgactg tctgccaatg atagacgtga ggatcggcaa tggcgcagat gaagtctcgc   1020

caggtcgtgt actgcccgat gccctggggc ccaaaaggtc caaagccgga cgtctgagac   1080

agatctgcgg cagcgatcgc gtccatggcc tcggccacgg gttgcaaaac ggcaggcaat   1140

tcagtttcgg gcagatcttg caacgtcact ccctgggctc ggcgcgagat gcagtacgtg   1200

agagattcgc taaactcccc aatgtccagt acctctggta tggggagagc ggcggaggcg   1260

aaatgacggt agacataccg atccttgtag aacccgtccg cacaactatt aaccctcaac   1320

acgtatcccc gacccctac gtcaaacgag aacgccctac tctcctctcc ctcgctcagt    1380

tgcatcaagt cggagacaga gtcgaacttc tcaataagga atttctccac ggacgtagcg   1440

gtcagttccg gtttcttccc catcgagctc ggtacccggg gatccatgat tgttgtatta   1500
```

```
tgtacctatg tttgtgatga gacaataaat atgagaagag aacgttgcgg ccactttttt   1560
ctccttcctt cgcgtgctca tgttggtggt ttgggaggca gaagatgcat ggagcgccac   1620
acattcggta ggacgaaaca gcctccccca caaagggacc atgggtagct aggatgacgc   1680
acaagcgagt tcccgctctc gaagggaaac ccaggcattt ccttcctctt ttcaagccac   1740
ttgttcacgt gtcaacacaa ttttggacta aaatgcccct cggaactcgg caggcctccc   1800
tctgctccgt tgtcctggtc gccgagaacg cgagaccgtg ccgcatgcca tcgatctgct   1860
cgtctgtact actaatcgtg tgcgtgttcg tgcttgtttc gcacgaaatt gtcctcgttc   1920
ggccctcaca acggtggaaa tcggtgctag aataaagtga ggtggcttat ttcaatggcg   1980
gccgtcatca tgcgggatca actgaagtac ggcgggttct cgagatttca tcgtgctcgt   2040
ccagagcagg tgttttgcct gcagctcttc atgtttaggg gtcatgattt catctgatat   2100
gccgtaagaa aaccaatatt cacttctcaa ttttccatgg aaaggtgaag gcctaggttg   2160
tgtgcgaggc aacgactggg gagggatcgc aacattcttg ctaacctccc ctctatcttg   2220
gccgctgtga atcggcatat ttaccgggct gaattgagaa agtgttttga gggaattaaa   2280
aggtggctgt cttgcaagct tggcttcagt gcctgcttaa ttcgaaccga tccagcttgt   2340
gatgaggcct tcctaagcct ggtagtcaga agcgacatgg cgctataaat ttcgtctcag   2400
ttggagagta gaaaagcatg attcgaacac ggttttcaac tgccaaagat atctccattg   2460
tttccttcaa tctgtacacc tgcacgggcc agtgaggcca ggaaataaag atggacagac   2520
ggcatgctag tagactttgt tgagattagt gtttgtgttc gtctttatgg ctttgagtgg   2580
gccccttaa cctatacaca catgacaatc aggtgacgag gaagctctcg actctccagg   2640
tctccaacac atcatgagga cgccgctctg ccaggaccct ccccgactcc ttcccaccct   2700
tattcttcac cggcatctgc atccggggtc ttgaaggcgt gctggtactc cacgatgccc   2760
agctcggtgt tgctgtgatc ctcctccacg cggcggaagg cgaacatggg gcccccgttc   2820
tgcaggatgc tggggtggat ggcgctcttg aagtgcatgt ggctgtccac cacggagctg   2880
tagtagccgc cgtcgcgcag gctgaaggtg cgggtgaagc tgccatccag atcgttatcg   2940
cccatggggt gcaggtgctc cacggtggcg ttgctgcgga tgatcttgtc ggtgaagatc   3000
acgctgtcct cggggaagcc ggtgcccatc accttgaagt cgccgatcac gcggccggcc   3060
tcgtagcggt agctgaagct cacgtgcagc acgccgccgt cctcgtactt ctcgatgcgg   3120
gtgttggtgt agccgccgtt gttgatggcg tgcaggaagg ggttctcgta gccgctgggg   3180
taggtgccga agtggtagaa gccgtagccc atcacgtggc tcagcaggta ggggctgaag   3240
gtcagggcgc ctttggtgct cttcatcttg ttggtcatgc ggccctgctc gggggtgccc   3300
tctccgccgc ccaccagctc gaactccacg ccgttcaggg tgccggtgat gcggcactcg   3360
atctccatgg cgggcaggcc gctctcgtcg ctctccaaca tgtaagctag gcttttggtg   3420
agagaatggg aaagaagtta gatgtaaaat tgaacttcgg ttgtcgaatt tcagaggtag   3480
tgcgcggtgc gtgcgcaacg aaggaccgtc tgcgacagtc ggagagaatt ggggtagcca   3540
ctagagtaga aaaccttcac tttcccgcct gagcaccgtt tctggaaagg atctgaagat   3600
tgagatatga tttttcgaac ttgcaccgat gtggccctcg tgtagaagac gaggcagagt   3660
ggatatagtg ccactgaaga catgcagcaa gctaccgaac aacgcgataa tggagactag   3720
cgcgtctgcc attggcaacc gtgctcgcct tctcgtgatc ttacgtgtcg cgtctcttca   3780
tctccgtaca cgaaaaatat tggtatgcgc gtgcattatg ctttcagtac gtgtaaatga   3840
gagacaggca atgccacact actggcgcag gacatgttat cctcatccgg gtcgcttttc   3900
```

```
ttgctctatg caaggaaagg ggcggaaatg atagagattg ataaattgat cgacgcggaa   3960

gagttattac tctgcatgac aatgaagtgt gcttttaaag ttttgtttat cgagaggcct   4020

cgtgcgagaa atttttgtcg cagcatgatt gacttgtagg atagatacta gctggactgg   4080

tcttcgacat ccctacacct cctgccaaac ggaaaaaaaa agcatctgtc ggctgcacac   4140

agattgcgac tacttataac ttcaaactat gctataagtg tccttttctt tctttctttt   4200

ctttccttgc cgtcctttat gcccctgcag ggtacgtttt agacggacta ggcagtataa   4260

cttcgtatag tataccttat acgaagttat ggcgcgccag gctacgttag ttcagcagct   4320

gagaacgacc acgaacggga a                                             4341
```

<210> SEQ ID NO 139
<211> LENGTH: 1707
<212> TYPE: DNA
<213> ORGANISM: Nannochloropsis gaditana
<220> FEATURE:
<221> NAME/KEY: misc_feature
<223> OTHER INFORMATION: cpSRP54 gene coding sequence

<400> SEQUENCE: 139

```
atgcttcggc agcagctgtt gcacagcggc aggcagccgg gtgcgacatg cagcttacta     60

acctgctcga catggcgacc gtctgccttg ttcggccgtc ctaagcccca aaaactgcac    120

agccagcgct tgcagcatca gggccgcccc tcccgcctcg tcgtgcgcag cgcaatgttc    180

gacaacctga gccgcagcct ggagagggcg tgggacatgg tgcgcaagga cgggcggcta    240

acggcggaca acatcaagga gcccatgcgg gagattcgca gggcgctgct tgaggcggat    300

gtgaggctgg gggcgccgct gatcagattc ttggtatcta cccccccccc ctcccaggtc    360

tccctccccg tggtgcgcaa gtttgtgaag gcggtggagg agaaggcgct gggttctgca    420

gtgaccaagg gtgtcacccc cgaccagcag ctggtgaagg tggtgtacga ccagctgcgg    480

gagctgatgg gggggcagca ggaagggctg gtgcccactt cgccagagga gccgcaggtg    540

atcttgatgg cggggctgca gggcacgggg aagacgacag ctgcggggaa gctggccttg    600

ttcctgcaga agaaggggca gaaggtgctg ctggtggcca ccgacatcta ccgccccgcc    660

gccatcgacc agctggtgaa gctgggcgac aggataggggg tgccggtgtt ccagctggga    720

acccaggtgc agccgccgga gattgcaagg caggggctgg agaaggcgcg agcagagggg    780

tttgacgccg tcatcgtcga cacggcgggg cggctgcaga tcgaccagag catgatggag    840

gagctggtgc agatcaagtc cacggtgaag ccctccgaca cgctgctagt ggtcgatgcg    900

atgacggggc aggaggcagc cgggctggtg aaggcgttca atgatgccgt ggacatcaca    960

ggcgccgtgc tgaccaagct tgacggggac agccgcggcg gcgccgcgct gagcgtgcgc   1020

caggtcagcg ggcggcccat caagtttgtg ggcatggggg agggcatgga ggcgctggag   1080

cccttctacc ccgagcgcat ggccagcagg attctgggca tgggtgacgt ggtcaccctg   1140

gtggagaagg ctgaggagag catcaaggaa gaggaggcgc aggagatatc gcggaagatg   1200

ctgtcggcca aatttgactt tgacgacttc ctgaagcagt acaagatggt ggcggggatg   1260

gggaacatgg cccaaatcat gaagatgctg ccaggcatga acaagtttac ggagaagcag   1320

ctggcgggcg ttgagaagca gtacaaggtg tacgagagca tgatccagag catgacggtg   1380

aaggagcgca agcagccgga gctgttggtg aagtcgccct ccaggaggcg gcgcatagcg   1440

cgcgggtcgg ggcgctcgga gcgggaggtc acagagctgc tgggggtgtt caccaacctg   1500

cggacgcaga tgcagagctt ctccaaaatg atggccatgg gggggatggg catgggctcc   1560
```

```
atgatgagcg acgaggagat gatgcaggcc acgctggcag gcgccggccc ccgccccgtg   1620

ccagctggca aggtgcggcg gaagaagctg gccgcggcgg gcgggtcgcg gggcatggct   1680

gagctggcat ccctgaaggc agaatga                                      1707
```

<210> SEQ ID NO 140
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting cpSRP54 gene, includes PAM

<400> SEQUENCE: 140

```
ggccacgccc ttgctccgtc                                                20
```

<210> SEQ ID NO 141
<211> LENGTH: 20
<212> TYPE: DNA
<213> ORGANISM: Nannochloropsis gaditana
<220> FEATURE:
<221> NAME/KEY: misc_feature
<223> OTHER INFORMATION: 5' Primer sequence for cpSRP54 gene

<400> SEQUENCE: 141

```
gcaggacaat gaaattgacg                                                20
```

<210> SEQ ID NO 142
<211> LENGTH: 20
<212> TYPE: DNA
<213> ORGANISM: Nannochloropsis gaditana
<220> FEATURE:
<221> NAME/KEY: misc_feature
<223> OTHER INFORMATION: 3' Primer sequence for cpSRP54 gene

<400> SEQUENCE: 142

```
gtggaggaac gtcagaggac                                                20
```

<210> SEQ ID NO 143
<211> LENGTH: 1551
<212> TYPE: DNA
<213> ORGANISM: Nannochloropsis gaditana
<220> FEATURE:
<221> NAME/KEY: misc_feature
<223> OTHER INFORMATION: Ftsy gene coding sequence

<400> SEQUENCE: 143

```
atgttgcagt atcacctcct cctcctacct ctcctgatgc tgccttgggc aggatggact     60

caagctgcat tcgttactcc aagagttgga ggcccaagat cttatggtga tggaagaaaa    120

tacagagtcg gtgtgccatt ctactcgtca atcgacgagg tagacagtcc tatctacacc    180

acggcatcac gatccagaag gcaaggtgaa agccacatga tggtattcga ttttattcga    240

aagcgggcag aagagggaat acaacaagta caaaacatcg ctactaaaac tgcggagggg    300

aagtttgtgg aagctctagg cgacacagcc tcctacgtca aaaagcgaca ggaaatcgac    360

gctgagaacc ttgcgaagct tcaagaaggc ttagcaaaga gcaggcagcg tctgatgggg    420

gacttggatg tgatttttgg tgtgagcgag gatgtgggcc tcacgaagac tttggataag    480

ctggaggaag tgctgatgat gtcggacata ggggcggcca cgacgggtga aatcatcgac    540

gacctccgca tggtcgccaa ggccgagaaa ctcgagcctg acgacgtcaa gtctgtcctc    600

cgtttgcgtt tgatcgaggc gttgacggcc aaggatagga gtatgcagtt gaaaaaggaa    660
```

```
gcgtccgcgg ggaatggaaa gagctaccct cgtgtcctct tcgtcatcgg tgcgaacggg    720

atgggcaaga cgacgacgat cgggaagatc gcctcccgcc tcaaaaatga agcgaatcag    780

agtgtgctgg ttgccgcctg tgacactttt cgcgccgccg ctgtcgacca gctggaggag    840

tggacggtgc gagccggcgt ggacatccac cggccagggg aagggcagac gaaacccgcg    900

cccgtgctgg aagaggctat cagtaaggcg atcgaaggag actacgacgt gctgattgtg    960

gacacatctg ggcggctttc aaataacgtg gccttgaacg aggagctcaa gaagttgaaa   1020

aggaccatcg cggacggcat ccctggtggc ccgcatgaga ccctactcgt cttagacggc   1080

gccgtgggca ggaatggggt agatcaggca aaggtctgga atcgagaggt tggaatcacg   1140

gggttggtca tcacgaaact tgacggcacg gccaggggag gtgtggtggt tagcatcgtg   1200

agggacgtgg gcgtccctgt gaagctcatt ggagtgggcg aggggattga tgacttgcgg   1260

gatttcaatc cagaggattt tgtggatgct ttgttgggat atgagcctga acaggtgctg   1320

gccttggagg cccggcttca agacatggtt caaggcaaac ttatcaagcc gaagagaggg   1380

gtaattgtac gctctgaagg tggtggacgc gataagaata tggatgcaga cgatatcagc   1440

gacaggatga gacggaaagt ccaaggacgg gggggccagg gcggttcctc ctcgcagcgt   1500

ggagggggaa aaggaggaaa aagcggtggt ggcaagaaaa agaggcggta a            1551
```

<210> SEQ ID NO 144
<211> LENGTH: 489
<212> TYPE: PRT
<213> ORGANISM: Nannochloropsis gaditana
<220> FEATURE:
<221> NAME/KEY: misc_feature
<223> OTHER INFORMATION: ALB3b polypeptide

<400> SEQUENCE: 144

```
Met Pro Gln Pro Phe Phe Trp Ser Cys Arg Glu Gln Cys Cys Asp Pro
1               5                   10                  15

Cys Leu Gln His Ser His Arg Ser Glu Leu Ser Tyr Leu Phe Asp Phe
            20                  25                  30

Phe His Ser Asn Arg Met Val Met Arg Thr His Gln Arg Glu Met Trp
        35                  40                  45

Arg Gln Gln Gln Cys Leu Gly Arg Arg Leu Gly Ser Cys Ile Phe Cys
    50                  55                  60

Leu Leu Met Ala Ser Leu Leu Phe Thr Ser Glu Val Val Thr Ala Phe
65                  70                  75                  80

Val Pro Val Ala Thr Arg Arg Pro Asp Leu Leu His Val Ser Arg Pro
                85                  90                  95

Pro Phe Pro Ser Arg Ala Thr Pro Gly Thr Arg Ala Leu Arg Met Val
            100                 105                 110

Leu Gln Pro His Asp Val Val Thr His Leu Asp Pro Ala Trp Leu Ser
        115                 120                 125

His Val Phe Gln Gly Val Ala Asp Ala Ala Val Thr Ser Leu Asp Ala
    130                 135                 140

Thr Asn Ala Ala Val Asp Ala Thr Thr Asp Ala Ala Ala Lys Glu Pro
145                 150                 155                 160

Gly Phe Phe Asp Lys Phe Val Asn Thr Val Met Gly Ala Ile Glu Gly
                165                 170                 175

Val His Ser Glu Leu Val Ser Leu Gly Val Pro Gly Ala Tyr Gly Leu
            180                 185                 190

Ala Ile Ile Leu Phe Thr Ala Gly Val Lys Leu Ala Leu Leu Pro Val
```

```
        195                 200                 205

Thr Tyr Lys Gln Met Glu Ser Ala Gln Arg Met Gln Ala Leu Ala Pro
    210                 215                 220

Lys Ala Lys Glu Leu Lys Asp Lys Tyr Gly Lys Asn Lys Ala Leu Leu
225                 230                 235                 240

Asn Gln Leu Thr Ala Lys Leu Tyr Glu Asp Ala Glu Val Asn Pro Leu
                245                 250                 255

Ala Gly Cys Leu Pro Ala Leu Ala Gln Ile Pro Ile Phe Ile Ala Leu
            260                 265                 270

Tyr Arg Ser Leu Ile Asn Leu Ala Gly Asn Ser Asp Phe Asn Glu Pro
        275                 280                 285

Phe Leu Trp Leu Pro Ser Leu Ala Gly Pro Leu Tyr Gly Gln Ala Arg
    290                 295                 300

Gly Thr Asp Trp Leu Phe Lys Asn Trp Val Asp Gly Val Pro Ala Leu
305                 310                 315                 320

Gly Trp His Asp Thr Ile Ala Phe Leu Thr Ile Pro Val Ile Leu Ile
                325                 330                 335

Leu Thr Gln Ser Ile Ser Gln Arg Leu Leu Thr Pro Pro Ser Asp Asp
            340                 345                 350

Pro Lys Thr Ala Gln Thr Gln Arg Val Leu Lys Tyr Leu Pro Ile Met
        355                 360                 365

Val Gly Tyr Phe Ser Leu Ser Val Pro Ser Gly Leu Gly Val Tyr Trp
    370                 375                 380

Ile Thr Asn Asn Leu Ile Ser Thr Ala Ile Ser Ile Ser Ile Lys Glu
385                 390                 395                 400

Lys Phe Ala Lys Gln Pro Ile Val Ile Asp Val Asp Val Asp Pro Glu
                405                 410                 415

Asp Leu Gly Tyr Asp Pro Ser Thr Val Ala Met Gly Phe Glu Glu Met
            420                 425                 430

Met Ala Glu Ala Thr Arg Asn Ala Leu Pro Ser Glu Gln Pro Lys Arg
        435                 440                 445

Asp Arg Pro Thr Pro Ser Ser Leu Leu Lys Ala Ser Glu Ser Val Val
    450                 455                 460

Ala Glu Glu Gly Gly Lys Arg Asp Glu Glu Ala Gly Arg Val Gly Glu
465                 470                 475                 480

Glu Arg Glu Lys Ala Gly Val Glu Ala
                485
```

<210> SEQ ID NO 145
<211> LENGTH: 1470
<212> TYPE: DNA
<213> ORGANISM: Nannochloropsis gaditana
<220> FEATURE:
<221> NAME/KEY: misc_feature
<223> OTHER INFORMATION: ALB3b gene coding sequence

<400> SEQUENCE: 145

```
atgccccaac cctttttttg gtcttgccgc gagcagtgct gtgatccgtg cctgcaacat     60

tcacatcgga gcgaactctc atatttgttc gatttttttcc attcaaacag gatggtcatg    120

cggacgcatc agcgtgagat gtggcgtcag cagcaatgtc tgggtagaag actagggtca    180

tgtatattct gtctcctgat ggcatccctt ttgtttactt ccgaggtggt cacagcattt    240

gtgcccgtcg ccacgcgtcg gcccgacctc ctccacgtct ctcgcccccc atttccttcg    300

agagccacgc caggtaccag agctttgcgc atggttttac agccgcacga tgtggtgacg    360
```

```
cacctggacc cagcgtggct ttcccacgtc tttcagggcg tggcagatgc ggccgtgact    420

tctttggatg cgacaaatgc cgcggtggac gccaccaccg atgccgccgc gaaggagccg    480

ggcttcttcg ataaattcgt gaacacggtc atgggcgcga tcgagggtgt gcacagtgaa    540

ctggtgtcgc tcggcgtccc tggcgcctac ggcttggcca tcatattgtt caccgcgggc    600

gtcaaactgg ccctgcttcc cgtcacctac aagcagatgg agtcagctca gcgtatgcag    660

gccctagcgc ccaaggcgaa ggagctcaag gacaagtacg ggaagaacaa ggcgctcctg    720

aaccagctga ccgccaagct ctacgaggac gcggaggtga accctctcgc cggctgcctt    780

cccgccctcg cccaaattcc cattttcatt gccctctacc gctccctgat caaccttgcg    840

gggaacagcg acttcaacga gccctttctc tggctgccga gtctggccgg gcctctctac    900

ggccaagccc gaggcacgga ctggctcttc aaaaactggg tggacggcgt cccggccctg    960

ggctggcacg acacaatcgc cttcctcacc atccccgtca tactgatcct cacgcagtct   1020

atctcccaac gactgctcac cccgcccagc gacgacccca agaccgcgca gacccagcgc   1080

gtcctcaaat atctgcccat catggtcggg tacttctctc tgagcgtgcc ctccggcctg   1140

ggtgtctact ggatcaccaa caatttgatc tccacggcca tctcgatcag catcaaggag   1200

aagttcgcca agcagccgat cgtgatcgac gtggatgtgg acccggagga cttgggctac   1260

gacccctcca cggtggccat gggcttcgaa gagatgatgg cggaggcgac gcgcaacgcg   1320

cttccaagcg agcagcccaa gcgggatcga ccgacgccat cctccctttt gaaagcgtca   1380

gagagtgtcg tggctgagga ggggggggaag agggacgagg aggccggccg cgtgggggag   1440

gagagagaaa aagcgggcgt ggaggcctga                                    1470
```

<210> SEQ ID NO 146
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting ALB3b gene, includes PAM

<400> SEQUENCE: 146

```
gggaaagcca cgctgggtcc                                                 20
```

<210> SEQ ID NO 147
<211> LENGTH: 1689
<212> TYPE: DNA
<213> ORGANISM: Nannochloropsis gaditana
<220> FEATURE:
<221> NAME/KEY: misc_feature
<223> OTHER INFORMATION: Cytosolic SRP54 gene coding sequence

<400> SEQUENCE: 147

```
atggtgttgc aggagctcgg tgacaagctt acgggggctc tacgccggct gcagaccacc     60

acggtcgtca acgacgacgt cctcaacgac ctgctccagg acgtatgccg tgcgttagtc    120

gaatccgatg tgaatatcaa ggtagtggcg accctaagaa agggcatcaa ggagaaagtc    180

aaccttgcag atgcccccgc tggcctgaac agacggaaaa tggtgcagcg ggcggtgatg    240

gaggaattgg tccgcctggt cgactcggga acaaagccgt accaaatgag gaagggaaag    300

tcgaacgtga tcatgtttgt gggcttgcaa ggctcgggga aaactaccac cattgccaaa    360

tacgccaact attaccagcg gaagggatgg aagacgtgca tggtgtgtgc cgataccttt    420

cgtgccggag ccttcgatca gctgaagcag aatgcgacaa aactccgtgt gcctttttac    480
```

```
ggctcctaca cggaggcgga cccggtacgg atcgccgagg agggcgtcca gcagttccgt    540

tcagagggat acgaggttat cattgtcgat acctcgggcc ggcacaagca ggaagaagcc    600

ctgtttgagg agatgaaaga gatccaagcg gcggtccgtc ccgacaacgt ggtgtacgtc    660

atggacgcca cccagggcca agccgtcttc gaccaggcac agggtttcca ccaggccgcc    720

gcggtgggct ccgtcattgt caccaagctg gacgggcacg ccaagggggg aggcgccttg    780

tcggccgtgg cggcgacggg ggcgcctatc atatttttgg gctcggggga gcattttgac    840

gacctggacg tcttcaaccc cgggagtttc atcagtcggt tgctgggctt gggggacatg    900

cggggttttt tggaggaagt gagcagcctg gggggcgaggg aaggagggaa agagaggcag    960

gaggccatgg cccagcggct cgtcaagggc cagttcaccc tccgcgacat gtacgagcag   1020

tttgagaacg tgatgaagct ggggcccctt tccaaggtca tgggcatgct gccgggcttt   1080

ccctcttttc tgatgggggg gggggaagga gggagggggg ggcaggacga agctgccacg   1140

ggccggctga agcgtttctt gaccatgatg gacagcatga cggacgcgga gctcgatggg   1200

aaggtggacc tgaacaagag cgagagccgc gtgaaccgga ttgctcgagg aagcggggca   1260

cacccgatgg aagtccaatt tttgctcaag acgtacgcgc aattctcgca aatgttcaag   1320

aagatgggcc cgatgatgtt gaaaggcggg gagggtggca tacagcggca gatggcacgc   1380

aacccgggag gcgtgatgaa tcagttgagc aaggcggtgg acccgcgaat gctacagcag   1440

atgggaggcg caaaaggaat gatggacatg atgaaagcga tgggaggagg aatggggggg   1500

gggcttgcgg acatgctgca gaacttgggg ggaggggggg gagggagagg gggaggaaga   1560

gggagtggac gaggaggggg tgggatggat ccagaacaga tgcaggcgca gatggcgcaa   1620

atggaagaga tgatgaaaag tatgggaatg ggtggaggag ggaaaggagg tggagggttc   1680

cctttctga                                                           1689
```

<210> SEQ ID NO 148
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting Cytosolic SRP54 gene

<400> SEQUENCE: 148

```
ggccagcggg ggcatctgca                                                 20
```

<210> SEQ ID NO 149
<211> LENGTH: 683
<212> TYPE: DNA
<213> ORGANISM: Nannochloropsis gaditana
<220> FEATURE:
<221> NAME/KEY: misc_feature
<223> OTHER INFORMATION: NITRITE/SULFITE REDUCTASE PROMOTER

<400> SEQUENCE: 149

```
ctggtgtcgt caacagccag ctgccacaag aaagtgaaca tgcgtctatt tatgacgtca     60

ttcatcaacc accccgtttc caaacaccgt cccacgcgct gttgagagat gatttttttga   120

atgccatatg gtgctcaaac atgtgcatcg acgctgtcgc acaagcagga gcgggcttgc    180

ccactcgttc ttgttaacgg cttgattcaa aatccccgcc cggaacaaaa tatgccggag    240

cgatccaacg aagcaaaagt caaccagagc ctctctttcc gtccaacacc cgtgttggtg    300

ccatgttaac aatagattca tgcatggata ggcgaagacg tgagaagtta cggagtttgg    360
```

```
gtcatgcttg cgtacatcac tcaacccttt tccccaaaaa aaaatcccgc catgcgattg    420

ccttcgttgc accgcaaaac ggaaattagt tatggcgtca ttgctcaaga ttactgtttt    480

tcgacaaggt gctgcacaac cttggaagaa aactctgcaa atccgtcaat cacatgagtt    540

gtagtttttt tcggcaaggc gggtgagcgt agtgaattat attccttgta aggcaaagcg    600

gatactaatt ttcacgtagt tgccctgacc tcctatgctc ggaaacgccg ccgtactgcc    660

ccacccgaac tcagatcacc agt                                            683


<210> SEQ ID NO 150
<211> LENGTH: 990
<212> TYPE: DNA
<213> ORGANISM: Nannochloropsis gaditana
<220> FEATURE:
<221> NAME/KEY: misc_feature
<223> OTHER INFORMATION: Nitrite/Sulfite Reductase Terminator

<400> SEQUENCE: 150

aggcagggtc cccgccaaaa agggtggcga ggacaagaag aagaaacagg aaggggggg      60

gcacgacgga ggacttgtcg agtccatcag ggaggtaggg gcgggaagcc tcgaatctgc    120

tagttggtag ggataaatag agttcaagga ccgaaggagg aggcgccagg atcagcgaaa    180

gcctggatta agagcgagac tccttgcgct gcagtcaagg cgattacagg acccccggtg    240

tctgggtttg gagatgacct cttggaggac ggcttgatgc gggtttttga ggaaggttgt    300

acatttttgt ttgaaatttg caaggaaagc gtcgcgctcc ggcatagagg gatagggga     360

ggaaagggca cttgtgcccg ctccgtctct gtacgggtct ttgaagaaaa gattcgagaa    420

accacccaaa gggcatcaaa tgcgaaacct ccctgaaaaa agtttcgatt ttctttattt    480

gttgaggagg agagggaaga gtggtatcca atgtggggtg tattcacgcc aacaaagcgg    540

ggggagctga cccagaggcc acctgccaca ggctccatcc aaacaagctt tcagggctga    600

ttccagaatt agggttagag taagaatgag ggctacgcca gcagtcatcc tttgcgggcg    660

tcttgagtcg caagaagctc tccaaggaaa gcgaaggcga attttcccca aaaacaaagg    720

cagtggcgag ctccttgtcc ctctttgagc accctcctc gctaatttc ttactctgat      780

tttttgggga agtgtttctc cttctttcgg agacgtggcc ttatgctcca tcgccttcgc    840

gcaccgactc gaccatgccc acacactctc cgtgcccccc ttccctctgc cacccttccc    900

tctcccccc tcccttcctc cctccctccc tccctccctc cctccctcct cccaggcaca     960

cccctattgt ccacttcgcg ccccaggctc                                     990
```